(12) United States Patent
Nagase et al.

(10) Patent No.: US 6,277,859 B1
(45) Date of Patent: Aug. 21, 2001

(54) MORPHINAN DERIVATIVE AND ITS PHARMACEUTICAL APPLICATIONS

(75) Inventors: Hiroshi Nagase; Koji Kawai; Kuniaki Kawamura, all of Kamakura; Jun Hayakawa, Yokohama; Takashi Endoh, Chigasaki, all of (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/541,793

(22) Filed: Mar. 31, 2000

Related U.S. Application Data

(63) Continuation of application No. 08/108,643, filed as application No. PCT/JP93/00080 on Jan. 22, 1993.

(30) Foreign Application Priority Data

Jan. 23, 1992 (JP) .................................. 4-10115
Nov. 2, 1992 (JP) .................................. 4-294308

(51) Int. Cl.$^7$ .................... C07D 489/00; A61K 31/4355
(52) U.S. Cl. .................. 514/282; 540/481; 540/597; 546/44; 546/45; 546/46
(58) Field of Search .................. 546/44, 45, 46; 514/282; 540/497, 481

(56) References Cited

U.S. PATENT DOCUMENTS

| | | | |
|---|---|---|---|
| 3,236,851 | 2/1966 | Sawa et al. | 514/289 |
| 4,241,066 | 12/1980 | Kobylecki et al. | 546/45 |
| 4,241,067 | 12/1980 | Kobylecki et al. | 546/45 |
| 4,362,870 | 12/1982 | Portoghese | 546/44 |
| 4,401,672 | 8/1983 | Portoghese | 514/279 |
| 4,730,048 | 3/1988 | Portoghese | 546/45 |
| 4,767,718 | 8/1988 | Meyers | 436/501 |
| 4,806,556 | 2/1989 | Portoghese | 546/45 |
| 4,816,586 | 3/1989 | Portoghese | 544/340 |
| 5,071,985 | 12/1991 | Andre et al. | 546/45 |
| 5,219,861 | 6/1993 | Kanematsu et al. | 514/282 |
| 5,258,386 | 11/1993 | Newman et al. | 514/289 |
| 5,739,145 | 4/1998 | Nagase et al. | 514/282 |

FOREIGN PATENT DOCUMENTS

| | | |
|---|---|---|
| 0622231 | 11/1935 | (DE) . |
| 2254298 | 5/1974 | (DE) . |
| 2812580 | 10/1978 | (DE) . |
| 3617182 | 11/1986 | (DE) . |
| 0242417 | 10/1987 | (EP) . |
| 0359647 | 3/1990 | (EP) . |
| 0374919 | 6/1990 | (EP) . |
| 0864107 | 3/1961 | (GB) . |
| 0919311 | 2/1963 | (GB) . |
| 2175898 | 12/1986 | (GB) . |
| 40-12629 | 6/1965 | (JP) . |
| 0417786 | 4/1966 | (JP) . |
| 41-66905 | 4/1966 | (JP) . |
| 4118826 | 10/1966 | (JP) . |
| 4732998 | 8/1972 | (JP) . |
| 53-119899 | 10/1978 | (JP) . |
| 0574991 | 1/1982 | (JP) . |
| 61-271275 | 12/1986 | (JP) . |
| 62-258380 | 11/1987 | (JP) . |
| 1149788 | 6/1989 | (JP) . |
| 2121993 | 5/1990 | (JP) . |
| 0290054 | 6/1965 | (NL) . |
| 9315081 | 5/1993 | (WO) . |
| 9501178 | 1/1995 | (WO) . |

OTHER PUBLICATIONS

Portoghese et al., J. Med. Chem., vol. 34, No. 7, p. 1996 (1991).
Olsen et al., J. Med. Chem., vol. 33, No. 2, pp. 737–741 (1990).
Chem. Pharm. Bull., vol. 36, No. 6, pp. 2282–2285 (1988).
Mohamed et al., J. Med. Chem., vol. 29, No. 8, pp. 1551–1553 (1986).
Sayre et al., J. Med. Chem., vol. 27, No. 10, pp. 1325–1335 (1984).
Sayre et al., J. Med. Chem., vol. 26, No. 9, pp. 1229–1235 (1983).
Erez et al., J. Med. Chem., vol. 25, No. 7, pp. 847–849 (1982).
Sayre et al., J. Org. Chem., vol. 45, No. 16, pp. 3366–3368 (1980).
J. Med. Chem., vol. 23, pp. 233–234 (1980).
Portoghese et al., J. Med. Chem., vol. 22, No. 2, pp. 168–173 (1979).
Jiang et al., J. Med. Chem., vol. 20, No. 8, pp. 1100–1102 (1977).
Australian (AIPO) Office Action, Mar. 29, 1994, citing prior art references.
Ko et al., J. Med. Chem., vol. 27, pp. 1727–1729 (1984).
Dykstra et al., Chemical Abstracts, vol. 107, No. 21, pp. 58–59 (1987).

(List continued on next page.)

*Primary Examiner*—John M. Ford
(74) *Attorney, Agent, or Firm*—Birch, Stewart, Kolasch & Birch, LLP

(57) ABSTRACT

A morphinan derivative or its pharmacologically allowed acid addition salt represented with compound I, (I)

[chemical structure]

an analgesic and diuretic having its derivative or its salt as the active ingredient, and its production process are described. The compound of the present invention possesses strong analgesic activity and diuretic action as a highly selective κ-opioid agonist, allowing it to be used as a useful analgesic and diuretic.

13 Claims, No Drawings

OTHER PUBLICATIONS

Burger, Ed., "Medicinal Chemistry" $2^{nd}$ Ed., Interscience, NY (1981), p. 43.

Hosztafi et al., Arzneim–Forsch, vol. 43, No. 11, pp. 1200–1203 (1993).

Hosztafi et al., Heterocycles, vol. 36, No. 7, pp. 1509–1519 (1993).

Hosztafi et al., Synth. Commun., vol. 22, No. 12, pp. 1673–1682 (1992).

Hosztafi et al., Monatsh. Chem., vol. 123, No. 5, pp. 435–441 (1992).

Simon et al., Synth. Commun., vol. 22, No. 6, pp. 913–921 (1992).

Dasher et al., J. Med. Chem., vol. 35, No. 13, pp. 2374–2384 (1992).

Fujii et al., Chem. Pharm. Bull., vol. 35, No. 6, pp. 2282–2285 (1988).

Abbot et al., Analyst (London), vol. 112, No. 4, pp. 397–406 (1987).

DeGraw et al., J. Med. Chem., vol. 21, No. 5, pp. 415–422 (1978).

Derwent Japanese, vol. 5, No. 44 Oct. 27, 1996 (JP 18,825/66).

Derwent, Week T34, p. 10, Mar. 23, 1972 (JP 54957T, 54959T and 54958T).

DeHaven–Hudkins et al., Society for Neuroscience, vol. 24, Part 1, Abstracts, $28^{th}$ Annual Meeting, (Nov. 7–12, 1998); Abstract No. 352.6.

Fujii et al., Chem. Abstr., vol. 110, Abstract 193151 (1988).

Merck Index, $11^{th}$ Ed., p. 6275, Compounds 6277 and 6278 (1989).

MORPHINAN DERIVATIVE AND ITS PHARMACEUTICAL APPLICATIONS

This application is a continuation of co-pending application Ser. No. 08/108,643, filed on Feb. 10, 1997. Application Ser. No. 08/108,643 is the national phase of PCT International Application No. PCT/JP93/00800 filed on Jan. 22, 1993 under 35 U.S.C. §371. The entire contents of each of the above-identified applications are hereby incorporated by reference.

TECHNICAL FIELD

The present invention relates to an analgesic and diuretic having as its active ingredient a morphinan derivative or a pharmacologically acceptable acid salt thereof.

BACKGROUND ART

Morphine has long been known as a powerful analgesic having a morphinan skeleton, and is widely used even at present. However, this drug has serious side effects that present clinical problems, including drug dependence, action that suppresses respiration and action that suppresses smooth muscle movement (constipation). Thus, there is a need for a powerful analgesic that acts on the central nervous system and that also can be used safely.

In addition, it has also been reported that drugs that act on opioid receptors effect urination (J. D. Leander, J. Pharmacol. Exp. Ther., 227, 35 (1983)), and thus, the effective use of that action is also desired.

DISCLOSURE OF THE INVENTION

The existence of opioid receptors has been clearly established as receptors involved in analgesic action on the central nervous system. Moreover, these receptors are known to be able to classified into the three types, $\mu$, $\delta$ and $\kappa$. In addition, $\sigma$ receptors are also known to demonstrate psychotomimetics. Those agonists having affinity for these $\kappa$-receptors or $\delta$-receptors have been shown to have strong analgesic activity, while not demonstrating serious side effects that present clinical problems, such as drug dependence, action that suppresses respiration and action that suppresses smooth muscle movement, that are observed in the case of morphin and so forth, which are $\mu$-receptor agonists. In addition, the psychotomimetics observed in existing $\kappa$-receptor agonists are reported to be caused by the affinity to $\sigma$-receptors. Moreover, $\kappa$-receptor agonists do not demonstrate cross tolerance with $\mu$-receptor agonists such as morphin. Analgesics free of such side effects having a high degree of usefulness since they can be applied in not only the control of pain in patients having post-operative pain and cancer patients suffering from cancer, but can also be widely applied for general pain. In addition, the absence of cross tolerance indicates that these analgesics are effective even in patients that have developed tolerance to analgesics such as morphin. Therefore, the object of the present invention is to provide a $\kappa$-receptor agonist or $\delta$-receptor agonist that has powerful analgesic action while not having serious side effects like those of morphin, not having cross tolerance with morphin and so forth, and not demonstrating any affinity whatsoever for $\sigma$-receptors. In addition, another object of the present invention is to provide a useful diuretic that takes advantage of the effects of opioid action drugs on urination.

As a result of earnest studies to solve the above-mentioned problems, the inventors of the present invention found that the morphinan derivatives indicated by the below formula (I) is a compound that demonstrates analgesic action and diuretic action having the excellent characteristics described above, thus leading to completion of the present invention.

Namely, the present invention relates to a morphinan derivative represented with general formula (I) below or pharmacologically acceptable acid salt thereof, its production process as well as its pharmaceutical applications:

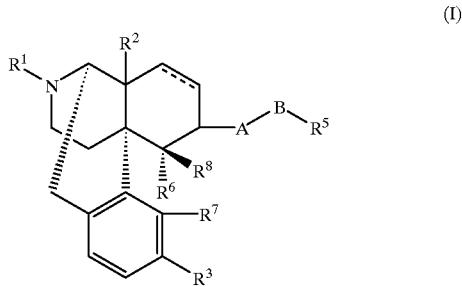

(I)

[wherein,—
represents a single or double bond; $R^1$ represents an alkyl group having 1–5 carbon atoms, a cycloalkylalkyl group having 4–7 carbon atoms, a cycloalkenylalkyl group having 5–7 carbon atoms, an aryl group having 6–12 carbon atoms, an aralkyl group having 7–13 carbon atoms, an alkenyl group having 4–7 carbon atoms, an allyl group, a furan-2-ylalkyl group having 1–5 carbon atoms, or a thiophen-2-ylalkyl group having 1–5 carbon atoms; $R^2$ represents a hydrogen atoms, a hydroxy group, a nitro group, an alkanoyloxy group having 1–5 carbon atoms, an alkoxy group having 1–5 carbon atoms, an alkyl group having 1–5 carbon atoms, or —$NR^9R^{10}$ wherein $R^9$ represents a hydrogen atom or an alkyl group having 1–5 carbon atoms, and $R^{10}$ represents a hydrogen atom, an alkyl group having 1–5 carbon atoms, or —$C(=O)R^{11}$ wherein $R^{11}$ represents a hydrogen atom, a phenyl group or an alkyl group having 1–5 carbon atoms; $R^3$ represents a hydrogen atom, a hydroxy group, an alkanoyloxy group having 1–5 carbon atoms, or an alkoxy group having 1–5 carbon atoms; A represents —XC(=Y)—, —XC(=Y)Z—, —X—, —XSO$_2$—, or —OC(OR$^4$)R$^4$— (where, X, Y and Z each independently represent NR$^4$, S or O wherein $R^4$ represents a hydrogen atom, a straight-chain or branched chain alkyl group having 1–5 carbon atoms or an aryl group having 6–12 carbon atoms, and wherein $R^4$ may be identical or different); B represents a valence bond, a straight-chain or branched chain alkylene group having 1–14 carbon atoms (which may be substituted with at least one type of substituent groups selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein 1 to 3 methylene groups may be replaced with carbonyl groups), an acyclic unsaturated hydrocarbon containing from 1 to 3 double bonds and/or triple bonds and having 2–14 carbon atoms (which may be substituted with at least one substituent group selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein from 1 to 3 methylene groups may be replaced with carbonyl groups), or a straight-chain or branched chain saturated or unsaturated hydrocarbon group containing from 1 to 5 thioether, ether and/or amino bonds and having 1–14 carbon atoms (wherein hetero atoms are not bonded directly to A, and 1 to 3 methylene groups may be replaced with carbonyl groups); $R^5$ represents a hydrogen atom or an organic group having the basic skeleton of (formula 1) (which may be substituted with at least one or more substituent groups selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, iodine, an amino group, a nitro group, a cyano group, an isothiocyanate group, a trifluoromethyl group and a methylenedioxy group),

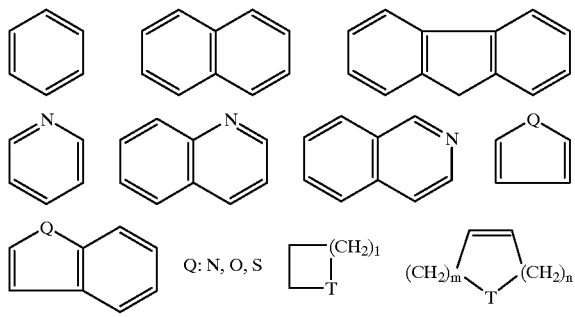

T: CH, N, S, O
l = 0–5
m, n ≥ 0
m + n ≤ 5

(Formula 1) Organic Group Represented by $R^5$
(Formula 1—1)

$R^6$ represents a hydrogen atom; $R^7$ represents a hydrogen atom, a hydroxy group, an alkoxy group having 1–5 carbon atoms, an alkanoyloxy group having 1–5 carbon atoms, or $R^6$ and $R^7$ together represent —O—, —CH$_2$— or —S—; $R^8$ represents a hydrogen atom, an alkyl group having 1–5 carbon atoms, or an alkanoyl group having 1–5 carbon atoms, and the general formula (I) includes the (+) form, (−) form and (±) form].

DETAILED DESCRIPTION

Here, preferable examples of $R^1$ include an alkyl group having 1–5 carbon atoms, a cycloalkylmethyl group having 4–7 carbon atoms, a cycloalkenylmethyl group having 5–7 carbon atoms, a phenylalkyl group having 7–13 carbon atoms, an alkenyl group having 4–7 carbon atoms, an allyl group, a furan-2-yl-alkyl group having 1–5 carbon atoms and a thiophen-2-yl-alkyl group having 1–5 carbon atoms, while particularly preferable examples of $R^1$ include methyl, ethyl, cyclopropylmethyl, cyclobutylmethyl, cyclopentylmethyl, cyclopentenylmethyl, cyclohexenylmethyl, benzyl, phenethyl, trans-2-butenyl, 2-methyl-2-butenyl, allyl, furan-2-yl-methyl and thiophen-2-yl-methyl groups.

Preferable examples of $R^2$ include a hydrogen atom, and hydroxy, nitro, acetoxy, methoxy, methyl, ethyl, propyl, amino, dimethylamino, acetylamino and benzoylamino groups, while particularly preferable examples include a hydrogen atom, and hydroxy, nitro, acetoxy, methyl and dimethylamino groups.

Preferable examples of $R^3$ include a hydrogen atom, and hydroxy, acetoxy and methoxy groups.

Preferable examples of A include —NR$^4$C(=O)—, —NR$^4$C(=S)—, —NR$^4$C(=O)O—, —NR$^4$C(=O)NR$^4$—, —NR$^4$C(=S)NR$^4$—, —NR$^4$C((=O)S—, —OC((=O)—, —OC(=O)O—, —SC(=O)—, —NR$^4$—, —O—, —NR$^4$SO$_2$— and —OSO$_2$—, while particularly preferable examples include —NR$^4$C(=O)—, —NR$^4$C(=S)—, —NR$^4$C(=O) O—, —NR$^4$C(=O)NR$^4$—, —NR$^4$C(=S)NR$^4$— and —NR$^4$SO$_2$—.

Preferable examples of $R^4$ include a hydrogen atom, a straight-chain or branched alkyl group having 1–5 carbon atoms and a phenyl group, while particularly preferable examples include a straight-chain or branched alkyl group having 1–5 carbon atoms, and particularly methyl, ethyl, propyl, isopropyl, butyl and isobutyl groups.

Preferable examples of B include —(CH$_2$)n— (n=0–6), —(CH$_2$)n—C(=O)— (n=1–4), —CH=CH—(CH$_2$)n— (n=0–4), —C≡C—(CH$_2$)n— (n=0–4), —CH$_2$—O—, —CH$_2$—S—, —CH$_2$—O—(CH$_2$)$_2$—O—(CH$_2$)$_2$—, —CH$_2$—O——CH$_2$—NH—CH$_2$—O—CH$_2$— and —CH$_2$—O—CH$_2$—S—CH$_2$—O—CH$_2$—, while particularly preferable examples include —(CH$_2$)n— (n=0–6), —CH=CH—(CH$_2$)n— (n=0–4), —C≡C—(CH$_2$)n— (n=0–4), —CH$_2$—O— and —CH$_2$—S—. Preferable examples of $R^5$ include a hydrogen atom and an organic group having the basic skeleton indicated in (formula 1–1) (which may be substituted with at least one or more substituent groups selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, an amino group, a nitro group, a cyano group, an isothiocyanate group and a trifluoromethyl group), (Formula 1-1)

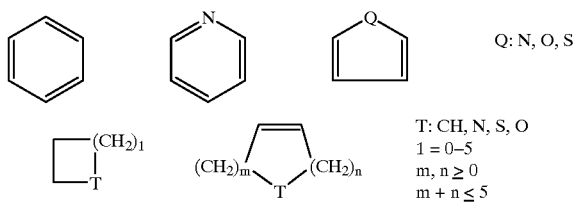

T: CH, N, S, O
l = 0–5
m, n ≥ 0
m + n ≤ 5 while particularly preferable examples include, a hydrogen atom and phenyl, 3,4-dichlorophenyl, 4-chlorophenyl, 3-chlorophenyl, 3,4-difluorophenyl, 4-fluorophenyl, 3-fluorophenyl, 2-fluorophenyl, 4-bromophenyl, 3-bromophenyl, 2-bromophenyl, 4-nitrophenyl, 3-nitrophenyl, 2-nitrophenyl, 4-trifluoromethylphenyl, 3-trifluoromethylphenyl, 2-trifluoromethylphenyl, 4-methylphenyl, 3-methylphenyl, 2-methylphenyl, 4-methoxyphenyl, 3-methoxyphenyl, 2-methoxy, 3-furanyl, 2-furanyl, 3-thienyl, 2-thienyl, cyclopentyl and cyclohexyl groups. But naturally the present invention is not limited to these examples.

Preferable examples of pharmacologically preferable acid addition salts include, but are naturally not limited to, inorganic acid salts such as hydrochloride, sulfate, nitrate, hydrobromide, hydroiodide and phosphate; organic carboxylates such as acetate, lactate, citrate, oxalate, glutarate, malate, tartrate, fumarate, mandelate, benzoate and phthalate; and, organic sulfonates such as methanesulfonate, ethanesulfonate, benzenesulfonate, p-toluenesulfonate and camphorsulfonate, while particularly preferable examples include hydrochloride, hydrobromate, phosphate, tartrate and methanesulfonate.

Among the compounds of the general formula (I) of the present invention, compound 1

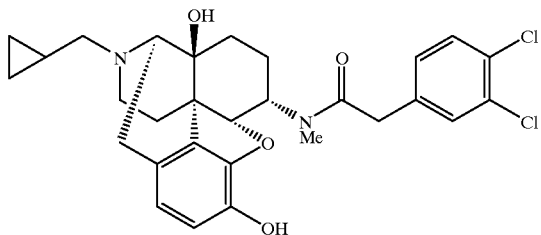

wherein—
is a single bond, $R^1$ is a cyclopropylmethyl group, $R^2$ and $R^3$ are hydroxy groups, A is $\alpha$-$NR^4C(=O)$—, $R^4$ is a methyl group, B is —$CH_2$—, $R^5$ is 3,4-dichlorophenyl, $R^6$ and $R^7$ are together —O— and $R^8$ is a hydrogen atom is named 17-cyclopropylmethyl-4,5α-epoxy-3,14β-dihydroxy-6α-(N-methyl-3,4-dichlorophenylacetamide)morphinane.

In accordance with the above nomenclature system, concrete examples of the compound of the present invention are as follows:

17-cyclopropylmethyl-4,5α-epoxy-3,14β-dihydroxy-6α-(N-methylcinnamamido)morphinan, 17-cyclopropylmethyl-4,5α-epoxy-3,14β-dihydroxy-6α-(N-methylbenzyloxycarbamido)-morphinan, 17-cyclopropylmethyl-4,5α-epoxy-3,14β-dihydroxy-6α-(N-methylphenylmethanesulfonamido)morphinan, 17-allyl-4,5α-epoxy-3,14β-dihydroxy-6α-(N-methyl-3,4-dichlorophenylacetamido)morphinan, 17-allyl-4,5α-epoxy-3,14β-dihydroxy-6α-(N-methylcinnamamido)morphinan, 17-allyl-4,5α-epoxy-3,14β-dihydroxy-6α-(N-methylbenzyloxycarbamido)morphinan, 17-allyl-4,5α-epoxy-3,14β-dihydroxy-6α-(N-methylphenylmethanesulfonamido)morphinan, 17-methyl-4,5α-epoxy-3,14β-dihydroxy-6α-(N-methyl-3,4-dichlorophenylacetamido)morphinan, 17-methyl-4,5α-epoxy-3,14β-dihydroxy-6α-(N-methylcinnamamido)morphinan, 17-methyl-4,5α-epoxy-3,14β-dihydroxy-6α-(N-methylbenzyloxycarbamido)morphinan, 17-methyl-4,5α-epoxy-3,14β-dihydroxy-6α-(N-methylphenylmethanesulfonamido)-morphinan, 17-phenethyl-4,5α-epoxy-3,14β-dihydroxy-6α-(N-methyl-3,4-dichlorophenylacetamido)morphinan, 17-phenethyl-4,5α-epoxy-3,14β-dihydroxy-6α-(N-methylcinnamamido)-morphinan, 17-phenethyl-4,5α-epoxy-3,14β-dihydroxy-6α-(N-methylbenzyloxycarbamido)morphinan, 17-phenethyl-4,5α-epoxy-3,14β-dihydroxy-6α-(N-methylphenylmethanesulfonamido)morphinan, 17-cyclopropylmetyl-4,5α-epoxy-3-hydroxy-14β-acetoxy-6α-(N-methyl-3,4-dichlorophenylacetamido)morphinan, 17-cyclopropylmethyl-4,5α-epoxy-3-hydroxy-14β-acetoxy-6α-(N-methylcinnamamido)morphinan, 17-cyclopropylmethyl-4,5α-epoxy-3-hydroxy-14β-acetoxy-6α-(N-methylbenzyloxycarbamido)morphinan, 17-cyclopropylmethyl-4,5α-epoxy-3-hydroxy-14β-acetoxy-6α-(N-methylphenylmethanesulfonamido) morphinan, 17-allyl-4,5α-epoxy-3-hydroxy-14β-acetoxy-6α-(N-methyl-3,4-dichlorophenylacetamido)morphinan, 17-allyl-4.5α-epoxy-3-hydroxy-14β-acetoxy-6α-(N-methylcinnamamido)morphinan, 17-allyl-4,5α-epoxy-3-hydroxy-14β-acetoxy-6α-(N-methylbenzyloxycarbamido)morphinan, 17-allyl-4,5α-epoxy-3-hydroxy-14β-acetoxy-6α-(N-methylphenylmethanesulfonamido)-morphinan, 17-methyl-4,5α-epoxy-3-hydroxy-14β-acetoxy-6α-(N-methyl-3,4-dichlorophenylacetamido)morphinan, 17-methyl-4,5α-epoxy-3-hydroxy-14β-acetoxy-6α-(N-methylcinnamamido)-morphinan, 17-methyl-4,5α-epoxy-3-hydroxy-14β-acetoxy-6α-(N-methylbenzyloxycarbamido) morphinan, 17-methyl-4,5α-epoxy-3-hydroxy-14β-acetoxy-6α-(N-methylphenylmethanesulfonamido) morphinan, 17-phenethyl-4,5α-epoxy-3-hydroxy-14β-acetoxy-6α-(N-methyl-3,4-dichlorophenylacetamido) morphinan, 17-phenethyl-4,5α-epoxy-3-hydroxy-14β-acetoxy-6α-(N-methylcinnamamido)morphinan, 17-phenethyl-4,5α-epoxy-3-hydroxy-14β-acetoxy-6α-(N-methylbenzyloxycarbamido)morphinan, 17-phenethyl-4,5α-epoxy-3-hydroxy-14β-acetoxy-6α-(N-methylphenylmethanesulfonamido)morphinan, 17-cyclopropylmethyl-4,5α-epoxy-14β-hydroxy-6α-(N-methyl-3,4-dichlorophenylacetamido)morphinan, 17-cyclopropylmetyl-4,5α-epoxy-14β-hydroxy-6α-(N-methylcinnamamido)morphinan, 17-cyclopropylmethyl-4,5α-epoxy-14βhydroxy-6α-(N-methylbenzyloxycarbamido)-morphinan, 17-cyclopropylmethyl-4,5α-epoxy-14β-hydroxy-6α-(N-methylphenylmethanesulfonamido)morphinan, 17-allyl-4,5α-epoxy-14βhydroxy-6α-(N-methyl-3,4-dichlorophenylacetamido)morphinan, 17-allyl-4,5α-epoxy-14β-hydroxy-6α-(N-methylcinnamamido)morphinan, 17-allyl-4,5α-epoxy-14βhydroxy-6α-(N-methylbenzyloxycarbamido)-morphinan, 17-allyl-4,5α-epoxy-14βhydroxy-6α-(N-methylphenylmethanesulfonamido)morphinan, 17-methyl-4,5α-epoxy-14βhydroxy-6α-(N-methyl-3,4-dichlorophenylacetoamido)morphinan, 17-methyl-4,5α-epoxy-14β-hydroxy-6α-(N-methylcinnamamido)morphinan, 17-methyl-4,5α-epoxy-14β-hydroxy-6α-(N-methylbenzyloxycarbamido) morphinan, 17-methyl-4,5α-epoxy-14β-hydroxy-6α-(N-methylphenylmethanesulfonamido)morphinan, 17-phenethyl-4,5α-epoxy-14β-hydroxy-6α-(N-methyl-3,4-dichlorophenylacetamido)morphinan, 17-phenethyl-4,5α-epoxy-14β-hydroxy-6α-(N-methylcinnamamido) morphinan, 17-phenethyl-4,5α-epoxy-14β-hydroxy-6α-(N-methylbenzyloxycarbamido)morphinan, 17-phenethyl-4,5α-epoxy-14β-hydroxy-6α-(N-methylphenylmethanesulfonamido)-morphinan, 17-cyclopropylmethyl-4,5α-epoxy-14β-acetoxy-6α-(N-methyl-3,4-dichlorophenylacetamido)morphinan, 17-cyclopropylmethyl-4,5α-epoxy-14β-acetoxy-6α-(N-methylcinnamamido)morphinan, 17-cyclopropylmethyl-4,5(α-epoxy-14β-acetoxy-6α-(N-methylbenzyloxycarbamido)-morphinan, 17-cyclopropylmethyl-4,5α-epoxy-14β-acetoxy-6α-(N-methylphenylmethanesulfonamido)morphinan, 17-allyl-4,5α-epoxy-14β-actoxy-6α-(N-methyl-3,4-dichlorophenylacetamido)morphinan, 17-allyl-4,5α-epoxy-14β-acetoxy-6α-(N-methylcinnamamido)morphinan, 17-allyl-4,5α-epoxy-14β-acetoxy-6α-(N-methylbenzyloxycarbamido)-morphinan, 17-allyl-4,5α-epoxy-14β-acetoxy-6α-(N-methylphenylmethanesulfonamido)morphinan, 17-methyl-4,5α-epoxy-14β-acetoxy-6α-(N-methyl-3,4-dichlorophenylacetamido)morphinan, 17-methyl-4,5α-epoxy-14β-acetoxy-6α-(N-methylcinnamamido)morphinan, 17-methyl-4,5α-epoxy-14β-acetoxy-6α-(N-methylbenzyloxycarbamido) morphinan, 17-methyl-4,5α-epoxy-14β-acetoxy-6α-(N-methylphenylmethanesulfonamido)morphinan, 17-phenethyl-4,5α-epoxy-14β-acetoxy-6α-(N-methyl-3,4-dichlorophenylacetamido)morphinan, 17-phenethyl-4,5α-epoxy-14β-acetoxy-6α-(N-methylcinnamamido)

morphinan, 17-phenethyl-4,5α-epoxy-14β-acetoxy-6α-(N-methylbenzyloxycarbamido)morphinan, 17-phenethyl-4,5α-epoxy-14β-acetoxy-6α-(N-methylphenylmethanesulfonamido)-morphinan, 17-cyclopropylmethyl-4,5α-epoxy-3-methoxy-14β-hydroxy-6α-N-methyl-3,4-dichlorophenylacetamido)morphinan, 17-cyclopropylmethyl-4,5α-epoxy-3-methoxy-14β-hydroxy-6α-(N-methylcinnamamido)morphinan, 17-cyclopropylmethyl-4,5α-epoxy-3-methoxy-14β-hydroxy-6α-(N-methylbenzyloxycarbamido)morphinan, 17-cyclopropylmethyl-4,5α-epoxy-3-methoxy-14β-hydroxy-6α-(N-methylphenylmethanesulfonamido)morphinan, 17-allyl-4,5α-epoxy-3-methoxy-14β-hydroxy-6α-(N-methyl-3,4-dichlorophenylacetamido)morphinan, 17-allyl-4,5α-epoxy-3-methoxy-14β-hydroxy-6α-(N-methylcinamamido)morphinan, 17-allyl-4,5α-epoxy-3-methoxy-14β-hydroxy-6α-(N-methylbenzyloxycarbamido)morphinan, 17-allyl-4,5α-epoxy-3-methoxy-14β-hydroxy-6α-(N-methylphenylmethanesulfonamido)-morphinan, 17-methyl-4,5α-epoxy-3-methoxy-14β-hydroxy-6α-(N-methyl-3,4-dichlorophenylacetamido)morphinan, 17-methyl-4,5α-epoxy-3-methoxy-14β-hydroxy-6α-(N-methylcinnamamido)-morphinan, 17-methyl-4,5α-epoxy-3-methoxy-14β-hydroxy-6α-(N-methylbenzyloxycarbamido)morphinan, 17-methyl-4,5α-epoxy-3-methoxy-14β-hydroxy-6α-(N-methylphenylmethanesulfonamido)morphinan, 17-phenethyl-4,5α-epoxy-3-methoxy-14β-hydroxy-6α-(N-methyl-3,4-dichlorophenylacetamido)morphinan, 17-phenethyl-4,5α-epoxy-3-methoxy-14β-hydroxy-6α-(N-methylcinnamamido)morphinan, 17-phenethyl-4,5α-epoxy-3-methoxy-14β-hydroxy-6α-(N-methylbenzyloxycarbamido)morphinan, 17-phenethyl-4,5α-epoxy-3-methoxy-14β-hydroxy-6α-(N-methylphenylmethanesulfonamido)morphinan, 17-cyclopropylmetyl-4,5α-epoxy-3-methoxy-14β-acetoxy-6α-(N-methyl-3,4-dichlorophenylacetamido)morphinan, 17-cyclopropylmethyl-4,5α-epoxy-3-methoxy-14β-acetoxy-6α-(N-methylcinnamamido)morphinan, 17-cyclopropylmethyl-4,5α-epoxy-3-methoxy-14β-acetoxy-6α-(N-methylbenzyloxycarbamido)morphinan, 17-cyclopropylmethyl-4,5α-epoxy-3-methoxy-14β-acetoxy-6α-(N-methylphenylmethanesulfonamido)morphinan, 17-allyl-4,5α-epoxy-3-methoxy-14β-acetoxy-6α-(N-methyl-3,4-dichlorophenylacetamido)morphinan, 17-allyl-4,5α-epoxy-3-methoxy-14β-acetoxy-6α-(N-methylcinnamamido)morphinan, 17-allyl-4,5α-epoxy-3-methoxy-14β-acetoxy-6α-(N-methylbenzyloxycarbamido)morphinan, 17-allyl-4,5α-epoxy-3-methoxy-14β-acetoxy-6α-(N-methylphenylmethanesulfonamido)-morphinan, 17-methyl-4,5α-epoxy-3-methoxy-14β-acetoxy-6α-(N-methyl-3,4-dichlorophenylacetamido)morphinan, 17-methyl-4,5α-epoxy-3-methoxy-14β-acetoxy-6α-(N-methylcinnamamido)-morphinan, 17-methyl-4,5α-epoxy-3-methoxy-14β-acetoxy-6α-(N-methylbenzyloxycarbamido)morphinan, 17-methyl-4,5α-epoxy-3-methoxy-14β-acetoxy-6α-(N-methylphenylmethanesulfonamido)morphinan, 17-phenethyl-4,5α-epoxy-3-methoxy-14β-acetoxy-6α-(N-methyl-3,4-dichlorophenylacetamido)morphinan, 17-phenethyl-4,5α-epoxy- 3-methoxy-14β-acetoxy-6α-(N-methylcinnamamido)morphinan, 17-phenethyl-4,5α-epoxy-3-methoxy-14β-acetoxy-6α-(N-methylbenzyloxycarbamido)morphinan, 17-phenethyl-4,5α-epoxy-3-methoxy-14β-acetoxy-6α-(N-methylphenylmethanesulfonamido)morphinan, 17-cyclopropylmethyl-4,5α-epoxy-3-acetoxy-14β-hydroxy-6α-(N-methyl-3,4-dichlorophenylacetamido)morphinan, 17-cyclopropylmethyl-4,5α-epoxy-3-acetoxy-14β-hydroxy-6α-(N-methylcinnamamido)morphinan, 17-cyclopropylmethyl-4,5α-epoxy-3-acetoxy-14β-hydroxy-6α-(N-methylbenzyloxycarbamido)morphinan, 17-cyclopropylmethyl-4,5α-epoxy-3-acetoxy-14β-hydroxy-6α-(N-methylphenylmethanesulfonamido)morphinan, 17-allyl-4,5α-epoxy-3-acetoxy-14β-hydroxy-6α-(N-methyl-3,4-dichlorophenylacetamido)morphinan, 17-allyl-4,5α-epoxy-3-acetoxy-14β-hydroxy-6α-(N-methylcinnamamido)morphinan, 17-allyl-4,5α-epoxy-3-acetoxy-14β-hydroxy-6α-(N-methylbenzyloxycarbamido)morphinan, 17-allyl-4,5α-epoxy-3-acetoxy-14β-hydroxy-6α-(N-methylphenylmethanesulfonamido)morphinan, 17-methyl-4,5α-epoxy-3-acetoxy-14β-hydroxy-6α-(N-methyl-3,4-dichlorophenylacetamido)morphinan, 17-methyl-4,5α-epoxy-3-acetoxy-14β-hydroxy-6α-(N-methylcinnamamido)morphinan, 17-methyl-4,5α-epoxy-3-acetoxy-14βhydroxy-6α-(N-methylbenzyloxycarbamido)morphinan, 17-methyl-4,5α-epoxy-3-acetoxy-14β-hydroxy-6α-(N-methylphenylmethanesulfonamido)-morphinan, 17-phenethyl-4,5α-epoxy-3-acetoxy-14β-hydroxy-6α-(N-methyl-3,4-dichlorophenylacetamido)morphinan, 17-phenethyl-4,5α-epoxy-3-acetoxy-14β-hydroxy-6α-(N-methylcinnamamido)morphinan, 17-phenethyl-4,5α-epoxy-3-acetoxy-14β-hydroxy-6α-(N-methylbenzyloxycarbamido)-morphinan, 17-phenethyl-4,5α-epoxy-3-acetoxy-14β-hydroxy-6α-(N-methylphenylmethanesulfonamido)morphinan, 17-cyclopropylmethyl-4,5α-epoxy-3,14β-diacetoxy-6α-(N-methyl-3,4-dichlorophenylacetamido)morphinan, 17-cyclopropylmethyl-4,5α-epoxy-3,14β-diacetoxy-6α-(N-methylcinnamamido)morphinan, 17-cyclopropylmethyl-4,5αepoxy-3,14β-diacetoxy-6α-(N-methylbenzyloxycarbamido)-morphinan, 17-cyclopropylmethyl-4,5α-epoxy-3,14β-diacetoxy-6α-(N-methylphenylmethanesulfonamido)morphinan, 17-allyl-4,5α-epoxy-3,14β-diacetoxy-6α-(N-methyl-3,4-dichlorophenylacetamido)morphinan, 17-allyl-4,5α-epoxy-3,14β-diacetoxy-6α-(N-methylcinnamamido)morphinan, 17-allyl-4,5α-epoxy-3,14β-diacetoxy-6α-(N-methylbenzyloxycarbamido)morphinan, 17-allyl-4,5α-epoxy-3,14β-diacetoxy-6α-(N-methylphenylmethanesulfonamido)-morphinan, 17-methyl-4,5α-epoxy-3,14β-diacetoxy-6α-(N-methyl-3,4-dichlorophenylacetamido)morphinan, 17-methyl-4,5α-epoxy-3,14β-diacetoxy-6α-(N-methylcinnamamido)morphinan, 17-methyl-4,5α-epoxy-3,14β-diacetoxy-6α-(N-methylbenzyloxycarbamido)morphinan, 17-methyl-4,5α-epoxy-3,14β-diacetoxy-6α-(N-methylphenylmethanesulfonamido)morphinan, 17-phenethyl-4,5α-epoxy-3,14β-diacetoxy-6α-(N-methyl-3,4-dichlorophenylacetamido)morphinan, 17-phenethyl-4,5α-epoxy-3,14β-diacetoxy-6α-(N-methylcinnamamido)morphinan, 17-phenethyl-4,5α-epoxy-3,14β-diacetoxy-6α-(N-methylbenzyloxycarbamido)morphinan, 17-phenethyl-4,5α-epoxy-3,14β-diacetoxy-6α-(N-methylphenylmethanesulfonamido)morphinan, 17-cyclopropylmethyl-4,5α-epoxy-3,14β-dihydroxy-6α-(N-isobutyl-3,4-dichlorophenylacetamido)morphinan, 17-cyclopropylmetyl-4,5α-epoxy-3,14β-dihydroxy-6α-(N-isobutylcinnamamido)morphinan, 17-cyclopropylmethyl-4,5α-epoxy-3,14β-dihydroxy-6α-(N-isobutylbenzyloxycarbamido)-morphinan, 17-cyclopropylmethyl-4,5α-epoxy-3,14β-dihydroxy-6α-(N-isobutylphenylmethanesulfonamido)morphinan, 17-allyl-4,5α-epoxy-3,14β-dihydroxy-6α-(N-isobutyl-3,4-dichlorophenylacetamido)morphinan, 17-allyl-4,5α-epoxy- 3,14β-dihydroxy-6α-(N-isobutylcinnamamido)morphinan, 17-allyl-4,5α-epoxy-3,14β-dihydroxy-6α-(N-isobutylbenzyloxycarbamido)morphinan, 17-allyl-4,5α-epoxy-3,14β-dihydroxy-6α-(N-isobutylphenylmethanesulfonamido)morphinan, 17-metyl-4,5α-epoxy-3,14β-dihydroxy-6α-(N-isobutyl-3,4-dichlorophenylacetamido)morphinan, 17-methyl-4,5α-epoxy-3,14β-dihydroxy-6α-(N-isobutylcinnamamido)morphinan, 17-metyl-4,5α-epoxy-3,14β-dihydroxy-6α-(N-isobutylbenzyloxycarbamido)morphinan, 17-metyl-4,5α-epoxy-3,14β-dihydroxy-6α-(N-isobutylphenylmethanesulfonamido)-morphinan, 17-phenethyl-4,5α-epoxy-3,14β-dihydroxy-6α-(N-isobutyl-3,4-dichlorophenylacetamido)morphinan, 17-phenethyl-4,5α-epoxy-3,14β-dihydroxy-6α-(N-isobutylcinnamamido)morphinan, 17-phenethyl-4,5α-epoxy-3,14β-dihydroxy-6α-(N-isobutylbenzyloxycarbamido)-morphinan, 17-phenethyl-4,5α-epoxy-3,14β-dihydroxy-6α-(N-isobutylphenylmethanesulfonamido)morphinan, 17-cyclopropylmethyl-4,5α-epoxy-3-hydroxy-14β-acetoxy-6α-(N-isobutyl-3,4-dichlorophenylacetamido)morphinan, 17-cyclopropylmetyl-4,5α-epoxy-3-hydroxy-14β-acetoxy-6α-(N-isobutylcinnamamido)morphinan, 17-cyclopropylmethyl-4,5α-epoxy-3-hydroxy-14β-acetoxy-6α-(N-isobutylbenzyloxycarbamido)morphinan, 17-cyclopropylmethyl-4,5α-epoxy-3-hydroxy-14β-acetoxy-6α-(N-isobutylphenylmethanesulfonamido)morphinan, 17-allyl-4,5α-epoxy-3-hydroxy-14β-acetoxy-6α-(N-isobutyl-3,4-dichlorophenylacetamido)morphinan, 17-allyl-4,5α-epoxy-3-hydroxy-14β-acetoxy-6α-(N-isobutylcinnamamido)morphinan, 17-allyl-4,5α-epoxy-3-hydroxy-14β-acetoxy-6α-(N-isobutylbenzyloxycarbamido)morphinan, 17-allyl-4,5α-epoxy-3-hydroxy-14β-acetoxy-6α-(N-isobutylphenylmethanesulfonamido)morphinan, 17-methyl-4,5α-epoxy-3-hydroxy-14β-acetoxy-6α-(N-isobutyl-3,4-dichlorophenylacetamido)morphinan, 17-methyl-4,5α-epoxy-3-hydroxy-14β-acetoxy-6α-(N-isobutylcinnamamido)morphinan, 17-methyl-4,5α-epoxy-3-hydroxy-14β-acetoxy-6α-(N-isobutylbenzyloxycarbamido)morphinane, 17-methyl-4,5α-epoxy-3-hydroxy-14β-acetoxy-6α-(N-isobutylphenylmethanesulfonamido)morphinan, 17-phenethyl-4,5α-epoxy-3-hydroxy-14β-acetoxy-6α-(N-isobutyl-3,4 -dichlorophenylacetamido)morphinan, 17-phenethyl-4,5α-epoxy-3-hydroxy-14β-acetoxy-6α-(N-isobutylcinnamamido)morphinan, 17-phenethyl-4,5α-epoxy-3-hydroxy-14β-acetoxy-6α-(N-isobutylbenzyloxycarbamido)morphinan, 17-phenethyl-4,5α-epoxy-3-hydroxy-14β-acetoxy-6α-(N-isobutylphenylmethanesulfonamido)morphinan, 17-cyclopropylmethyl-4,5α-epoxy-14β-hydroxy-6α-(N-isobutyl-3,4-dichlorophenylacetamido)morphinan, 17-cyclopropylmethyl-4,5α-epoxy-14β-hydroxy-6α-(N-isobutylcinnamamido)morphinan, 17-cyclopropylmethyl-4,5α-epoxy-14β-hydroxy-6α-(N-isobutylbenzyloxycarbamido)-morphinan, 17-cyclopropylmethyl-4,5α-epoxy-14β-hydroxy-6α-(N-isobutylphenylmethanesulfonamido)morphinan, 17-allyl-4,5α-epoxy-14β-hydroxy-6α-(N-isobutyl-3,4-dichlorophenylacetamido)morphinan, 17-allyl-4,5α-epoxy-14β-hydroxy-6α-(N-isobutylcinnamamido)morphinan, 17-allyl-4,5α-epoxy-14β-hydroxy-6α-(N-isobutylbenzyloxycarbamido)-morphinan, 17-allyl-4,5α-epoxy-14β-hydroxy-6α-(N-isobutylphenylmethanesulfonamido)morphinan, 17-methyl-4,5α-epoxy-14β-hydroxy-6α-(N-isobutyl-3,4-dichlorophenylacetamido)morphinan, 17-methyl-4,5α-epoxy-14β-hydroxy-6α-(N-isobutylcinnamamido)morphinan, 17-methyl-4,5α-epoxy-14β-hydroxy-6α-(N-isobutylbenzyloxycarbamido)morphinan, 17-methyl-4,5α-epoxy-14β-hydroxy-6α-(N-isobutylphenylmethanesulfonamido)-morphinan, 17-phenethyl-4,5α-epoxy-14β-hydroxy-6α-(N-isobutyl-3,4-dichlorophenylacetamido)morphinan, 17-phenethyl-4,5α-epoxy-14β-hydroxy-6α-(N-isobutylcinnamamido)morphinan, 17-phenethyl-4,5α-epoxy-14β-hydroxy-6α-(N-isobutylbenzyloxycarbamido)morphinan, 17-phenethyl-4,5α-epoxy-14β-hydroxy-6α-(N-isobutylphenylmethanesulfonamido)morphinan, 17-cyclopropylmethyl-4,5α-epoxy-14β-acetoxy-6α-(N-isobutyl-3,4-dichlorophenylacetamido)morphinan, 17-cyclopropylmethyl-4,5α-epoxy-14β-acetoxy-6α-(N-isobutylcinnamamido)morphinan, 17-cyclopropylmethyl-4,5α-epoxy-14β-acetoxy-6α-(N-isobutylbenzyloxycarbamido)-morphinan, 17-cyclopropylmethyl-4,5α-epoxy-14β-acetoxy-6α-(N-isobutylphenylmethanesulfonamido)morphinan, 17-allyl-4,5α-epoxy-14β-acetoxy-6α-(N-isobutyl-3,4-dichlorophenylacetamido)morphinan, 17-allyl-4,5α-epoxy-14β-acetoxy-6α-(N-isobutylcinnamamido)morphinan, 17-allyl-4,5α-epoxy-14β-acetoxy-6α-(N-isobutylbenzyloxycarbamido)-morphinan, 17-allyl-4,5α-epoxy-14β-acetoxy-6α-(N-isobutylphenylmethanesulfonamido)morphinan, 17-methyl-4,5α-epoxy-14β-acetoxy-6α-(N-isobutyl-3,4-dichlorophenylacetamido)morphinan, 17-methyl-4,5α-epoxy-14β-acetoxy-6α-(N-isobutylcinnamamido)morphinan, 17-methyl-4,5α-epoxy-14β-acetoxy-6α-(N-isobutylbenzyloxycarbamido)morphinan, 17-methyl-4,5α-epoxy-14β-acetoxy-6α-(N-isobutylphenylmethanesulfonamido)morphinan, 17-phenethyl-4,5α-epoxy-14β-acetoxy-6α-(N-isobutyl-3,4-dichlorophenylacetamido)morphinan, 17-phenethyl-4,5α-epoxy-14β-acetoxy-6α-(N-isobutylcinnamamido)morphinan, 17-phenethyl-4,5α-epoxy-14β-acetoxy-6α-(N-isobutylbenzyloxycarbamido)morphinan, 17-phenethyl-4,5α-epoxy-14β-acetoxy-6α-(N-isobutylphenylmethanesulfonamido)-morphinan, 17-cyclopropylmethyl-4,5α-epoxy-3-methoxy-14β-hydroxy-6α-(N-isobutyl-3,4-dichlorophenylacetamido)-morphinan, 17-cyclopropylmethyl-4,5α-epoxy-3-methoxy-14β-hydroxy-6α-(N-isobutylcinnamamido)morphinan, 17-cyclopropylmethyl-4,5α-epoxy-3-methoxy-14β-hydroxy-6α-(N-isobutylbenzyloxycarbamido)morphinan, 17-cyclopropylmethyl-4,5α-epoxy-3-methoxy-14β-hydroxy-6α-(N-isobutylphenylmethanesulfonamido)morphinan, 17-allyl-4,5α-epoxy-3-methoxy-14β-hydroxy-6α-(N-isobutyl-3,4-dichlorophenylacetamido)morphinan, 17-allyl-4,5α-epoxy-3-methoxy-14β-hydroxy-6α-(N-isobutylcinnamamido)morphinan, 17-allyl-4,5α-epoxy-3-methoxy-14β-hydroxy-6α-(N-isobutylbenzyloxycarbamido)morphinan, 17-allyl-4,5α-epoxy-3-methoxy-14β-hydroxy-6α-(N-isobutylphenylmethanesulfonamido)morphinan, 17-methyl-4,5α-epoxy-3-methoxy-14β-hydroxy-6α-(N-isobutyl-3,4-dichlorophenylacetamido)morphinan, 17-methyl-4,5α-epoxy-3-methoxy-14β-hydroxy-6α-(N-isobutylcinnamamido)morphinan, 17-methyl-4,5α-epoxy-3-methoxy-14β-hydroxy-6α-(N-isobutylbenzyloxycarbamido)-morphinan, 17-methyl-4,5α-epoxy-3-methoxy-14β-hydroxy-6α-(N- isobutylphenylmethanesulfonamido)morphinan, 17-phenethyl-4,5α-epoxy-3-methoxy-14β-hydroxy-6α-(N-isobutyl-3,4-dichlorophenylacetamido)morphinan, 17-phenethyl-4,5α-epoxy-3-methoxy-14β-hydroxy-6α-(N-isobutylcinnamamido)-morphinan, 17-phenethyl-4,5α-epoxy-3-methoxy-14β-hydroxy-6α-(N-isobutylbenzyloxycarbamido)morphinan, 17-phenethyl-4,5α-epoxy-3-methoxy-14β-hydroxy-6α-(N-isobutylphenylmethanesulfonamido)morphinan, 17-cyclopropylmethyl-4,5α-epoxy-3-methoxy-14β-acetoxy-6α-(N-isobutyl-3,4-dichlorophenylacetamido)-morphinan, 17-cyclopropylmethyl-4,5α-epoxy-3-methoxy-14β-acetoxy-6α-(N-isobutylcinnamamido)morphinan, 17-cyclopropylmethyl-4,5α-epoxy-3-methoxy-14β-acetoxy-6α-(N-isobutylbenzyloxycarbamido)morphinan, 17-cyclopropylmethyl-4,5α-epoxy-3-methoxy-14β-acetoxy-6α-(N-isobutylphenylmethanesulfonamido)morphinan, 17-allyl-4,5α-epoxy-3-methoxy-14β-acetoxy-6α-(N-isobutyl-3,4-dichlorophenylacetamido)morphinan, 17-allyl-4,5α-epoxy-3-methoxy-14β-acetoxy-6α-(N-isobutylcinnamamido)morphinan, 17-allyl-4,5α-epoxy-3-methoxy-14β-acetoxy-6α-(N-isobutylbenzyloxycarbamido)morphinan, 17-allyl-4,5α-epoxy-3-methoxy-14β-acetoxy-6α-(N-isobutylphenylmethanesulfonamido)morphinan, 17-methyl-4,5α-epoxy-3-methoxy-14β-acetoxy-6α-(N-isobutyl-3,4-dichlorophenylacetamido)morphinan, 17-methyl-4,5α-epoxy-3-methoxy-14β-acetoxy-6α-(N-isobutylcinnamamido)morphinan, 17-methyl-4,5α-epoxy-3-methoxy-14β-acetoxy-6α-(N-isobutylbenzyloxycarbamido)-morphinan, 17-methyl-4,5α-epoxy-3-methoxy-14β-acetoxy-6α-(N-isobutylphenylmethanesulfonamido)morphinan, 17-phenethyl-4,5α-epoxy-3-methoxy-14β-acetoxy-6α-(N-isobutyl-3,4-dichlorophenylacetamido)morphinan, 17-phenethyl-4,5α-epoxy-3-methoxy-14β-acetoxy-6α-(N-isobutylcinnamamido)-morphinan, 17-phenethyl-4,5α-epoxy-3-methoxy-14β-acetoxy-6α-(N-isobutylbenzyloxycarbamido)morphinan, 17-phenethyl-4,5α-epoxy-3-methoxy-14β-acetoxy-6α-(N-isobutylphenylmethanesulfonamido)morphinan, 17-cyclopropylmethyl-4,5α-epoxy-3-acetoxy-14β-hydroxy-6α-(N-isobutyl-3,4-dichlorophenylacetamido)-morphinan, 17-cyclopropylmethyl-4,5α-epoxy-3-acetoxy-14β-hydroxy-6α-(N-isobutylcinnamamido)morphinan, 17-cyclopropylmethyl-4,5α-epoxy-3-acetoxy-14β-hydroxy-6α-(N-isobutylbenzyloxycarbamido)morphinan, 17-cyclopropylmethyl-4,5α-epoxy-3-acetoxy-14β-hydroxy-6α-(N-isobutylphenylmethanesulfonamido)morphinan, 17-allyl-4,5α-epoxy-3-acetoxy-14β-hydroxy-6α-(N-isobutyl-3,4-dichlorophenylacetamido)morphinan, 17-allyl-4,5α-epoxy-3-acetoxy-14β-hydroxy-6α-(N-isobutylcinnamamido)morphinan, 17-allyl-4,5α-epoxy-3-acetoxy-14β-hydroxy-6α-(N-isobutylbenzyloxycarbamido)morphinan, 17-allyl-4,5α-epoxy-3-acetoxy-14β-hydroxy-6α-(N-isobutylphenylmethanesulfonamido)morphinan, 17-methyl-4,5α-epoxy-3-acetoxy-14β-hydroxy-6α-(N-isobutyl-3,4-dichlorophenylacetamido)morphinan, 17-methyl-4,5α-epoxy-3-acetoxy-14β-hydroxy-6α-(N-isobutylcinnamamido)morphinan, 17-methyl-4,5α-epoxy-3-acetoxy-14β-hydroxy-6α-(N-isobutylbenzyloxycarbamido)-morphinan, 17-methyl-4,5α-epoxy-3-acetoxy-14β-hydroxy-6α-(N-isobutylphenylmethanesulfonamido)morphinan, 17-phenethyl-4,5α-epoxy-3-acetoxy-14β-hydroxy-6α-(N-isobutyl-3,4-dichlorophenylacetamido)morphinan, 17-phenethyl-4,5α-epoxy-3-acetoxy-14β-hydroxy-6α-(N-isobutylcinnamamido)morphinan, 17-phenethyl-4,5α-epoxy-3-acetoxy-14β-hydroxy-6α-(N-isobutylbenzyloxycarbamido)morphinan, 17-phenethyl-4,5α-epoxy-3-acetoxy-14β-hydroxy-6α-(N-isobutylphenylmethanesulfonamido)morphinan, 17-cyclopropylmethyl-4,5α-epoxy-3,14-diacetoxy-6α-(N-isobutyl-3,4-dichlorophenylacetamido)morphinan, 17-cyclopropylmethyl-4,5α-epoxy-3,14β-diacetoxy-6α-(N-isobutylcinnamamido)morphinan, 17-cyclopropylmethyl-4,5α-epoxy-3,14β-diacetoxy-6α-(N-isobutylbenzyloxycarbamido)-morphinan, 17-cyclopropylmethyl-4,5α-epoxy-3,14β-diacetoxy-6α-(N-isobutylphenylmethanesulfonamido)morphinan, 17-allyl-4,5α-epoxy-3,14β-diacetoxy-6α-(N-isobutyl-3,4-dichlorophenylacetamido)morphinan, 17-allyl-4,5α-epoxy-3,14β-diacetoxy-6α-(N-isobutylcinnamamido)morphinan, 17-allyl-4,5α-epoxy-3,14β-diacetoxy-6α-(N-isobutylbenzyloxycarbamido)morphinan, 17-allyl-4,5α-epoxy-3,14β-diacetoxy-6α-(N-isobutylphenylmethanesulfonamido)-morphinan, 17-methyl-4,5α-epoxy-3,14β-diacetoxy-6α-(N-isobutyl-3,4-dichlorophenylacetamido)morphinan, 17-methyl-4,5α-epoxy-3,14β-diacetoxy-6α-(N-isobutylcinnamamido)morphinan, 17-methyl-4,5α-epoxy-3,14β-diacetoxy-6α-(N-isobutylbenzyloxycarbamido)morphinan, 17-methyl-4,5α-epoxy-3,14β-diacetoxy-6α-(N-isobutylphenylmethanesulfonamido)-morphinan, 17-phenethyl-4,5α-epoxy-3,14β-diacetoxy-6α-(N-isobutyl-3,4-dichlorophenylacetamido)morphinan, 17-phenethyl-4,5α-epoxy-3,14β-diacetoxy-6α-(N-isobutylcinnamamido)morphinan, 17-phenethyl-4,5α-epoxy-3,14β-diacetoxy-6α-(N-isobutylbenzyloxycarbamido)morphinan, 17-phenethyl-4,5α-epoxy-3,14β-diacetoxy-6α-(N-isobutylphenylmethanesulfonamido)morphinan, 17-cyclopropylmethyl-4,5α-epoxy-3,14β-dihydroxy-6β-(N-methyl-3,4-dichlorophenylacetamido)morphinan, 17-cyclopropylmethyl-4,5α-epoxy-3,14β-dihydroxy-6β-(N-methylcinnamamido)morphinan, 17-cyclopropylmethyl-4,5α-epoxy-3,14β-dihydroxy-62-(N-methylbenzyloxycarbamido)-morphinan, 17-cyclopropylmethyl-4,5α-epoxy-3,14β-dihydroxy-6β-(N-metylphenylmethanesulfonamido)morphinan, 17-allyl-4,5α-epoxy-3,14β-dihydroxy-6β-(N-methyl-3,4-dichlorophenylacetamido)morphinan, 17-allyl-4,5α-epoxy-3,14β-dihydroxy-6β-(N-methylcinnamamido)morphinan, 17-allyl-4,5α-epoxy-3,14β-dihydroxy-6β-(N-methylbenzyloxycarbamido)morphinan, 17-allyl-4,5α-epoxy-3,14β-dihydroxy-60-(N-methylphenylmethanesulfonamido)morphinan, 17-methyl-4,5α-epoxy-3,14β-dihydroxy-6β-(N-methyl-3,4-dichlorophenylacetamido)morphinan, 17-methyl-4,5α-epoxy-3,14β-dihydroxy-60-(N-methylcinnamamido)morphinan, 17-methyl-4,5α-epoxy-3,14β-dihydroxy-6β-(N-methylbenzyloxycarbamido)morphinan, 17-methyl-4,5α-epoxy-3,14β-dihydroxy-6β-(N-methylphenylmethanesulfonamido)-morphinan, 17-phenethyl-4,5α-epoxy-3,14β-dihydroxy-6β-(N-methyl-3,4-dichlorophenylacetamido)morphinan, 17-phenethyl-4,5α-epoxy-3,14β-dihydroxy-6β-(N-methylcinnamamido)morphinan, 17-phenethyl-4,5α-epoxy-3,14β-dihydroxy-6β-(N-methylbenzyloxycarbamido)morphinan, 17-phenethyl-4,5α-epoxy-3,14β-dihydroxy-6β-(N-methylphenylmethanesulfonamido)morphinan, 17-cyclopropylmethyl-4,5α-epoxy-3-hydroxy-14β-acetoxy-6β-(N-methyl-3,4-dichlorophenylacetamido)-morphinan, 17-cyclopropylmethyl-4,5α-epoxy-3-hydroxy-14β-acetoxy-6β-(N-methylcinnamamido)morphinan, 17-cyclopropylmethyl-4,5α-epoxy-3-hydroxy-14β- acetoxy-6β-(N-methylbenzyloxycarbamido)morphinan, 17-cyclopropylmethyl-4,5α-epoxy-3-hydroxy-14β-acetoxy-6β-(N-methylphenylmethanesulfonamido) morphinan, 17-allyl-4,5α-epoxy-3-hydroxy-14β-acetoxy-6β-(N-methyl-3,4-dichlorophenylacetamido)morphinan, 17-allyl-4,5α-epoxy-3-hydroxy-14β-acetoxy-6β-(N-methylcinnamamido)morphinan, 17-allyl-4,5α-epoxy-3-hydroxy-14β-acetoxy-6β-(N-methylbenzyloxycarbamido)morphinan, 17-allyl-4,5α-epoxy-3-hydroxy-14β-acetoxy-6β-(N-methylphenylmethanesulfonamido)morphinan, 17-methyl-4,5α-epoxy-3-hydroxy-14β-acetoxy-6β-(N-methyl-3,4-dichlorophenylacetamido)morphinan, 17-methyl-4,5α-epoxy-3-hydroxy-14β-acetoxy-6β-(N-methylcinnamamido)morphinan, 17-methyl-4,5α-epoxy-3-hydroxy-14β-acetoxy-6β-(N-methylbenzyloxycarbamido)morphinan, 17-methyl-4,5α-epoxy-3-hydroxy-14β-acetoxy-6β-(N-methylphenylmethanesulfonamido)-morphinan, 17-phenethyl-4,5α-epoxy-3-hydroxy-14β-acetoxy-6β-(N-methyl-3,4-dichlorophenylacetamido)morphinan, 17-phenethyl-4,5α-epoxy-3-hydroxy-14β-acetoxy-6β-(N-methylcinnamamido)morphinan, 17-phenethyl-4,5α-epoxy-3-hydroxy-14β-acetoxy-6β-(N-methylbenzyloxycarbamido)-morphinan, 17-phenethyl-4,5α-epoxy-3-hydroxy-14β-acetoxy-6β-(N-methylphenylmethanesulfonamido)morphinan, 17-cyclopropylmethyl-4,5α-epoxy-14β-hydroxy-6β-(N-methyl-3,4-dichlorophenylacetamido)morphinan, 17-cyclopropylmethyl-4,5α-epoxy-14β-hydroxy-6β-(N-methylcinnamamido)morphinan, 17-cyclopropylmethyl-4,5α-epoxy-14β-hydroxy-6β-(N-methylbenzyloxycarbamido)-morphinan, 17-cyclopropylmethyl-4,5α-epoxy-14β-hydroxy-6β-(N-methylphenylmethanesulfonamido)morphinan, 17-allyl-4,5α-epoxy-14β-hydroxy-6β-(N-methyl-3,4-dichlorophenylacetamido)morphinan, 17-allyl-4,5α-epoxy-14β-hydroxy-6β-(N-methylcinnamamido)morphinan, 17-allyl-4,5α-epoxy-14β-hydroxy-6β-(N-methylbenzyloxycarbamido)-morphinan, 17-allyl-4,5α-epoxy-14β-hydroxy-6β-(N-methylphenylmethanesulfonamido)morphinan, 17-methyl-4,5α-epoxy-14β-hydroxy-6β-(N-methyl-3,4-dichlorophenylacetamido)morphinan, 17-methyl-4,5α-epoxy-14β-hydroxy-6β-(N-methylcinnamamido)morphinan, 17-methyl-4,5α-epoxy-14β-hydroxy-6β-(N-methylbenzyloxycarbamido)-morphinan, 17-methyl-4,5α-epoxy-14β-hydroxy-6β-(N-methylphenylmethanesulfonamido)morphinan, 17-phenethyl-4,5α-epoxy-14β-hydroxy-6β-(N-methyl-3,4-dichlorophenylacetamido)morphinan, 17-phenethyl-4,5α-epoxy-14β-hydroxy-6β-(N-methylcinnamamido)morphinan, 17-phenethyl-4,5α-epoxy-14β-hydroxy-6β-(N-methylbenzyloxycarbamido)morphinan, 17-phenethyl-4,5α-epoxy-14β-hydroxy-6β-(N-methylphenylmethanesulfonamido)-morphinan, 17-cyclopropylmethyl-4,5α-epoxy-14β-acetoxy-6β-(N-methyl-3,4-dichlorophenylacetamido)morphinan, 17-cyclopropylmethyl-4,5α-epoxy-14β-acetoxy-6β-(N-methylcinnamamido)morphinan, 17-cyclopropylmethyl-4,5α-epoxy-14β-acetoxy-6β-(N-methylbenzyloxycarbamido)-morphinan, 17-cyclopropylmethyl-4,5α-epoxy-14β-acetoxy-6β-(N-methylphenylmethanesulfonamido)morphinan, 17-allyl-4,5α-epoxy-14β-acetoxy-6β-(N-methyl-3,4-dichlorophenylacetamido)morphinan, 17-allyl-4,5α-epoxy-14β-acetoxy-6β-(N-methylcinnamamido)morphinan, 17-allyl-4,5α-epoxy-14β-acetoxy-6β-(N-methylbenzyloxycarbamido)-morphinan, 17-allyl-4,5α-epoxy-14β-acetoxy-6β-(N-methylphenylmethanesulfonamido)morphinan, 17-methyl-4,5α-epoxy-14β-acetoxy-6β-(N-methyl-3,4-dichlorophenylacetamido)morphinan, 17-methyl-4,5α-epoxy-14β-acetoxy-6β-(N-methylcinnamamido)morphinan, 17-methyl-4,5α-epoxy-14β-acetoxy-6β-(N-methylbenzyloxycarbamido)-morphinan, 17-methyl-4,5α-epoxy-14β-acetoxy-6β-(N-methylphenylmethanesulfonamido)morphinan, 17-phenethyl-4,5α-epoxy-14-acetoxy-6β-(N-methylcinnamamido)morphinan, 17-phenethyl-4,5α-epoxy-14β-acetoxy-6β-(N-methylbenzyloxycarbamido)morphinan, 17-phenethyl-4,5α-epoxy-14β-acetoxy-6β-(N-methylphenylmethanesulfonamido)-morphinan, 17-cyclopropylmethyl-4,5α-epoxy-3-methoxy-14β-hydroxy-6β-(N-methyl-3,4-dichlorophenylacetamido)-morphinan, 17-cyclopropylmethyl-4,5α-epoxy-3-methoxy-14β-hydroxy-6β-(N-methylcinnamamido)morphinan, 17-cyclopropylmethyl-4,5α-epoxy-3-methoxy-14β-hydroxy-6β-(N-methylbenzyloxycarbamido)morphinan, 17-cyclopropylmethyl-4,5α-epoxy-3-methoxy-14β-hydroxy-6β-(N-methylphenylmethanesulfonamido)morphinan, 17-allyl-4,5α-epoxy-3-methoxy-14β-hydroxy-6β-(N-methyl-3,4-dichlorophenylacetamido)morphinan, 17-allyl-4,5α-epoxy-3-methoxy-14β-hydroxy-6β-(N-methylcinnamamido)morphinan, 17-allyl-4,5α-epoxy-3-methoxy-14β-hydroxy-6β-(N-methylbenzyloxycarbamido)morphinan, 17-allyl-4,5α-epoxy-3-methoxy-14β-hydroxy-6β-(N-methylphenylmethanesulfonamido)-morphinan, 17-methyl-4,5α-epoxy-3-methoxy-14β-hydroxy-6β-(N-methyl-3,4-dichlorophenylacetamido)morphinan, 17-methyl-4,5α-epoxy-3-methoxy-14β-hydroxy-6β-(N-methylcinnamamido)morphinan, 17-methyl-4,5α-epoxy-3-methoxy-14β-hydroxy-6β-(N-methylbenzyloxycarbamido)-morphinan, 17-methyl-4,5α-epoxy-3-methoxy-14β-hydroxy-6β-(N-methylphenylmethanesulfonamido)morphinan, 17-phenethyl-4,5α-epoxy-3-methoxy-14β-hydroxy-6β-(N-methyl-3,4-dichlorophenylacetamido)morphinan, 17-phenethyl-4,5α-epoxy-3-methoxy-14β-hydroxy-6β-(N-methylcinnamamido)morphinan, 17-phenethyl-4,5α-epoxy-3-methoxy-14β-hydroxy-6β-(N-methylbenzyloxycarbamido)morphinan, 17-phenethyl-4,5α-epoxy-3-methoxy-14β-hydroxy-6β-(N-methylphenylmethanesulfonamido)morphinan, 17-cyclopropylmethyl-4,5α-epoxy-3-methoxy-14β-acetoxy-6β-(N-methyl-3,4-dichlorophenylacetamido)-morphinan, 17-cyclopropylmethyl-4,5α-epoxy-3-methoxy-14β-acetoxy-6β-(N-methylcinnamamido)morphinan, 17-cyclopropylmethyl-4,5α-epoxy-3-methoxy-14β-acetoxy-6β-(N-methylbenzyloxycarbamido)morphinan, 17-cyclopropylmethyl-4,5α-epoxy-3-methoxy-14β-acetoxy-6β-(N-methylphenylmethanesulfonamido) morphinan, 17-allyl-4,5α-epoxy-3-methoxy-14β-acetoxy-6β-(N-methyl-3,4-dichlorophenylacetamido)morphinan, 17-allyl-4,5α-epoxy-3-methoxy-14β-acetoxy-6β-(N-methylcinnamamido)morphinan, 17-allyl-4,5α-epoxy-3-methoxy-14β-acetoxy-6β-(N-methylbenzyloxycarbamido) morphinan, 17-allyl-4,5α-epoxy-3-methoxy-14β-acetoxy-6β-(N-methylphenylmethanesulfonamido)morphinan, 17-methyl-4,5α-epoxy-3-methoxy-14β-acetoxy-6β-(N-methyl-3,4-dichlorophenylacetamido)morphinan, 17-methyl-4,5α-epoxy-3-methoxy-14β-acetoxy-6β-(N-methylcinnamamido)morphinan, 17-methyl-4,5α-epoxy-3- methoxy-14β-acetoxy-6β-(N-methylbenzyloxycarbamido) morphinan, 17-methyl-4,5α-epoxy-3-methoxy-14β-acetoxy-6β-(N-methylphenylmethanesulfonamido)-morphinan, 17-phenethyl-4,5α-epoxy-3-methoxy-14β-acetoxy-6β-(N-methyl-3,4-dichlorophenylacetamido) morphinan, 17-phenethyl-4,5α-epoxy-3-methoxy-14β-acetoxy-6β-(N-methylcinnamamido)morphinan, 17-phenethyl-4,5α-epoxy-3-methoxy-14β-acetoxy-6β-(N-methylbenzyloxycarbamido)-morphinan, 17-phenethyl-4,5α-epoxy-3-methoxy-14β-acetoxy-6β-(N-methylphenylmethanesulfonamido)morphinan, 17-cyclopropylmethyl-4,5α-epoxy-3-acetoxy-14β-hydroxy-6β-(N-methyl-3,4-dichlorophenylacetamido)-morphinan, 17-cyclopropylmethyl-4,5α-epoxy-3-acetoxy-14β-hydroxy-6β-(N-methylcinnamamido)morphinan, 17-cyclopropylmethyl-4,5α-epoxy-3-acetoxy-14β-hydroxy-6β-(N-methylbenzyloxycarbamido)morphinan, 17-cyclopropylmethyl-4,5α-epoxy-3-acetoxy-14β-hydroxy-6β-(N-methylphenylmethanesulfonamido) morphinan, 17-allyl-4,5α-epoxy-3-acetoxy-14β-hydroxy-6β-(N-methyl-3,4-dichlorophenylacetamido)morphinan, 17-allyl-4,5α-epoxy-3-acetoxy-14β-hydroxy-6β-(N-methylcinnamamido)morphinan, 17-allyl-4,5α-epoxy-3-acetoxy-14β-hydroxy-6β-(N-methylbenzyloxycarbamido)morphinan, 17-allyl-4,5α-epoxy-3-acetoxy-14β-hydroxy-6β-(N-methylphenylmethanesulfonamido)morphinan, 17-methyl-4,5α-epoxy-3-acetoxy-14β-hydroxy-6β-(N-methyl-3,4-dichlorophenylacetamido)morphinan, 17-methyl-4,5α-epoxy-3-acetoxy-14β-hydroxy-6β-(N-methylcinnamamido) morphinan, 17-methyl-4,5α-epoxy-3-acetoxy-14β-hydroxy-6β-(N-methylbenzyloxycarbamido)morphinan, 17-methyl-4,5α-epoxy-3-acetoxy-14β-hydroxy-6β-(N-methylphenylmethanesulfonamido)-morphinan, 17-phenethyl-4,5α-epoxy-3-acetoxy-14β-hydroxy-6β-(N-methyl-3,4-dichlorophenylacetamido)morphinan, 17-phenethyl-4,5α-epoxy-3-acetoxy-14β-hydroxy-6β-(N-methylcinnamamido)morphinan, 17-phenethyl-4,5α-epoxy-3-acetoxy-14β-hydroxy-6β-(N-methylbenzyloxycarbamido)-morphinan, 17-phenethyl-4,5α-epoxy-3-acetoxy-14β-hydroxy-6β-(N-methylphenylmethanesulfonamido)morphinan, 17-cyclopropylmethyl-4,5α-epoxy-3,14β-diacetoxy-6β-(N-methyl-3,4-dichlorophenylacetamido)morphinan, 17-cyclopropylmethyl-4,5α-epoxy-3,14β-diacetoxy-6β-(N-methylcinnamamido)morphinan, 17-cyclopropylmethyl-4,5α-epoxy-3,14β-diacetoxy-6β-(N-methylbenzyloxycarbamido)-morphinan, 17-cyclopropylmethyl-4,5α-epoxy-3,14β-diacetoxy-6β-(N-methylphenylmethanesulfonamido)morphinan, 17-allyl-4,5α-epoxy-3,14β-diacetoxy-6β-(N-methyl-3,4-dichlorophenylacetamido)morphinan, 17-allyl-4,5α-epoxy-3,14β-diacetoxy-6β-(N-methylcinnamamido)morphinan, 17-allyl-4,5α-epoxy-3,14β-diacetoxy-6β-(N-methylbenzyloxycarbamido)morphinan, 17-allyl-4,5α-epoxy-3,14β-diacetoxy-6β-(N-methylphenylmethanesulfonamido)morphinan, 17-methyl-4,5α-epoxy-3,14β-diacetoxy-6β-(N-methyl-3,4-dichlorophenylacetamido)morphinan, 17-methyl-4,5α-epoxy-3,14β-diacetoxy-6β-(N-methylcinnamamido) morphinan, 17-methyl-4,5α-epoxy-3,14β-diacetoxy-6β-(N-methylbenzyloxycarbamido)morphinan, 17-methyl-4,5α-epoxy-3,14β-diacetoxy-6β-(N-methylphenylmethanesulfonamido)-morphinan, 17-phenethyl-4,5α-epoxy-3,14β-diacetoxy-6β-(N-methyl-3,4-dichlorophenylacetamido)morphinan, 17-phenethyl-4,5α-epoxy-3,14β-diacetoxy-6β-(N-methylcinnamamido)-morphinan, 17-phenethyl-4,5α-epoxy-3,14β-diacetoxy-6β-(N-methylbenzyloxycarbamido)morphinan, 17-phenethyl-4,5α-epoxy-3,14β-diacetoxy-6β-(N-methylphenylmethanesulfonamido)morphinan, 17-cyclopropylmethyl-4,5α-epoxy-3,14β-dihydroxy-6β-(N-isobutyl-3,4-dichlorophenylacetamido)morphinan, 17-cyclopropylmethyl-4,5α-epoxy-3,14β-dihydroxy-6β-(N-isobutylcinnamamido)morphinan, 17-cyclopropylmethyl-4,5α-epoxy-3,14β-dihydroxy-6β-(N-isobutylbenzyloxycarbamido)-morphinan, 17-cyclopropylmethyl-4,5α-epoxy-3,14β-dihydroxy-6β-(N-isobutylphenylmethanesulfonamido)morphinan, 17-allyl-4,5α-epoxy-3,14β-dihydroxy-6β-(N-isobutyl-3,4-dichlorophenylacetamido)morphinan, 17-allyl-4,5α-epoxy-3,14β-dihydroxy-6β-(N-isobutylcinnamamido)morphinan, 17-allyl-4,5α-epoxy-3,14β-dihydroxy-6β-(N-isobutylbenzyloxycarbamido)morphinan, 17-allyl-4,5α-epoxy-3,14β-dihydroxy-6β-(N-isobutylphenylmethanesulfonamido)-morphinan, 17-methyl-4,5α-epoxy-3,14β-dihydroxy-6β-(N-isobutyl-3,4-dichlorophenylacetamido)morphinan, 17-methyl-4,5α-epoxy-3,14β-dihydroxy-6β-(N-isobutylcinnamamido) morphinan, 17-methyl-4,5α-epoxy-3,14β-dihydroxy-6β-(N-isobutylbenzyloxycarbamido)morphinan, 17-methyl-4,5α-epoxy-3,14-dihydroxy-6β-(N-isobutylphenylmethanesulfonamido)-morphinan, 17-phenethyl-4,5α-epoxy-3,14β-dihydroxy-6β-(N-isobutyl-3,4-dichlorophenylacetamido)morphinan, 17-phenethyl-4,5α-epoxy-3,14β-dihydroxy-6β-(N-isobutylcinnamamido) morphinan, 17-phenethyl-4,5α-epoxy-3,14β-dihydroxy-6β-(N-isobutylbenzyloxycarbamido)morphinan, 17-phenethyl-4,5α-epoxy-3,14β-dihydroxy-6β-(N-isobutylphenylmethanesulfonamido)morphinan, 17-cyclopropylmethyl-4,5α-epoxy-3-hydroxy-14β-acetoxy-6β-(N-isobutyl-3,4-dichlorophenylacetamido)-morphinan, 17-cyclopropylmethyl-4,5α-epoxy-3-hydroxy-14β-acetoxy-6β-(N-isobutylcinnamamido)morphinan, 17-cyclopropylmethyl-4,5α-epoxy-3-hydroxy-14β-acetoxy-6β-(N-isobutylbenzyloxycarbamido)morphinan, 17-cyclopropylmethyl-4,5α-epoxy-3-hydroxy-14β-acetoxy-6β-(N-isobutylphenylmethanesulfonamido) morphinan, 17-allyl-4,5α-epoxy-3-hydroxy-14β-acetoxy-6β-(N-isobutyl-3,4-dichlorophenylacetamido)morphinan, 17-allyl-4,5α-epoxy-3-hydroxy-14β-acetoxy-6β-(N-isobutylcinnamamido)morphinan, 17-allyl-4,5α-epoxy-3-hydroxy-14β-acetoxy-6β-(N-isobutylbenzyloxycarbamido) morphinan, 17-allyl-4,5α-epoxy-3-hydroxy-14β-acetoxy-6β-(N-isobutylphenylmethanesulfonamido)morphinan, 17-methyl-4,5α-epoxy-3-hydroxy-14β-acetoxy-6β-(N-isobutyl-3,4-dichlorophenylacetamido)morphinan, 17-methyl-4,5α-epoxy-3-hydroxy-14β-acetoxy-6β-(N-isobutylcinnamamido)morphinan, 17-methyl-4,5α-epoxy-3-hydroxy-14β-acetoxy-6β-(N-isobutylbenzyloxycarbamido)-morphinan, 17-methyl-4,5α-epoxy-3-hydroxy-14β-acetoxy-6β-(N-isobutylphenylmethanesulfonamido)morphinan, 17-phenethyl-4,5α-epoxy-3-hydroxy-14β-acetoxy-6β-(N-isobutyl-3,4-dichlorophenylacetamido)morphinan, 17-phenethyl-4,5α-epoxy-3-hydroxy-14β-acetoxy-6β-(N-isobutylcinnamamido)-morphinan, 17-phenethyl-4,5α-epoxy-3-hydroxy-14β-acetoxy-6β-(N-isobutylbenzyloxycarbamido)morphinan, 17-phenethyl-4,5α-epoxy-3-hydroxy-14β-acetoxy-6β-(N-isobutylphenylmethanesulfonamido)morphinan, 17-cyclopropylmethyl-4,5α-epoxy-14β-hydroxy-6β-(N-isobutyl-3,4-dichlorophenylacetamido)morphinan, 17-cyclopropylmethyl-4,5α-epoxy-14β-hydroxy-6β-(N- isobutylcinnamamido)morphinan, 17-cyclopropylmethyl-4,5α-epoxy-14β-hydroxy-6β-(N-isobutylbenzyloxycarbamido)-morphinan, 17-cyclopropylmethyl-4,5α-epoxy-14β-hydroxy-6β-(N-isobutylphenylmethanesulfonamido)morphinan, 17-allyl-4,5α-epoxy-14β-hydroxy-6β-(N-isobutyl-3,4-dichlorophenylacetamido)morphinan, 17-allyl-4,5α-epoxy-14β-hydroxy-6β-(N-isobutylcinnamamido)morphinan, 17-allyl-4,5α-epoxy-14β-hydroxy-6β-(N-isobutylbenzyloxycarbamido)-morphinan, 17-allyl-4,5α-epoxy-14β-hydroxy-6β-(N-isobutylphenylmethanesulfonamido)morphinan, 17-methyl-4,5α-epoxy-14β-hydroxy-6β-(N-isobutyl-3,4-dichlorophenylacetamido)morphinan, 17-methyl-4,5α-epoxy-14β-hydroxy-6β-(N-isobutylcinnamamido)morphinan, 17-methyl-4,5α-epoxy-14β-hydroxy-6β-(N-isobutylbenzyloxycarbamido)-morphinan, 17-methyl-4,5α-epoxy-14β-hydroxy-6β-(N-isobutylphenylmethanesulfonamido)morphinan, 17-phenethyl-4,5α-epoxy-14β-hydroxy-6β-(N-isobutyl-3,4-dichlorophenylacetamido)morphinan, 17-phenethyl-4,5α-epoxy-14β-hydroxy-6β-(N-isobutylcinnamamido)morphinan, 17-phenethyl-4,5α-epoxy-14β-hydroxy-6β-(N-isobutylbenzyloxycarbamido)morphinan, 17-phenethyl-4,5α-epoxy-14β-hydroxy-6β-(N-isobutylphenylmethanesulfonamido)-morphinan, 17-cyclopropylmethyl-4,5α-epoxy-14β-acetoxy-6β-(N-isobutyl-3,4-dichlorophenylacetamido)morphinan, 17-cyclopropylmethyl-4,5α-epoxy-14β-acetoxy-6β-(N-isobutylcinnamamido)morphinan, 17-cyclopropylmethyl-4,5α-epoxy-14β-acetoxy-6β-(N-isobutylbenzyloxycarbamido)-morphinan, 17-cyclopropylmethyl-4,5α-epoxy-14β-acetoxy-6β-(N-isobutylphenylmethanesulfonamido)morphinan, 17-allyl-4,5α-epoxy-14β-acetoxy-6β-(N-isobutyl-3,4-dichlorophenylacetamido)morphinan, 17-allyl-4,5α-epoxy-14β-acetoxy-6β-(N-isobutylcinnamamido)morphinan, 17-allyl-4,5α-epoxy-14β-acetoxy-6β-(N-isobutylbenzyloxycarbamido)-morphinan, 17-allyl-4,5α-epoxy-14β-acetoxy-6β-(N-isobutylphenylmethanesulfonamido)morphinan, 17-methyl-4,5α-epoxy-14β-acetoxy-6β-(N-isobutyl-3,4-dichlorophenylacetamido)morphinan, 17-methyl-4,5α-epoxy-14β-acetoxy-6β-(N-isobutylcinnamamido)morphinan, 17-methyl-4,5α-epoxy-14β-acetoxy-6β-(N-isobutylbenzyloxycarbamido)-morphinan, 17-methyl-4,5α-epoxy-14β-acetoxy-6β-(N-isobutylphenylmethanesulfonamido)morphinan, 17-phenethyl-4,5α-epoxy-14β-acetoxy-6β-(N-isobutyl-3,4-dichlorophenylacetamido)morphinan, 17-phenethyl-4,5α-epoxy-14β-acetoxy-6β-(N-isobutylcinnamamido)morphinan, 17-phenethyl-4,5α-epoxy-14β-acetoxy-6β-(N-isobutylbenzyloxycarbamido)morphinan, 17-phenethyl-4,5α-epoxy-14β-acetoxy-6β-(N-isobutylphenylmethanesulfonamido)-morphinan, 17-cyclopropylmethyl-4,5α-epoxy-3-methoxy-14β-hydroxy-6β-(N-isobutyl-3,4-dichlorophenylacetamido)-morphinan, 17-cyclopropylmethyl-4,5α-epoxy-3-methoxy-14β-hydroxy-6β-(N-isobutylcinnamamido)morphinan, 17-cyclopropylmethyl-4,5α-epoxy-3-methoxy-14β-hydroxy-6β-(N-isobutylbenzyloxycarbamido)morphinan, 17-cyclopropylmethyl-4,5α-epoxy-3-methoxy-14β-hydroxy-6β-(N-isobutylphenylmethanesulfonamido)morphinan, 17-allyl-4,5α-epoxy-3-methoxy-14β-hydroxy-6β-(N-isobutyl-3,4-dichlorophenylacetamido)morphinan, 17-allyl-4,5α-epoxy-3-methoxy-14β-hydroxy-6β-(N-isobutylcinnamamido)morphinan, 17-allyl-4,5α-epoxy-3-methoxy-14β-hydroxy-6β-(N-isobutylbenzyloxycarbamido)morphinan, 17-allyl-4,5α-epoxy-3-methoxy-14β-hydroxy-6β-(N-isobutylphenylmethanesulfonamido)morphinan, 17-methyl-4,5α-epoxy-3-methoxy-14β-hydroxy-6β-(N-isobutyl-3,4-dichlorophenylacetamido)morphinan, 17-methyl-4,5α-epoxy-3-methoxy-14β-hydroxy-6β-(N-isobutylcinnamamido)morphinan, 17-methyl-4,5α-epoxy-3-methoxy-14β-hydroxy-6β-(N-isobutylbenzyloxycarbamido)-morphinan, 17-methyl-4,5α-epoxy-3-methoxy-14β-hydroxy-6β-(N-isobutylphenylmethanesulfonamido)morphinan, 17-phenethyl-4,5α-epoxy-3-methoxy-14β-hydroxy-6β-(N-isobutyl-3,4-dichlorophenylacetamido)morphinan, 17-phenethyl-4,5α-epoxy-3-methoxy-14β-hydroxy-6β-(N-isobutylcinnamamido)-morphinan, 17-phenethyl-4,5α-epoxy-3-methoxy-14β-hydroxy-6β-(N-isobutylbenzyloxycarbamido)morphinan, 17-phenethyl-4,5α-epoxy-3-methoxy-14β-hydroxy-6β-(N-isobutylphenylmethanesulfonamido)morphinan, 17-cyclopropylmethyl-4,5α-epoxy-3-methoxy-14β-acetoxy-6β-(N-isobutyl-3,4-dichlorophenylacetamido)-morphinan, 17-cyclopropylmethyl-4,5α-epoxy-3-methoxy-14β-acetoxy-6β-(N-isobutylcinnamamido)morphinan, 17-cyclopropylmethyl-4,5α-epoxy-3-methoxy-14β-acetoxy-6β-(N-isobutylbenzyloxycarbamido)morphinan, 17-cyclopropylmethyl-4,5α-epoxy-3-methoxy-14β-acetoxy-6β-(N-isobutylphenylmethanesulfonamido)morphinan, 17-allyl-4,5α-epoxy-3-methoxy-14β-acetoxy-6β-(N-isobutyl-3,4-dichlorophenylacetamido)morphinan, 17-allyl-4,5α-epoxy-3-methoxy-14β-acetoxy-6β-(N-isobutylcinnamamido)morphinan, 17-allyl-4,5α-epoxy-3-methoxy-14β-acetoxy-6β-(N-isobutylbenzyloxycarbamido)morphinan, 17-allyl-4,5α-epoxy-3-methoxy-14β-acetoxy-6β-(N-isobutylphenylmethanesulfonamido)morphinan, 17-methyl-4,5α-epoxy-3-methoxy-14β-acetoxy-6β-(N-isobutyl-3,4-dichlorophenylacetamido)morphinan, 17-methyl-4,5α-epoxy-3-methoxy-14β-acetoxy-6β-(N-isobutylcinnamamido)morphinan, 17-methyl-4,5α-epoxy-3-methoxy-14β-acetoxy-6β-(N-isobutylbenzyloxycarbamido)-morphinan, 17-methyl-4,5α-epoxy-3-methoxy-14β-acetoxy-6β-(N-isobutylphenylmethanesulfonamido)morphinan, 17-phenethyl-4,5α-epoxy-3-methoxy-14β-acetoxy-6β-(N-isobutyl-3,4-dichlorophenylacetamido)morphinan, 17-phenethyl-4,5α-epoxy-3-methoxy-14β-acetoxy-6β-(N-isobutylcinnamamido)-morphinan, 17-phenethyl-4,5α-epoxy-3-methoxy-14β-acetoxy-6β-(N-isobutylbenzyloxycarbamido)morphinan, 17-phenethyl-4,5α-epoxy-3-methoxy-14β-acetoxy-6β-(N-isobutylphenylmethanesulfonamido)morphinan, 17-cyclopropylmethyl-4,5α-epoxy-3-acetoxy-14β-hydroxy-6β-(N-isobutyl-3,4-dichlorophenylacetamido)-morphinan, 17-cyclopropylmethyl-4,5α-epoxy-3-acetoxy-14β-hydroxy-6β-(N-isobutylcinnamamido)morphinan, 17-cyclopropylmethyl-4,5α-epoxy-3-acetoxy-14β-hydroxy-6β-(N-isobutylbenzyloxycarbamido)morphinan, 17-cyclopropylmethyl-4,5α-epoxy-3-acetoxy-14β-hydroxy-6β-(N-isobutylphenylmethanesulfonamido)morphinan, 17-allyl-4,5α-epoxy-3-acetoxy-14β-hydroxy-6β-(N-isobutyl-3,4-dichlorophenylacetamido)morphinan, 17-allyl-4,5α-epoxy-3-acetoxy-14β-hydroxy-6β-(N-isobutylcinnamamido)morphinan, 17-allyl-4,5α-epoxy-3-acetoxy-14β-hydroxy-6β-(N-isobutylbenzyloxycarbamido)morphinan, 17-allyl-4,5α-epoxy-3-acetoxy-14β-hydroxy-6β-(N-isobutylphenylmethanesulfonamido)morphinan, 17-methyl-4,5α-epoxy-3-acetoxy-14β-hydroxy-6β-(N-isobutyl-3,4-dichlorophenylacetamido)morphinan, 17-methyl-4,5α-epoxy-3-acetoxy-14β-hydroxy-6β-(N-isobutylcinnamamido)morphinan, 17-methyl-4,5α-epoxy-3-acetoxy-14β-hydroxy-6β-(N-isobutylbenzyloxycarbamido)-morphinan, 17-methyl-4,5α-epoxy-3-acetoxy-14β-hydroxy-6β-(N-isobutylphenylmethanesulfonamido)morphinan, 17-phenethyl-4,5α-epoxy-3-acetoxy-14β-hydroxy-6β-(N-isobutyl-3,4-dichlorophenylacetamido)morphinan, 17-phenethyl-4,5α-epoxy-3-acetoxy-14β-hydroxy-6β-(N-isobutylcinnamamido)-morphinan, 17-phenethyl-4,5α-epoxy-3-acetoxy-14β-hydroxy-6β-(N-isobutylbenzyloxycarbamido)morphinan, 17-phenethyl-4,5α-epoxy-3-acetoxy-14β-hydroxy-6β-(N-isobutylphenylmethanesulfonamido)morphinan, 17-cyclopropylmethyl-4,5α-epoxy-3,14β-diacetoxy-6β-(N-isobutyl-3,4-dichlorophenylacetamido)morphinan, 17-cyclopropylmethyl-4,5α-epoxy-3,14β-diacetoxy-6β-(N-isobutylcinnamamido)morphinan, 17-cyclopropylmethyl-4,5α-epoxy-3,14β-diacetoxy-6β-(N-isobutylbenzyloxycarbamido)-morphinan, 17-cyclopropylmethyl-4,5α-epoxy-3,14β-diacetoxy-6β-(N-isobutylphenylmethanesulfonamido)morphinan, 17-allyl-4,5α-epoxy-3,14β-diacetoxy-6β-(N-isobutyl-3,4-dichlorophenylacetamido)morphinan, 17-allyl-4,5α-epoxy-3,14β-diacetoxy-6β-(N-isobutylcinnamamido)morphinan, 17-allyl-4,5α-epoxy-3,14β-diacetoxy-6β-(N-isobutylbenzyloxycarbamido)morphinan, 17-allyl-4,5α-epoxy-3,14β-diacetoxy-6β-(N-isobutylphenylmethanesulfonamido)-morphinan, 17-methyl-4,5α-epoxy-3,14β-diacetoxy-6β-(N-isobutyl-3,4-dichlorophenylacetamido)morphinan, 17-methyl-4,5α-epoxy-3,14β-diacetoxy-6β-(N-isobutylcinnamamido)morphinan, 17-methyl-4,5α-epoxy-3,14β-diacetoxy-6β-(N-isobutylbenzyloxycarbamido)morphinan, 17-methyl-4,5α-epoxy-3,14β-diacetoxy-6β-(N-isobutylphenylmethanesulfonamido)-morphinan, 17-phenethyl-4,5α-epoxy-3,14β-diacetoxy-6β-(N-isobutyl-3,4-dichlorophenylacetamido)morphinan, 17-phenethyl-4,5α-epoxy-3,14β-diacetoxy-6β-(N-isobutylcinnamamido)morphinan, 17-phenethyl-4,5α-epoxy-3,14β-diacetoxy-6β-(N-isobutylbenzyloxycarbamido)morphinan, 17-phenethyl-4,5α-epoxy-3,14β-diacetoxy-6β-(N-isobutylphenylmethanesulfonamido)morphinan, 17-cyclopropylmethyl-4,5α-epoxy-3,14β-dihydroxy-6α-(N-methyl-3,4-dichlorobenzamido)morphinan, 17-allyl-4,5α-epoxy-3,14β-dihydroxy-6α-(N-methyl-3,4-dichlorobenzamido)-morphinan, 17-cyclopropylmethyl-4,5α-epoxy-3,14β-dihydroxy-6β-(N-methyl-3,4-dichlorobenzamido)morphinan, 17-allyl-4,5α-epoxy-3,14β-dihydroxy-6β-(N-methyl-3,4-dichlorobenzamido)morphinan, 17-cyclopropylmethyl-4,5α-epoxy-3,14β-dihydroxy-6α-(N-ethyl-3,4-dichlorophenylacetamido)morphinan, 17-allyl-4,5α-epoxy-3,14β-dihydroxy-6α-(N-ethyl-3,4-dichlorophenylacetamido)-morphinan, 17-cyclopropylmethyl-4,5α-epoxy-3,14β-dihydroxy-6β-(N-ethyl-3,4-dichlorophenylacetamido)morphinan, 17-allyl-4,5α-epoxy-3,14β-dihydroxy-6β-(N-ethyl-3,4-dichlorophenylacetamido)morphinan, 17-cyclopropylmethyl-4,5α-epoxy-3,14β-dihydroxy-6α-(N-methyl-3-phenylpropionamido)morphinan, 17-allyl-4,5α-epoxy-3,14β-dihydroxy-6α-(N-methyl-3-phenylpropionamido)-morphinan, 17-cyclopropylmethyl-4,5α-epoxy-3,14β-dihydroxy-6β-(N-methyl-3-phenylpropionamido)morphinan, 17-allyl-4,5α-epoxy-3,14β-dihydroxy-6β-(N-methyl-3-phenylpropionamido)morphinan, 17-cyclopropylmethyl-4,5α-epoxy-3,14β-dihydroxy-6α-[N-methyl-3-(5-chlorobenzo[b]thienyl)acetamido]morphinan, 17-allyl-4,5α-epoxy-3,14β-dihydroxy-6α-[N-methyl-3-(5-chlorobenzo[b]thienyl)acetamido]morphinan, 17-cyclopropylmethyl-4,5α-epoxy-3,14β-dihydroxy-6β-[N-methyl-3-(5-chlorobenzo[b]thienyl)acetamido]morphinan, 17-allyl-4,5α-epoxy-3,14β-dihydroxy-6β-[N-methyl-3-(5-chlorobenzo[b]thienyl)acetamido]morphinan, 17-cyclopropylmethyl-4,5α-epoxy-3,14β-dihydroxy-6α-(N-methylphenylacetamido)morphinan, 17-allyl-4,5α-epoxy-3,14β-dihydroxy-6α-(N-methylphenylacetamido)morphinan, 17-cyclopropylmethyl-4,5α-epoxy-3,14β-dihydroxy-6β-(N-methylphenylacetamido)morphinan, 17-allyl-4,5α-epoxy-3,14β-dihydroxy-6β-(N-methylphenylacetamido)morphinan, 17-cyclopropylmethyl-4,5α-epoxy-3,14β-dihydroxy-6α-(N-methylcyclohexylacetamido)morphinan, 17-allyl-4,5α-epoxy-3,14β-dihydroxy-6α-(N-methylcyclohexylacetamido)-morphinan, 17-cyclopropylmethyl-4,5α-epoxy-3,14β-dihydroxy-6β-(N-methylcyclohexylacetamido)morphinan, 17-allyl-4,5α-epoxy-3,14β-dihydroxy-6β-(N-methylcyclohexylacetamido)-morphinan, 17-cyclopropylmethyl-4,5α-epoxy-3,14β-dihydroxy-6α-(N-methyl-3-bromophenylacetamido)morphinan, 17-allyl-4,5α-epoxy-3,14β-dihydroxy-6α-(N-methyl-3-bromophenylacetamido)-morphinan, 17-cyclopropylmethyl-4,5α-epoxy-3,14β-dihydroxy-6β-(N-methyl-3-bromophenylacetamido)morphinan, 17-allyl-4,5α-epoxy-3,14β-dihydroxy-6β-(N-methyl-3-bromophenylacetamido)morphinan, 17-cyclopropylmethyl-4,5α-epoxy-3,14β-dihydroxy-6α-(N-methyl-4-benzo[b]thienylacetamido)morphinan, 17-allyl-4,5α-epoxy-3,14β-dihydroxy-6α-(N-methyl-4-benzo[b]thienylacetamido)-morphinan, 17-cyclopropylmethyl-4,5α-epoxy-3,14β-dihydroxy-6β-(N-methyl-4-benzo[b]thienylacetamido)morphinan, 17-allyl-4,5α-epoxy-3,14β-dihydroxy-6β-(N-methyl-4-benzo[b]thienylacetamido)morphinan, 17-cyclopropylmethyl-4,5α-epoxy-3,14β-dihydroxy-6α-(N-methyl-3,4-dichlorocinnamamido)morphinan, 17-allyl-4,5α-epoxy-3,14β-dihydroxy-6α-(N-methyl-3,4-dichlorocinnamamido)morphinan, 17-cyclopropylmethyl-4,5α-epoxy-3,14β-dihydroxy-6β-(N-methyl-3,4-dichlorocinnamamido)morphinan, 17-allyl-4,5α-epoxy-3,14β-dihydroxy-6β-(N-methyl-3,4-dichlorocinnamamido)morphinan, 17-cyclopropylmethyl-4,5α-epoxy-3,14β-dihydroxy-6α-(N-methyl-4-bromophenylacetamido)morphinan, 17-allyl-4,5α-epoxy-3,14β-dihydroxy-6α-(N-methyl-4-bromophenylacetamido)-morphinan, 17-cyclopropylmethyl-4,5α-epoxy-3,14β-dihydroxy-6β-(N-methyl-4-bromophenylacetamido)morphinan, 17-allyl-4,5α-epoxy-3,14β-dihydroxy-6β-(N-methyl-4-bromophenylacetamido)morphinan, 17-cyclopropylmethyl-4,5α-epoxy-3,14β-dihydroxy-6α-[(R)-N-methyl-2-phenylpropionamido]morphinan, 17-allyl-4,5α-epoxy-3,14β-dihydroxy-6α-[(R)-N-methyl-2-phenylpropionamido]morphinan, 17-cyclopropylmethyl-4,5α-epoxy-3,14β-dihydroxy-6β-[(R)-N-methyl-2-phenylpropionamido]morphinan, 17-allyl-4,5α-epoxy-3,14β-dihydroxy-6β-[(R)-N-methyl-2-phenylpropionamido]morphinan, 17-cyclopropylmethyl-4,5α-epoxy-3,14β-dihydroxy-6α-[(R)-N-methylmethoxyphenylacetamido]morphinan, 17-allyl-4,5α-epoxy-3,14β-dihydroxy-6α-[(R)-N-methylmethoxyphenylacetamido]morphinan, 17-cyclopropylmethyl-4,5α-epoxy-3,14β-dihydroxy-6β-[(R)-N-methylmethoxyphenylacetamido]morphinan, 17-allyl-4,5α-epoxy-3,14β-dihydroxy-6β-[(R)-N-methylmethoxyphenylacetamido]morphinan, 17-cyclopropylmethyl-4,5α-epoxy-3,14β-dihydroxy-6α-[(S)-N-methylmethoxyphenylacetamido]morphinan, 17-allyl- 4,5α-epoxy-3,14β-dihydroxy-6α-[(S)-N-methylmethoxyphenylacetamido]morphinan, 17-cyclopropylmethyl-4,5α-epoxy-3,14β-dihydroxy-6β-[(S)-N-methylmethoxyphenylacetamido]morphinan, 17-allyl-4,5α-epoxy-3,14β-dihydroxy-6β-[(S)-N-methylmethoxyphenylacetamido]morphinan, 17-cyclopropylmethyl-4,5α-epoxy-3,14β-dihydroxy-6α-(3,4-dichlorophenylacetamido)morphinan, 17-allyl-4,5α-epoxy-3,14β-dihydroxy-6α-(3,4-dichlorophenylacetamido)-morphinan, 17-cyclopropylmethyl-4,5α-epoxy-3,14β-dihydroxy-6β-(3,4-dichlorophenylacetamido)morphinan, 17-allyl-4,5α-epoxy-3,14β-dihydroxy-6β-(3,4-dichlorophenylacetamido)morphinan, 17-cyclopropylmethyl-4,5α-epoxy-3,14β-dihydroxy-6α-(N-methyl-3,4-difluorophenylacetamido)morphinan, 17-allyl-4,5α-epoxy-3,14β-dihydroxy-6α-(N-methyl-3,4-difluorophenylacetamido)morphinan, 17-cyclopropylmethyl-4,5α-epoxy-3,14β-dihydroxy-6β-(N-methyl-3,4-difluorophenylacetamido)morphinan, 17-allyl-4,5α-epoxy-3,14β-dihydroxy-6β-(N-methyl-3,4-difluorophenylacetamido)-morphinan, 17-cyclopropylmethyl-4,5α-epoxy-3,14β-dihydroxy-6α-(N-methyl-3-trifluoromethylphenylacetamido)morphinan, 17-allyl-4,5α-epoxy-3,14β-dihydroxy-6α-(N-methyl-3-trifluoromethylphenylacetamido)morphinan, 17-cyclopropylmethyl-4,5α-epoxy-3,14β-dihydroxy-6β-(N-methyl-3-trifluoromethylphenylacetamido)morphinan, 17-allyl-4,5α-epoxy-3,14β-dihydroxy-6β-(N-methyl-3-trifluoromethylphenylacetamido)morphinan, 17-cyclopropylmethyl-4,5α-epoxy-3,14β-dihydroxy-6α-[(S)-N-methyl-2-phenylpropionamido]morphinan, 17-allyl-4,5α-epoxy-3,14β-dihydroxy-6α-[(S)-N-methyl-2-phenylpropionamido]morphinan, 17-cyclopropylmethyl-4,5α-epoxy-3,14β-dihydroxy-6β-[(S)-N-methyl-2-phenylpropionamido]morphinan, 17-allyl-4,5α-epoxy-3,14β-dihydroxy-6β-[(S)-N-methyl-2-phenylpropionamido]morphinan, 17-cyclopropylmethyl-4,5α-epoxy-3,14β-dihydroxy-6α-[N-methyl-N-2-(3,4dichlorophenyl)ethylamino]morphinan, 17-allyl-4,5α-epoxy-3,14β-dihydroxy-6α-[N-methyl-N-2-(3,4-dichlorophenyl)ethylamino]morphinan, 17-cyclopropylmethyl-4,5α-epoxy-3,14β-dihydroxy-6β-[N-methyl-N-2-(3,4-dichlorophenyl)ethylamino]morphinan, 17-allyl-4,5α-epoxy-3,14β-dihydroxy-6β-[N-methyl-N-2-(3,4-dichlorophenyl)ethylamino]morphinan, 17-cyclopropylmethyl-4,5α-epoxy-3,14β-dihydroxy-6α-(N-methyl-4-nitrophenylacetamido)morphinan, 17-allyl-4,5α-epoxy-3,14β-dihydroxy-6α-(N-methyl-4-nitrophenylacetamido)-morphinan, 17-cyclopropylmethyl-4,5α-epoxy-3,14β-dihydroxy-6β-(N-methyl-4-nitrophenylacetamido)morphinan, 17-allyl-4,5α-epoxy-3,14β-dihydroxy-6β-(N-methyl-4-nitrophenylacetamido)morphinan, 17-cyclopropylmethyl-4,5α-epoxy-3,14β-dihydroxy-6α-(N-methyl-4-aminophenylacetamido)morphinan, 17-allyl-4,5α-epoxy-3,14β-dihydroxy-6α-(N-methyl-4-aminophenylacetamido)morphinan, 17-cyclopropylmethyl-4,5α-epoxy-3,14β-dihydroxy-6β-(N-methyl-4-aminophenylacetamido)morphinan, 17-allyl-4,5α-epoxy-3,14β-dihydroxy-6β-(N-methyl-4-aminophenylacetamido)-morphinan, 17-cyclopropylmethyl-4,5α-epoxy-3,14β-dihydroxy-6α-(N-methylcyclohexylcarboxyamido)morphinan, 17-allyl-4,5α-epoxy-3,14β-dihydroxy-6α-(N-methylcyclohexylcarboxyamido)-morphinan, 17-cyclopropylmethyl-4,5α-epoxy-3,14β-dihydroxy-6β-(N-methylcyclohexylcarboxyamido)morphinan, 17-allyl-4,5α-epoxy-3,14β-dihydroxy-6β-(N-methylcyclohexylcarboxyamido)morphinan, 17-cyclopropylmethyl-4,5α-epoxy-3,14β-dihydroxy-6α-(N-methylbenzamido)morphinan, 17-allyl-4,5α-epoxy-3,14β-dihydroxy-6α-(N-methylbenzamido)morphinan, 17-cyclopropylmethyl-4,5α-epoxy-3,14β-dihydroxy-6β-(N-methylbenzamido)morphinan, 17-allyl-4,5α-epoxy-3,14β-dihydroxy-6β-(N-methylbenzamido)morphinan, 17-cyclopropylmethyl-4,5α-epoxy-3,14β-dihydroxy-6α-(N-methyl-4-phenylbutyroamido)morphinan, 17-allyl-4,5α-epoxy-3,14β-dihydroxy-6α-(N-methyl-4-phenylbutyroamido))-morphinan, 17-cyclopropylmethyl-4,5α-epoxy-3,14β-dihydroxy-6β(N-methyl-4-phenylbutyroamido)morphinan, 17-allyl-4,5α-epoxy-3,14β-dihydroxy-6β-(N-methyl-4-phenylbutyroamido)morphinan, 17-cyclopropylmethyl-4,5α-epoxy-3,14βdihydroxy-6α-(N-methyl-2-bromophenylacetamido)morphinan, 17-allyl-4,5α-epoxy-3,14β-dihydroxy-6α-(N-methyl-2-bromophenylacetamido))-morphinan, 17-cyclopropylmethyl-4,5α-epoxy-3,14β-dihydroxy-6β-(N-methyl-2-bromophenylacetamido)morphinan, 17-allyl-4,5α-epoxy-3,14β-dihydroxy-6β-(N-methyl-2-bromophenylacetamido)morphinan, 17-cyclopropylmethyl-4,5α-epoxy-3,14β-dihydroxy-6α-(N-methyl-6-phenylhexanamido)morphinan, 17-allyl-4,5α-epoxy-3,14β-dihydroxy-6α-(N-methyl-6-phenylhexanamido)-morphinan, 17-cyclopropylmethyl-4,5α-epoxy-3,14βdihydroxy-6β-(N-methyl-6-phenylhexanamido)morphinan, 17-allyl-4,5α-epoxy-3,14β-dihydroxy-6β(N-methyl-6-phenylhexanamido)morphinan, 17-cyclopropylmethyl-4,5α-epoxy-3,14βdihydroxy-6α-(N-methyl-3-fluorophenylacetamido)morphinan, 17-allyl-4,5α-epoxy-3,14βdihydroxy-6α-(N-methyl-3-fluorophenylacetamido)morphinan, 17-cyclopropylmethyl-4,5α-epoxy-3,14β-dihydroxy-60(N-methyl-3-fluorophenylacetamido)morphinan, 17-allyl-4,5α-epoxy-3,14β-dihydroxy-6β(N-methyl-3-fluorophenylacetamido)morphinan, 17-cyclopropylmethyl-4,5α-epoxy-3,14β-dihydroxy-6α-[N-methyl-N'-(3,4-dichlorophenyl)ureido]morphinan, 17-allyl-4,5α-epoxy-3,14βdihydroxy-6α-[N-methyl-N'-(3,4-dichlorophenyl)ureido]morphinan, 17-cyclopropylmethyl-4,5α-epoxy-3,14β-dihydroxy-6β[N-methyl-N'-(3,4-dichlorophenyl)ureido]morphinan, 17-allyl-4,5α-epoxy-3,14β-dihydroxy-6β-[N-methyl-N'-(3,4-dichlorophenyl)ureido]morphinan, 17-cyclopropylmethyl-4,5α-epoxy-3,14β-dihydroxy-6α-(N-methyl-N'-benzylureido)morphinan, 17-allyl-4,5α-epoxy-3,14β-dihydroxy-6α-(N-methyl-N'-benzylureido)morphinan, 17 -cyclopropylmethyl-4,5α-epoxy-3,14β-dihydroxy-6β-(N-methyl-N'-benzylureido)morphinan, 17-allyl-4,5α-epoxy-3,14β-dihydroxy-6β-(N-methyl-N'-benzylureido)morphinan, 17-cyclopropylmethyl-4,5α-epoxy-3,14β-dihydroxy-6α-(N-methyl-3-nitrophenylacetamido)morphinan, 17-allyl-4,5α-epoxy-3,14β-dihydroxy-6α-(N-methyl-3-nitrophenylacetamido)morphinan, 17-cyclopropylmethyl-4,5α-epoxy-3,14β-dihydroxy-6α-(N-methyl-3-nitrophenylacetamido)morphinan, 17-allyl-4,5α-epoxy-3,14β-dihydroxy-6β-(N-methyl-3-nitrophenylacetamido)morphinan, 17-cyclopropylmethyl-4,5α-epoxy-3,14β-dihydroxy-6α-(N-methyl-4-pyridylacetamido)morphinan, 17-allyl-4,5α-epoxy-3,14β-dihydroxy-6α-(N-methyl-4-pyridylacetamido)morphinan, 17-cyclopropylmethyl-4,5α- epoxy-3,14β-dihydroxy-6β-(N-methyl-4-pyridylacetamido) morphinan, 17-allyl-4,5α-epoxy-3,14β-dihydroxy-6β-(N-methyl-4-pyridylacetamido)morphinan, 17-cyclopropylmethyl-4,5α-epoxy-3,14β-dihydroxy-6α-[N-methyl-trans-3-(3-thienyl)acrylamido]morphinan, 17-allyl-4,5α-epoxy-3,14β-dihydroxy-6α-[N-methyl-trans-3-(3-thienyl)acrylamido]morphinan, 17-cyclopropylmethyl-4,5α-epoxy-3,14β-dihydroxy-6β-[N-methyl-trans-3-(3-thienyl)acrylamido]morphinan, 17-allyl-4,5α-epoxy-3,14β-dihydroxy-6β-[N-methyl-trans-3-(3-thienyl)acrylamido]morphinan, 17-cyclopropylmethyl-4,5α-epoxy-3,14β-dihydroxy-6α-(N-methylthiophenoxyacetamido)morphinan, 17-allyl-4,5α-epoxy-3,14β-dihydroxy-6α-(N-methylthiophenoxyacetamido)morphinan, 17-cyclopropylmethyl-4,5α-epoxy-3,14β-dihydroxy-6β-(N-methylthiophenoxyacetamido)morphinan, 17-allyl-4,5α-epoxy-3,14β-dihydroxy-6β-(N-methylthiophenoxyacetamido)morphinan, 17-cyclopropylmethyl-4,5α-epoxy-3,14β-dihydroxy-6α-(N-methylphenoxyacetamido)morphinan, 17-allyl-4,5α-epoxy-3,14β-dihydroxy-6α-(N-methylphenoxyacetamido)morphinan, 17-cyclopropylmethyl-4,5α-epoxy-3,14β-dihydroxy-6β-(N-methylphenoxyacetamido)morphinan, 17-allyl-4,5α-epoxy-3,14β-dihydroxy-6β-(N-methylphenoxyacetamido)-morphinan, 17-cyclopropylmethyl-4,5α-epoxy-3,14β-dihydroxy-6α-(N-methyl-4-nitrobenzyloxycarbamido)morphinan, 17-allyl-4,5α-epoxy-3,14β-dihydroxy-6α-(N-methyl-4-nitrobenzyloxycarbamido)morphinan, 17-cyclopropylmethyl-4,5α-epoxy-3,14β-dihydroxy-6β-(N-methyl-4-nitrobenzyloxycarbamido)morphinan, 17-allyl-4,5α-epoxy-3,14β-dihydroxy-6β-(N-methyl-4-nitrobenzyloxycarbamido)morphinan, 17-cyclopropylmethyl-4,5α-epoxy-3,14β-dihydroxy-6α-(N-methyl-3-pyridylmethoxycarbamido)morphinan, 17-allyl-4,5α-epoxy-3,14β-dihydroxy-6α-(N-methyl-3-pyridylmethoxycarbamido)morphinan, 17-cyclopropylmethyl-4,5α-epoxy-3,14β-dihydroxy-6β-(N-methyl-3-pyridylmethoxycarbamido)morphinan, 17-allyl-4,5α-epoxy-3,14β-dihydroxy-6β-(N-methyl-3-pyridylmethoxycarbamido)morphinan, 17-cyclopropylmethyl-4,5α-epoxy-3,14β-dihydroxy-6α-(N-methyl-3,4-dichlorophenylmethane-sulfonamido)-morphinan, 17-allyl-4,5α-epoxy-3,14β-dihydroxy-6α-(N-methyl-3,4-dichlorophenylmethane-sulfonamido)morphinan, 17-cyclopropylmethyl-4,5α-epoxy-3,14β-dihydroxy-6β-(N-methyl-3,4-dichlorophenylmethanesulfonamido)morphinan, 17-allyl-4,5α-epoxy-3,14β-dihydroxy-6β-(N-methyl-3,4-dichlorophenylmethanesulfonamido)morphinan, 17-cyclopropylmethyl-4,5α-epoxy-3,14β-dihydroxy-6α-(N-methyl-N'-benzylthioureido)morphinan, 17-ally-4,5α-epoxy-3,14β-dihydroxy-6α-(N-methyl-N'-benzylthioureido)morphinan, 17-cyclopropylmethyl-4,5α-epoxy-3,14β-dihydroxy-6β-(N-methyl-N'-benzylthioureido)morphinan, 17-allyl-4,5α-epoxy-3,14β-dihydroxy-6β-N-methyl-N'-benzylthioureido)morphinan, 17-cyclopropylmethyl-4,5α-epoxy-3,14β-dihydroxy-6α-(N-methylhexanamido)morphinan, 17-allyl-4,5α-epoxy-3,14β-dihydroxy-6α-(N-methylhexanamido)morphinan, 17-cyclopropylmethyl-4,5α-epoxy-3,14β-dihydroxy-6β-(N-methylhexanamido)morphinan, 17-allyl-4,5α-epoxy-3,14β-dihydroxy-6β-(N-methylhexanamido)morphinan, 17-cyclopropylmethyl-4,5α-epoxy-3,14β-dihydroxy-6α-(N-methylheptanamido)morphinan, 17-allyl-4,5α-epoxy-3,14β-dihydroxy-6α-(N-methylheptanamido)-morphinan, 17-cyclopropylmethyl-4,5α-epoxy-3,14β-dihydroxy-69-(N-methylheptanamido)morphinan, 17-allyl-4,5α-epoxy-3,14β-dihydroxy-6β-(N-methylheptanamido)morphinan, 17-cyclopropylmethyl-4,5α-epoxy-3,14β-dihydroxy-6α-(N-methyl-3-aminophenylacetamido)morphinan, 17-allyl-4,5α-epoxy-3,14β-dihydroxy-6α-(N-methyl-3-aminophenylacetamido)morphinan, 17-cyclopropylmethyl-4,5α-epoxy-3,14β-dihydroxy-6β-(N-methyl-3-aminophenylacetamido)morphinan, 17-allyl-4,5α-epoxy-3,14β-dihydroxy-6β-(N-methyl-3-aminophenylacetamido)-morphinan, 17-cyclopropylmethyl-4,5α-epoxy-3,14β-dihydroxy-6α-(N-methyl-2-pyridylacetamido)morphinan, 17-allyl-4,5α-epoxy-3,14β-dihydroxy-6α-(N-methyl-2-pyridylacetamido)morphinan, 17-cyclopropylmethyl-4,5α-epoxy-3,14β-dihydroxy-6β-(N-methyl-2-pyridylacetamido)morphinan, 17-allyl-4,5α-epoxy-3,14β-dihydroxy-6β-(N-methyl-2-pyridylacetamido)morphinan, 17-cyclopropylmethyl-4,5α-epoxy-3,14β-dihydroxy-6α-[N-methyl-3-β-pyridyl)propionamido]morphinan, 17-allyl-4,5α-epoxy-3,14β-dihydroxy-6α-[N-methyl-3-β-pyridyl)propionamido]morphinan, 17-cyclopropylmethyl-4,5α-epoxy-3,14β-dihydroxy-6β-[N-methyl-3-(3-pyridyl)propionamido]morphinan, 17-allyl-4,5α-epoxy-3,14β-dihydroxy-6β-[N-methyl-3-(3-pyridyl)propionamido]morphinan, 17-cyclopropylmethyl-4,5α-epoxy-3,14β-dihydroxy-6α-(3-phenylpropioyloxy)morphinan, 17-allyl-4,5α-epoxy-3,14β-dihydroxy-6α-(3-phenylpropioyloxy)-morphinan, 17-cyclopropylmethyl-4,5α-epoxy-3,14β-dihydroxy-6β-(3-phenylpropioyloxy)morphinan, 17-allyl-4,5α-epoxy-3,14β-dihydroxy-6β-(3-phenylpropioyloxy)morphinan, 17-cyclopropylmethyl-4,5α-epoxy-3,14β-dihydroxy-6α-[2-(3-furyl)ethenylsulfonyloxy]morphinan, 17-allyl-4,5α-epoxy-3,14β-dihydroxy-6α-[2-(3-furyl)ethenylsulfonyloxy]morphinan, 17-cyclopropylmethyl-4,5α-epoxy-3,14β-dihydroxy-6β-[2-(3-furyl)ethenylsulfonyloxy]morphinan, 17-allyl-4,5α-epoxy-3,14β-dihydroxy-6β-[2-(3-furyl)ethenylsulfonyloxy]morphinan, 17-cyclopropylmethyl-4,5α-epoxy-3,14β-dihydroxy-6α-(N-methyl-3-trifluoromethylcinnamamido)morphinan, 17-cyclopropylmethyl-4,5α-epoxy-3,14β-dihydroxy-6α-[N-methyl-trans-3-(3-furyl)acrylamido]morphinan, 17-cyclopropylmethyl-4,5α-epoxy-3,14β-dihydroxy-6α-(N-methyl-4-trifluoromethylcinnamamido)morphinan, 17-cyclopropylmethyl-4,5α-epoxy-3,14β-dihydroxy-6α-(N-methyl-3-phenylpropiolamido)morphinan, 17-allyl-4,5α-epoxy-3,14β-dihydroxy-6α-(N-methyl-3-trifluoromethylcinnamamido)morphinan, 17-allyl-4,5α-epoxy-3,14β-dihydroxy-6α-[N-methyl-trans-3-(3-furyl)acrylamido]morphinan, 17-allyl-4,5α-epoxy-3,14β-dihydroxy-6α-(N-methyl-4-trifluoromethylcinnamamido)morphinan, 17-allyl-4,5α-epoxy-3,14β-dihydroxy-6α-(N-methyl-3-phenylpropiolamido)morphinan, 17-methyl-4,5α-epoxy-3,14β-dihydroxy-6α-(N-methyl-3-trifluoromethylcinnamamido)morphinan, 17-methyl-4,5α-epoxy-3,14β-dihydroxy-6α-[N-methyl-trans-3-(3-furyl)acrylamido]morphinan, 17-methyl-4,5α-epoxy-3,14β-dihydroxy-6α-(N-methyl-4-trifluoromethylcinnamamido)morphinan, 17-methyl-4,5α-epoxy-3,14β-dihydroxy-6α-(N-methyl-3-phenylpropiolamido)morphinan, 17-phenethyl-4,5α-epoxy-3,14β-dihydroxy-6α-(N-methyl-3-trifluoromethylcinnamamido)morphinan, 17-phenethyl-4,5α-epoxy-3,14β-dihydroxy-6α-[N-methyl-trans-3-(3-furyl)acrylamido]morphinan, 17-phenethyl-4,5α-epoxy-3,14β-dihydroxy-6α-(N-methyl-4-trifluoromethyl-cinnamamido)morphinan, 17-phenethyl-4,5α-epoxy-3,14β-dihydroxy-6α-(N-methyl-3-phenylpropiolamido)-morphinan, 17-cyclopropylmethyl-4,5α-epoxy-3-hydroxy-14β-acetoxy-6α-(N-methyl-3-trifluoromethylcinnamamido)morphinan, 17-cyclopropylmethyl-4,5α-epoxy-3-hydroxy-14β-acetoxy-6α-[N-methyl-trans-3-(3-furyl)acrylamido]morphinan, 17-cyclopropylmethyl-4,5α-epoxy-3-hydroxy-14β-acetoxy-6α-(N-methyl-4-trifluoromethylcinnamamido)morphinan, 17-cyclopropylmethyl-4,5α-epoxy-3-hydroxy-14β-acetoxy-6α-(N-methyl-3-phenylpropiolamido)morphinan, 17-allyl-4,5α-epoxy-3-hydroxy-14β-acetoxy-6α-(N-methyl-3-trifluoromethylcinnamamido)morphinan, 17-allyl-4,5α-epoxy-3-hydroxy-14β-acetoxy-6α-[N-methyl-trans-3-(3-furyl)acrylamido]morphinan, 17-allyl-4,5α-epoxy-3-hydroxy-14β-acetoxy-6α-(N-methyl-4-trifluoromethylcinnamamido)morphinan, 17-allyl-4,5α-epoxy-3-hydroxy-14β-acetoxy-6α-(N-methyl-3-phenylpropiolamido)morphinan, 17-methyl-4,5α-epoxy-3-hydroxy-14β-acetoxy-6α-(N-methyl-3-trifluoromethylcinnamamido)morphinan, 17-methyl-4,5α-epoxy-3-hydroxy-14β-acetoxy-6α-[N-methyl-trans-3-(3-furyl)acrylamido]morphinan, 17-methyl-4,5α-epoxy-3-hydroxy-14β-acetoxy-6α-(N-methyl-4-trifluoromethylcinnamamido)morphinan, 17-methyl-4,5α-epoxy-3-hydroxy-14β-acetoxy-6α-(N-methyl-3-phenylpropiolamido)morphinan, 17-phenethyl-4,5α-epoxy-3-hydroxy-14β-acetoxy-6α-(N-methyl-3-trifluoromethylcinnamamido)morphinan, 17-phenethyl-4,5α-epoxy-3-hydroxy-14β-acetoxy-6α-[N-methyl-trans-3-β-furyl)acrylamido]morphinan, 17-phenethyl-4,5α-epoxy-3-hydroxy-14β-acetoxy-6α-(N-methyl-4-trifluoromethylcinnamamido)morphinan, 17-phenethyl-4,5α-epoxy-3-hydroxy-14β-acetoxy-6α-(N-methyl-3-phenylpropiolamido)morphinan, 17-cyclopropylmethyl-4,5α-epoxy-14β-hydroxy-6α-(N-methyl-3-trifluoromethylcinnamamido)morphinan, 17-cyclopropylmethyl-4,5α-epoxy-14β-hydroxy-6α-[N-methyl-trans-3-(3-furyl)acrylamido]morphinan, 17-cyclopropylmethyl-4,5α-epoxy-14β-hydroxy-6α-(N-methyl-4-trifluoromethylcinnamamido)morphinan, 17-cyclopropylmethyl-4,5α-epoxy-14β-hydroxy-6α-(N-methyl-3-phenylpropiolamido)morphinan, 17-allyl-4,5α-epoxy-14β-hydroxy-6α-(N-methyl-3-trifluoromethylcinnamamido)morphinan, 17-allyl-4,5α-epoxy-14β-hydroxy-6α-[N-methyl-trans-3-(3-furyl)acrylamido]morphinan, 17-allyl-4,5α-epoxy-14β-hydroxy-6α-(N-methyl-4-trifluoromethyl-cinnamamido)morphinan, 17-allyl-4,5α-epoxy-14β-hydroxy-6α-(N-methyl-3-phenylpropiolamido)morphinan, 17-methyl-4,5α-epoxy-14β-hydroxy-6α-(N-methyl-3-trifluoromethylcinnamamido)morphinan, 17-methyl-4,5α-epoxy-14β-hydroxy-6α-[N-methyl-trans-3-β-furyl)acrylamido]morphinan, 17-methyl-4,5α-epoxy-14β-hydroxy-6α-(N-methyl-4-trifluoromethylcinnamamido)morphinan, 17-methyl-4,5α-epoxy-14β-hydroxy-6α-(N-methyl-3-phenylpropiolamido)morphinan, 17-phenethyl-4,5α-epoxy-14β-hydroxy-6α-(N-methyl-3-trifluoromethylcinnamamido)morphinan, 17-phenethyl-4,5α-epoxy-14β-hydroxy-6α-[N-methyl-trans-3-(3-furyl)acrylamido]morphinan, 17-phenethyl-4,5α-epoxy-14β-hydroxy-6α-(N-methyl-4-trifluoromethylcinnamamido)morphinan, 17-phenethyl-4,5α-epoxy-14β-hydroxy-6α-(N-methyl-3-phenylpropiolamido)morphinan, 17-cyclopropylmethyl-4,5α-epoxy-14β-acetoxy-6α-(N-methyl-3-trifluoromethylcinnamamido)morphinan, 17-cyclopropylmethyl-4,5α-epoxy-14β-acetoxy-6α-[N-methyl-trans-3-(3-furyl)acrylamido]morphinan, 17-cyclopropylmethyl-4,5α-epoxy-14β-acetoxy-6α-(N-methyl-4-trifluoromethylcinnamamido)morphinan, 17-cyclopropylmethyl-4,5α-epoxy-14β-acetoxy-6α-(N-methyl-3-phenylpropiolamido)morphinan, 17-allyl-4,5α-epoxy-14β-acetoxy-6α-(N-methyl-3-trifluoromethylcinnamamido) morphinan, 17-allyl-4,5α-epoxy-14β-acetoxy-6α-[N-methyl-trans-3-(3-furyl)acrylamido]morphinan, 17-allyl-4,5α-epoxy-14β-acetoxy-6α-(N-methyl-4-trifluoromethylcinnamamido)morphinan, 17-allyl-4,5α-epoxy-14β-acetoxy-6α-(N-methyl-3-phenylpropiolamido)-morphinan, 17-methyl-4,5α-epoxy-14β-acetoxy-6α-(N-methyl-3-trifluoromethylcinnamamido)morphinan, 17-methyl-4,5α-epoxy-14β-acetoxy-6α-[N-methyl-trans-3-(3-furyl)acrylamido]morphinan, 17-methyl-4,5α-epoxy-14β-acetoxy-6α-(N-methyl-4-trifluoromethylcinnamamido)morphinan, 17-methyl-4,5α-epoxy-14β-acetoxy-6α-(N-methyl-3-phenylpropiolamido)morphinan, 17-phenethyl-4,5α-epoxy-14β-acetoxy-6α-(N-methyl-3-trifluoromethylcinnamamido)morphinan, 17-phenethyl-4,5α-epoxy-14β-acetoxy-6α-[N-methyl-trans-3-(3-furyl)acrylamido]morphinan, 17-phenethyl-4,5α-epoxy-14β-acetoxy-6α-(N-methyl-4-trifluoromethylcinnamamido)morphinan, 17-phenethyl-4,5α-epoxy-14β-acetoxy-6α-(N-methyl-3-phenylpropiolamido)morphinan, 17-cyclopropylmethyl-4,5α-epoxy-3-methoxy-14β-hydroxy-6α-(N-methyl-3-trifluoromethylcinnamamido)morphinan, 17-cyclopropylmethyl-4,5α-epoxy-3-methoxy-14β-hydroxy-6α-[N-methyl-trans-3-3-furyl)acrylamido]morphinan, 17-cyclopropylmethyl-4,5α-epoxy-3-methoxy-14β-hydroxy-6α-(N-methyl-4-trifluoromethylcinnamamido)morphinan, 17-cyclopropylmethyl-4,5α-epoxy-3-methoxy-14β-hydroxy-6α-(N-methyl-3-phenylpropiolamido)morphinan, 17-allyl-4,5α-epoxy-3-methoxy-14β-hydroxy-6α-(N-methyl-3-trifluoromethylcinnamamido)morphinan, 17-allyl-4,5α-epoxy-3-methoxy-14β-hydroxy-6α-[N-methyl-trans-3-(3-furyl)acrylamido]morphinan, 17-allyl-4,5α-epoxy-3-methoxy-14β-hydroxy-6α-(N-methyl-4-trifluoromethylcinnamamido)morphinan, 17-allyl-4,5α-epoxy-3-methoxy-14β-hydroxy-6α-(N-methyl-3-phenylpropiolamido)morphinan, 17-methyl-4,5α-epoxy-3-methoxy-14β-hydroxy-6α-(N-methyl-3-trifluoromethylcinnamamido)morphinan, 17-methyl-4,5α-epoxy-3-methoxy-14β-hydroxy-6α-[N-methyl-trans-3-(3-furyl)acrylamido]morphinan, 17-methyl-4,5α-epoxy-3-methoxy-14β-hydroxy-6α-(N-methyl-4-trifluoromethyl-cinnamamido)morphinan, 17-methyl-4,5α-epoxy-3-methoxy-14β-hydroxy-6α-(N-methyl-3-phenylpropiolamido)-morphinan, 17-phenethyl-4,5α-epoxy-3-methoxy-14β-hydroxy-6α-(N-methyl-3-trifluoromethylcinnamamido)-morphinan, 17-phenethyl-4,5α-epoxy-3-methoxy-14β-hydroxy-6α-[N-methyl-trans-3-3-furyl)acrylamido]-morphinan, 17-phenethyl-4,5α-epoxy-3-methoxy-14β-hydroxy-6α-(N-methyl-4-trifluoromethylcinnamamido)morphinan, 17-phenethyl-4,5α-epoxy-3-methoxy-14β-hydroxy-6α-(N-methyl-3-phenylpropiolamido)morphinan, 17-cyclopropylmethyl-4,5α-epoxy-3-methoxy-14β-acetoxy-6α-(N-methyl-3-trifluoromethylcinnamamido)morphinan, 17-cyclopropylmethyl-4,5α-epoxy-3-methoxy-14β-acetoxy-6α-[N-methyl-trans-3-(3-furyl)acrylamido]morphinan, 17-cyclopropylmethyl-4,5α-epoxy-3-methoxy-14β-acetoxy-6α-(N-methyl-4-trifluoromethylcinnamamido)morphinan, 17-cyclopropylmethyl-4,5α-epoxy-3-methoxy-14β-acetoxy-6α-(N-methyl-3-phenylpropionamido)morphinan, 17-allyl-4,5α-epoxy-3-methoxy-14β-acetoxy-6α-(N-methyl-3-trifluoromethylcinnamamido)morphinan, 17-allyl- 4,5α-epoxy-3-methoxy-14β-acetoxy-6α-[N-methyl-trans-3-(3-furyl)acrylamido]morphinan, 17-allyl-4,5α-epoxy-3-methoxy-14β-acetoxy-6α-(N-methyl-4-trifluoromethylcinnamamido)morphinan, 17-allyl-4,5α-epoxy-3-methoxy-14β-acetoxy-6α-(N-methyl-3-phenylpropiolamido)morphinan, 17-methyl-4,5α-epoxy-3-methoxy-14β-acetoxy-6α-(N-methyl-3-trifluoromethylcinnamamido)morphinan, 17-methyl-4,5α-epoxy-3-methoxy-14β-acetoxy-6α-[N-methyl-trans-3-(3-furyl)acrylamido]morphinan, 17-methyl-4,5α-epoxy-3-methoxy-14β-acetoxy-6α-(N-methyl-4-trifluoromethylcinnamamido)morphinan, 17-methyl-4,5α-epoxy-3-methoxy-14β-acetoxy-6α-(N-methyl-3-phenylpropiolamido) morphinan, 17-phenethyl-4,5α-epoxy-3-methoxy-14β-acetoxy-6α-(N-methyl-3-trifluoromethylcinnamamido)morphinan, 17-phenethyl-4,5α-epoxy-3-methoxy-14β-acetoxy-6α-[N-methyl-trans-3-(3-furyl)acrylamido]morphinan, 17-phenethyl-4,5α-epoxy-3-methoxy-14β-acetoxy-6α-(N-methyl-4-trifluoromethylcinnamamido)morphinan, 17-phenethyl-4,5α-epoxy-3-methoxy-14β-acetoxy-6α-(N-methyl-3-phenylpropiolamido)morphinan, 17-cyclopropylmethyl-4,5α-epoxy-3-acetoxy-14β-hydroxy-6α-(N-methyl-3-trifluoromethylcinnamamido)morphinan, 17-cyclopropylmethyl-4,5α-epoxy-3-acetoxy-14β-hydroxy-6α-[N-methyl-trans-3-(3-furyl)acrylamido]morphinan, 17-cyclopropylmethyl-4,5α-epoxy-3-acetoxy-14β-hydroxy-6α-(N-methyl-4-trifluoromethylcinnamamido)morphinan, 17-cyclopropylmethyl-4,5α-epoxy-3-acetoxy-14β-hydroxy-6α-(N-methyl-3-phenylpropiolamido)morphinan, 17-allyl-4,5α-epoxy-3-acetoxy-14β-hydroxy-6α-(N-methyl-3-trifluoromethylcinnamamido)morphinan, 17-allyl-4,5α-epoxy-3-acetoxy-14β-hydroxy-6α-[N-methyl-trans-3-(3-furyl)acrylamido]morphinan, 17-allyl-4,5α-epoxy-3-acetoxy-14β-hydroxy-6α-(N-methyl-4-trifluoromethylcinnamamido)morphinan, 17-allyl-4,5α-epoxy-3-acetoxy-14β-hydroxy-6α-(N-methyl-3-phenylpropiolamido)morphinan, 17-methyl-4,5α-epoxy-3-acetoxy-14β-hydroxy-6α-(N-methyl-3-trifluoromethylcinnamamido)morphinan, 17-methyl-4,5α-epoxy-3-acetoxy-14β-hydroxy-6α-[N-methyl-trans-3-(3-furyl)acrylamido]morphinan, 17-methyl-4,5α-epoxy-3-acetoxy-14β-hydroxy-6α-(N-methyl-4-trifluoromethylcinnamamido)morphinan, 17-methyl-4,5α-epoxy-3-acetoxy-14β-hydroxy-6α-(N-methyl-3-phenylpropiolamido)morphinan, 17-phenethyl-4,5α-epoxy-3-acetoxy-14β-hydroxy-6α-(N-methyl-3-trifluoromethylcinnamamido)morphinan, 17-phenethyl-4,5α-epoxy-3-acetoxy-14β-hydroxy-6α-[N-methyl-trans-3-(3-furyl)acrylamido]morphinan, 17-phenethyl-4,5α-epoxy-3-acetoxy-14β-hydroxy-6α-(N-methyl-4-trifluoromethylcinnamamido)morphinan, 17-phenethyl-4,5α-epoxy-3-acetoxy-14β-hydroxy-6α-(N-methyl-3-phenylpropiolamido)morphinan, 17-cyclopropylmethyl-4,5α-epoxy-3,14β-diacetoxy-6α-(N-methyl-3-trifluoromethylcinnamamido)morphinan, 17-cyclopropylmethyl-4,5α-epoxy-3,14β-diacetoxy-6α-[N-methyl-trans-3-(3-furyl)acrylamido]morphinan, 17-cyclopropylmethyl-4,5α-epoxy-3,14β-diacetoxy-6α-(N-methyl-4-trifluoromethylcinnamamido)morphinan, 17-cyclopropylmethyl-4,5α-epoxy-3,14β-diacetoxy-6α-(N-methyl-3-phenylpropiolamido)morphinan, 17-allyl-4,5α-epoxy-3,14β-diacetoxy-6α-(N-methyl-3-trifluoromethylcinnamamido)morphinan, 17-allyl-4,5α-epoxy-3,14β-diacetoxy-6α-[N-methyl-trans-3-(3-furyl)acrylamido]morphinan, 17-allyl-4,5α-epoxy-3,14β-diacetoxy-6α-(N-methyl-4-trifluoromethylcinnamamido)morphinan, 17-allyl-4,5α-epoxy-3,14β-diacetoxy-6α-(N-methyl-3-phenylpropiolamido)morphinan, 17-methyl-4,5α-epoxy-3,14β-diacetoxy-6α-(N-methyl-3-trifluoromethylcinnamamido)morphinan, 17-methyl-4,5α-epoxy-3,14β-diacetoxy-6α-[N-methyl-trans-3-(3-furyl)acrylamido]morphinan, 17-methyl-4,5α-epoxy-3,14β-diacetoxy-6α-(N-methyl-4-trifluoromethylcinnamamido)morphinan, 17-methyl-4,5α-epoxy-3,14β-diacetoxy-6α-(N-methyl-3-phenylpropiolamido)morphinan, 17-phenethyl-4,5α-epoxy-3,14β-diacetoxy-6α-(N-methyl-3-trifluoromethylcinnamamido)morphinan, 17-phenethyl-4,5α-epoxy-3,14β-diacetoxy-6α-[N-methyl-trans-3-(3-furyl)acrylamido]morphinan, 17-phenethyl-4,5α-epoxy-3,14β-diacetoxy-6α-(N-methyl-4-trifluoromethyl-cinnamamido) morphinan, 17-phenethyl-4,5α-epoxy-3,14β-diacetoxy-6α-(N-methyl-3-phenylpropiolamido)-morphinan, 17-cyclopropylmethyl-4,5α-epoxy-3,14β-dihydroxy-6α-(N-isobutyl-3-trifluoromethylcinnamamido)-morphinan, 17-cyclopropylmethyl-4,5α-epoxy-3,14β-dihydroxy-6α-[N-isobutyl-trans-3-(3-furyl)acrylamido]-morphinan, 17-cyclopropylmethyl-4,5α-epoxy-3,14β-dihydroxy-6α-(N-isobutyl-4-trifluoromethylcinnamamido)morphinan, 17-cyclopropylmethyl-4,5α-epoxy-3,14β-dihydroxy-6α-(N-isobutyl-3-phenylpropiolamido)morphinan, 17-allyl-4,5α-epoxy-3,14β-dihydroxy-6α-(N-isobutyl-3-trifluoromethylcinnamamido)morphinan, 17-allyl-4,5α-epoxy-3,14β-dihydroxy-6α-[N-isobutyl-trans-3-(3-furyl)acrylamido]morphinan, 17-allyl-4,5α-epoxy-3,14β-dihydroxy-6α-(N-isobutyl-4-trifluoromethylcinnamamido) morphinan, 17-allyl-4,5α-epoxy-3,14β-dihydroxy-6α-(N-isobutyl-3-phenylpropiolamido)morphinan, 17-methyl-4,5α-epoxy-3,14β-dihydroxy-6α-(N-isobutyl-3-trifluoromethylcinnamamido)morphinan, 17-methyl-4,5α-epoxy-3,14β-dihydroxy-6α-[N-isobutyl-trans-3-(3-furyl)acrylamido]morphinan, 17-methyl-4,5α-epoxy-3,14β-dihydroxy-6α-(N-isobutyl-4-trifluoromethylcinnamamido)morphinan, 17-methyl-4,5α-epoxy-3,14β-dihydroxy-6α-(N-isobutyl-3-phenylpropiolamido)morphinan, 17-phenethyl-4,5α-epoxy-3,14β-dihydroxy-6α-(N-isobutyl-3-trifluoromethylcinnamamido)morphinan, 17-phenethyl-4,5α-epoxy-3,14β-dihydroxy-6α-[N-isobutyl-trans-3-(3-furyl)acrylamido]morphinan, 17-phenethyl-4,5α-epoxy-3,14β-dihydroxy-6α-(N-isobutyl-4-trifluoromethyl-cinnamamido)morphinan, 17-phenethyl-4,5α-epoxy-3,14β-dihydroxy-6α-(N-isobutyl-3-phenylpropiolamido)-morphinan, 17-cyclopropylmethyl-4,5α-epoxy-3-hydroxy-14β-acetoxy-6α-(N-isobutyl-3-trifluoromethylcinnamamido)-morphinan, 17-cyclopropylmethyl-4,5α-epoxy-3-hydroxy-14β-acetoxy-6α-[N-isobutyl-trans-3-(3-furyl)acrylamido]morphinan, 17-cyclopropylmethyl-4,5α-epoxy-3-hydroxy-14β-acetoxy-6α-(N-isobutyl-4-trifluoromethylcinnamamido)morphinan, 17-cyclopropylmethyl-4,5α-epoxy-3-hydroxy-14β-acetoxy-6α-(N-isobutyl-3-phenylpropiolamido)morphinan, 17-allyl-4,5α-epoxy-3-hydroxy-14β-acetoxy-6α-(N-isobutyl-3-trifluoromethylcinnamamido)morphinan, 17-allyl-4,5α-epoxy-3-hydroxy-14β-acetoxy-6α-[N-isobutyl-trans-3-(3-furyl)acrylamido]morphinan, 17-allyl-4,5α-epoxy-3-hydroxy-14β-acetoxy-6α-(N-isobutyl-4-trifluoromethylcinnamamido)morphinan, 17-allyl-4,5α-epoxy-3-hydroxy-14β-acetoxy-6α-(N-isobutyl-3-phenylpropiolamido)morphinan, 17-methyl-4,5α-epoxy-3-hydroxy-14β-acetoxy-6α-(N-isobutyl-3-trifluoromethylcinnamamido)morphinan, 17-methyl-4,5α-epoxy-3-hydroxy-14β-acetoxy-6α-[N-isobutyl-trans-3-(3-furyl)acrylamido]morphinan, 17-methyl-4,5α-epoxy-3- hydroxy-14β-acetoxy-6α-(N-isobutyl-4-trifluoromethylcinnamamido)morphinan, 17-methyl-4,5α-epoxy-3-hydroxy-14β-acetoxy-6α-(N-isobutyl-3-phenylpropiolamido)-morphinan, 17-phenethyl-4,5α-epoxy-3-hydroxy-14β-acetoxy-6α-(N-isobutyl-3-trifluoromethylcinnamamido)-morphinan, 17-phenethyl-4,5α-epoxy-3-hydroxy-14β-acetoxy-6α-[N-isobutyl-trans-3-(3-furyl)acrylamido]-morphinan, b 17-phenethyl-4,5α-epoxy-3-hydroxy-14β-acetoxy-6α-(N-isobutyl-4-trifluoromethylcinnamamido)morphinan, 17-phenethyl-4,5α-epoxy-3-hydroxy-14β-acetoxy-6α-(N-isobutyl-3-phenylpropiolamido)morphinan, 17-cyclopropylmethyl-4,5α-epoxy-14β-hydroxy-6α-(N-isobutyl-3-trifluoromethylcinnamamido)morphinan, 17-cyclopropylmethyl-4,5α-epoxy-14β-hydroxy-6α-[N-isobutyl-trans-3-(3-furyl)acrylamido]morphinan, 17-cyclopropylmethyl-4,5α-epoxy-14β-hydroxy-6α-(N-isobutyl-4-trifluoromethylcinnamamido)morphinan, 17-cyclopropylmethyl-4,5α-epoxy-14β-hydroxy-6α-(N-isobutyl-3-phenylpropiolamido)morphinan, 17-allyl-4,5α-epoxy-14β-hydroxy-6α-(N-isobutyl-3-trifluoromethylcinnamamido)morphinan, 17-allyl-4,5α-epoxy-14β-hydroxy-6α-[N-isobutyl-trans-3-(3-furyl)acrylamido]morphinan, 17-allyl-4,5α-epoxy-14β-hydroxy-6α-(N-isobutyl-4-trifluoromethylcinnamamido)morphinan, 17-allyl-4,5α-epoxy-14β-hydroxy-6α-(N-isobutyl-3-phenylpropiolamido)-morphinan, 17-methyl-4,5α-epoxy-14β-hydroxy-6α-(N-isobutyl-3-trifluoromethylcinnamamido)morphinan, 17-methyl-4,5α-epoxy-14β-hydroxy-6α-[N-isobutyl-trans-3-3-furyl)acrylamido]morphinan, 17-methyl-4,5α-epoxy-14β-hydroxy-6α-(N-isobutyl-4-trifluoromethylcinnamamido)morphinan, 17-methyl-4,5α-epoxy-14β-hydroxy-6α-(N-isobutyl-3-phenylpropiolamido)morphinan, 17-phenethyl-4,5α-epoxy-14β-hydroxy-6α-(N-isobutyl-3-trifluoromethylcinnamamido)morphinan, 17-phenethyl-4,5α-epoxy-14β-hydroxy-6α-[N-isobutyl-trans-3-(3-furyl)acrylamido]morphinan, 17-phenethyl-4,5α-epoxy-14β-hydroxy-6α-(N-isobutyl-4-trifluoromethylcinnamamido)morphinan, 17-phenethyl-4,5α-epoxy-14β-hydroxy-6α-(N-isobutyl-3-phenylpropiolamido)morphinan, 17-cyclopropylmethyl-4,5α-epoxy-14β-acetoxy-6α-(N-isobutyl-3-trifluoromethylcinnamamido)morphinan, 17-cyclopropylmethyl-4,5α-epoxy-14β-acetoxy-6α-[N-isobutyl-trans-3-(3-furyl)acrylamido]morphinan, 17-cyclopropylmethyl-4,5α-epoxy-14β-acetoxy-6α-(N-isobutyl-4-trifluoromethylcinnamamido)morphinan, 17cyclopropylmethyl-4,5α-epoxy-14β-acetoxy-6α-(N-isobutyl-3-phenylpropiolamido)morphinan, 17-allyl-4,5α-epoxy-14β-acetoxy-6α-(N-isobutyl-3-trifluoromethylcinnamamido)morphinan, 17-allyl-4,5α-epoxy-14β-acetoxy-6α-[N-isobutyl-trans-3-(3-furyl)acrylamido]morphinan, 17-allyl-4,5α-epoxy-14β-acetoxy-6α-(N-isobutyl-4-trifluoromethylcinnamamido)morphinan, 17-allyl-4,5α-epoxy-14β-acetoxy-6α-(N-isobutyl-3-phenylpropiolamido)-morphinan, 17-methyl-4,5α-epoxy-14β-acetoxy-6α-(N-isobutyl-3-trifluoromethylcinnamamido)morphinan, 17-methyl-4,5α-epoxy-14β-acetoxy-6α-[N-isobutyl-trans-3-(3-furyl)acrylamido]morphinan, 17-methyl-4,5α-epoxy-14β-acetoxy-6α-(N-isobutyl-4-trifluoromethylcinnamamido)morphinan, 17-methyl-4,5α-epoxy-14β-acetoxy-6α-(N-isobutyl-3-phenylpropiolamido)morphinan, 17-phenethyl-4,5α-epoxy-14β-acetoxy-6α-(N-isobutyl-3-trifluoromethylcinnamamido)morphinan, 17-phenethyl-4,5α-epoxy-14β-acetoxy-6α-[N-isobutyl-trans-3-(3-furyl)acrylamido]morphinan, 17-phenethyl-4,5α-epoxy-14β-acetoxy-6α-(N-isobutyl-4-trifluoromethylcinnamamido)morphinan, 17-phenethyl-4,5α-epoxy-14β-acetoxy-6α-(N-isobutyl-3-phenylpropiolamido)morphinan, 17-cyclopropylmethyl-4,5α-epoxy-3-methoxy-14β-hydroxy-6α-(N-isobutyl-3-trifluoromethylcinnamamido)morphinan, 17-cyclopropylmethyl-4,5α-epoxy-3-methoxy-14β-hydroxy-6α-[N-isobutyl-trans-3-(3-furyl)acrylamido]morphin, 17-cyclopropylmethyl-4,5α-epoxy-3-methoxy-14β-hydroxy-6α-(N-isobutyl-4-trifluoromethylcinnamamido)morphinan, 17-cyclopropylmethyl-4,5α-epoxy-3-methoxy-14β-hydroxy-6α-(N-isobutyl-3-phenylpropiolamido)morphinan, 17-allyl-4,5α-epoxy-3-methoxy-14β-hydroxy-6α-(N-isobutyl-3-trifluoromethylcinnamamido)morphinan, 17-allyl-4,5α-epoxy-3-methoxy-14β-hydroxy-6α-[N-isobutyl-trans-3-(3-furyl)acrylamido]morphinan, 17-allyl-4,5α-epoxy-3-methoxy-14β-hydroxy-6α-(N-isobutyl-4-trifluoromethylcinnamamido)morphinan, 17-allyl-4,5α-epoxy-3-methoxy-14β-hydroxy-6α-(N-isobutyl-3-phenylpropiolamido)morphinan, 17-methyl-4,5α-epoxy-3-methoxy-14β-hydroxy-6α-(N-isobutyl-3-trifluoromethylcinnamamido)morphinan, 17-methyl-4,5α-epoxy-3-methoxy-14β-hydroxy-6α-[N-isobutyl-trans-3-(3-furyl)acrylamido]morphinan, 17-methyl-4,5α-epoxy-3-methoxy-14β-hydroxy-6α-(N-isobutyl-4-trifluoromethylcinnamamido)morphinan, 17-methyl-4,5α-epoxy-3-methoxy-14β-hydroxy-6α-(N-isobutyl-3-phenylpropiolamido)morphinan, 17-phenethyl-4,5α-epoxy-3-methoxy-14β-hydroxy-6α-(N-isobutyl-3-trifluoromethylcinnamamido)morphinan, 17-phenethyl-4,5α-epoxy-3-methoxy-14β-hydroxy-6α-[N-isobutyl-trans-3-(3-furyl)acrylamido]morphinan, 17-phenethyl-4,5α-epoxy-3-methoxy-14β-hydroxy-6α-(N-isobutyl-4-trifluoromethylcinnamamido)morphinan, 17-phenethyl-4,5α-epoxy-3-methoxy-14β-hydroxy-6α-(N-isobutyl-3-phenylpropiolamido)morphinan, 17-cyclopropylmethyl-4,5α-epoxy-3-methoxy-14β-acetoxy-6α-(N-isobutyl-3-trifluoromethylcinnamamido)morphinan, 17-cyclopropylmethyl-4,5α-epoxy-3-methoxy-14β-acetoxy-6α-[N-isobutyl-trans-3-(3-furyl)acrylamido]morphinan, 17-cyclopropylmethyl-4,5α-epoxy-3-methoxy-14β-acetoxy-6α-(N-isobutyl-4-trifluoromethylcinnamamido)morphinan, 17-cyclopropylmethyl-4,5α-epoxy-3-methoxy-14β-acetoxy-6α-(N-isobutyl-3-phenylpropiolamido)morphinan, 17-allyl-4,5α-epoxy-3-methoxy-14β-acetoxy-6α-(N-isobutyl-3-trifluoromethylcinnamamido)morphinan, 17-allyl-4,5α-epoxy-3-methoxy-14β-acetoxy-6α-[N-isobutyl-trans-3-(3-furyl)acrylamido]morphinan, 17-allyl-4,5α-epoxy-3-methoxy-14β-acetoxy-6α-(N-isobutyl-4-trifluoromethylcinnamamido)morphinan, 17-allyl-4,5α-epoxy-3-methoxy-14β-acetoxy-6α-(N-isobutyl-3-phenylpropiolamido)morphinan, 17-methyl-4,5α-epoxy-3-methoxy-14β-acetoxy-6α-(N-isobutyl-3-trifluoromethylcinnamamido)morphinan, 17-methyl-4,5α-epoxy-3-methoxy-14β-acetoxy-6α-[N-isobutyl-trans-3-(3-furyl)acrylamido]morphinan, 17-methyl-4,5α-epoxy-3-methoxy-14β-acetoxy-6α-(N-isobutyl-4-trifluoromethyl-cinnamamido)morphinan, 17-methyl-4,5α-epoxy-3-methoxy-14β-acetoxy-6α-(N-isobutyl-3-phenylpropiolamido)morphinan, 17-phenethyl-4,5α-epoxy-3-methoxy-14β-acetoxy-6α-(N-isobutyl-3-trifluoromethylcinnamamido)morphinan, 17-phenethyl-4,5α-epoxy-3-methoxy-14β-acetoxy-6α-[N-isobutyl-trans-3-

(3-furyl)acrylamido]morphinan, 17-phenethyl-4,5α-epoxy-3-methoxy-14β-acetoxy-6α-(N-isobutyl-4-trifluoromethylcinnamamido)morphinan, 17-phenethyl-4,5α-epoxy-3-methoxy-14β-acetoxy-6α-(N-isobutyl-3-phenylpropiolamido)morphinan, 17-cyclopropylmethyl-4,5α-epoxy-3-acetoxy-14β-hydroxy-6α-(N-isobutyl-3-trifluoromethylcinnamamido)morphinan, 17-cyclopropylmethyl-4,5α-epoxy-3-acetoxy-14β-hydroxy-6α-[N-isobutyl-trans-3-(3-furyl)acrylamido]morphinan, 17-cyclopropylmethyl-4,5α-epoxy-3-acetoxy-14β-hydroxy-6α-(N-isobutyl-4-trifluoromethylcinnamamido)morphinan, 17-cyclopropylmethyl-4,5α-epoxy-3-acetoxy-14β-hydroxy-6α-(N-isobutyl-3-phenylpropiolamido)morphinan, 17-allyl-4,5α-epoxy-3-acetoxy-14β-hydroxy-6α-(N-isobutyl-3-trifluoromethylcinnamamido)morphinan, 17-allyl-4,5α-epoxy-3-acetoxy-14β-hydroxy-6α-[N-isobutyl-trans-3-(3-furyl)acrylamido]morphinan, 17-allyl-4,5α-epoxy-3-acetoxy-14β-hydroxy-6α-(N-isobutyl-4-trifluoromethylcinnamamido)morphinan, 17-allyl-4,5α-epoxy-3-acetoxy-14β-hydroxy-6α-(N-isobutyl-3-phenylpropiolamido)morphinan, 17-methyl-4,5α-epoxy-3-acetoxy-14β-hydroxy-6α-(N-isobutyl-3-trifluoromethylcinnamamido)morphinan, 17-methyl-4,5α-epoxy-3-acetoxy-14β-hydroxy-6α-[N-isobutyl-trans-3-(3-furyl)acrylamido]morphinan, 17-methyl-4,5α-epoxy-3-acetoxy-14β-hydroxy-6α-(N-isobutyl-4-trifluoromethylcinnamamido)morphinan, 17-methyl-4,5α-epoxy-3-acetoxy-14β-hydroxy-6α-(N-isobutyl-3-phenylpropiolamido)morphinan, 17-phenethyl-4,5α-epoxy-3-acetoxy-14β-hydroxy-6α-(N-isobutyl-3-trifluoromethylcinnamamido)morphinan, 17-phenethyl-4,5α-epoxy-3-acetoxy-14β-hydroxy-6α-[N-isobutyl-trans-3-(3-furyl)acrylamido]morphinan, 17-phenethyl-4,5α-epoxy-3-acetoxy-14β-hydroxy-6α-(N-isobutyl-4-trifluoromethylcinnamamido)morphinan, 17-phenethyl-4,5α-epoxy-3-acetoxy-14β-hydroxy-6α-(N-isobutyl-3-phenylpropiolamido)morphinan, 17-cyclopropylmethyl-4,5α-epoxy-3,14β-diacetoxy-6α-(N-isobutyl-3-trifluoromethylcinnamamido)morphinan, 17-cyclopropylmethyl-4,5α-epoxy-3,14β-diacetoxy-6α-[N-isobutyl-trans-3-(3-furyl)acrylamido]morphinan, 17-cyclopropylmethyl-4,5α-epoxy-3,14β-diacetoxy-6α-(N-isobutyl-4-trifluoromethylcinnamamido)morphinan, 17-cyclopropylmethyl-4,5α-epoxy-3,14β-diacetoxy-6α-(N-isobutyl-3-phenylpropiolamido)morphinan, 17-allyl-4,5α-epoxy-3,14β-diacetoxy-6α-(N-isobutyl-3-trifluoromethylcinnamamido)morphinan, 17-allyl-4,5α-epoxy-3,14β-diacetoxy-6α-[N-isobutyl-trans-3-(3-furyl)acrylamido]morphinan, 17-allyl-4,5α-epoxy-3,14β-diacetoxy-6α-(N-isobutyl-4-trifluoromethylcinnamamido)morphinan, 17-allyl-4,5α-epoxy-3,14β-diacetoxy-6α-(N-isobutyl-3-phenylpropiolamido)morphinan, 17-methyl-4,5α-epoxy-3,14β-diacetoxy-6α-(N-isobutyl-3-trifluoromethylcinnamamido)morphinan, 17-methyl-4,5α-epoxy-3,14β-diacetoxy-6α-[N-isobutyl-trans-3-(3-furyl)acrylamido]morphinan, 17-methyl-4,5α-epoxy-3,14β-diacetoxy-6α-(N-isobutyl-4-trifluoromethylcinnamamido)morphinan, 17-methyl-4,5α-epoxy-3,14β-diacetoxy-6α-(N-isobutyl-3-phenylpropiolamido)morphinan, 17-phenethyl-4,5α-epoxy-3,14β-diacetoxy-6α-(N-isobutyl-3-trifluoromethylcinnamamido)morphinan, 17-phenethyl-4,5α-epoxy-3,14β-diacetoxy-6α-[N-isobutyl-trans-3-(3-furyl)acrylamido]morphinan, 17-phenethyl-4,5α-epoxy-3,14β-diacetoxy-6α-(N-isobutyl-4-trifluoromethylcinnamamido)morphinan, 17-phenethyl-4,5α-epoxy-3,14β-diacetoxy-6α-(N-isobutyl-3-phenylpropiolamido)morphinan, 17-cyclopropylmethyl-4,5α-epoxy-3,14β-dihydroxy-6β-(N-methyl-3-trifluoromethylcinnamamido)morphinan, 17-cyclopropylmethyl-4,5α-epoxy-3,14β-dihydroxy-6β-[N-methyl-trans-3-(3-furyl)acrylamido]morphinan, 17-cyclopropylmethyl-4,5α-epoxy-3,14β-dihydroxy-6β-(N-methyl-4-trifluoromethylcinnamamido)morphinan, 17-cyclopropylmethyl-4,5α-epoxy-3,14β-dihydroxy-6β-(N-methyl-3-phenylpropiolamido)morphinan, 17-allyl-4,5α-epoxy-3,14β-dihydroxy-6β-(N-methyl-3-trifluoromethyl-cinnamamido)morphinan, 17-allyl-4,5α-epoxy-3,14β-dihydroxy-6β-[N-methyl-trans-3-(3-furyl)acrylamido]-morphinan, 17-allyl-4,5α-epoxy-3,14β-dihydroxy-6β-(N-methyl-4-trifluoromethylcinnamamido)morphinan, 17-allyl-4,5α-epoxy-3,14β-dihydroxy-6β-(N-methyl-3-phenylpropiolamido)morphinan, 17-methyl-4,5α-epoxy-3,14β-dihydroxy-6β-(N-methyl-3-trifluoromethylcinnamamido)morphinan, 17-methyl-4,5α-epoxy-3,14β-dihydroxy-6β-[N-methyl-trans-3-(3-furyl)acrylamido]morphinan, 17-methyl-4,5α-epoxy-3,14β-dihydroxy-6β-(N-methyl-4-trifluoromethyl-cinnamamido)morphinan, 17-methyl-4,5α-epoxy-3,14β-dihydroxy-6β-(N-methyl-3-phenylpropiolamido)-morphinan, 17-phenethyl-4,5α-epoxy-3,14β-dihydroxy-6β-(N-methyl-3-trifluoromethylcinnamamido)morphinan, 17-phenethyl-4,5α-epoxy-3,14β-dihydroxy-6β-[N-methyl-trans-3-(3-furyl)acrylamido]morphinan, 17-phenethyl-4,5α-epoxy-3,14β-dihydroxy-6β-(N-methyl-4-trifluoromethylcinnamamido)morphinan, 17-phenethyl-4,5α-epoxy-3,14β-dihydroxy-6β-(N-methyl-3-phenylpropiolamido)morphinan, 17-cyclopropylmethyl-4,5α-epoxy-3-hydroxy-14β-acetoxy-6β-(N-methyl-3-trifluoromethylcinnamamido)-morphinan, 17-cyclopropylmethyl-4,5α-epoxy-3-hydroxy-14β-acetoxy-6β-[N-methyl-trans-3-(3-furyl)acrylamido]morphinan, 17-cyclopropylmethyl-4,5α-epoxy-3-hydroxy-14β-acetoxy-6β-(N-methyl-4-trifluoromethylcinnamamido)morphinan, 17-cyclopropylmethyl-4,5α-epoxy-3-hydroxy-14β-acetoxy-6β-(N-methyl-3-phenylpropiolamido)morphinan, 17-allyl-4,5α-epoxy-3-hydroxy-14β-acetoxy-6β-(N-methyl-3-trifluoromethylcinnamamido)morphinan, 17-allyl-4,5α-epoxy-3-hydroxy-14β-acetoxy-6β-[N-methyl-trans-3-(3-furyl)acrylamido]morphinan, 17-allyl-4,5α-epoxy-3-hydroxy-14β-acetoxy-6β-(N-methyl-4-trifluoromethylcinnamamido)morphinan, 17-allyl-4,5α-epoxy-3-hydroxy-14β-acetoxy-6β-(N-methyl-3-phenylpropiolamido)morphinan, 17-methyl-4,5α-epoxy-3-hydroxy-14β-acetoxy-6β-(N-methyl-3-trifluoromethylcinnamamido)morphinan, 17-methyl-4,5α-epoxy-3-hydroxy-14β-acetoxy-6β-[N-methyl-trans-3-(3-furyl)acrylamido]morphinan, 17-methyl-4,5α-epoxy-3-hydroxy-14β-acetoxy-6β-(N-methyl-4-trifluoromethylcinnamamido)morphinan, 17-methyl-4,5α-epoxy-3-hydroxy-14β-acetoxy-6β-(N-methyl-3-phenylpropiolamido)morphinan, 17-phenethyl-4,5α-epoxy-3-hydroxy-14β-acetoxy-6β-(N-methyl-3-trifluoromethylcinnamamido)morphinan, 17-phenethyl-4,5α-epoxy-3-hydroxy-14β-acetoxy-6β-[N-methyl-trans-3-(3-furyl)acrylamido]morphinan, 17-phenethyl-4,5α-epoxy-3-hydroxy-14β-acetoxy-6β-(N-methyl-4-trifluoromethylcinnamamido)morphinan, 17-phenethyl-4,5α-epoxy-3-hydroxy-14β-acetoxy-6β-(N-methyl-3-phenylpropiolamido)morphinan, 17-cyclopropylmethyl-4,5α-epoxy-14β-hydroxy-6β-(N-methyl-3-trifluoromethylcinnamamido)morphinan, 17-cyclopropylmethyl-4,5α-epoxy-14β-hydroxy-6β-[N-methyl-trans-3-(3-furyl)acrylamido]morphinan, 17-cyclopropylmethyl-4,5α-epoxy-14β-hydroxy-6β-(N-methyl-4-trifluoromethylcinnamamido)morphinan, 17-cyclopropylmethyl-4,5α-epoxy-14β-hydroxy-6β-(N-methyl-3-phenylpropiolamido)morphinan, 17-allyl-4,5α-epoxy-14β-hydroxy-6β-(N-methyl-3-trifluoromethylcinnamamido)morphinan, 17-allyl-4,5α-epoxy-14β-hydroxy-6β-[N-methyl-trans-3-(3-furyl)acrylamido]morphinan, 17-allyl-4,5α-epoxy-14β-hydroxy-6β-(N-methyl-4-trifluoromethyl-cinnamamido)morphinan, 17-allyl-4,5α-epoxy-14β-hydroxy-6β-(N-methyl-3-phenylpropiolamido)morphinan, 17-methyl-4,5α-epoxy-14β-hydroxy-6β-(N-methyl-3-trifluoromethylcinnamamido)morphinan, 17-methyl-4,5α-epoxy-14β-hydroxy-6β-[N-methyl-trans-3-(3-furyl)acrylamido]morphinan, 17-methyl-4,5α-epoxy-14β-hydroxy-6β-(N-methyl-4-trifluoromethyl-cinnamamido)morphinan, 17-methyl-4,5α-epoxy-14β-hydroxy-6β-(N-methyl-3-phenylpropiolamido)morphinan, 17-phenethyl-4,5α-epoxy-14β-hydroxy-6β-(N-methyl-3-trifluoromethylcinnamamido)morphinan, 17-phenethyl-4,5α-epoxy-14β-hydroxy-6β-[N-methyl-trans-3-(3-furyl)acrylamido]morphinan, 17-phenethyl-4,5α-epoxy-14β-hydroxy-6β-(N-methyl-4-trifluoromethylcinnamamido)morphinan, 17-phenethyl-4,5α-epoxy-14β-hydroxy-6β-(N-methyl-3-phenylpropiolamido)morphinan, 17-cyclopropylmethyl-4,5α-epoxy-14β-acetoxy-6β-(N-methyl-3-trifluoromethylcinnamamido)morphinan, 17-cyclopropylmethyl-4,5α-epoxy-14β-acetoxy-6β-[N-methyl-trans-3-(3-furyl)acrylamido]morphinan, 17-cyclopropylmethyl-4,5α-epoxy-14β-acetoxy-6β-(N-methyl-4-trifluoromethylcinnamamido)morphinan, 17-cyclopropylmethyl-4,5α-epoxy-14β-acetoxy-6β-(N-methyl-3-phenylpropiolamido)morphinan, 17-allyl-4,5α-epoxy-14β-acetoxy-6β-(N-methyl-3-trifluoromethylcinnamamido)) morphinan, 17-allyl-4,5α-epoxy-14β-acetoxy-6β-[N-methyl-trans-3-(3-furyl)acrylamido]morphinan, 17-allyl-4,5α-epoxy-14β-acetoxy-6β-(N-methyl-4-trifluoromethylcinnamamido)morphinan, 17-allyl-4,5α-epoxy-14β-acetoxy-6β-(N-methyl-3-phenylpropiolamido)-morphinan, 17-methyl-4,5α-epoxy-14β-acetoxy-6β-(N-methyl-3-trifluoromethylcinnamamido)morphinan, 17-methyl-4,5α-epoxy-14β-acetoxy-6β-[N-methyl-trans-3-(3-furyl)acrylamido]morphinan, 17-methyl-4,5α-epoxy-14β-acetoxy-6β-(N-methyl-4-trifluoromethylcinnamamido)morphinan, 17-methyl-4,5α-epoxy-14β-acetoxy-6β-(N-methyl-3-phenylpropiolamido)morphinan, 17-phenethyl-4,5α-epoxy-14β-acetoxy-6β-(N-methyl-3-trifluoromethylcinnamamido)morphinan, 17-phenethyl-4,5α-epoxy-14β-acetoxy-6β-[N-methyl-trans-3-(3-furyl)acrylamido]-morphinan, 17-phenethyl-4,5α-epoxy-14β-acetoxy-6β-(N-methyl-4-trifluoromethylcinnamamido)morphinan, 17-phenethyl-4,5α-epoxy-14β-acetoxy-6β-(N-methyl-3-phenylpropiolamido)morphinan, 17-cyclopropylmethyl-4,5α-epoxy-3-methoxy-14β-hydroxy-6β-(N-methyl-3-trifluoromethylcinnamamido)-morphinan, 17-cyclopropylmethyl-4,5α-epoxy-3-methoxy-14β-hydroxy-6β-[N-methyl-trans-3-(3-furyl)acrylamido]-morphinan, 17-cyclopropylmethyl-4,5α-epoxy-3-methoxy-14β-hydroxy-6β-(N-methyl-4-trifluoromethylcinnamamido)morphinan, 17-cyclopropylmethyl-4,5α-epoxy-3-methoxy-14β-hydroxy-6β-(N-methyl-3-phenylpropiolamido)morphinan, 17-allyl-4,5α-epoxy-3-methoxy-14β-hydroxy-6β-(N-methyl-3-trifluoromethylcinnamamido)morphinan, 17-allyl-4,5α-epoxy-3-methoxy-14β-hydroxy-6β-[N-methyl-trans-3-(3-furyl)acrylamido]morphinan, 17-allyl-4,5α-epoxy-3-methoxy-14β-hydroxy-6β-(N-methyl-4-trifluoromethylcinnamamido)morphinan, 17-allyl-4,5α-epoxy-3-methoxy-14β-hydroxy-6β-(N-30 methyl-3-phenylpropiolamido)morphinan, 17-methyl-4,5α-epoxy-3-methoxy-14β-hydroxy-6β-(N-methyl-3-trifluoromethylcinnamamido)morphinan, 17-methyl-4,5α-epoxy-3-methoxy-14β-hydroxy-6β-[N-methyl-trans-3-(3-furyl)acrylamido]morphinan, 17-methyl-4,5α-epoxy-3-methoxy-14β-hydroxy-6β-(N-methyl-4-trifluoromethyl-cinnamamido)morphinan, 17-methyl-4,5α-epoxy-3-methoxy-14β-hydroxy-6β-(N-methyl-3-phenylpropiolamido)-morphinan, 17-phenethyl-4,5α-epoxy-3-methoxy-14β-hydroxy-6β-(N-methyl-3-trifluoromethylcinnamamido)-morphinan, 17-phenethyl-4,5α-epoxy-3-methoxy-14β-hydroxy-6β-[N-methyl-trans-3-(3-furyl)acrylamido]-morphinan, 17-phenethyl-4,5α-epoxy-3-methoxy-14β-hydroxy-6β-(N-methyl-4-trifluoromethylcinnamamido)morphinan, 17-phenethyl-4,5α-epoxy-3-methoxy-14β-hydroxy-6β-(N-methyl-3-phenylpropiolamido)morphinan, 17-cyclopropylmethyl-4,5α-epoxy-3-methoxy-14β-acetoxy-6β-(N-methyl-3-trifluoromethylcinnamamido)morphinan, 17-cyclopropylmethyl-4,5α-epoxy-3-methoxy-14β-acetoxy-6β-[N-methyl-trans-3-(3-furyl)acrylamido]morphinan, 17-cyclopropylmethyl-4,5α-epoxy-3-methoxy-14β-acetoxy-6β-(N-methyl-4-trifluoromethylcinnamamido)morphinan, 17-cyclopropylmethyl-4,5α-epoxy-3-methoxy-14β-acetoxy-6β-(N-methyl-3-phenylpropiolamido)morphinan, 17-allyl-4,5α-epoxy-3-methoxy-14β-acetoxy-6β-(N-methyl-3-trifluoromethylcinnamamido)morphinan, 17-allyl-4,5α-epoxy-3-methoxy-14β-acetoxy-6β-[N-methyl-trans-3-(3-furyl)acrylamido]morphinan, 17-allyl-4,5α-epoxy-3-methoxy-14β-acetoxy-6β-(N-methyl-4-trifluoromethylcinnamamido)morphinan, 17-allyl-4,5α-epoxy-3-methoxy-14β-acetoxy-6β-(N-methyl-3-phenylpropiolamido)morphinan, 17-methyl-4,5α-epoxy-3-methoxy-14β-acetoxy-6β-(N-methyl-3-trifluoromethyl-cinnamamido)morphinan, 17-methyl-4,5α-epoxy-3-methoxy-14β-acetoxy-6β-[N-methyl-trans-3-(3-furyl)acrylamido]-morphinan, 17-methyl-4,5α-epoxy-3-methoxy-14β-acetoxy-6β-(N-methyl-4-trifluoromethylcinnamamido)morphinan, 17-methyl-4,5α-epoxy-3-methoxy-14β-acetoxy-6β-(N-methyl-3-phenylpropiolamido)morphinan, 17-phenethyl-4,5α-epoxy-3-methoxy-14β-acetoxy-6β-(N-methyl-3-trifluoromethylcinnamamido)morphinan, 17-phenethyl-4,5α-epoxy-3-methoxy-14β-acetoxy-6β-[N-methyl-trans-3-(3-furyl)acrylamido]morphinan, 17-phenethyl-4,5α-epoxy-3-methoxy-14β-acetoxy-6β-(N-methyl-4-trifluoromethylcinnamamido)morphinan, 17-phenethyl-4,5α-epoxy-3-methoxy-14β-acetoxy-6β-(N-methyl-3-phenylpropiolamido)morphinan, 17-cyclopropylmethyl-4,5α-epoxy-3-acetoxy-14β-hydroxy-6β-(N-methyl-3-trifluoromethylcinnamamido)morphinan, 17-cyclopropylmethyl-4,5α-epoxy-3-acetoxy-14β-hydroxy-6β-[N-methyl-trans-3-(3-furyl)acrylamido]morphinan, 17-cyclopropylmethyl-4,5α-epoxy-3-acetoxy-14β-hydroxy-6β-(N-methyl-4-trifluoromethylcinnamamido)morphinan, 17-cyclopropylmethyl-4,5α-epoxy-3-acetoxy-14β-hydroxy-6β-(N-methyl-3-phenylpropiolamido)morphinan, 17-allyl-4,5α-epoxy-3-acetoxy-14β-hydroxy-6β-(N-methyl-3-trifluoromethylcinnamamido)morphinan, 17-allyl-4,5α-epoxy-3-acetoxy-14β-hydroxy-6β-[N-methyl-trans-3-(3-furyl)acrylamido]morphinan, 17-allyl-4,5α-epoxy-3-acetoxy-14β-hydroxy-6β-(N-methyl-4-trifluoromethylcinnamamido)morphinan, 17-allyl-4,5α-epoxy-3-acetoxy-14β-hydroxy-6β-(N-methyl-3-phenylpropiolamido)morphinan, 17-methyl-4,5α-epoxy-3- acetoxy-14β-hydroxy-6β-(N-methyl-3-trifluoromethylcinnamamido)morphinan, 17-methyl-4,5α-epoxy-3-acetoxy-14β-hydroxy-6β-[N-methyl-trans-3-(3-furyl)acrylamido]morphinan, 17-methyl-4,5α-epoxy-3-acetoxy-14β-hydroxy-6β-(N-methyl-4-trifluoromethylcinnamamido)morphinan, 17-methyl-4,5α-epoxy-3-acetoxy-14β-hydroxy-6β-(N-methyl-3-phenylpropiolamido)morphinan, 17-phenethyl-4,5α-epoxy-3-acetoxy-14β-hydroxy-6β-(N-methyl-3-trifluoromethylcinnamamido)morphinan, 17-phenethyl-4,5α-epoxy-3-acetoxy-14β-hydroxy-6β-[N-methyl-trans-3-(3-furyl)acrylamido]morphinan, 17-phenethyl-4,5α-epoxy-3-acetoxy-14β-hydroxy-6β-(N-methyl-4-trifluoromethylcinnamamido)morphinan, 17-phenethyl-4,5α-epoxy-3-acetoxy-14β-hydroxy-6β-(N-methyl-3-phenylpropiolamido)morphinan, 17-cyclopropylmethyl-4,5α-epoxy-3,14β-diacetoxy-6β-(N-methyl-3-trifluoromethylcinnamamido)morphinan, 17-cyclopropylmethyl-4,5α-epoxy-3,14β-diacetoxy-6β-[N-methyl-trans-3-(3-furyl)acrylamido]morphinan, 17-cyclopropylmethyl-4,5α-epoxy-3,14β-diacetoxy-6β-(N-methyl-4-trifluoromethylcinnamamido)morphinan, 17-cyclopropylmethyl-4,5α-epoxy-3,14β-diacetoxy-6β-(N-methyl-3-phenylpropiolamido)morphinan, 17-allyl-4,5α-epoxy-3,14β-diacetoxy-6β-(N-methyl-3-trifluoromethylcinnamamido)morphinan, 17-allyl-4,5α-epoxy-3,14β-diacetoxy-6β-[N-methyl-trans-3-(3-furyl)acrylamido]morphinan, 17-allyl-4,5α-epoxy-3,14β-diacetoxy-6β-(N-methyl-4-trifluoromethylcinnamamido)morphinan, 17-allyl-4,5α-epoxy-3,14β-diacetoxy-6β-(N-methyl-3-phenylpropiolamido)morphinan, 17-methyl-4,5α-epoxy-3,14β-diacetoxy-6β-(N-methyl-3-trifluoromethylcinnamamido)morphinan, 17-methyl-4,5α-epoxy-3,14β-diacetoxy-6β-[N-methyl-trans-3-(3-furyl)acrylamido]morphinan, 17-methyl-4,5α-epoxy-3,14β-diacetoxy-6β-(N-methyl-4-trifluoromethylcinnamamido)morphinan, 17-methyl-4,5α-epoxy-3,14β-diacetoxy-6β-(N-methyl-3-phenylpropiolamido)morphinan, 17-phenethyl-4,5α-epoxy-3,14β-diacetoxy-6β-(N-methyl-3-trifluoromethylcinnamamido)morphinan, 17-phenethyl-4,5α-epoxy-3,14β-diacetoxy-6β-[N-methyl-trans-3-(3-furyl)acrylamido]morphinan, 17-phenethyl-4,5α-epoxy-3,14β-diacetoxy-6β-(N-methyl-4-trifluoromethylcinnamamido)morphinan, 17-phenethyl-4,5α-epoxy-3,14β-diacetoxy-6β-(N-methyl-3-phenylpropiolamido)morphinan, 17-cyclopropylmethyl-4,5α-epoxy-3,14β-dihydroxy-6β-(N-isobutyl-3-trifluoromethylcinnamamido)-morphinan, 17-cyclopropylmethyl-4,5α-epoxy-3,14β-dihydroxy-6β-[N-isobutyl-trans-3-(3-furyl)acrylamido]-morphinan, 17-cyclopropylmethyl-4,5α-epoxy-3,14β-dihydroxy-6β-(N-isobutyl-4-trifluoromethylcinnamamido)morphinan, 17-cyclopropylmethyl-4,5α-epoxy-3,14β-dihydroxy-6β-(N-isobutyl-3-phenylpropiolamido)morphinan, 17-allyl-4,5α-epoxy-3,14β-dihydroxy-6β-(N-isobutyl-3-trifluoromethylcinnamamido)morphinan, 17-allyl-4,5α-epoxy-3,14β-dihydroxy-6β-[N-isobutyl-trans-3-(3-furyl)acrylamido]morphinan, 17-allyl-4,5α-epoxy-3,14β-dihydroxy-6β-(N-isobutyl-4-trifluoromethylcinnamamido)morphinan, 17-allyl-4,5α-epoxy-3,14β-dihydroxy-6β-(N-isobutyl-3-phenylpropiolamido)morphinan, 17-methyl-4,5α-epoxy-3,14β-dihydroxy-6β-(N-isobutyl-3-trifluoromethylcinnamamido)morphinan, 17-methyl-4,5α-epoxy-3,14β-dihydroxy-6β-[N-isobutyl-trans-3-(3-furyl)acrylamido]morphinan, 17-methyl-4,5α-epoxy-3,14β-dihydroxy-6β-(N-isobutyl-4-trifluoromethylcinnamamido)morphinan, 17-methyl-4,5α-epoxy-3,14β-dihydroxy-6β-(N-isobutyl-3-phenylpropiolamido)morphinan, 17-phenethyl-4,5α-epoxy-3,14β-dihydroxy-6β-(N-isobutyl-3-trifluoromethylcinnamamido)morphinan, 17-phenethyl-4,5α-epoxy-3,14β-dihydroxy-6β-[N-isobutyl-trans-3-(3-furyl)acrylamido]morphinan, 17-phenethyl-4,5α-epoxy-3,14β-dihydroxy-6β-(N-isobutyl-4-trifluoromethylcinnamamido)morphinan, 17-phenethyl-4,5α-epoxy-3,14β-dihydroxy-6β-(N-isobutyl-3-phenylpropiolamido)morphinan, 17-cyclopropylmethyl-4,5α-epoxy-3-hydroxy-14β-acetoxy-6β-(N-isobutyl-3-trifluoromethylcinnamamido)-morphinan, 17-cyclopropylmethyl-4,5α-epoxy-3-hydroxy-14β-acetoxy-6β-[N-isobutyl-trans-3-(3-furyl)acrylamido]morphinan, 17-cyclopropylmethyl-4,5α-epoxy-3-hydroxy-14β-acetoxy-6β-(N-isobutyl-4-trifluoromethylcinnamamido)morphinan, 17-cyclopropylmethyl-4,5α-epoxy-3-hydroxy-14β-acetoxy-6β-(N-isobutyl-3-phenylpropiolamido)morphinan, 17-allyl-4,5α-epoxy-3-hydroxy-14β-acetoxy-6β-(N-isobutyl-3-trifluoromethylcinnamamido)morphinan, 17-allyl-4,5α-epoxy-3-hydroxy-14β-acetoxy-6β-[N-isobutyl-trans-3-(3 furyl)acrylamido]morphinan, 17-allyl-4,5α-epoxy-3-hydroxy-14β-acetoxy-6β-(N-isobutyl-4-trifluoromethyl-cinnamamido)morphinan, 17-allyl-4,5α-epoxy-3-hydroxy-14β-acetoxy-6β-(N-isobutyl-3-phenylpropiolamido)morphinan, 17-methyl-4,5α-epoxy-3-hydroxy-14β-acetoxy-6β-(N-isobutyl-3-trifluoromethylcinnamamido)morphinan, 17-methyl-4,5α-epoxy-3-hydroxy-14β-acetoxy-6β-[N-isobutyl-trans-3-(3-furyl)acrylamido]morphinan, 17-methyl-4,5α-epoxy-3-hydroxy-14β-acetoxy-6β-(N-isobutyl-4-trifluoromethyl-cinnamamido)morphinan, 17-methyl-4,5α-epoxy-3-hydroxy-14β-acetoxy-6β-(N-isobutyl-3-phenylpropiolamido)morphinan, 17-phenethyl-4,5α-epoxy-3-hydroxy-14β-acetoxy-6β-(N-isobutyl-3-trifluoromethylcinnamamido)morphinan, 17-phenethyl-4,5α-epoxy-3-hydroxy-14β-acetoxy-6β-[N-isobutyl-trans-3-(3-furyl)acrylamido]morphinan, 17-phenethyl-4,5α-epoxy-3-hydroxy-14β-acetoxy-6β-(N-isobutyl-4-trifluoromethylcinnamamido)morphinan, 17-phenethyl-4,5α-epoxy-3-hydroxy-14β-acetoxy-6β-(N-isobutyl-3-phenylpropiolamido)morphinan, 17-cyclopropylmethyl-4,5α-epoxy-14β-hydroxy-6β-(N-isobutyl-3-trifluoromethylcinnamamido)morphinan, 17-cyclopropylmethyl-4,5α-epoxy-14β-hydroxy-6β-[N-isobutyl-trans-3-(3-furyl)acrylamido]morphinan, 17-cyclopropylmethyl-4,5α-epoxy-14β-hydroxy-6β-(N-isobutyl-4-trifluoromethylcinnamamido)morphinan, 17-cyclopropylmethyl-4,5α-epoxy-14β-hydroxy-6β-(N-isobutyl-3-phenylpropiolamido)morphinan, 17-allyl-4,5α-epoxy-14β-hydroxy-6β-(N-isobutyl-3-trifluoromethylcinnamamido)morphinan, 17-allyl-4,5α-epoxy-14β-hydroxy-6β-[N-isobutyl-trans-3-(3-furyl)acrylamido]morphinan, 17-allyl-4,5α-epoxy-14β-hydroxy-6β-(N-isobutyl-4-trifluoromethyl-cinnamamido)morphinan, 17-allyl-4,5α-epoxy-14β-hydroxy-6β-(N-isobutyl-3-phenylpropiolamido)-morphinan, 17-methyl-4,5α-epoxy-14β-hydroxy-6β-(N-isobutyl- 3-trifluoromethylcinnamamido)morphinan, 17-methyl-4,5α-epoxy-14β-hydroxy-6β-[N-isobutyl-trans-3-(3-furyl)acrylamido]morphinan, 17-methyl-4,5α-epoxy-14β-hydroxy-6β-(N-isobutyl-4-trifluoromethyl-cinnamamido)morphinan, 17-methyl-4,5α-epoxy-14β-hydroxy-6β-(N-isobutyl-3-phenylpropiolamido)-morphinan, 17-phenethyl-4,5α-epoxy-14β-hydroxy-6β-(N-isobutyl-3-trifluoromethylcinnamamido)morphinan, 17-phenethyl-4,5α-epoxy-14β-hydroxy-6β-[N-isobutyl-trans-3-(3-furyl)acrylainido]morphinan,
17-phenethyl-4,5α-epoxy-14β-hydroxy-6β-(N-isobutyl-4-trifluoromethylcinnamamido)morphinan, 17-phenethyl-4,5α-epoxy-14β-hydroxy-6β-(N-isobutyl-3-phenylpropiolamido)morphinan, 17-cyclopropylmethyl-4,5α-epoxy-14β-acetoxy-6β-(N-isobutyl-3-trifluoromethylcinnamamido)morphinan, 17-cyclopropylmethyl-4,5α-epoxy-14β-acetoxy-6β-[N-isobutyl-trans-3-(3-furyl)acrylamido]morphinan, 17-cyclopropylmethyl-4,5α-epoxy-14β-acetoxy-6β-(N-isobutyl-4-trifluoromethylcinnamamido)morphinan, 17-cyclopropylmethyl-4,5α-epoxy-14β-acetoxy-6β-(N-isobutyl-3-phenylpropiolamido)morphinan, 17-allyl-4,5α-epoxy-14β-acetoxy-6β-(N-isobutyl-3-trifluoromethylcinnamamido)morphinan,
17-allyl-4,5α-epoxy-14β-acetoxy-6β-[N-isobutyl-trans-3-(3-furyl)acrylamido]morphinan, 17-allyl-4,5α-epoxy-14β-acetoxy-6β-(N-isobutyl-4-trifluoromethylcinnamamido)morphinan, 17-allyl-4,5α-epoxy-14β-acetoxy-6β-(N-isobutyl-3-phenylpropiolamido)-morphinan, 17-methyl-4,5α-epoxy-14β-acetoxy-6β-(N-isobutyl-3-trifluoromethylcinnamamido)morphinan, 17-methyl-4,5α-epoxy-14β-acetoxy-6β-[N-isobutyl-trans-3-(3-furyl)acrylamido]morphinan, 17-methyl-4,5α-epoxy-14β-acetoxy-6β-(N-isobutyl-4-trifluoromethylcinnamamido)morphinan, 17-methyl-4,5α-epoxy-14β-acetoxy-6β-(N-isobutyl-3-phenylpropiolamido)morphinan, 17-phenethyl-4,5α- epoxy- 14β-acetoxy-6β-(N-isobutyl-3-trifluoromethylcinnamamido)morphinan,
17-phenethyl-4,5α-epoxy-14β-acetoxy-6β- [N-isobutyl-trans-3-(3-furyl)acrylamido]morphinan, 17-phenethyl-4,5α-epoxy-14β-acetoxy-6β-(N-isobutyl-4-trifluoromethylcinnamamido)morphinan, 17-phenethyl-4,5α-epoxy-14β-acetoxy-6β-(N-isobutyl-3-phenylpropiolamido)morphinan, 17-cyclopropylmethyl-4,5α-epoxy-3-methoxy-14β-hydroxy-6β-(N-isobutyl-3-trifluoromethylcinnamamido)morphinan, 17-cyclopropylmethyl-4,5α-epoxy-3-methoxy-14β-hydroxy-6β-[N-isobutyl-trans-3-(3-furyl)acrylamido]morphinan, 17-cyclopropylmethyl-4,5α-epoxy-3-methoxy-14β-hydroxy-6β-(N-isobutyl-4-trifluoromethylcinnamamido)morphinan,
17-cyclopropylmethyl-4,5α-epoxy-3-methoxy-14β-hydroxy-6β-(N-isobutyl-3-phenylpropiolamido)-morphinan, 17-allyl-4,5α-epoxy-3-methoxy-14β-hydroxy-6β-(N-isobutyl-3-trifluoromethylcinnamamido)-morphinan, 17-allyl-4,5α-epoxy-3-methoxy-14β-hydroxy-6β-[N-isobutyl-trans-3-(3-furyl)acrylamido]morphinan, 17-allyl-4,5α-epoxy-3-methoxy-14β-hydroxy-6β-(N-isobutyl-4-trifluoromethylcinnamamido)morphinan, 17-allyl-4,5α-epoxy-3-methoxy-14β-hydroxy-6β-(N-isobutyl-3-phenylpropiolamido)morphinan, 17-methyl-4,5α-epoxy-3-methoxy-14β-hydroxy-6β-(N-isobutyl-3-trifluoromethylcinnamamido)morphinan, 17-methyl-4,5α-epoxy-3-methoxy-14β-hydroxy-6β-[N-isobutyl-trans-3-(3-furyl) acrylamido] morphinan,
17-methyl-4,5α-epoxy-3-methoxy-14β-hydroxy-6β-(N-isobutyl-4-trifluoromethylcinnamamido)morphinan, 17-methyl-4,5α-epoxy-3-methoxy-14β-hydroxy-6β-(N-isobutyl-3-phenylpropiolamido)morphinan, 17-phenethyl-4,5α-epoxy-3-methoxy-14β-hydroxy-6β-(N-isobutyl-3-trifluoromethylcinnamamido)morphinan, 17-phenethyl-4,5α-epoxy-3-methoxy-14β-hydroxy-6β-[N-isobutyl-trans-3-(3-furyl)acrylamido]morphinan, 17-phenethyl-4,5α-epoxy-3-methoxy-14β-hydroxy-6β-(N-isobutyl-4 -trifluoromethylcinnamainido)morphinan, 17-phenethyl-4,5α-epoxy-3-methoxy-14β-hydroxy-6β-(N-isobutyl-3-phenylpropiolamido)morphinan,
17-cyclopropylmethyl-4,5α-epoxy-3-methoxy-14β-acetoxy-6β-(N-isobutyl-3-trifluoromethylcinnamamido)-morphinan, 17-cyclopropylmethyl-4,5α-epoxy-3-methoxy-14β-acetoxy-6F-[N-isobutyl-trans-3-(3-furyl)acrylamido]morphinan, 17-cyclopropylmethyl-4,5α-epoxy-3-methoxy-14β-acetoxy-6β-(N-isobutyl-4-trifluoromethylcinnamamido)morphinan, 17-cyclopropylmethyl-4,5α-epoxy-3-methoxy-14β-acetoxy-6β-(N-isobutyl-3-phenylpropiolamido)morphinan, 17-allyl-4,5α-epoxy-3-methoxy-14β-acetoxy-6β-(N-isobutyl-3-trifluoromethylcinnamamido)morphinan, 17-allyl-4,5α-epoxy-3-methoxy-14β-acetoxy-6β-[N-isobutyl-trans-3-(3-furyl)acrylamido]morphinan, 17-allyl-4,5α-epoxy-3-methoxy-14β-acetoxy-6β-(N-isobutyl-4-trifluoromethyl-cinnamamido)morphinan, 17-allyl-4,5α-epoxy-3-methoxy-14β-acetoxy-6β-(N-isobutyl-3-phenylpropiolamido)-morphinan,
17-methyl-4,5α-epoxy-3-methoxy-14β-acetoxy-6β-(N-isobutyl-3-trifluoromethylcinnamamido)morphinan, 17-methyl-4,5α-epoxy-3-methoxy-14β-acetoxy-6β-[N-isobutyl-trans-3-(3-furyl)acrylamido]morphinan, 17-methyl-4,5α-epoxy-3-methoxy-14β-acetoxy-6β-(N-isobutyl-4-trifluoromethylcinnamamido)morphinan, 17-methyl-4,5α-epoxy-3-methoxy-14β-acetoxy-6β-(N-isobutyl-3-phenylpropiolamido)morphinan, 17-phenethyl-4,5α-epoxy-3-methoxy-14β-acetoxy-6β-(N-isobutyl-3-trifluoromethylcinnamamido)morphinan, 17-phenethyl-4,5α-epoxy-3-methoxy-14β-acetoxy-6β-[N-isobutyl-trans-3-(3-furyl)acrylamido]morphinan, 17-phenethyl-4,5α-epoxy-3-methoxy-14β-acetoxy-6β-(N-isobutyl-4-trifluoromethylcinnamamido)morphinan, 17-phenethyl-4,5α-epoxy-3-methoxy-14β-acetoxy-6β-(N-isobutyl-3-phenylpropiolamido)morphinan,
17-cyclopropylmethyl-4,5α-epoxy-3-acetoxy-14β-hydroxy-6β-(N-isobutyl-3-trifluoromethylcinnamamido)-morphinan, 17-cyclopropylmethyl-4,5α-epoxy-3-acetoxy-14β-hydroxy-6β-[N-isobutyl-trans-3-(3-furyl)acrylamido]morphinan, 17-cyclopropylmethyl-4,5α-epoxy-3-acetoxy-14β-hydroxy-6β-(N-isobutyl-4-trifluoromethylcinnamamido)morphinan, 17-cyclopropylmethyl-4,5α-epoxy-3-acetoxy-14β-hydroxy-6β-(N-isobutyl-3-phenylpropiolamido)morphinan, 17-allyl-4,5α-epoxy-3-acetoxy-14β-hydroxy-6β-(N-isobutyl-3-trifluoromethylcinnamamido)morphinan, 17-allyl-4,5α-epoxy-3-acetoxy-14β-hydroxy-6β-[N-isobutyl-trans-3-(3-furyl)acrylamido]morphinan, 17-allyl-4,5α-epoxy-3-acetoxy-14β-hydroxy-6β-(N-isobutyl-4-trifluoromethylcinnamamido)morphinan, 17-allyl-4,5α-epoxy-3-acetoxy-14β-hydroxy-6β-(N-isobutyl-3-phenylpropiolamido)morphinan,
17-methyl-4,5α-epoxy-3-acetoxy-14β-hydroxy-6β-(N-isobutyl-3-trifluoromethylcinnamamido)morphinan, 17-methyl-4,5α-epoxy-3-acetoxy-14β-hydroxy-6β-[N-isobutyl-trans-3-(3-furyl)acrylamido]morphinan, 17-methyl-4,5α-epoxy-3-acetoxy-14β-hydroxy-6β-(N-isobutyl-4-trifluoromethylcinnamamido)morphinan, 17-methyl-4,5α-epoxy-3-acetoxy-14β-hydroxy-6β-(N-isobutyl-3-phenylpropiolamido)morphinan, 17-phenethyl-4,5α-epoxy-3-acetoxy-14β-hydroxy-6β-(N-isobutyl-3-trifluoromethylcinnamamido)morphinan, 17-phenethyl-4,5α-epoxy-3-acetoxy-14β-hydroxy-6β-[N-isobutyl-trans-3-(3-furyl)acrylamido]morphinan, 17-phenethyl-4,5α-epoxy-3-acetoxy-14β-hydroxy-6β-(N-isobutyl-4-trifluoromethylcinnamaido)morphinan, 17-phenethyl-4,5α-epoxy-3-acetoxy-14β-hydroxy-6β-(N-isobutyl-3-phenylpropiolamido)morphinan, 17-cyclopropylmethyl-4,5α-epoxy-3,14β-diacetoxy-6β-(N-isobutyl-3-trifluoromethylcinnamamido)-morphinan, 17-cyclopropylmethyl-4,5α-epoxy-3,14β-diacetoxy-6β-[N-isobutyl-trans-3-(3-furyl)acrylamido]morphinan, 17-cyclopropylmethyl-4,5α-epoxy- 3,14β-diacetoxy-6β-(N-isobutyl-4-trifluoromethylcinnamamido)morphinan, 17-cyclopropylmethyl-4,5α-epoxy-3,14β-diacetoxy-6β-(N-isobutyl-3-phenylpropiolamido)morphinan, 17-allyl-4,5α-epoxy-3,14β-diacetoxy-6β-(N-isobutyl-3-trifluoromethylcinnamamido)morphinan, 17-allyl-4,5α-epoxy-3,14β-diacetoxy-6β-[N-isobutyl-trans-3-(3-furyl)acrylamido]morphinan, 17-allyl-4,5α-epoxy-3,14β-diacetoxy-6β-(N-isobutyl-4-trifluoromethyl-cinnamamido)morphinan, 17-allyl-4,5α-epoxy-3,14β-diacetoxy-6β-(N-isobutyl-3-phenylpropiolamido)morphinan, 17-methyl-4,5α-epoxy-3,14β-diacetoxy-6β-(N-isobutyl-3-trifluoromethylcinnamamido)morphinan, 17-methyl-4,5α-epoxy-3,14β-diacetoxy-6β-[N-isobutyl-trans-3-(3-furyl)acrylamido]morphinan, 17-methyl-4,5α-epoxy-3,14β-diacetoxy-6β-(N-isobutyl-4-trifluoromethylcinnamamido)morphinan, 17-methyl-4,5α-epoxy-3,14β-diacetoxy-6β-(N-isobutyl-3-phenylpropiolamido)morphinan, 17-phenethyl-4,5α-epoxy-3,14β-diacetoxy-6β-(N-isobutyl-3-trifluoromethylcinnamamido)morphinan, 17-phenethyl-4,5α-epoxy-3,14β-diacetoxy-6β-[N-isobutyl-trans-3-(3-furyl)acrylamido]morphinan, 17-phenethyl-4,5α-epoxy-3,14β-diacetoxy-6β-(N-isobutyl-4-trifluoromethylcinnamamido)morphinan, 17-phenethyl-4,5α-epoxy-3,14β-diacetoxy-6β-(N-isobutyl-3-phenylpropiolamido)morphinan, 17-cyclopropylmethyl-4,5α-epoxy-3,14β-dihydroxy-6α-(N-methyl-3-cyclohexylpropionamido)morphinan, 17-allyl-4,5α-epoxy-3,14β-dihydroxy-6α-(N-methyl-3-cyclohexylpropionamido)morphinan, 17-cyclopropylmethyl-4,5α-epoxy-3,14β-dihydroxy-6β-(N-methyl-3-cyclohexylpropionamido)morphinan, 17-allyl-4,5α-epoxy-3,14β-dihydroxy-6β-(N-methyl-3-cyclohexylpropionamido)morphinan, 17-cyclopropylmethyl-4,5α-epoxy-3,14β-dihydroxy-6α-(N-methylbutyloxycarbamido)morphinan, 17-allyl-4,5α-epoxy-3,14β-dihydroxy-6α-(N-methylbutyloxycarbamido)morphinan, 17-cyclopropylmethyl-4,5α-epoxy-3,14β-dihydroxy-6β-(N-methylbutyloxycarbamido)morphinan, 17-allyl-4,5α-epoxy-3,14β-dihydroxy-6β-(N-methylbutyloxy-carbamido)morphinan, 17-cyclopropylmethyl-4,5α-epoxy-3,14β-dihydroxy-6α-(N-methyl-3-isothiocyanatophenylacetamido)-morphinan, 17-allyl-4,5α-epoxy-3,14β-dihydroxy-6α-(N-methyl-3-isothiocyanatophenylacetamido)morphinan, 17-cyclopropylmethyl-4,5α-epoxy-3,14β-dihydroxy-6β-(N-methyl-3-isothiocyanatophenylacetamido)morphinan, 17-allyl-4,5α-epoxy-3,14β-dihydroxy-6β-(N-methyl-3-isothiocyanatophenylacetamido)morphinan, 17-cyclopropylmethyl-4,5α-epoxy-3,14β-dihydroxy-6α-(N-methyl-2-hexenamido)morphinan, 17-allyl-4,5α-epoxy-3,14β-dihydroxy-6α-(N-methyl-2-hexenamido)-morphinan, 17-cyclopropylmethyl-4,5α-epoxy-3,14β-dihydroxy-6β-(N-methyl-2-hexenamido)morphinan, 17-allyl-4,5α-epoxy-3,14β-dihydroxy-6β-(N-methyl-2-hexenamido)morphinan, 17-cyclopropylmethyl-4,5α-epoxy-3,14β-dihydroxy-6α-(N-methyl-3-fluorocinnamamido)morphinan, 17-allyl-4,5α-epoxy-3,14β-dihydroxy-6α-(N-methyl-3-fluorocinnamamido)morphinan, 17-cyclopropylmethyl-4,5α-epoxy-3,14β-dihydroxy-6β-(N-methyl-3-fluorocinnamamido)morphinan, 17-allyl-4,5α-epoxy-3,14β-dihydroxy-6β-(N-methyl-3-fluorocinnamamido)-morphinan, 17-cyclopropylmethyl-4,5α-epoxy-3,14β-dihydroxy-6α-(N-methyl-3-methoxycinnamamido)morphinan, 17-allyl-4,5α-epoxy-3,14β-dihydroxy-6α-(N-methyl-3-methoxycinnamamido)morphinan, 17-cyclopropylmethyl-4,5α-epoxy-3,14β-dihydroxy-6β-(N-methyl-3-methoxycinnamamido)morphinan, 17-allyl-4,5α-epoxy-3,14β-dihydroxy-6β-(N-methyl-3-methoxycinnamamido)-morphinan, 17-cyclopropylmethyl-4,5α-epoxy-3,14β-dihydroxy-6α-(N-methyl-2-cyclopentylpropionamido)morphinan, 17-allyl-4,5α-epoxy-3,14β-dihydroxy-6α-(N-methyl-2-cyclopentylpropionamido)morphinan, 17-cyclopropylmethyl-4,5α-epoxy-3,14β-dihydroxy-6β-(N-methyl-2-cyclopentylpropionamido)morphinan, 17-allyl-4,5α-epoxy-3,14β-dihydroxy-6β-(N- methyl-2-cyclopentylpropionamido)morphinan, 17-cyclopropylmethyl-4,5α-epoxy-3,14β-dihydroxy-6α-(N-methyl-2-naphthamido)morphinan, 17-allyl-4,5α-epoxy-3,14β-dihydroxy-6α-(N-methyl-2-naphthamido)-morphinan, 17-cyclopropylmethyl-4,5α-epoxy-3,14β-dihydroxy-6β-(N-methyl-2-naphthamido)morphinan, 17-allyl-4,5α-epoxy-3,14β-dihydroxy-6β-(N-methyl-2-naphthamido)morphinan, 17-cyclopropylmethyl-4,5α-epoxy-3,14β-dihydroxy-6α-(N-methyl-3-nitrocinnamamido)morphinan, 17-allyl-4,5α-epoxy-3,14β-dihydroxy-6α-(N-methyl-3-nitrocinnamamido)morphinan, 17-cyclopropylmethyl-4,5α-epoxy-3,14β-dihydroxy-6β-(N-methyl-3-nitrocinnamamido)morphinan, 17-allyl-4,5α-epoxy-3,14β-dihydroxy-6β-(N-methyl-3-nitrocinnamamido)morphinan, 17-cyclopropylmethyl-4,5α-epoxy-3,14β-dihydroxy-6α-(N-methyl-2-methoxyethoxycarbamido)morphinan, 17-allyl-4,5α-epoxy-3,14β-dihydroxy-6α-(N-methyl-2-methoxyethoxycarbamido)morphinan, 17-cyclopropylmethyl-4,5α-epoxy-3,14β-dihydroxy-6β-(N-methyl-2-methoxyethoxycarbamido)morphinan, 17-allyl-4,5α-epoxy-3,14β-dihydroxy-6β-(N-methyl-2-methoxyethoxycarbamido)morphinan, 17-cyclopropylmethyl-4,5α-epoxy-3,14β-dihydroxy-6α-(N-methyl-trans-3-cyclohexylacrylamido)morphinan, 17-allyl-4,5α-epoxy-3,14β-dihydroxy-6α-(N-methyl-trans-3-cyclohexylacrylamido)morphinan, 17-cyclopropylmethyl-4,5α-epoxy-3,14β-dihydroxy-6β-(N-methyl-trans-3-cyclohexylacrylamido)morphinan, 17-allyl-4,5α-epoxy- 3,14β-dihydroxy-6β-(N-methyl-trans-3-cyclohexylacrylamido)morphinan, 17-cyclopropylmethyl-4,5α-epoxy-3,14β-dihydroxy-6α-(N-methylbenzoylacetamido)morphinan, 17-allyl-4,5α-epoxy-3,14β-dihydroxy-6α-(N-methylbenzoylacetamido)-morphinan, 17-cyclopropylmethyl-4,5α-epoxy-3,14β-dihydroxy-6β-(N-methylbenzoylacetamido)morphinan, 17-allyl-4,5α-epoxy-3,14β-dihydroxy-6β-(N-methylbenzoylacetamido)morphinan, 17-cyclopropylmethyl-4,5α-epoxy-3,14β-dihydroxy-6α-[N-methyl-trans-3-(2-furyl)acrylamido]morphinan, 17-allyl-4,5α-epoxy-3,14β-dihydroxy-6α-[N-methyl-trans-3-(2-furyl)acrylamido]morphinan, 17-cyclopropylmethyl-4,5α-epoxy-3,14β-dihydroxy-6β-[N-methyl-trans-3-(2-furyl)acrylamido]morphinan, 17-allyl-4,5α-epoxy-3,14β-dihydroxy-6β-[N-methyl-trans-3-(2-furyl)acrylamido]morphinan, 17-cyclopropylmethyl-4,5α-epoxy-3,14β-dihydroxy-6α-(N-methyl-2-trifluoromethylcinnamamido)morphinan, 17-allyl-4,5α-epoxy-3,14β-dihydroxy-6α-(N-methyl-2-trifluoromethylcinnamamido)morphinan, 17-cyclopropylmethyl-4,5α-epoxy-3,14β-dihydroxy-6β-(N-methyl-2-trifluoromethylcinnamamido)morphinan, 17-allyl-4, 5α-epoxy-3,14β-dihydroxy-6β-(N-methyl-2-trifluoromethylcinnamamido)morphinan,
17-cyclopropylmethyl-4,5α-epoxy-3,14β-dihydroxy-6α-(N-methyl-3-isothiocyanatocinnamamido)morphinan,
17-allyl-4,5α-epoxy-3,14β-dihydroxy-6α-(N-methyl-3-isothiocyanatocinnamamido)morphinan,
17-cyclopropylmethyl-4,5α-epoxy-3,14β-dihydroxy-6β-(N-methyl-3-isothiocyanatocinnamamido)morphinan,
17-allyl-4,5α-epoxy-3,14β-dihydroxy-6β-(N-methyl-3-isothiocyanatocinnamamido)morphinan,
17-cyclopropylmethyl-4,5α-epoxy-3,14β-dihydroxy-6α-(N-methyl-3-methylcinnamamido)morphinan, 17-cyclopropylmethyl-4,5α-epoxy-3,14β-dihydroxy-6α-[N-methyl-3-(4-trifluoromethylphenyl)propiolamido]morphinan, 17-allyl-4,5α-epoxy-3,14β-dihydroxy-6α-(N-methyl-3-methylcinnamamido)morphinan, 17-allyl-4,5α-epoxy-3,14β-dihydroxy-6α-[N-methyl-3-(4-trifluoromethylphenyl)propiolamido]morphinan, 17-methyl-4,5α-epoxy-3,14β-dihydroxy-6α-(N-methyl-3-methylcinnamamido)morphinan, 17-methyl-4,5α-epoxy-3,14β-dihydroxy-6α-[N-methyl-3-(4-trifluoromethylphenyl)propiolamido]morphinan, 17-phenethyl-4,5α-epoxy-3,14β-dihydroxy-6α-(N-methyl-3-methylcinnamamido)morphinan, 17-phenethyl-4,5α-epoxy-3,14β-dihydroxy-6α-[N-methyl-3-(4-trifluoromethylphenyl)propiolamido]morphinan, 17-cyclopropylmethyl-4,5α-epoxy-14β-acetoxy-3-hydroxy-6α-(N-methyl-3-methylcinnamamido)morphinan, 17-cyclopropylmethyl-4,5α-epoxy-14β-acetoxy-3-hydroxy-6α-[N-methyl-3-(4-trifluoromethylphenyl)propiolamido]-morphinan, 17-allyl-4,5α-epoxy-14β-acetoxy-3-hydroxy-6α-(N-methyl-3-methylcinnamamido)morphinan, 17-allyl-4,5α-epoxy-14β-acetoxy-3-hydroxy-6α-[N-methyl-3-(4-trifluoromethylphenyl)propiolamido]morphinan, 17-methyl-4,5α-epoxy-14β-acetoxy-3-hydroxy-6α-(N-methyl-3-methylcinnamamido)morphinan, 17-methyl-4,5α-epoxy-14β-acetoxy-3-hydroxy-6α-[N-methyl-3-(4-trifluoromethylphenyl)propiolamido]morphinan, 17-phenethyl-4,5α-epoxy-14β-acetoxy-3-hydroxy-6α-(N-methyl-3-methylcinnamamido)morphinan, 17-phenethyl-4,5α-epoxy-14β-acetoxy-3-hydroxy-6α-[N-methyl-3-(4-trifluoromethylphenyl)propiolamido]morphinan, 17-cyclopropylmethyl-4,5α-epoxy-14β-hydroxy-6α-(N-methyl-3-methylcinnamamido)morphinan, 17-cyclopropylmethyl-4,5α-epoxy-14β-hydroxy-6α-[N-methyl-3-(4-trifluoromethylphenyl)propiolamido]morphinan, 17-allyl-4,5α-epoxy-14β-hydroxy-6α-(N-methyl-3-methylcinnamamido)morphinan, 17-allyl-4,5α-epoxy-14β-hydroxy-6α-[N-methyl-3-(4-trifluoromethylphenyl)-propiolamido]morphinan, 17-methyl-4,5α-epoxy-14β-hydroxy-6α-(N-methyl-3-methylcinnamamido)morphinan, 17-methyl-4,5α-epoxy-14β-hydroxy-6α-[N-methyl-3-(4-trifluoromethylphenyl)propiolamido]morphinan, 17-phenethyl-4,5α-epoxy-14β-hydroxy-6α-(N-methyl-3-methylcinnamamido)morphinan, 17-phenethyl-4,5α-epoxy-14β-hydroxy-6α-[N-methyl-3-(4-trifluoromethylphenyl)-propiolamido]morphinan, 17-cyclopropylmethyl-4,5α-epoxy-14β-acetoxy-6α-(N-methyl-3-methylcinnamamido)-morphinan, 17-cyclopropylmethyl-4,5α-epoxy-14β-acetoxy-6α-[N-methyl-3-(4-trifluoromethylphenyl)propiolamido]-morphinan, 17-allyl-4,5α-epoxy-14β-acetoxy-6α-(N-methyl-3-methylcinnamamido)morphinan, 17-allyl-4,5α-epoxy-14β-acetoxy-6α-[N-methyl-3-(4-trifluoromethylphenyl)propiolamido]morphinan, 17-methyl-4,5α-epoxy-14β-acetoxy-6α-(N-methyl-3-methylcinnamamido)morphinan, 17-methyl-4,5α-epoxy-14β-acetoxy-6α-[N-methyl-3-(4-trifluoromethylphenyl)propiolamido]morphinan, 17-phenethyl-4,5α-epoxy-14β-acetoxy-6α-(N-methyl-3-methylcinnamamido)morphinan, 17-phenethyl-4,5α-epoxy-14β-acetoxy-6α-[N-methyl-3-(4-trifluoromethylphenyl)-propiolamido]morphinan, 17-cyclopropylmethyl-4,5α-epoxy-14β-hydroxy-3-methoxy-6α-(N-methyl-3-methylcinnamamido)morphinan, 17-cyclopropylmethyl-4,5α-epoxy-14β-hydroxy-3-methoxy-6α-[N-methyl-3-(4-trifluoromethylphenyl)-propiolamido]morphinan, 17-allyl-4,5α-epoxy-14β-hydroxy-3-methoxy-6α-(N-methyl-3-methylcinnamamido)-morphinan, 17-allyl-4,5α-epoxy-14β-hydroxy-3-methoxy-6α-[N-methyl-3-(4-trifluoromethylphenyl)-propiolamido]morphinan, 17-methyl-4,5α-epoxy-14β-hydroxy-3-methoxy-6α-(N-methyl-3-methylcinnamamido)morphinan, 17-methyl-4,5α-epoxy-14β-hydroxy-3-methoxy-6α-[N-methyl-3-(4-trifluoromethyl -phenyl)propiolamido]morphinan, 17-phenethyl-4,5α-epoxy-14β-hydroxy-3-methoxy-6α-(N-methyl-3-methylcinnamamido)morphinan, 17-phenethyl-4,5α-epoxy- 14β-hydroxy-3-methoxy-6α-[N-methyl-3-(4-trifluoromethylphenyl)propiolamido]morphinan, 17-cyclopropylmethyl-4,5α-epoxy-14β-acetoxy-3-methoxy-6α-(N-methyl-3-methylcinnamamido)morphinan, 17-cyclopropylmethyl-4,5α-epoxy-14β-acetoxy-3-methoxy-6α-[N-methyl-3-(4-trifluoromethylphenyl)propiolamido]-morphinan, 17-allyl-4,5α-epoxy-14β-acetoxy-3-methoxy-6α-(N-methyl-3-methylcinnamamido)morphinan, 17-allyl-4,5α-epoxy-14β-acetoxy-3-methoxy-6α-[N-methyl-3-(4-trifluoromethylphenyl)propiolamido]morphinan, 17-methyl-4,5α-epoxy-14β-acetoxy-3-methoxy-6α-(N-methyl-3-methylcinnamamido)morphinan, 17-methyl-4,5α-epoxy-14β-acetoxy-3-methoxy-6α-[N-methyl-3-(4-trifluoromethylphenyl)propiolamido]morphinan, 17-phenethyl-4,5α-epoxy-14β-acetoxy-3-methoxy-6α-(N-methyl-3-methylcinnamamido)morphinan, 17-phenethyl-4,5α-epoxy-14β-acetoxy-3-methoxy-6α-[N-methyl-3-(4-trifluoromethylphenyl)propiolamido]morphinan, 17-cyclopropylmethyl-4,5α-epoxy-14β-hydroxy-3-acetoxy-6α-(N-methyl-3-methylcinnamamido)morphinan, 17-cyclopropylmethyl-4,5α-epoxy-14β-hydroxy-3-acetoxy-6α-[N-methyl-3-(4-trifluoromethylphenyl)propiolamido]-morphinan, 17-allyl-4,5α-epoxy-14β-hydroxy-3-acetoxy-6α-(N-methyl-3-methylcinnamamido)morphinan, 17-allyl-4,5α-epoxy-14β-hydroxy-3-acetoxy-6α-[N-methyl-3-(4-trifluoromethylphenyl)propiolamido]morphinan, 17-methyl-4,5α-epoxy-14β-hydroxy-3-acetoxy-6α-(N-methyl-3-methylcinnamamido)morphinan, 17-methyl-4,5α-epoxy-14β-hydroxy-3-acetoxy-6α-[N-methyl-3-(4-trifluoromethyl-phenyl)propiolamido]morphinan, 17-phenethyl-4,5α-epoxy-14β-hydroxy-3-acetoxy-6α-(N-methyl-3-methylcinnamamido)morphinan, 17-phenethyl-4,5α-epoxy-14β-hydroxy-3-acetoxy-6α-[N-methyl-3-(4-trifluoromethylphenyl)propiolamido]morphinan, 17-cyclopropylmethyl-4,5α-epoxy-3,14β-diacetoxy-6α-(N-methyl-3-methylcinnamamido)morphinan, 17-cyclopropylmethyl-4,5α-epoxy-3,14β-diacetoxy-6α-[N-methyl- 3-(4-trifluoromethylphenyl)propiolamido]-morphinan, 17-allyl-4,5α-epoxy-3,14β-diacetoxy-6α-(N-methyl-3-methylcinnamamido)morphinan, 17-allyl-4,5α-epoxy-3,14β-diacetoxy-6α-[N-methyl-3-(4-trifluoromethylphenyl)propiolamido]morphinan, 17-methyl-4,5α-epoxy-3,14β-diacetoxy-6α-(N-methyl-3-methylcinnamamido)morphinan, 17-methyl-4,5α-epoxy-3, 14β-diacetoxy-6α-[N-methyl-3-(4-trifluoromethylphenyl) propiolamido]morphinan, 17-phenethyl-4,5α-epoxy-3,14β-diacetoxy-6α-(N-methyl-3-methylcinnamamido) morphinan, 17-phenethyl-4,5α-epoxy-3,14β-diacetoxy-6α-[N-methyl-3-(4-trifluoromethylphenyl)propiolamido] morphinan, 17-cyclopropylmethyl-4,5α-epoxy-3,14β-dihydroxy-6α-(N-isobutyl-3-methylcinnamamido)morphinan, 17-cyclopropylmethyl-4,5α-epoxy-3,14α-dihydroxy-6α-[N-isobutyl-3-(4-trifluoromethylphenyl)propiolamido]-morphinan, 17-allyl-4,5α-epoxy-3,14β-dihydroxy-6α-(N-isobutyl-3-methylcinnamamido)morphinan, 17-allyl-4,5α-epoxy-3,14β-dihydroxy-6α-[N-isobutyl-3-(4-trifluoromethylphenyl)propiolamido]morphinan, 17-methyl-4,5α-epoxy-3,14β-dihydroxy-6α-(N-isobutyl-3-methylcinnamamido)morphinan, 17-methyl-4,5α-epoxy-3,14β-dihydroxy-6α-[N-isobutyl-3-(4-trifluoromethylphenyl) propiolamido]morphinan, 17-phenethyl-4,5α-epoxy-3,14β-dihydroxy-6α-(N-isobutyl-3-methylcinnamamido) morphinan, 17-phenethyl-4,5α-epoxy-3,14β-dihydroxy-6α-[N-isobutyl-3-(4-trifluoromethylphenyl)propiolamido]-morphinan, 17-cyclopropylmethyl-4,5α-epoxy-14β-acetoxy-3-hydroxy-6α-(N-isobutyl-3-methylcinnamamido)-morphinan, 17-cyclopropylmethyl-4,5α-epoxy-14β-acetoxy-3-hydroxy-6α-[N-isobutyl-3-(4-trifluoromethylphenyl)propiolamido]morphinan, 17-allyl-4,5α-epoxy-14β-acetoxy-3-hydroxy-6α-(N-isobutyl-3-methylcinnamamido)morphinan, 17-allyl-4,5α-epoxy-14β-acetoxy-3-hydroxy-6α-[N-isobutyl-3-(4-trifluoromethylphenyl)propiolamido]morphinan, 17-methyl-4,5α-epoxy-14β-acetoxy-3-hydroxy-6α-(N-isobutyl-3-methylcinnamamido)morphinan, 17-methyl-4,5α-epoxy-14β-acetoxy-3-hydroxy-6α-[N-isobutyl-3-(4-trifluoromethylphenyl)propiolamido]morphinan, 17-phenethyl-4,5α-epoxy-14β-acetoxy-3-hydroxy-6α-(N-isobutyl-3-methylcinnamamido)morphinan, 17-phenethyl-4,5α-epoxy-14β-acetoxy-3-hydroxy-6α-[N-isobutyl-3-(4-trifluoromethylphenyl)propiolamido]morphinan, 17-cyclopropylmethyl-4,5α-epoxy-14β-hydroxy-6α-(N-isobutyl-3-methylcinnamamido)morphinan, 17-cyclopropylmethyl-4,5α-epoxy-14β-hydroxy-6α-[N-isobutyl-3-(4-trifluoromethylphenyl)propiolamido]-morphinan, 17-allyl-4,5α-epoxy-14β-hydroxy-6α-(N-isobutyl-3-methylcinnamamido)morphinan, 17-allyl-4,5α-epoxy-14β-hydroxy-6α-[N-isobutyl-3-(4-trifluoromethylphenyl)propiolamido]morphinan, 17-methyl-4,5α-epoxy-14β-hydroxy-6α-(N-isobutyl-3-methylcinnamamido)morphinan, 17-methyl-4,5α-epoxy-14β-hydroxy-6α-[N-isobutyl-3-(4-trifluoromethylphenyl) propiolamido]morphinan, 17-phenethyl-4,5α-epoxy-14β-hydroxy-6α- (N-isobutyl-3-methylcinnamainido) morphinan, 17-phenethyl-4,5α-epoxy-14β-hydroxy-6α-[N-isobutyl-3-(4-trifluoromethylphenyl)propiolamido] morphinan, 17-cyclopropylmethyl-4,5α-epoxy-14β-acetoxy-6α-(N-isobutyl-3-methylcinnamamido)morphinan, 17-cyclopropylmethyl-4,5α-epoxy-14β-acetoxy-6α-[N-isobutyl-3-(4-trifluoromethylphenyl)propiolamido]-morphinan, 17-allyl-4,5α-epoxy-14β-acetoxy-6α-(N-isobutyl-3-methylcinnamamido)morphinan, 17-allyl-4,5α-epoxy-14β-acetoxy-6α-[N-isobutyl-3-(4-trifluoromethylphenyl)propiolamido]morphinan, 17-methyl-4,5α-epoxy-14β-acetoxy-6α-(N-isobutyl-3-methylcinnamamido)morphinan, 17-methyl-4,5α-epoxy-14β-acetoxy-6α-[N-isobutyl-3-(4-trifluoromethylphenyl) propiolamido]morphinan, 17 -phenethyl-4,5α-epoxy-14β-acetoxy-6α- (N-isobutyl-3-methylcinnamamido) morphinan, 17-phenethyl-4,5α-epoxy-14β-acetoxy-6α-[N-isobutyl-3-(4-trifluoromethyl-phenyl)propiolamido] morphinan, 17-cyclopropylmethyl-4,5α-epoxy-14β-hydroxy-3-methoxy-6α-(N-isobutyl-3-methylcinnamamido) morphinan, 17-cyclopropylmethyl-4,5α-epoxy-14β-hydroxy-3-methoxy-6α-[N-isobutyl-3-(4-trifluoromethylphenyl)-propiolamido]morphinan, 17-allyl-4,5α-epoxy-14β-hydroxy-3-methoxy-6α-(N-isobutyl-3-methylcinnamamido)morphinan, 17-allyl-4,5α-epoxy-14β-hydroxy-3-methoxy-6α- N-isobutyl-3-(4-trifluoromethylphenyl)propiolamido]morphinan, 17-methyl-4,5α-epoxy-14β-hydroxy-3-methoxy-6α-(N-isobutyl-3-methylcinnamamido)morphinan, 17-methyl-4,5α-epoxy-14β-hydroxy-3-methoxy-6α-[N-isobutyl-3-(4-trifluoromethylphenyl)propiolamido]morphinan, 17-phenethyl-4,5α-epoxy-14β-hydroxy-3-methoxy-6α-(N-isobutyl-3-methylcinnamamido)morphinan, 17-phenethyl-4,5α-epoxy-14β-hydroxy-3-methoxy-6α-[N-isobutyl-3-(4-trifluoromethylphenyl)propiolamido]morphinan, 17-cyclopropylmethyl-4,5α-epoxy-14β-acetoxy-3-methoxy-6α-(N-isobutyl-3-methylcinnamamido) morphinan, 17-cyclopropylmethyl-4,5α-epoxy-14β-acetoxy-3-methoxy-6α-[N-isobutyl-3-(4-trifluoromethylphenyl)-propiolamido]morphinan, 17-allyl-4,5α-epoxy-14β-acetoxy-3-methoxy-6α-(N-isobutyl-3-methylcinnamamido)morphinan, 17-allyl-4,5α-epoxy-14β-acetoxy-3-methoxy-6α-[N-isobutyl-3-(4-trifluoromethylphenyl)propiolainido]morphinan, 17-methyl-4,5α-epoxy-14β-acetoxy-3-methoxy-6α-(N-isobutyl-3-methylcinnamamido)morphinan, 17-methyl-4,5α-epoxy-14β-acetoxy-3-methoxy-6α-[N-isobutyl-3-(4-trifluoromethylphenyl)propiolamido]morphinan, 17-phenethyl-4,5α-epoxy-14β-acetoxy-3-methoxy-6α-(N-isobutyl-3-methylcinnamamido)morphinan, 17-phenethyl-4,5α-epoxy-14β-acetoxy-3-methoxy-6α- [N-isobutyl-3-(4-trifluoromethylphenyl)propiolamido]morphinan, 17-cyclopropylmethyl-4,5α-epoxy-14β-hydroxy-3-acetoxy-6α-(N-isobutyl-3-methylcinnamamido)morphinan, 17-cyclopropylmethyl-4,5α-epoxy-14β-hydroxy-3-acetoxy-6α-[N-isobutyl-3-(4-trifluoromethylphenyl)-propiolamido]morphinan, 17-allyl-4,5α-epoxy-14β-hydroxy-3-acetoxy-6α-(N-isobutyl-3-methylcinnamamido)-morphinan, 17-allyl-4,5α-epoxy-14β-hydroxy-3-acetoxy-6α-[N-isobutyl-3-(4-trifluoromethylphenyl)-propiolamido]morphinan, 17-methyl-4,5α-epoxy-14β-hydroxy-3-acetoxy-6α-(N-isobutyl-3-methylcinnamamido)-morphinan, 17-methyl-4,5α-epoxy-14β-hydroxy-3-acetoxy-6α-[N-isobutyl-3-(4-trifluoromethylphenyl) propiolamido]morphinan, 17-phenethyl-4,5α-epoxy-14β-hydroxy-3-acetoxy-6α-(N-isobutyl-3-methylcinnamamido)morphinan, 17-phenethyl-4,5α-epoxy-14β-hydroxy-3-acetoxy-6α-[N-isobutyl-3-(4-trifluoromethylphenyl)propiolamido]morphinan, 17-cyclopropylmethyl-4,5α-epoxy-3,14β-diacetoxy-6α-(N-isobutyl-3-methylcinnamamido)morphinan, 17-cyclopropylmethyl-4,5α-epoxy-3,14β-diacetoxy-6α-[N-isobutyl-3-(4-trifluoromethylphenyl)propiolamido]-morphinan, 17-allyl-4,5α-epoxy-3,14β-diacetoxy-6α-(N-isobutyl-3-methylcinnamamido)morphinan, 17-allyl-4,5α-epoxy-3,14β-diacetoxy-6α-[N-isobutyl-3-(4-trifluoromethylphenyl)propiolamido]morphinan, 17-methyl-4,5α-epoxy-3,14β-diacetoxy-6α-(N-isobutyl-3-methylcinnamamido)morphinan, 17-methyl-4,5α-epoxy-3,14β-diacetoxy-6α-[N-isobutyl-3-(4-trifluoromethylphenyl) propiolamido]morphinan, 17-phenethyl-4,5α-epoxy-3,14β- diacetoxy-6α-(N-isobutyl-3-methylcinnamamido) morphinan, 17-phenethyl-4,5α-epoxy-3,14-diacetoxy-6α-[N-isobutyl-3-(4-trifluoromethylphenyl)propiolamido] morphinan, 17-cyclopropylmethyl-4,5α-epoxy-3,14β-dihydroxy-6β-(N-methyl-3-methylcinnamamido)morphinan, 17-cyclopropylmethyl-4,5α-epoxy-3,14β-dihydroxy-6β-[N-methyl- 3-(4-trifluoromethylphenyl)propiolamido]-morphinan, 17-allyl-4,5α-epoxy-3,14β-dihydroxy-6β-(N-methyl-3-methylcinnamamido)morphinan, 17-allyl-4,5α-epoxy-3,14β-dihydroxy-6β-[N-methyl-3-(4-trifluoromethylphenyl)propiolamido]morphinan, 17-methyl-4,5α-epoxy-3,14β-dihydroxy-6β-(N-methyl-3-methylcinnamamido)morphinan, 17-methyl-4,5α-epoxy-3,14β-dihydroxy-6β-[N-methyl-3-(4-trifluoromethylphenyl) propiolamido]morphinan, 17-phenethyl-4,5α-epoxy-3,14β-dihydroxy-6β-(N-methyl-3-methylcinnamamido) morphinan, 17-phenethyl-4,5α-epoxy-3,14β-dihydroxy-6β-[N-methyl-3-(4-trifluoromethylphenyl)propiolamido] morphinan, 17-cyclopropylmethyl-4,5α-epoxy-14β-acetoxy-3-hydroxy-6β-(N-methyl-3-methylcinnamamido)morphinan, 17-cyclopropylmethyl-4,5α-epoxy-14β-acetoxy-3-hydroxy-6β-[N-methyl-3-(4-trifluoromethylphenyl) propiolamido]-morphinan, 17-allyl-4,5α-epoxy-14β-acetoxy-3-hydroxy-6β-(N-methyl-3-methylcinnamamido) morphinan, 17-allyl-4,5α-epoxy-14β-acetoxy-3-hydroxy-6β-[N-methyl-3-(4-trifluoromethylphenyl)propiolamido] morphinan, 17-methyl-4,5α-epoxy-14β-acetoxy-3-hydroxy-6β-(N-methyl-3-methylcinnamamido)morphinan, 17-methyl-4,5α-epoxy-14β-acetoxy-3-hydroxy-6β-[N-methyl-3-(4-trifluoromethylphenyl)propiolamido] morphinan, 17-phenethyl-4,5α-epoxy-14β-acetoxy-3-hydroxy-6β-(N-methyl-3-methylcinnamamido)morphinan, 17-phenethyl-4,5α-epoxy-14β-acetoxy-3-hydroxy-6β-[N-methyl-3-(4-trifluoromethylphenyl)propiolamido] morphinan, 17-cyclopropylmethyl-4,5α-epoxy-14β-hydroxy-6β-(N-methyl-3-methylcinnamamido)morphinan, 17-cyclopropylmethyl-4,5α-epoxy-14β-hydroxy-60-[N-methyl-3-(4-trifluoromethylphenyl)propiolamido] morphinan, 17-allyl-4,5α-epoxy-14β-hydroxy-6β-(N-methyl-3-methylcinnamamido)morphinan, 17-allyl-4,5α-epoxy-14β-hydroxy-6β-[N-methyl-3-(4-trifluoromethylphenyl)-propiolamido]morphinan, 17-methyl-4,5α-epoxy-14β-hydroxy-6β-(N-methyl-3-methylcinnamamido)morphinan, 17-methyl-4,5α-epoxy-14β-hydroxy-6β-[N-methyl-3-(4-trifluoromethylphenyl) propiolamido]morphinan, 17-phenethyl-4,5α-epoxy-14β-hydroxy-6β-(N-methyl-3-methylcinnamamido)morphinan, 17-phenethyl-4,5α-epoxy-14β-hydroxy-6β-[N-methyl-3-(4-trifluoromethylphenyl)-propiolamido]morphinan, 17-cyclopropylmethyl-4,5α-epoxy-14β-acetoxy-6β-(N-methyl-3-methylcinnamamido)-morphinan, 17-cyclopropylmethyl-4,5α-epoxy-14β-acetoxy-6β-[N-methyl-3-(4-trifluoromethylphenyl)propiolamido]-morphinan, 17-allyl-4,5α-epoxy-14β-acetoxy-6β-(N-methyl-3-methylcinnamamido)morphinan, 17-allyl-4,5α-epoxy-14β-acetoxy-6β-[N-methyl-3-(4-trifluoromethylphenyl)propiolamido]morphinan, 17-methyl-4,5α-epoxy-14β-acetoxy-6β-(N-methyl-3-methylcinnaimamido) morphinan, 17-methyl-4,5α-epoxy-14β-acetoxy-6β-[N-methyl-3-(4-trifluoromethylphenyl)-propiolamido]morphinan, 17-phenethyl-4,5α-epoxy-14β-acetoxy-6β-(N-methyl-3-methylcinnamamido)morphinan, 17-phenethyl-4,5α-epoxy-14β-acetoxy-6β-[N-methyl-3-(4-trifluoromethylphenyl)propiolamido]morphinan, 17-cyclopropylmethyl-4,5α-epoxy-14β-hydroxy-3-methoxy-6β-(N-methyl-3-methylcinnamamido)morphinan, 17-cyclopropylmethyl-4,5α-epoxy-14β-hydroxy-3-methoxy-6β- [N-methyl-3-(4-trifluoromethylphenyl) propiolamido]-morphinan, 17-allyl-4,5α-epoxy-14β-hydroxy-3-methoxy-6β-(N-methyl-3-methylcinnamamido) morphinan, 17-allyl-4,5α-epoxy-14β-hydroxy-3-methoxy-6β-[N-methyl-3-(4-trifluoromethylphenyl)propiolamido] morphinan, 17-methyl-4,5α-epoxy-14β-hydroxy-3-methoxy-6β-(N-methyl-3-methylcinnamamido)morphinan, 17-methyl-4,5α-epoxy-14β-hydroxy-3-methoxy-6β-[N-methyl-3-(4-trifluoromethylphenyl)propiolamido] morphinan, 17-phenethyl-4,5α-epoxy-14β-hydroxy-3-methoxy-6β-(N-methyl-3-methylcinnamamido)morphinan, 17-phenethyl-4,5α-epoxy-14β-hydroxy-3-methoxy-6β-[N-methyl-3-(4 -trifluoromethylphenyl)propiolamido] morphinan, 17-cyclopropylmethyl-4,5α-epoxy-14β-acetoxy-3-methoxy-6β-(N-methyl-3-methylcinnamamido)morphinan, 17-cyclopropylmethyl-4,5α-epoxy-14β-acetoxy-3-methoxy-6β-[N-methyl-3-(4-trifluoromethylphenyl) propiolamido]-morphinan, 17-allyl-4,5α-epoxy-14β-acetoxy-3-methoxy-6β-(N-methyl-3-methylcinnamnido) morphinan, 17-allyl-4,5α-epoxy-14β-acetoxy-3-methoxy-6β-[N-methyl-3-(4-trifluoromethylphenyl)propiolamido] morphinan, 17-methyl-4,5α-epoxy-14β-acetoxy-3-methoxy-6β-(N-methyl-3-methylcinnamamido)morphinan, 17-methyl-4,5α-epoxy-14β-acetoxy-3-methoxy-6β-[N-methyl-3-(4-trifluoromethylphenyl)propiolamido] morphinan, 17-phenethyl-4,5α-epoxy-14β-acetoxy-3-methoxy-6β-(N-methyl-3-methylcinnamamido)morphinan, 17-phenethyl-4,5α-epoxy-14β-acetoxy-3-methoxy-6β-[N-methyl-3-(4-trifluoromethylphenyl)propiolamido] morphinan, 17-cyclopropylmethyl-4,5α-epoxy-14β-hydroxy-3-acetoxy-6β-(N-methyl-3-methylcinnamamido)morphinan, 17-cyclopropylmethyl-4,5α-epoxy-14β-hydroxy-3-acetoxy-6β-[N-methyl-3-(4-trifluoromethylphenyl) propiolamido]-morphinan, 17-allyl-4,5α-epoxy-14β-hydroxy-3-acetoxy-6β-(N-methyl-3-methylcinnamamido) morphinan, 17-allyl-4,5α-epoxy-14β-hydroxy-3-acetoxy-6β-[N-methyl-3-(4-trifluoromethylphenyl)propiolamido] morphinan, 17-methyl-4,5α-epoxy-14β-hydroxy-3-acetoxy-6β-(N-methyl-3-methylcinnamamido)morphinan, 17-methyl-4,5α-epoxy-14β-hydroxy-3-acetoxy-6β-[N-methyl-3-(4-trifluoromethylphenyl)propiolamido] morphinan, 17-phenethyl-4,5α-epoxy-14β-hydroxy-3-acetoxy-6β-(N-methyl-3-methylcinnamamido)morphinan, 17-phenethyl-4,5α-epoxy-14β-hydroxy-3-acetoxy-6β-[N-methyl-3-(4-trifluoromethylphenyl)propiolamido] morphinan, 17-cyclopropylmethyl-4,5α-epoxy-3,14β-diacetoxy-6β-(N-methyl-3-methylcinnamamido)morphinan, 17-cyclopropylmethyl-4,5α-epoxy-3,14β-diacetoxy-6β-[N-methyl-3-(4-trifluoromethylphenyl)propiolamido]-morphinan, 17-allyl-4,5α-epoxy-3,14β-diacetoxy-6β-(N-methyl-3-methylcinnamamido)morphinan, 17-allyl-4,5α-epoxy-3,14β-diacetoxy-6β-[N-methyl-3-(4-trifluoromethylphenyl)propiolamido]morphinan, 17-methyl-4,5α-epoxy-3,14β-diacetoxy-6β-(N-methyl-3-methylcinnamamido)morphinan, 17-methyl-4,5α-epoxy-3,14β-diacetoxy-6β-[N-methyl-3-(4-trifluoromethylphenyl) propiolamido]morphinan, 17-phenethyl-4,5α-epoxy-3,14β-diacetoxy-6β-(N-methyl-3-methylcinnamamido) morphinan, 17-phenethyl-4,5α-epoxy-3,14β-diacetoxy-6β-[N-methyl-3-(4-trifluoromethylphenyl)propiolamido] morphinan, 17-cyclopropylmethyl-4,5α-epoxy-3,14β-dihydroxy-6β-(N-isobutyl-3-methylcinnamamido)morphinan, 17-cyclopropylmethyl-4,5α-epoxy-3,14β-dihydroxy-6β-[N-isobutyl-3-(4-trifluoromethylphenyl)propiolamido]morphinan, 17-allyl-4,5α-epoxy-3,14β-dihydroxy-6β-(N-isobutyl-3-methylcinnamamido)morphinan, 17-allyl-4,5α-epoxy-3,14β-dihydroxy-6β-[N-isobutyl-3-(4-trifluoromethylphenyl)propiolamido]morphinan, 17-methyl-4,5α-epoxy-3,14β-dihydroxy-6β-(N-isobutyl-3-methylcinnamamido)morphinan, 17-methyl-4,5α-epoxy-3,14β-dihydroxy-6β-[N-isobutyl-3-(4-trifluoromethylphenyl)propiolamido]morphinan, 17-phenethyl-4,5α-epoxy-3,14β-dihydroxy-6β-(N-isobutyl-3-methylcinnamamido)morphinan, 17-phenethyl-4,5α-epoxy-3,14β-dihydroxy-6β-[N-isobutyl-3-(4-trifluoromethylphenyl)propiolamido]morphinan, 17-cyclopropylmethyl-4,5α-epoxy-14β-acetoxy-3-hydroxy-6β-(N-isobutyl-3-methylcinnamamido)morphinan, 17-cyclopropylmethyl-4,5α-epoxy-14β-acetoxy-3-hydroxy-6β-[N-isobutyl-3-(4-trifluoromethylphenyl)propiolamido]morphinan, 17-allyl-4,5α-epoxy-14β-acetoxy-3-hydroxy-6β-(N-isobutyl-3-methylcinnamamido)morphinan, 17-allyl-4,5α-epoxy-14β-acetoxy-3-hydroxy-6β-[N-isobutyl-3-(4-trifluoromethylphenyl)propiolamido]morphinan, 17-methyl-4,5α-epoxy-14β-acetoxy-3-hydroxy-6β-(N-isobutyl-3-methylcinnamamido)morphinan, 17-methyl-4,5α-epoxy-14β-acetoxy-3-hydroxy-6β-[N-isobutyl-3-(4-trifluoromethylphenyl)propiolamido]morphinan, 17-phenethyl-4,5α-epoxy-14β-acetoxy-3-hydroxy-6β-(N-isobutyl-3-methylcinnamamido)morphinan, 17-phenethyl-4,5α-epoxy-14β-acetoxy-3-hydroxy-6β-[N-isobutyl-3-(4-trifluoromethylphenyl)propiolamido]morphinan, 17-cyclopropylmethyl-4,5α-epoxy-14β-hydroxy-6β-(N-isobutyl-3-methylcinnamamnido)morphinan, 17-cyclopropylmethyl-4,5α-epoxy-14β-hydroxy-6β-(N-isobutyl-3-(4-trifluoromethylphenyl)propiolamido]morphinan, 17-allyl-4,5α-epoxy-14β-hydroxy-6β-(N-isobutyl-3-methylcinnamamido)morphinan, 17-allyl-4,5α-epoxy-14β-hydroxy-6β-[N-isobutyl-3-(4-trifluoromethylphenyl)propiolamido]morphinan, 17-methyl-4,5α-epoxy-14β-hydroxy-6β-(N-isobutyl-3-methylcinnamamido)morphinan, 17-methyl-4,5α(-epoxy-14β-hydroxy-6β-[N-isobutyl-3-(4-trifluoromethylphenyl)propiolamido]morphinan, 17-phenethyl-4,5α-epoxy-14β-hydroxy-6β-(N-isobutyl-3-methylcinnamamido)morphinan, 17-phenethyl-4,5α-epoxy-14β-hydroxy-6β-[N-isobutyl-3-(4-trifluoromethylphenyl)propiolamido]morphinan, 17-cyclopropylmethyl-4,5α-epoxy-14β-acetoxy-6β-(N-isobutyl-3-methylcinnamamido)morphinan, 17-cyclopropylmethyl-4,5α-epoxy-14β-acetoxy-6β-[N-isobutyl-3-(4-trifluoromethylphenyl)propiolamido]morphinan, 17-allyl-4,5α-epoxy-14β-acetoxy-6β-(N-isobutyl-3-methylcinnamamido)morphinan, 17-allyl-4,5α-epoxy-14β-acetoxy-6β-[N-isobutyl-3-(4-trifluoromethylphenyl)propiolamido]morphinan, 17-methyl-4,5α-epoxy-14β-acetoxy-6β-(N-isobutyl-3-methylcinnamamido)morphinan, 17-methyl-4,5α-epoxy-14β-acetoxy-6β-[N-isobutyl-3-(4-trifluoromethylphenyl)propiolamido]morphinan, 17-phenethyl-4,5α-epoxy-14β-acetoxy-6β-(N-isobutyl-3-methylcinnamamido)morphinan, 17-phenethyl-4,5α-epoxy-14β-acetoxy-6β[N-isobutyl-3-(4-trifluoromethylphenyl)propiolamido]morphinan, 17-cyclopropylmethyl-4,5α-epoxy-14β-hydroxy-3-methoxy-6β-(N-isobutyl-3-methylcinnamamido)morphinan, 17-cyclopropylmethyl-4,5α-epoxy-14β-hydroxy-3-methoxy-6β-[N-isobutyl-3-(4-trifluoromethylphenyl)-propiolamido]morphinan, 17-allyl-4,5α-epoxy-14β-hydroxy-3-methoxy-6β-(N-isobutyl-3-methylcinnamamido)morphinan, 17-allyl-4,5α-epoxy-14β-hydroxy-3-methoxy-6β-[N-isobutyl-3-(4-trifluoromethylphenyl)propiolamido]morphinan, 17-methyl-4,5α-epoxy-14β-hydroxy-3-methoxy-6β-(N-isobutyl-3-methylcinnamamido)morphinan, 17-methyl-4,5α-epoxy-14β-hydroxy-3-methoxy-6β-[N-isobutyl-3-(4-trifluoromethylphenyl)propiolamido]morphinan, 17-phenethyl-4,5α-epoxy-14β-hydroxy-3-methoxy-6β-(N-isobutyl-3-methylcinnamamido)morphinan, 17-phenethyl-4,5α-epoxy-14β-hydroxy-3-methoxy-6β-[N-isobutyl-3-(4-trifluoromethylphenyl)propiolamido]morphinan, 17-cyclopropylmethyl-4,5α-epoxy-14β-acetoxy-3-methoxy-6β-(N-isobutyl-3-methylcinnamamido)morphinan, 17-cyclopropylmethyl-4,5α-epoxy-14β-acetoxy-3-methoxy-6β-[N-isobutyl-3-(4-trifluoromethylphenyl)-propiolamido]morphinan, 17-allyl-4,5α-epoxy-14β-acetoxy-3-methoxy-6β-(N-isobutyl-3-methylcinnamamido)morphinan, 17-allyl-4,5α-epoxy-14β-acetoxy-3-methoxy-6β-[N-isobutyl-3-(4-trifluoromethylphenyl)propiolamido]morphinan, 17-methyl-4,5α-epoxy-14β-acetoxy-3-methoxy-6β-(N-isobutyl-3-methylcinnamamido)morphinan, 17-methyl-4,5α-epoxy-14β-acetoxy-3-methoxy-6β-[N-isobutyl-3-(4-trifluoromethylphenyl)propiolamido]morphinan, 17-phenethyl-4,5α-epoxy-14β-acetoxy-3-methoxy-6β-(N-isobutyl-3-methylcinnamamido)morphinan, 17-phenethyl-4,5α-epoxy-14β-acetoxy-3-methoxy-6β-[N-isobutyl-3-(4-trifluoromethylphenyl)propiolamido]morphinan, 17-cyclopropylmethyl-4,5α-epoxy-14β-hydroxy-3-acetoxy-6β-(N-isobutyl-3-methylcinnamamido)morphinan, 17-cyclopropylmethyl-4,5α-epoxy-14β-hydroxy-3-acetoxy-6β-[N-isobutyl-3-(4-trifluoromethylphenyl)-propiolamido]morphinan, 17-allyl-4,5α-epoxy-14β-hydroxy-3-acetoxy-6β-(N-isobutyl-3-methylcinnanamido)morphinan, 17-allyl-4,5α-epoxy-14β-hydroxy-3-acetoxy-6β-[N-isobutyl-3-(4-trifluoromethylphenyl)-propiolamido]morphinan, 17-methyl-4,5α-epoxy-14β-hydroxy-3-acetoxy-6β-(N-isobutyl-3-methylcinnamamido)morphinan, 17-methyl-4,5α-epoxy-14β-hydroxy-3-acetoxy-6β-[N-isobutyl-3-(4-trifluoromethylphenyl)propiolamido]morphinan, 17-phenethyl-4,5α-epoxy-14β-hydroxy-3-acetoxy-6β-(N-isobutyl-3-methylcinnamamido)morphinan, 17-phenethyl-4,5α-epoxy-14β-hydroxy-3-acetoxy-6β-[N-isobutyl-3-(4-trifluoromethylphenyl)propiolamido]morphinan, 17-cyclopropylmethyl-4,5α-epoxy-3,14β-diacetoxy-6β-(N-isobutyl-3-methylcinnamamido)morphinan, 17-cyclopropylmethyl-4,5α-epoxy-3,14β-diacetoxy-6β-[N-isobutyl-3-(4-trifluoromethylphenyl)propiolamido]morphinan, 17-allyl-4,5α-epoxy-3,14β-diacetoxy-6β-(N-isobutyl-3-methylcinnamamido)morphinan, 17-allyl-4,5α-epoxy-3,14β-diacetoxy-6β-[N-isobutyl-3-(4-triflucromethylphenyl)propiolamido]morphinan, 17-methyl-4,5α-epoxy-3,14β-diacetoxy-6β-(N-isobutyl-3-methylcinnamamido)morphinan, 17-methyl-4,5α-epoxy-3,14β-diacetoxy-6β-[N-isobutyl-3- (4-trifluoromethylphenyl)propiolamido]morphinan, 17-phenethyl-4,5α-epoxy-3,14β-diacetoxy-6β-(N-isobutyl-3-methylcinnamamido)morphinan, 17-phenethyl-4,5α-epoxy-3,14β-diacetoxy-6β-[N-isobutyl-3-(4-trifluoromethylphenyl)propiolamido]morphinan, 17-cyclopropylmethyl-4,5α-epoxy-3,14β-dihydroxy-6α-[N-methyl-3-(3-trifluoromethylphenyl)propiolamido]-morphinan, 17-allyl-4,5α-epoxy-3,14β-dihydroxy-6α-[N-methyl-3-(3-trifluoromethylphenyl)propiolamido]- morphinan, 17-cyclopropylmethyl-4,5α-epoxy-3,14β-dihydroxy-6β-[N-methyl-3-(3-trifluoromethylphenyl)-propiolamido]morphinan, 17-allyl-4,5α(-epoxy-3,14β-dihydroxy-6β-[N-methyl-3-(3-trifluoromethylphenyl)-propiolamido]morphinan, 17-cyclopropylmethyl-4,5α-epoxy-3,14β-dihydroxy-6α-[N-methyl-trans-3-(2-thienyl)acrylamido]morphinan, 17-allyl-4,5α-epoxy-3,14β-dihydroxy-6α-[N-methyl-trans-3-(2-thienyl)acrylamido]morphinan, 17-cyclopropylmethyl-4,5α-epoxy-3,14β-dihydroxy-6β-[N-methyl-trans-3-(2-thienyl)acrylamido]morphinan, 17-allyl-4,5α-epoxy-3,14β-dihydroxy-6β-[N-methyl-trans-3-(2-thienyl)acrylamido]morphinan, 17-cyclopropylmethyl-4,5α-epoxy-3-hydroxy-6α-(N-methyl-3-trifluoromethylcinnamamido)morphinan, 17-cyclopropylmethyl-4,5α-epoxy-3-hydroxy-6α-[N-methyl-trans-3-(3-furyl)acrylamido]morphinan, 17-cyclopropylmethyl-4,5α-epoxy-3-hydroxy-6α-(N-methyl-3-methylcinnamamido)morphinan, 17-cyclopropylmethyl-4,5α-epoxy-3-hydroxy-6α-[N-methyl-3-(4-trifluoromethylphenyl)propiolamido]morphinan, 17-allyl-4,5α-epoxy-3-hydroxy-6α-(N-methyl-3-trifluoromethylcinnamamido)morphinan, 17-allyl-4,5α-epoxy-3-hydroxy-6α-[N-methyl-trans-3-(3-furyl)acrylamido]morphinan, 17-allyl-4,5α-epoxy-3-hydroxy-6α-(N-methyl-3-methylcinnamamido)morphinan, 17-allyl-4,5α-epoxy-3-hydroxy-6α-[N-methyl-3-(4-trifluoromethylphenyl)propiolamido]morphinan, 17-methyl-4,5α-epoxy-3-hydroxy-6α-(N-methyl-3-trifluoromethylcinnamamido)morphinan, 17-methyl-4,5α-epoxy-3-hydroxy-6α-[N-methyl-trans-3-(3-furyl)acrylamido]morphinan, 17-methyl-4,5α-epoxy-3-hydroxy-6α-(N-methyl-3-methylcinnamamido)morphinan, 17-methyl-4,5α-epoxy-3-hydroxy-6α-[N-methyl-3-(4-trifluoromethylphenyl)propiolamido]morphinan, 17-phenethyl-4,5α-epoxy-3-hydroxy-6α-(N-methyl-3-trifluoromethylcinnamamido)morphinan, 17-phenethyl-4,5α-epoxy-3-hydroxy-6α-[N-methyl-trans-3-(3-furyl)acrylamido]morphinan, 17-phenethyl-4,5α-epoxy-3-hydroxy-6α-(N-methyl-3-methylcinnamamido)morphinan, 17-phenethyl-4,5α-epoxy-3-hydroxy-6α-[N-methyl-3-(4-trifluoromethylphenyl)propiolamido]morphinan, 17-cyclopropylmethyl-4,5α-epoxy-3-hydroxy-14β-nitro-6α-(N-methyl-3-trifluoromethylcinnamamido)-morphinan, 17-cyclopropylmethyl-4,5α-epoxy-3-hydroxy-14β-nitro-6α-[N-methyl-trans-3-(3-furyl)acrylamido]-morphinan, 17-cyclopropylmethyl-4,5α-epoxy-3-hydroxy-14β-nitro-6α-(N-methyl-3-methylcinnamamido)morphinan, 17-cyclopropylmethyl-4,5α-epoxy-3-hydroxy-14β-nitro-6α-[N-methyl-3-(4-trifluoromethylphenyl)propiolamido]-morphinan, 17-allyl-4,5α-epoxy-3-hydroxy-14β-nitro-6β-(N-methyl-3-trifluoromethylcinnamamido)morphinan, 17-allyl-4,5α-epoxy-3-hydroxy-14β-nitro-6α-[N-methyl-trans-3-(3-furyl)acrylamido]morphinan, 17-allyl-4,5α-epoxy-3-hydroxy-14β-nitro-6α-(N-methyl-3-methylcinnamamido)morphinan, 17-allyl-4,5α-epoxy-3-hydroxy-14β-nitro-6α-[N-methyl-3-(4-trifluoromethylphenyl)propiolamido]morphinan, 17-methyl-4,5α-epoxy-3-hydroxy-14β-nitro-6α-(N-methyl-3-trifluoromethylcinnamamido)morphinan, 17-methyl-4,5α-epoxy-3-hydroxy-14β-nitro-6α-[N-methyl-trans-3-(3-furyl)acrylamido]morphinan, 17-methyl-4,5α-epoxy-3-hydroxy-14β-nitro-6α-(N-methyl-3-methylcinnamamido)-morphinan, 17-methyl-4,5α-epoxy-3-hydroxy-14β-nitro-6α-[N-methyl-3-(4-trifluoromethylphenyl)propiolamido]-morphinan, 17-phenethyl-4,5α-epoxy-3-hydroxy-14β-nitro-6α-(N-methyl-3-trifluoromethylcinnamamido)-morphinan, 17-phenethyl-4,5α-epoxy-3-hydroxy-14β-nitro-6α-[N-methyl-trans-3-(3-furyl)acrylamido]-morphinan, 17-phenethyl-4,5α-epoxy-3-hydroxy-14β-nitro-6α-(N-methyl-3-methylcinnamamido)morphinan, 17-phenethyl-4,5α-epoxy-3-hydroxy-14β-nitro-6β-[N-methyl-3-(4-trifluoromethylphenyl)propiolamido]morphinan, 17-cyclopropylmethyl-4,5α-epoxy-3-hydroxy-14β-dimethylamino-6α-(N-methyl-3-trifluoromethylcinnamamido)morphinan, 17-cyclopropylmethyl-4,5α-epoxy-3-hydroxy-14β-dimethylamino-6α-[N-methyl-trans-3-(3-furyl)acrylamido]morphinan, 17-cyclopropylmethyl-4,5α-epoxy-3-hydroxy-14β-dimethylamino-6α-(N-methyl-3-methylcinnamamido)morphinan, 17-cyclopropylmethyl-4,5α-epoxy-3-hydroxy-14β-dimethylamino-6α-[N-methyl-3-(4-trifluoromethylphenyl)propiolamido]morphinan, 17-allyl-4,5α-epoxy-3-hydroxy-14β-dimethylamino-6α-(N-methyl-3-trifluoromethylcinnamamido)morphinan, 17-allyl-4,5α-epoxy-3-hydroxy-14β-dimethylamino-6α-[N-methyl-trans-3-(3-furyl)acrylamido]morphinan, 17-allyl-4,5α-epoxy-3-hydroxy-14β-dimethylamino-6α-(N-methyl-3-methylcinnamamido)morphinan, 17-allyl-4,5α-epoxy-3-hydroxy-14β-dimethylamino-6α-[N-methyl-3-(4-trifluoromethylphenyl)propiolamido]morphinan, 17-methyl-4,5α-epoxy-3-hydroxy-14β-dimethylamino-6α-(N-methyl-3-trifluoromethylcinnamamido)morphinan, 17-methyl-4,5α-epoxy-3-hydroxy-14β-dimethylamino-6α-[N-methyl-trans-3-(3-furyl)acrylamido]morphinan, 17-methyl-4,5α-epoxy-3-hydroxy-14β-dimethylamino-6α-(N-methyl-3-methylcinnamamido)morphinan, 17-methyl-4,5α-epoxy-3-hydroxy-14β-dimethylamino-6α-[N-methyl-3-(4-trifluoromethylphenyl)propiolamido]morphinan, 17-phenethyl-4,5α-epoxy-3-hydroxy-14β-dimethylamino-6α-(N-methyl-3-trifluoromethylcinnamamido)morphinan, 17-phenethyl-4,5α-epoxy-3-hydroxy-14β-dimethylamino-6α-[N-methyl-trans-3-(3-furyl)acrylamido]morphinan, 17-phenethyl-4,5α-epoxy-3-hydroxy-14β-dimethylamino-6α-(N-methyl-3-methylcinnamamido)morphinan, 17-phenethyl-4,5α-epoxy-3-hydroxy-14β-dimethylamino-6α-[N-methyl-3-(4-trifluoromethylphenyl)propiolamido]morphinan, 17-cyclopropylmethyl-4,5α-epoxy-3-hydroxy-14β-methyl-6α-(N-methyl-3-trifluoromethylcinnamamido)-morphinan, 17-cyclopropylmethyl-4,5α-epoxy-3-hydroxy-14β-methyl-6α-[N-methyl-trans-3-(3-furyl)acrylamido]-morphinan, 17-cyclopropylmethyl-4,5α-epoxy-3-hydroxy-14β-methyl-6α-(N-methyl-3-methylcinnamamido)-morphinan, 17-cyclopropylmethyl-4,5α-epoxy-3-hydroxy-14β-methyl-6α-[N-methyl-3-(4-trifluoromethylphenyl)-propiolamido]morphinan, 17-allyl-4,5α-epoxy-3-hydroxy-14β-methyl-6α-(N-methyl-3-trifluoromethylcinnamamido)morphinan, 17-allyl-4,5α-epoxy-3-hydroxy-14β-methyl-6α-[N-methyl-trans-3-(3-furyl)acrylamido]morphinan, 17-allyl-4,5α-epoxy-3-hydroxy-14β-methyl-6α-(N-methyl-3-methylcinnamamido)morphinan, 17-allyl-4,5α-epoxy-3-hydroxy-14β-methyl-6α-[N-methyl-3-(4-trifluoromethylphenyl)propiolamido]morphinan, 14β,17-dimethyl-4,5α-epoxy-3-hydroxy-6α-(N-methyl-3-trifluoromethylcinnamamido)morphinan, 14β,17-dimethyl-4,5α-epoxy-3-hydroxy-6α-[N-methyl-trans-3-(3-furyl)acrylamido]morphinan, 14β,17-dimethyl-4,5α-epoxy-3-hydroxy-6α-(N-methyl-3-methylcinnamamido)-morphinan, 14β,17-dimethyl-4,5α-epoxy-3-hydroxy-6α-[N-methyl-3-(4-trifluoromethylphenyl)propiolamido]-morphinan, 17-phenethyl-4,5α-epoxy-3-hydroxy-14β-methyl-6α-(N-methyl-3-trifluoromethylcinnamamido)-morphinan, 17-phenethyl-4,5α-epoxy-3-hydroxy-14β-methyl-6α-[N-methyl-trans-3-(3-furyl)acrylamido]morphinan, 17-phenethyl-4,5α-epoxy-3-hydroxy-14β-methyl-6α-(N-methyl-3-methylcinnamamido)morphinan, 17-phenethyl-4,5α-epoxy-3-hydroxy-14β-methyl-6α-[N-methyl-3-(4-trifluoromethylphenyl)propiolamido]morphinan, 17-cyclopropylmethyl-3,14β-dihydroxy-6α-(N-methyl-3-trifluoromethylcinnamamido)morphinan, 17-cyclopropylmethyl-3,14β-dihydroxy-6α-[N-methyl-trans-3-(3-furyl)acrylamido]morphinan, 17-cyclopropylmethyl-3,14β-dihydroxy-6α-(N-methyl-3-methylcinnamamido)morphinan, 17-cyclopropylmethyl-3,14β-dihydroxy-6α-[N-methyl-3-(4-trifluoromethylphenyl)propiolamido]morphinan, 17-allyl-3,14β-dihydroxy-6α-(N-methyl-3-trifluoromethyl-cinnamamido)morphinan, 17-allyl-3,14β-dihydroxy-6α-[N-methyl-trans-3-(3-furyl)acrylamido]morphinan, 17-allyl-3,14β-dihydroxy-6α-(N-methyl-3-methylcinnamamido)morphinan, 17-allyl-3,14β-dihydroxy-6α-[N-methyl-3-(4-trifluoromethylphenyl)-propiolamido]morphinan, 17-methyl-3,14β-dihydroxy-6α-(N-methyl-3-trifluoromethylcinnamamido)morphinan, 17-methyl-3,14β-dihydroxy-6O-[N-methyl-trans-3-(3-furyl)acrylamido]morphinan, 17-methyl-3,14β-dihydroxy-6α- (N-methyl-3-methylcinnamamido)morphinan, 17-methyl-3,14β-dihydroxy-6α-[N-methyl-3-(4-trifluoromethylphenyl)propiolamido]morphinan, 17-phenethyl-3,14β-dihydroxy-6α-(N-methyl-3-trifluoromethylcinnamamido)morphinan, 17-phenethyl-3,14β-dihydroxy-6α-[N-methyl-trans-3-(3-furyl)acrylamido]morphinan, 17-phenethyl-3,14-dihydroxy-6α-(N-methyl-3-methylcinnamamido)morphinan, 17-phenethyl-3,14β-dihydroxy-6α-[N-methyl-3-(4-trifluoromethylphenyl)propiolamido]morphinan, 17-cyclopropylmethyl-3,14β-dihydroxy-4-methoxy-6α-(N-methyl-3-trifluoromethylcinnamamido)morphinan, 17-cyclopropylmethyl-3,14β-dihydroxy-4-methoxy-6α-[N-methyl-trans-3-(3-furyl)acrylamido]morphinan, 17-cyclopropylmethyl-3,14β-dihydroxy-4-methoxy-6α-(N-methyl-3-methylcinnamamido)morphinan, 17-cyclopropylmethyl-3,14β-dihydroxy-4-methoxy-6α-[N-methyl-3-(4-trifluoromethylphenyl)propiolamido]morphinan, 17-allyl-3,14β-dihydroxy-4-methoxy-6α-(N-methyl-3-trifluoromethylcinnamamido)morphinan, 17-allyl-3,14β-dihydroxy-4-methoxy-6α-[N-methyl-trans-3-(3-furyl)acrylamido]morphinan, 17-allyl-3,14β-dihydroxy-4-methoxy-6α-(N-methyl-3-methylcinnamamido)-morphinan, 17-allyl-3,14β-dihydroxy-4-methoxy-6α-[N-methyl-3-(4-trifluoromethylphenyl)propiolamido]morphinan, 17-methyl-3,14β-dihydroxy-4-methoxy-6α-(N-methyl-3-trifluoromethylcinnamamido)morphinan, 17-methyl-3,14β-dihydroxy-4-methoxy-6α-[N-methyl-trans-3-(3-furyl)acrylamido]morphinan, 17-methyl-3,14β-dihydroxy-4-methoxy-6α-(N-methyl-3-methylcinnamamido)morphinan, 17-methyl-3,14β-dihydroxy-4-methoxy-6α-[N-methyl-3-(4-trifluoromethylphenyl)propiolamido]morphinan, 17-phenethyl-3,14β-dihydroxy-4-methoxy-6α-(N-methyl-3-trifluoromethylcinnamamido)morphinan, 17-phenethyl-3,14β-dihydroxy-4-methoxy-6α-[N-methyl-trans-3-(3-furyl)acrylamido]morphinan, 17-phenethyl-3,14β-dihydroxy-4-methoxy-6α-(N-methyl-3-methylcinnamamido)morphinan, 17-phenethyl-3,14β-dihydroxy-4-methoxy-6α-[N-methyl-3-(4-trifluoromethylphenyl)propiolamido]morphinan, 17-cyclopropylmethyl-4,5α-epoxy-3,14β-dihydroxy-5β-methyl-6α-(N-methyl-3-trifluoromethylcinnamamido)-morphinan, 17-cyclopropylmethyl-4,5α-epoxy-3,14β-dihydroxy-5β-methyl-6α-[N-methyl-trans-3-(3-furyl)acrylamido]morphinan, 17-cyclopropylmethyl-4,5α-epoxy-3,14β-dihydroxy-5β-methyl-6α-(N-methyl-3-methylcinnamamido)morphinan, 17-cyclopropylmethyl-4,5α-epoxy-3,14β-dihydroxy-5β-methyl-6α-[N-methyl-3-(4-trifluoromethylphenyl)propiolamido]morphinan, 17-allyl-4,5α-epoxy-3,14β-dihydroxy-5β-methyl-6α-(N-methyl-3-trifluoromethylcinnamamido)morphinan, 17-allyl-4,5α-epoxy-3,14β-dihydroxy-5β-methyl-6α-[N-methyl-trans-3-(3-furyl)acrylamido]morphinan, 17-allyl-4,5α-epoxy-3,14β-dihydroxy-5β-methyl-6α-(N-methyl-3-methylcinnamamido)morphinan, 17-allyl-4,5α-epoxy-3,14β-dihydroxy-5β-methyl-6α-[N-methyl-3-(4-trifluoromethylphenyl)propiolamido]morphinan, 5β,17-dimethyl-4,5α-epoxy-3,14β-dihydroxy-6α-(N-methyl-3-trifluoromethylcinnamamido)morphinan, 5β,17-dimethyl-4,5α-epoxy-3,14β-dihydroxy-6α-[N-methyl-trans-3-(3-furyl)acrylamido]morphinan, 5β,17-dimethyl-4,5α-epoxy-3,14β-dihydroxy-6α-(N-methyl-3-methylcinnamamido)morphinan, 5β,17-dimethyl-4,5α-epoxy-3,14β-dihydroxy-6α-[N-methyl-3-(4-trifluoromethylphenyl)propiolamido]morphinan, 17-phenethyl-4,5α-epoxy-3,14β-dihydroxy-5β-methyl-6α-(N-methyl-3-trifluoromethylcinnamamido)-morphinan, 17-phenethyl-4,5α-epoxy-3,14β-dihydroxy-5β-methyl-6α-[N-methyl-trans-3-(3-furyl)acrylamido]-morphinan, 17-phenethyl-4,5α-epoxy-3,14β-dihydroxy-5β-methyl-6α-(N-methyl-3-methylcinnamamido)morphinan, 17-phenethyl-4,5α-epoxy-3,14β-dihydroxy-5β-methyl-6α-[N-methyl-3-(4-trifluoromethylphenyl)propiolamido]-morphinan, 17-cyclopropylmethyl-7,8-didehydro-4,5α-epoxy-3,14β-dihydroxy-6α-(N-methyl-3-trifluoromethyl-cinnamamido)morphinan, 17-cyclopropylmethyl-7,8-didehydro-4,5α-epoxy-3,14β-dihydroxy-6α-[N-methyl-trans-3-(3-furyl)acrylamido]morphinan, 17-cyclopropylmethyl-7,8-didehydro-4,5α-epoxy-3,14β-dihydroxy-6α-(N-methyl-3-methylcinnamamido)morphinan, 17-cyclopropylmethyl-7,8-didehydro-4,5α-epoxy-3,14β-dihydroxy-6α-[N-methyl-3-(4-trifluoromethylphenyl)propiolamido]morphinan, 17-allyl-7,8-didehydro-4,5α-epoxy-3,14β-dihydroxy-6α-(N-methyl-3-trifluoromethylcinnamamido)morphinan, 17-allyl-7,8-didehydro-4,5α-epoxy-3,14β-dihydroxy-6α-[N-methyl-trans-3-(3-furyl)acrylamido]morphinan, 17-allyl-7,8-didehydro-4,5α-epoxy-3,14β-dihydroxy-6α-(N-methyl-3-methylcinnamamido)morphinan, 17-allyl-7,8-didehydro-4,5α-epoxy-3,14β-dihydroxy-6α-[N-methyl-3-(4-trifluoromethylphenyl)propiolamido]morphinan, 17-methyl-7,8-didehydro-4,5α-epoxy-3,14β-dihydroxy-6α-(N-methyl-3-trifluoromethylcinnamamido)morphinan, 17-methyl-7,8-didehydro-4,5α-epoxy-3,14β-dihydroxy-6α-[N-methyl-trans-3-(3-furyl)acrylamido]morphinan, 17-methyl-7,8-didehydro-4,5α-epoxy-3,14β-dihydroxy-6α-( N-methyl-3-methylcinnamamido)morphinan, 17-methyl-7,8-didehydro-4,5α-epoxy-3,14β-dihydroxy-6α-[N-methyl- 3- (4-trifluoromethylphenyl)propiolamido]-morphinan, 17-phenethyl-7,8-didehydro-4,5α-epoxy-3,14β-dihydroxy-6α-(N-methyl-3-trifluoromethylcinnamamido)morphinan, 17-phenethyl-7,8-didehydro-4,5α-epoxy-3,14β-dihydroxy-6α-[N-methyl-trans-3-(3-furyl)acrylamido]morphinan, 17-phenethyl-7,8-didehydro-4,5α-epoxy-3,14β-dihydroxy-6α-(N-methyl-3-methylcinnamamido)morphinan, 17-phenethyl-7,8-didehydro-4,5α-epoxy-3,14β-dihydroxy-6α-[N-methyl-3-(4-trifluoromethylphenyl)propiolamido]morphinan, 17-cyclopropylmethyl-4,5α-epoxy-3-hydroxy-6β-(N-methyl-3-trifluoromethylcinnamamido)morphinan, 17-cyclopropylmethyl-4,5α-epoxy-3-hydroxy-6β-[N- methyl-trans-3-(3-furyl)acrylamido]morphinan, 17-cyclopropylmethyl-4,5α-epoxy-3-hydroxy-6β-(N-methyl-3-methylcinnamamido)morphinan, 17-cyclopropylmethyl-4,5α-epoxy-3-hydroxy-6β-[N-methyl-3-(4-trifluoromethylphenyl)propiolamido] morphinan, 17-allyl-4,5α-epoxy-3-hydroxy-6β-(N-methyl-3-trifluoromethylcinnamamido)morphinan, 17-allyl-4,5α-epoxy-3-hydroxy-6β-[N-methyl-trans-3-(3-furyl)acrylamido]morphinan, 17-allyl-4,5α-epoxy-3-hydroxy-6β-(N-methyl-3-methylcinnamamido)morphinan, 17-allyl-4,5α-epoxy-3-hydroxy-6β-[N-methyl-3-(4-trifluoromethylphenyl)propiolamido]morphinan, 17-methyl-4,5α-epoxy-3-hydroxy-6β-(N-methyl-3-trifluoromethylcinnamamido)morphinan, 17-methyl-4,5α-epoxy-3-hydroxy-6β-[N-methyl-trans-3-(3-furyl)acrylamido]morphinan, 17-methyl-4,5α-epoxy-3-hydroxy-6β-(N-methyl-3-methylcinnamamido)morphinan, 17-methyl-4,5α-epoxy-3-hydroxy-6β-[N-methyl-3-(4-trifluoromethylphenyl)propiolamido]morphinan, 17-phenethyl-4,5α-epoxy-3-hydroxy-6β-(N-methyl-3-trifluoromethylcinnamamido)morphinan, 17-phenethyl-4,5α-epoxy-3-hydroxy-6β-[N-methyl-trans-3-(3-furyl)acrylamido]morphinan, 17-phenethyl-4,5α-epoxy-3-hydroxy-6β-(N-methyl-3-methylcinnamamido)morphinan, 17-phenethyl-4,5α-epoxy-3-hydroxy-6β-[N-methyl-3-(4-trifluoromethylphenyl)propiolamido]morphinan, 17-cyclopropylmethyl-4,5α-epoxy-3-hydroxy-14β-nitro-6β-(N-methyl-3-trifluoromethylcinnamamido)-morphinan, 17-cyclopropylmethyl-4,5α-epoxy-3-hydroxy-14β-nitro-6β-[N-methyl-trans-3-(3-furyl)acrylamido]-morphinan, 17-cyclopropylmethyl-4,5α-epoxy-3-hydroxy-14β-nitro-6β-(N-methyl-3-methylcinnamamido)morphinan, 17-cyclopropylmethyl-4,5α-epoxy-3-hydroxy-14β-nitro-6β-[N-methyl-3-(4-trifluoromethylphenyl)propiolamido]-morphinan, 17-allyl-4,5α-epoxy-3-hydroxy-14β-nitro-6β-(N-methyl-3-trifluoromethylcinnamamido)morphinan, 17-allyl-4,5α-epoxy-3-hydroxy-14β-nitro-6β-[N-methyl-trans-3-(3-furyl)acrylamido]morphinan, 17-allyl-4,5α-epoxy-3-hydroxy-14β-nitro-6β-(N-methyl-3-methylcinnamamido)morphinan, 17-allyl-4,5α-epoxy-3-hydroxy-14β-nitro-6β-[N-methyl-3-(4-trifluoromethylphenyl)propiolamido]morphinan, 17-methyl-4,5α-epoxy-3-hydroxy-14β-nitro-6β-(N-methyl-3-trifluoromethylcinnamamido)morphinan, 17-methyl-4,5α-epoxy-3-hydroxy-14β-nitro-6β-[N-methyl-trans-3-(3-furyl)acrylamido]morphinan, 17-methyl-4,5α-epoxy-3-hydroxy-14β-nitro-6β-(N-methyl-3-methylcinnamamido)morphinan, 17-methyl-4,5α-epoxy-3-hydroxy-14β-nitro-6β-[N-methyl-3-(4-trifluoromethylphenyl)propiolamido]morphinan, 17-phenethyl-4,5α-epoxy-3-hydroxy-14β-nitro-6β-(N-methyl-3-trifluoromethylcinnamamido)-morphinan, 17-phenethyl-4,5α-epoxy-3-hydroxy-14β-nitro-6β-[N-methyl-trans-3-(3-furyl)acrylaraido]-morphinan, 17-phenethyl-4,5α-epoxy-3-hydroxy-14β-nitro-6β-(N-methyl-3-methylcinnamamido)morphinan, 17-phenethyl-4,5α-epoxy-3-hydroxy-14β-nitro-6β-[N-methyl-3-(4-trifluoromethylphenyl)propiolamido]morphinan, 17-cyclopropylmethyl-4,5α-epoxy-3-hydroxy-14β-dimethylamino-6β-(N-methyl-3-trifluoromethylcinnamamido)morphinan, 17-cyclopropylmethyl-4,5α-epoxy-3-hydroxy-14β-dimethylamino-6β-[N-methyl-trans-3-(3-furyl)acrylamido]morphinan, 17-cyclopropylmethyl-4,5α-epoxy-3-hydroxy-14β-dimethylamino-6β-(N-methyl-3-methylcinnamamido)morphinan, 17-cyclopropylmethyl-4,5α-epoxy-3-hydroxy-14β-dimethylamino-6β- [N-methyl-3-(4-trifluoromethylphenyl)propiolamido]morphinan, 17-allyl-4,5α-epoxy-3-hydroxy-14β-dimethylamino-6β-(N-methyl-3-trifluoromethylcinnamnamido)morphinan, 17-allyl-4,5α-epoxy-3-hydroxy-14β-dimethylamino-6β-[N-methyl-trans-3-(3-furyl)acrylamido]morphinan, 17-allyl-4,5α-epoxy-3-hydroxy-14β-dimethylamino-6β-(N-methyl-3-methylcinnamamido)morphinan, 17-allyl-4,5α-epoxy-3-hydroxy-14β-dimethylamino-6β-[N-methyl-3-(4-trifluoromethylphenyl)propiolamido]morphinan, 17-methyl-4,5α-epoxy-3-hydroxy-14β-dimethylamino-6β-(N-methyl-3-trifluoromethylcinnamamido)morphinan, 17-methyl-4,5α-epoxy-3-hydroxy-14β-dimethylamino-6β-[N-methyl-trans-3-(3-furyl)acrylamido]morphinan, 17-methyl-4,5α-epoxy-3-hydroxy-14β-dimethylamino-6β-(N-methyl-3-methylcinnamamido)morphinan, 17-methyl-4,5α-epoxy-3-hydroxy-14β-dimethylamino-6β-[N-methyl-3-(4-trifluoromethylphenyl)propiolamido] morphinan, 17-phenethyl-4,5α-epoxy-3-hydroxy-14β-dimethylamino-6β-(N-methyl-3-trifluoromethylcinnamamido)morphinan, 17-phenethyl-4,5α-epoxy-3-hydroxy-14β-dimethylamino-6β-[N-methyl-trans-3-(3-furyl)acrylamido]morphinan, 17-phenethyl-4,5α-epoxy-3-hydroxy-14β-dimethylamino-6β-(N-methyl-3-methylcinnamamido)morphinan, 17-phenethyl-4,5α-epoxy-3-hydroxy-14β-dimethylamino-6β-[N-methyl-3-(4-trifluoromethylphenyl)propiolamido]morphinan, 17-cyclopropylmethyl-4,5α-epoxy-3-hydroxy-14β-methyl-6β-(N-methyl-3-trifluoromethylcinnamamido)-morphinan, 17-cyclopropylmethyl-4,5α-epoxy-3-hydroxy-14β-methyl-6β-[N-methyl-trans-3-(3-furyl)acrylamido]-morphinan, 17-cyclopropylmethyl-4,5α-epoxy-3-hydroxy-14β-methyl-6β-(N-methyl-3-methylcinnamamido)-morphinan, 17-cyclopropylmethyl-4,5α-epoxy-3-hydroxy-14β-methyl-6β-[N-methyl-3-(4-trifluoromethylphenyl)-propiolamido]morphinan, 17-allyl-4,5α-epoxy-3-hydroxy-14β-methyl-6β-(N-methyl-3-trifluoromethylcinnamamido)morphinan, 17-allyl-4,5α-epoxy-3-hydroxy-14β-methyl-6β-[N-methyl-trans-3-(3-furyl)acrylamido]morphinan, 17-allyl-4,5α-epoxy-3-hydroxy-14β-methyl-6β-(N-methyl-3-methylcinnamamido)-morphinan, 17-allyl-4,5α-epoxy-3-hydroxy-14β-methyl-6β-[N-methyl-3-(4-trifluoromethylphenyl)propiolamido]-morphinan, 14β,17-dimethyl-4,5α-epoxy-3-hydroxy-6β-(N-methyl-3-trifluoromethylcinnamamido)morphinan, 14β,17-dimethyl-4,5α-epoxy-3-hydroxy-6β-[N-methyl-trans-3-(3-furyl)acrylamido]morphinan, 14β,17-dimethyl-4,5α-epoxy-3-hydroxy-6β-(N-methyl-3-methylcinnamamido)morphinan, 14β,17-dimethyl-4,5α-epoxy-3-hydroxy-6β-[N-methyl-3-(4-trifluoromethylphenyl)propiolamido] morphinan, 17-phenethyl-4,5α-epoxy-3-hydroxy-14β-methyl-6β-(N-methyl-3-trifluoromethylcinnamamido) morphinan, 17-phenethyl-4,5α-epoxy-3-hydroxy-14β-methyl-6β-[N-methyl-trans-3-(3-furyl)acrylamido] morphinan, 17-phenethyl-4,5α-epoxy-3-hydroxy-14β-methyl-6β-(N-methyl-3-methylcinnamamido)morphinan, 17-phenethyl-4,5α-epoxy-3-hydroxy-14β-methyl-6β-[N-methyl-3-(4-trifluoromethylphenyl)propiolamido]-morphinan, 17-cyclopropylmethyl-3,14β-dihydroxy-6β-(N-methyl-3-trifluoromethylcinnamamido)morphinan, 17-cyclopropylmethyl-3,14β-dihydroxy-6β-[N-methyl-trans-3-(3-furyl)acrylamido]morphinan, 17-cyclopropylmethyl-3,14β-dihydroxy-6β-(N-methyl-3-methylcinnamamido)-morphinan, 17-cyclopropylmethyl-3,14β-dihydroxy-6β-[N-methyl-3-(4-trifluoromethylphenyl)propiolamido]-morphinan, 17-allyl-3,14β-dihydroxy-6β-(N-methyl-3-trifluoromethylcinnamamido)morphinan, 17-allyl-3,14β-dihydroxy-6β-[N-methyl-trans-3-(3-furyl)acrylamido]-morphinan, 17-allyl-3,14β-dihydroxy-6β-(N- methyl-3-methylcinnamamido)morphinan, 17-allyl-3,14β-dihydroxy-6β-[N-methyl-3-(4-trifluoromethylphenyl)-propiolamido]morphinan, 17-methyl-3,14β-dihydroxy-6β-(N-methyl-3-trifluoromethylcinnamamido)morphinan, 17-methyl-3,14β-dihydroxy-6β-[N-methyl-trans-3-(3-furyl)acrylamido]morphinan, 17-methyl-3,14β-dihydroxy-6β-(N-methyl-3-methylcinnamamido)morphinan, 17-methyl-3,14β-dihydroxy-6β-[N-methyl-3-(4-trifluoromethylphenyl)propiolamido]morphinan, 17-phenethyl-3,14β-dihydroxy-6β-(N-methyl-3-trifluoromethylcinnamamido)morphinan, 17-phenethyl-3,14β-dihydroxy-6β-[N-methyl-trans-3-(3-furyl)acrylamido]morphinan, 17-phenethyl-3,14β-dihydroxy-6β-(N-methyl-3-methylcinnamamido)morphinan, 17-phenethyl-3,14β-dihydroxy-6β-[N-methyl-3-(4-trifluoromethylphenyl)propiolamido]morphinan, 17-cyclopropylmethyl-3,14β-dihydroxy-4-methoxy-6β-(N-methyl-3-trifluoromethylcinnamamido)morphinan, 17-cyclopropylmethyl-3,14β-dihydroxy-4-methoxy-6β-[N-methyl-trans-3-(3-furyl)acrylamido]morphinan, 17-cyclopropylmethyl-3,14β-dihydroxy-4-methoxy-6β-(N-methyl-3-methylcinnamamido)morphinan, 17-cyclopropylmethyl-3,14β-dihydroxy-4-methoxy-6β-[N-methyl-3-(4-trifluoromethylphenyl)propiolamido]morphinan, 17-allyl-3,14β-dihydroxy-4-methoxy-6β-(N-methyl-3-trifluoromethylcinnamamido)morphinan, 17-allyl-3,14β-dihydroxy-4-methoxy-6β-[N-methyl-trans-3-(3-furyl)acrylamido]morphinan, 17-allyl-3,14β-dihydroxy-4-methoxy-6β-(N-methyl-3-methylcinnamamido)morphinan, 17-allyl-3,14β-dihydroxy-4-methoxy-6β-[N-methyl-3-(4-trifluoromethylphenyl)propiolamido]morphinan, 17-methyl-3,14β-dihydroxy-4-methoxy-6β-(N-methyl-3-trifluoromethylcinnamamido)morphinan, 17-methyl-3,14β-dihydroxy-4-methoxy-6β-[N-methyl-trans-3-(3-furyl)acrylamido]morphinan, 17-methyl-3,14β-dihydroxy-4-methoxy-6β-(N-methyl-3-methylcinnamamido)morphinan, 17-methyl-3,14β-dihydroxy-4-methoxy-6β-[N-methyl-3-(4-trifluoromethylphenyl)propiolamido]morphinan, 17-phenethyl-3,14β-dihydroxy-4-methoxy-6β-(N-methyl-3-trifluoromethylcinnamamido)morphinan, 17-phenethyl-3,14β-dihydroxy-4-methoxy-6β-[N-methyl-trans-3-(3-furyl)acrylamido]morphinan, 17-phenethyl-3,14β-dihydroxy-4-methoxy-6β-(N-methyl-3-methylcinnamamido)morphinan, 17-phenethyl-3,14β-dihydroxy-4-methoxy-6β-[N-methyl-3-(4-trifluoromethylphenyl)propiolamido]morphinan, 17-cyclopropylmethyl-4,5α-epoxy-3,14β-dihydroxy-5β-methyl-6β-(N-methyl-3-trifluoromethylcinnamamido)morphinan, 17-cyclopropylmethyl-4,5α-epoxy-3,14β-dihydroxy-5β-methyl-6β-[N-methyl-trans-3-(3-furyl)acrylamido]morphinan, 17-cyclopropylmethyl-4,5α-epoxy-3,14β-dihydroxy-5β-methyl-6β-(N-methyl-3-methylcinnamamido)morphinan, 17-cyclopropylmethyl-4,5α-epoxy-3,14β-dihydroxy-5β-methyl-6β-[N-methyl-3-(4-trifluoromethylphenyl)propiolamido]morphinan, 17-allyl-4,5α-epoxy-3,14β-dihydroxy-5β-methyl-6β-(N-methyl-3-trifluoromethylcinnamamido)morphinan, 17-allyl-4,5α-epoxy-3,14β-dihydroxy-5β-methyl-6β-[N-methyl-trans-3-(3-furyl)acrylamido]morphinan, 17-allyl-4,5α-epoxy-3,14β-dihydroxy-5β-methyl-6β-(N-methyl-3-methylcinnamamido)morphinan, 17-allyl-4,5α-epoxy-3,14β-dihydroxy-5β-methyl-6β-[N-methyl-3-(4-trifluoromethylphenyl)propiolamido]morphinan, 5β,17-dimethyl-4,5α-epoxy-3,14β-dihydroxy-6β-(N-methyl-3-trifluoromethylcinnamamido)morphinan, 5β,17-dimethyl-4,5α-epoxy-3,14β-dihydroxy-6β-[N-methyl-trans-3-(3-furyl)acrylamido]morphinan, 5β,17-dimethyl-4,5α-epoxy-3,14β-dihydroxy-6β-(N-methyl-3-methylcinnamamido)morphinan, 5β,17-dimethyl-4,5α-epoxy-3,14β-dihydroxy-6β-[N-methyl-3-(4-trifluoromethylphenyl)propiolamido]morphinan, 17-phenethyl-4,5α-epoxy-3,14β-dihydroxy-5β-methyl-6β-(N-methyl-3-trifluoromethylcinnamamido)morphinan, 17-phenethyl-4,5α-epoxy-3,14β-dihydroxy-5β-methyl-6β-[N-methyl-trans-3-(3-furyl)acrylamido]morphinan, 17-phenethyl-4,5α-epoxy-3,14β-dihydroxy-5β-methyl-6β-(N-methyl-3-methylcinnamamido)morphinan, 17-phenethyl-4,5α-epoxy-3,14β-dihydroxy-5β-methyl-6β-[N-methyl-3-(4-trifluoromethylphenyl)propiolamido]morphinan, 17-cyclopropylmethyl-7,8-didehydro-4,5α-epoxy-3,14β-dihydroxy-6β-(N-methyl-3-trifluoromethyl-cinnamamido)morphinan, 17-cyclopropylmethyl-7,8-didehydro-4,5α-epoxy-3,14β-dihydroxy-6β-[N-methyl-trans-3-(3-furyl)acrylamido]morphinan, 17-cyclopropylmethyl-7,8-didehydro-4,5α-epoxy-3,14β-dihydroxy-6β-(N-methyl-3-methylcinnamamido)-morphinan, 17-cyclopropylmethyl-7,8-didehydro-4,5α-epoxy-3,14β-dihydroxy-6β-[N-methyl-3-(4-trifluoromethylphenyl)propiolamido]morphinan, 17-allyl-7,8-didehydro-4,5α-epoxy-3,14β-dihydroxy-6β(N-methyl-3-trifluoromethylcinnamamido)morphinan, 17-allyl-7,8-didehydro-4,5α-epoxy-3,14β-dihydroxy-6β-[N-methyl-trans-3-(3-furyl)acrylamido]morphinan, 17-allyl-7,8-didehydro-4,5α-epoxy-3,14β-dihydroxy-6β-(N-methyl-3-methylcinnamamido)morphinan, 17-allyl-7,8-didehydro-4,5α-epoxy-3,14β-dihydroxy-6β-[N-methyl-3-(4-trifluoromethylphenyl)propiolamido]morphinan, 17-methyl-7,8-didehydro-4,5α-epoxy-3,14β-dihydroxy-6β-(N-methyl-3-trifluoromethylcinnamamido)-morphinan, 17-methyl-7,8-didehydro-4,5α-epoxy-3,14β-dihydroxy-6β-[N-methyl-trans-3-(3-furyl)acrylamido]-morphinan, 17-methyl-7,8-didehydro-4,5α-epoxy-3,14β-dihydroxy-6β-(N-methyl-3-methylcinnamamido)morphinan, 17-methyl-7,8-didehydro-4,5α-epoxy-3,14β-dihydroxy-6β-[N-methyl-3-(4-trifluoromethylphenyl)propiolamido]morphinan, 17-phenethyl-7,8-didehydro-4,5α-epoxy-3,14β-dihydroxy-6β-(N-methyl-3-trifluoromethylcinnamamido)morphinan, 17-phenethyl-7,8-didehydro-4,5α-epoxy-3,14β-dihydroxy-6β-[N-methyl-trans-3-(3-furyl)acrylamido]morphinan, 17-phenethyl-7,8-didehydro-4,5α-epoxy-3,14β-dihydroxy-6β-(N-methyl-3-methylcinnamamido)morphinan, and 17-phenethyl-7,8-didehydro-4,5α-epoxy-3,14β-dihydroxy-6β-[N-methyl-3-(4-trifluoromethylphenyl)propiolamido]morphinan.

However, the present invention is not limited to these examples. Furthermore, the compounds of the present invention include the (+), (−) and (±) forms.

The compounds of general formula (I) of the present invention can be obtained, specifically, according to the methods described below.

Among the compounds represented by the general formula (I) of the present invention, those wherein A is —XC(=Y)—, —XC(=Y)Z— or —XSO$_2$— (wherein X represents NR$^4$ or O, Y represents O or S, Z represents O, NH or S, and R$^4$ is the same as previously defined) can be obtained, specifically, according to the methods described below.

In general, as shown in Chart 1, said compounds can be obtained by condensing a carboxylic acid derivative represented by the general formula (III) (wherein B and R$^5$ are the same as previously defined), a formic acid derivative represented by the general formula (IV) (wherein Z, B and R$^5$ are the same as previously defined), an isocyanic acid or isothiocyanic acid derivative represented by the general formula (V) (wherein B and R$^5$ are the same as previously defined) or a sulfonic acid derivative represented by the general formula (VI) (wherein B and $R^5$ are the same as previously defined), with a 6-amino or 6-hydroxy compound represented by the general formula (II) (wherein $R^1$, $R^2$, $R^3$, $R^6$, $R^7$ and $R^8$ are the same as previously defined, and E represents $NHR^4$ (wherein $R^4$ is the same as previously defined) or OH).

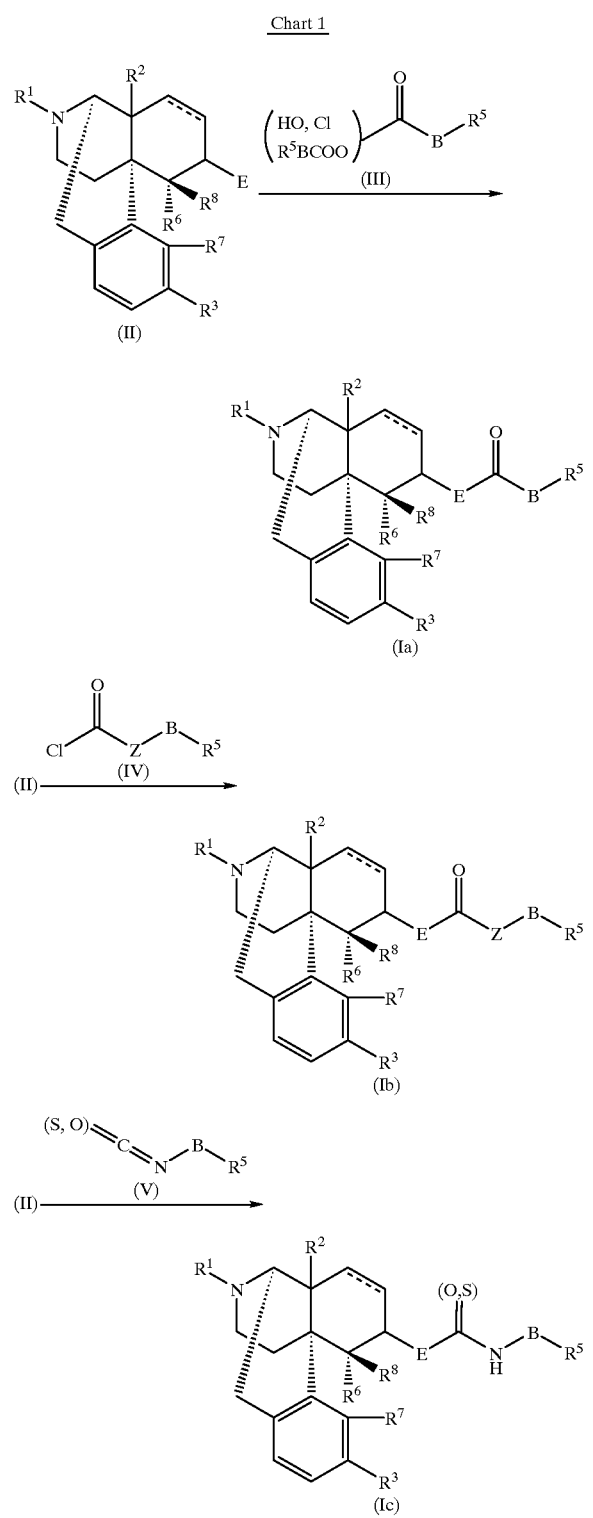

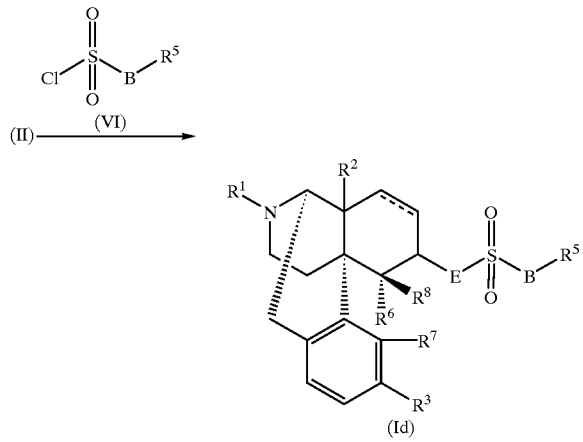

The 6-amino and 6-hydroxy compound used in this condensation can be obtained, specifically, by the processes described below.

As shown in Chart 2, a 6α-amino compound represented by the general formula (IIaα) (wherein $R^1$, $R^2$, $R^3$, $R^6$, $R^7$ and $R^8$ are the same as previously described, and $R^4$ represents a straight-chain or branched alkyl group having 1–5 carbon atoms or an aryl group having 6–12 carbon atoms) is obtained by mixing a 6-keto compound represented the general formula (VIIa) (wherein $R^1$, $R^2$, $R^3$, $R^6$, $R^7$ and $R^8$ are the same as previously defined) and a primary amine represented by the general formula (VIII) (wherein $R^4$ is the same as previously defined) in a solvent and hydrogenating in the presence of suitable amounts of acid and metal catalyst, or reducing with a metal hydride. reducing agent in the presence of acid. The hydrogenation reaction is more preferable in order to obtain the α-amino isomer with high selectivity. However, although the ratio varies according to the substrate, in the case of reduction using a metal hydride reducing agent, both the α form and β isomer are obtained simultaneously. Thus, this method is preferable in that it makes it possible to obtain a compound having the desired stereochemistry by using ordinary separation and purification techniques. In addition, the method in which the amine is obtained is also useful in the case of substrates having functional groups, such as olefins and so on, that react under hydrogenation conditions.

In the case of reduction using a hydrogenation reaction, 1–30 equivalents, and preferably 1–10 equivalents, of amine are used. Although any solvent including alcohols such as methanol and ethanol, ethers such as THF, ether, DME and dioxane, or aromatic hydrocarbons such as benzene and toluene, can be used as a reaction solvent as long as it is inert under hydrogenation conditions, alcohols are preferably used, with methanol used particularly preferably. Although any acid including inorganic acids such as hydrochloric acid, hydrobromic acid, sulfuric acid and phosphoric acid, or organic acids such as sulfonic acids including methanesulfonic acid and p-toluenesulfonic acid, benzoic acid, acetic acid or oxalic acid, can be used as long as it forms a salt with an amine, hydrochloric acid, sulfuric acid and methanesulfonic acid are preferably used. Normally, the use of hydrochloric acid in an amount of I equivalent less than the total amount of base yields satisfactory results. These acids can also be added to a reaction system after converting the substrate and reaction agents into salts in advance. Although all catalysts, including platinum catalysts such as platinum oxide and platinum hydroxide, palladium catalysts such as palladium hydroxide and palladium-carbon, and nickel catalysts such as Raney nickel, that are normally used in hydrogenation reactions can be used as a metal catalyst, platinum catalysts, and particularly platinum oxide, are used preferably. The reaction temperature is −30° C. to 80° C., and preferably −10° C. to 50° C., and the hydrogen pressure is 1–100 atmospheres and preferably 1–30 atmospheres. However, carrying out the reaction at room temperature and atmospheric pressure normally yields preferable results.

When reducing with a metal hydride, 1–30 equivalents, and preferably 1–15 equivalents, of amine are used. Although alcohols solvents such as methanol and ethanol, ethers such as THF, ether, DME and dioxane, or aromatic hydrocarbons such as benzene and toluene, can be used for as a solvent, alcohols are used preferably, with methanol used particularly preferably. Although any acid, including inorganic acids such as hydrochloric acid, hydrobromic acid, sulfuric acid and phosphoric acid, and organic acids such as sulfonic acids including methanesulfonic acid, p-toluenesulfonic acid, benzoic acid, acetic acid and oxalic acid, may be used in the reaction provided that it normally forms a salt with amines, hydrochloric acid, sulfuric acid and methanesulfonic acid are preferably used. In addition, these acids may also be added to the reaction system after converting the substrate and reaction agents into salts in advance. The metal hydride reducing agent used is that which allows the reaction to be carried out relatively stably in the presence of acid, examples of which include sodium borohydride, sodium cyanoborohydride, zinc borohydride, sodium triacetoxyborohydride, tetramethylammonium triacetoxyborohydride and borane-pyridine, with sodium cyanoborohydride used particularly preferably. Although the reaction can be carried out at a reaction temperature of −30° C. to 100° C. and preferably −10° C. to 50° C., satisfactory results can normally be obtained at room temperature.

Chart 2

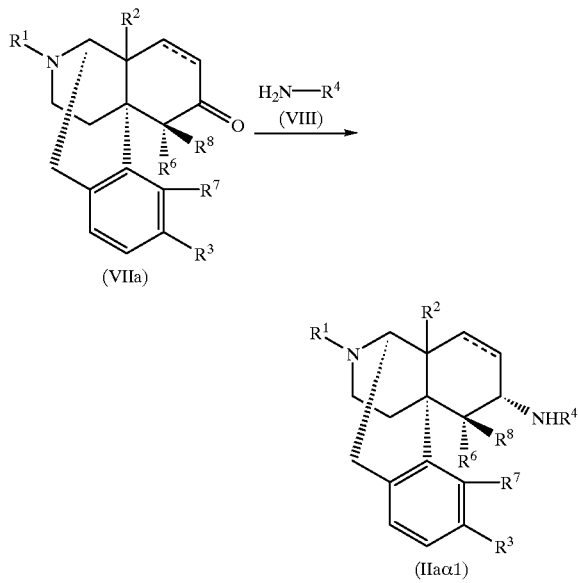

(VIIa)

(IIaα1)

As shown in Chart 3, a 6β-amino compound represented by the general formula (IIaβ2) (wherein $R^1$, $R^2$, $R^3$, $R^6$, $R^7$ and $R^8$ are the same as previously defined, and $R^4$ represents a straight-chain or branched alkyl group having 1–5 carbon atoms or an aryl group having 6–12 carbon atoms) can be obtained from a 6-keto compound represented by the general formula (VIIb) (wherein $R^1$, $R^2$, $R^3$, $R^6$, $R^7$ and $R^8$ are the same as previously defined) with the 3 steps described below.

Step 1 involves the obtaining of an iminium intermediate represented by the general formula (X) (wherein $R^1$, $R^2$, $R^3$, $R^4$, $R^6$, $R^7$ and $R^8$ are the same as previously defined) by reaction of a keto compound with a secondary amine compound having at least one benzyl substituent group represented by the general formula (IX) (wherein $R^4$ is the same as defined above) in the presence of acid. It is desirable that the reaction be carried out while removing water produced either by azeotropic distillation or in the presence of a dehydrating agent. 1–30 equivalents, and preferably 1–10 equivalents, of secondary amine are used. Although any acid, including inorganic acids such as hydrochloric acid, hydrobromic acid, sulfuric acid and phosphoric acid, or organic acids such as sulfonic acids including methanesulfonic acid and p-toluenesulfonic acid, benzoic acid, acetic acid and oxalic acid, can be used in the reaction as long as it forms a salt with amine, hydrochloric acid, sulfuric acid, methanesulfonic acid and benzoic acid are used preferably, with hydrochloric acid and benzoic acid used particularly preferably. A method wherein these acids are added to the system after converting the substrate and reaction agents into salts in advance is also preferably carried out.

Moreover, in the case of carrying out the reaction in the presence of a weak acid, there are cases wherein preferable results are obtained if a strong acid such as inorganic acids such as hydrochloric acid, hydrobromic acid, sulfuric acid and phosphoric acid, or sulfonic acids such as methanesulfonic acid, p-toluenesulfonic acid and campher-sulfonic acid especially a strong acid such as p-toluenesulfonic acid is added as an acid catalyst. Examples of reaction solvents that can be used include ethers such as THF, ether, DME and dioxane, halocarbons such as dichloromethane and chloroform, aromatic hydrocarbons such as benzene, toluene and xylene, esters such as ethyl acetate and methyl acetate, or mixtures thereof. When using a conventional Dean-Stark water separator for the purpose of removing water, solvents are used preferably that have excellent azeotropic efficiency and water separation efficiency, such as aromatic hydrocarbons such as benzene and toluene. In this case, the mixing of a solvent such as ethyl acetate, THF or the like, for the purpose of lowering the azeotropic temperature, in amounts that do not lower water separation efficiency may provide preferable results. Although a temperature of 40–200° C., and preferably 50–150° C., can be considered as a reaction temperature, satisfactory results can be obtained at a reaction temperature of 50–130° C. In addition, it has also been found that a new method is effective wherein a dehydrating agent is packed into a Soxhlet type extractor followed by continuous removal of water. Although any of the solvents mentioned above can be used as a solvent in this case, ethers, esters and aromatic hydrocarbons, and particularly THF, DME, ethyl acetate, benzene and toluene, are preferably used. Although examples of dehydrating agents include molecular sieves and inorganic dehydrating agents such as anhydrous calcium sulfate, anhydrous copper sulfate, anhydrous sodium sulfate, anhydrous magnesium sulfate and calcium chloride, molecular sieves are used particularly preferably. The amount used is 1–100 times, and preferably 1–30 times as calculated from their water retentivity and the amount of moisture theoretically produced. Although a temperature of 40–200° C., and preferably 50–150° C., can be considered as a reaction temperature, satisfactory results are obtained at a reaction temperature of 50–120° C. In addition, a method can also be carried out wherein the reaction is allowed to proceed by directly adding dehydrating agent to the reaction system. Examples of dehydrating agents include molecular sieves, inorganic dehydrating agents such as anhydrous calcium sulfate, anhydrous copper sulfate, anhydrous sodium sulfate, anhydrous magnesium sulfate and calcium chloride, or titanium compounds having dehydration ability such as tetraisopropoxytitanium and titanium tetrachloride. In this case also, an amount used is 1–100 times, and preferably 1–30 times as calculated from the water retentivity and the amount of moisture theoretically produced. Although a temperature of −80–100° C. can be considered as a reaction temperature, satisfactory results are obtained at a reaction temperature of −30–50° C.

Step 2 is a step involving conversion to a 6-N-alkyl-N-benzylamino compound represented by the general formula (XI) (wherein $R^1$, $R^2$, $R^3$, $R^4$, $R^6$, $R^7$ and $R^8$ are the same as previously defined) by reducing with metal hydride reducing agent without isolating iminium salt. Although the same solvent used in step 1 may be used as is for the reaction solvent of this step, preferable results are obtained by reacting after mixing an alcohols such as methanol or ethanol, and particularly methanol. Naturally, the reaction may also be carried out with only alcohols such as methanol or ethanol after distilling off the reaction solvent of step 1 under reduced pressure. The reaction can be carried out with metal hydride reducing agent that is relatively stable under conditions in the presence of acid, such as sodium borohydride, sodium cyanoborohydride, zinc borohydride, sodium triacetoxyborohydride, tetramethylammonium triacetoxyborohydride and borane-pyridine, particularly preferably sodium cyanoborohydride. The reaction is carried out a reaction temperature of −20–150° C., and preferably 0–120° C. The resulting 6-N-alkyl-N-benzylamino compound represented by the general formula (XI) (wherein $R^1$, $R^2$, $R^3$, $R^4$, $R^6$, $R^7$ and $R^8$ are the same as previously defined) can also be obtained using a secondary amine by performing reductive amination using the metal hydride reducing agents of Chart 2. Moreover, if this step is performed using a corresponding secondary amine, the compound of general formula (I) can be obtained wherein A is —$NR^4$—.

Step 3 involves removing a benzyl group under reducing conditions to form a 6β-amino form (IIaβ2). In this step, reacting the substrate either after converting into a salt in advance using an inorganic acid such as hydrochloric acid, hydrobromic acid, sulfuric acid or phosphoric acid, or an organic acid such as sulfonic acids including methanesulfonic acid, p-toluenesulfonic acid or campher-sulfonic acid, benzoic acid, acetic acid, oxalic acid or phthalic acid, and preferably hydrochloric acid or phthalic acid, or adding suitable amount of these acids prior to the reaction, yields favorable results. Since there are cases in which a resulting secondary amine salt can be purified as a crystal depending on the acid, selection of acid is important. For example, when phthalic acid is used with a compound wherein $R^1$ is a cyclopropylmethyl group, $R^2$ and $R^3$ are hydroxy groups, $R^4$ is a methyl group, $R^6$ and $R^7$ are together —O— and $R^8$ is a hydrogen atom, a crystalline salt is obtained that is easily purified. Although any solvent such as alcohol-based solvents such as methanol and ethanol, ethers such as THF, ether, DME and dioxane, and organic hydrocarbons such as benzene and toluene, can be used as a reaction solvent provided it is inert under hydrogenation conditions, alcohols are used preferably, with methanol used particularly preferably. Although any catalyst that is used in normal hydrogenation reactions, such as, platinum catalysts such as platinum oxide and platinum hydroxide, palladium catalysts such as palladium hydroxide and palladium-carbon, and nickel catalysts such as Raney nickel, can be used as a metal catalyst, palladium catalysts, and particularly palladium-carbon, are particularly preferably used. The reaction temperature is −30 to 80° C., and preferably −10 to 50° C. while hydrogen pressure is 1 to 100 atmospheres, and preferably 1 to 30 atmospheres. However, carrying out the reaction at room temperature and atmospheric pressure normally yields favorable results.

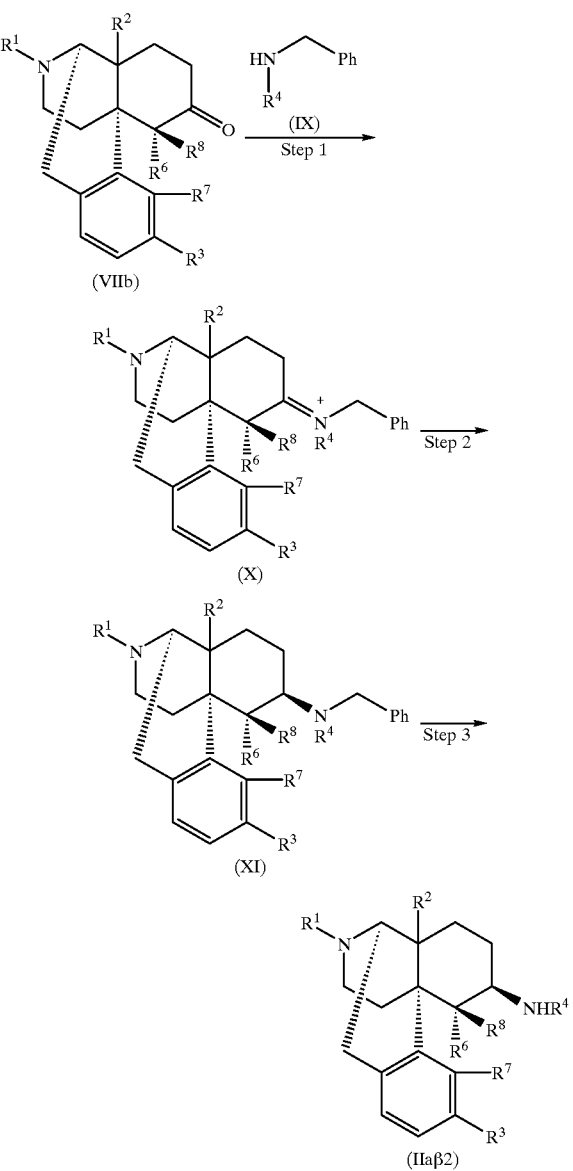

Chart 3

In addition, when ammonium acetate is used in place of primary amine in the reductive amination reaction shown in Chart 2, when dibenzylamine is used in the method shown in Chart 3, or after converting ketone into oxime using the method described in the literature (J. Med. Chem., 27, 1727 (1984)), a primary amine can be obtained by reducing with borane or under hydrogenation conditions. This primary amine can be converted into a secondary amine by effecting the acylation and reduction of step 2. This is also useful as an alternative route for obtaining the secondary amine.

As shown in Chart 4, a 6-α-alcohol represented by the general formula (IIbα) (wherein $R^1$, $R^2$, $R^3$, $R^6$, $R^7$ and $R^8$ are the same as previously defined) is obtained either by reducing with metal hydride reducing agent or hydrogenation in the presence of acid and metal catalyst. Although metal hydride reducing agents including sodium borohydride, sodium cyanoborohydride, zinc borohydride, sodium triacetoxyborohydride, L-selectride and lithium aluminum hydride can be used, sufficiently satisfactory results are obtained with sodium borohydride. Although solvents including alcohols such as methanol and ethanol, and ethers such as THF, ether, DME and dioxane are used, alcohols, and particularly methanol, are preferably used. In the case of hydrogenation, examples of solvents that are used include alcohols such as methanol and ethanol, and ethers such as THF, ether and dioxane, with alcohols being used preferably, and methanol being used particularly preferably.

Although acids such as inorganic acids such as hydrochloric acid, hydrobromic acid, sulfuric acid or phosphoric acid, and organic acids such as sulfonic acids including methanesulfonic acid and p-toluenesulfonic acid, benzoic acid are used, acetic acid or oxalic acid, hydrochloric acid is preferably used. Although all catalysts that are used in normal hydrogenation reactions such as platinum catalysts such as platinum oxide or platinum hydroxide, palladium catalysts such as palladium hydroxide or palladium-carbon, and nickel catalysts such as Raney nickel can be used as a metal catalyst, platinum catalysts, and particularly platinum oxide are preferably used. Although the reaction can be carried out at a reaction temperature of −30–80° C., and preferably −10–50° C., and under a hydrogen pressure of 1–100 atmospheres, and preferably 1–30 atmospheres, favorable results are normally obtained at room temperature and under atmospheric pressure.

Chart 4

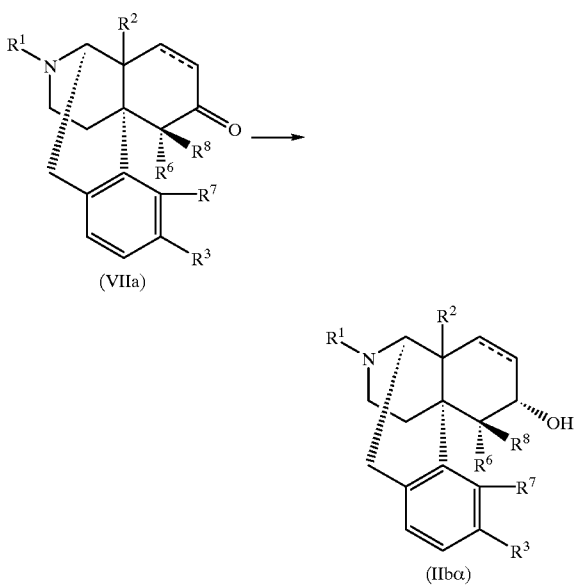

As shown in Chart 5, a 6β-hydroxy form represented by the general formula (IIbβ) (wherein $R^1$, $R^2$, $R^3$, $R^6$, $R^7$ and $R^8$ are the same as previously defined) can be obtained by reacting a 6-keto form represented by the general formula (VIIa) (wherein $R^1$, $R^2$, $R^3$, $R^6$, $R^7$ and $R^8$ are the same as previously defined) with formamidine sulfinic acid in the presence of a base. Preferable examples of a base used include inorganic bases such as sodium hydroxide, potassium hydroxide, potassium carbonate and sodium bicarbonate, with sodium hydroxide being used particularly preferably. Although examples of reaction solvents used include water, alcohols such as methanol and ethanol, and aprotic, dipolar solvents such as DMF and DMSO, the use of water normally yields satisfactory results. Although a temperature of 0–150° C. is considered as a reaction temperature, a temperature of 60–100° C. is preferable.

Chart 5

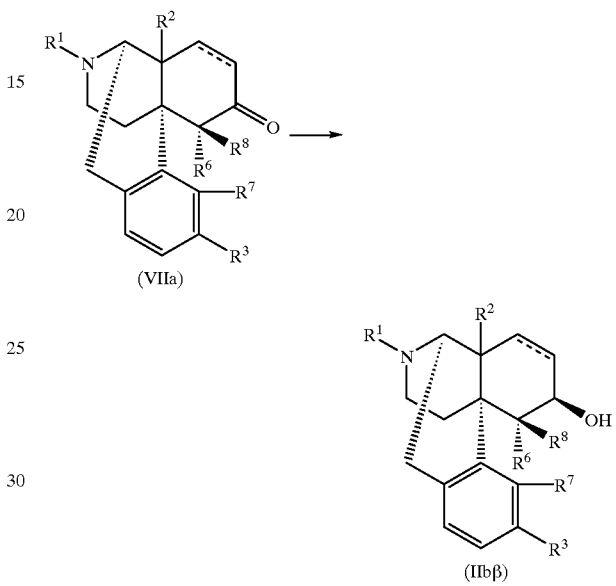

Among the 6-amino or 6-hydroxy compound synthesized in the above method, particularly a compound wherein $R^3$ is a hydrogen atom, is obtained by methods similar to those shown in Charts 2, 3, 4 and 5, using as a starting material a 3-dehydroxy-6-keto compound represented by the general formula (VIIe) (wherein $R^1$, $R^2$, $R^6$, $R^7$ and $R^8$ are the same as previously defined, provided that $R^7$ is not a hydroxy group), obtained by using as a substrate a 3-hydroxy-6-keto compound represented by the general formula (VIIc) (wherein $R^1$, $R^2$, $R^6$, $R^7$ and $R^8$ are the same as previously defined, provided that $R^7$ is not a hydroxy group) according to the scheme shown in Chart 6. In addition, an intermediate, wherein $R^3$ is a siloxy group, can be obtained by methods similar to those shown in Charts 2, 3, 4 and 5, by using for as a starting material a 3-siloxy-6-keto form represented by the general formula (VIIf) (wherein $R^1$, $R^2$, $R^6$, $R^7$ and $R^8$ are the same as previously defined, provided that $R^7$ is not a hydroxy group and G represents an alkylsilyl group), obtained from a 3-hydroxy-6-keto compound (VIIc) by the scheme shown in Chart 7.

Namely, as shown in Chart 6, the first step for obtaining a 3-dehydroxy-6-keto compound represented by the general formula (VIIe) (wherein $R^1$, $R^2$, $R^6$, $R^7$ and $R^8$ are the same as previously defined, provided that $R^7$ is not a hydroxy group) is a step wherein trifluoromethane sulfonic anhydride is caused to act on a phenolic hydroxyl group in the presence of a base to form a trifrate form represented by the general formula (VIId) (wherein $R^1$, $R^2$, $R^6$, $R^7$ and $R^8$ are the same as previously defined, provided that $R^7$ is not a hydroxy group). Although solvents such as halocarbons such as dichloromethane and chloroform, ethers such as THF, ether, DME and dioxane, and amines having large steric hindrances that can be used as solvents such as 2,6-lutidine and diisopropylethylamine, can be considered for use as a reaction solvent, halocarbons, and particularly dichloromethane, are preferably used.

Although tertiary amines such as triethylamine, diisopropylethyl amine and proton sponge, as well as pyridine, 2,6-lutidine and imidazole are used as a coexisting base, 2,6-lutidine is preferably used. Although the reaction can be carried out at −30–50° C., satisfactory results can be normally attained at a temperature of 0° C. to room temperature normally yields. Step 2 is a step wherein a trifrate form is reduced with formic acid in the presence of phosphorous ligand and a base using a palladium catalyst. Although amines usable as solvents such as triethylamine and diisopropylethylamine, ethers such as THF, ether, DME and dioxane, aromatic hydrocarbons such as benzene and toluene, and aprotic dipolar solvents such as DMF and DMSO are used for the reaction solvent, DMF is particularly preferably used. Although zero-valent complexes such as tetrakuistriphenylphosphine palladium and bisbenzylideneacetone palladium, and bivalent complexes such as palladium acetate and palladium chloride are frequently used for the palladium catalyst, palladium acetate is used normally.

Although monodentate phosphines such as trimethylphosphine, triethylphosphine, triphenylphosphine and tris-o-toluphosphine, and bidentate phosphines such as bis-(diphenylphosphino)methane, 1,2-bis-(diphenylphosphino) ethane, 1,3-bis-(diphenylphosphino) propane and 1,1'-bis-diphenylphosphinoferrocene, are used as a phosphorous ligand, 1,1'-bis-diphenylphosphinoferrocene is particularly preferably used. Although amines such as triethylamine and diisopropylethylamine, and inorganic salts such as silver carbonate, sodium acetate and potassium acetate, are used as a base used in the reaction, triethylamine is preferably used. The reaction is carried out at a reaction temperature of 0–150° C., and satisfactory results are normally obtained at a room temperature to 80° C.

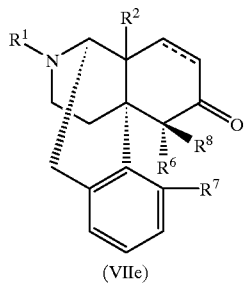

(VIIe)

As shown in Chart 7, a 3-hydroxy-6-keto form represented by the general formula (VIIc) (wherein $R^1$, $R^2$, $R^6$, $R^7$ and $R^8$ are the same as previously defined) may be reacted with silylchloride in the presence of a base to obtain a 3-siloxy-6-keto form represented by the general formula (VIIf) (wherein $R^1$, $R^2$, $R^6$, $R^7$ and $R^8$ are the same as previously defined, provided that $R^7$ is not a hydroxy group and G represents an allcylsilyl group). Although trimethylsilylchloride, triphenylsilylchloride, t-butyldimethylsilylchloride and diphenylmethylsilylchloride are mentioned as silylchlorides, t-butyldimethylsilylchloride is preferably used. Although tertiary amines such as triethylamine, diisopropylethylamine and proton sponges, as well as pyridine, dimethylaminopyridine and imidazole are used as a base, imidazole is preferably used. Although halocarbons such as dichloromethane, chloroform, carbon tetrachloride and 1,2-dichloroethane, ethers, such as ether, THF, DME and dioxane, and pyridine are used as a solvent, dichloromethane is preferably used. The reaction can be carried out within a range of −80–100° C., and preferable results are obtained particularly in the vicinity of 0° C. to room temperature. Although the reaction can be carried out in 5–300 minutes, since there are cases in which 6th position ketone groups are also enolsilylated when reaction time is lengthened particularly with respect to compounds wherein—
is a single bond and R6 and R7 together are —O—, a reaction time of 5–60 minutes is preferable.

Chart 6

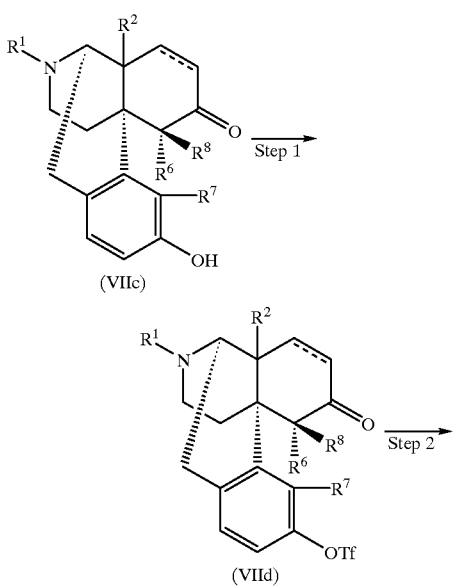

Chart 7

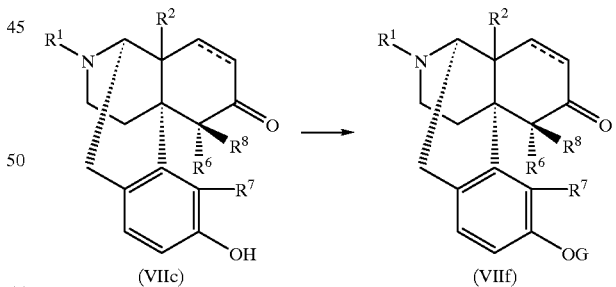

As shown in Chart 8, compounds wherein X is $NR^4$ can be obtained by condensing a 6-amino form represented by the general formula (IIa) (wherein $R^1$, $R^2$, $R^3$, $R^6$, $R^7$ and $R^8$ are the same as previously defined, and $R^4$ represents a straight-chain or branched alkyl group having 1–5 carbon atoms or an aryl group having 6–12 carbon atoms), obtained by the methods shown in Charts 2 and 3, with a carboxylic acid and carboxylic acid derivative represented by the general formula (III) (wherein B and $R^5$ are the same as previously defined), or with a formic acid derivative represented by the general formula (IV) (wherein Z, B and $R^5$ are the same as previously defined), or with a isocyanic acid or isothiocyanic acid derivative represented by the general formula (V) (wherein B and $R^5$ are the same as previously defined), or with a sulfonic acid derivative represented by the general formula (VI) (wherein B and $R^5$ are the same as previously defined), etc.

Condensation with a carboxylic acid derivative can be performed by reacting a 6-amino form with an acid chloride or acid anhydride that reacts in the presence of a base, or by reacting with carboxylic acid itself using, for example, N,N'-dicyclohexylcarbodiimide (abbreviated as DCC), 1,1'-carbonyldiimidazole, or bis-(2-oxo-3-oxazolidinyl) phosphinate chloride (abbreviated as BOPC), etc. Acid chloride or acid anhydride is used in an amount of 1–20 equivalents, and preferably 1–5 equivalents. Although halocarbons such as dichloromethane, chloroform, carbon tetrachloride and 1,2-dichloroethane, ethers such as ether, THF, DME and dioxane, pyridine, water or a mixture of these are used as reaction solvents, when using acid chloride, chloroform or a mixed solvent of THF and water is used preferably. In the case of using acid anhydride, pyridine is preferably used both as base and solvent. Although organic bases such as tertiary amines including triethylamine, diisopropylethylamine and proton sponges, pyridine, dimethylaminopyridine and imidazole, and inorganic bases such as potassium carbonate, sodium carbonate, sodium bicarbonate, sodium hydroxide and potassium hydroxide are used as bases, when using chloroform as the solvent, trimethylamine is normally used in an amount of 1–20 equivalents, and preferably 1–5 equivalents. In the case of using a mixed solvent of THF and water, the use of potassium carbonate, sodium carbonate or sodium bicarbonate in an amount of 1–20 equivalents, and preferably 1–5 equivalents, provides satisfactory results. The reaction can be carried out within a range of –80–100° C., and preferable results are obtained particularly at a temperature of from 0° C. to room temperature. In the case of using DCC as a condensing agent, an amount of 1–20 equivalents preferably 1–5 equivalents is used. Although halocarbons such as dichloromethane, chloroform, carbon tetrachloride and 1,2-dichloroethane, and ethers such as ether, THF, DME and dioxane are used as reaction solvents, dichloromethane and chloroform are particularly preferably used. Although organic bases such as tertiary amines including triethylamine, diisopropylethylamine and proton sponges, as well as pyridine, dimethylaminopyridine and imidazole are used as coexisting bases, dimethylaminopyridine in an amount of 0.01–2 equivalents is used particularly preferably. The reaction can be carried out within a range of –80–100° C., and preferable results are obtained in the vicinity of 0° C. to room temperature in particular.

In the case of using 1,1'-carbonyldiimidazole as a condensing agent, an amount of 1–20 equivalents, and preferably 1–5 equivalents is used. Although ethers such as ether, THF, DME and dioxane, and halocarbons such as dichloromethane, chloroform, carbon tetrachloride and 1,2-dichloroethane are used as reaction solvents, THF is particularly preferably used. The reaction can be carried out within a range of –20–120° C., and a temperature in the vicinity of room temperature to 100° C. is particularly preferable. In the case of using BOPCL as a condensing agent, it is used in an amount of 1–20 equivalents, and preferably 1–5 equivalents. Examples of solvents used for the reaction (solvent) include halocarbons such as dichloromethane, chloroform, carbon tetrachloride and 1,2-dichloroethane, and ethers such as ether, THF, DME and dioxane, though dichloromethane and chloroform are particularly preferably used. Although organic bases such as tertiary amines including triethylamine, diisopropylethylamine, proton sponge and N-ethylpiperidine, as well as pyridine, dimethylaminopyridine and imidazole are used as coexisting bases, N-ethylpiperidine in an amount of 1–20 equivalents, and preferably 1–5 equivalents, is particularly preferably used. The reaction can be carried out within a range of –80–100° C., and preferable results are obtained at 0–50° C. in particular.

Condensation with a formic acid derivative can be performed by reacting a 6-amino form with 1–20 equivalents and preferably 1–5 equivalents of an acid chloride that reacts in the presence of base. Although halocarbons such as dichloromethane, chloroform, carbon tetrachloride and 1,2-dichloroethane, ethers such as ether, THF, DME and dioxane, water or mixtures of these solvents are used as reaction solvents, chloroform and a mixed solvent of THF and water are particularly preferably used. Although organic bases such as tertiary amines including triethylamine, diisopropylethylamine and proton sponge, pyridine, dimethylaminopyridine and imidazole, and inorganic bases such as potassium carbonate, sodium carbonate and sodium bicarbonate are used as bases, triethylamine in an amount of 1–20 equivalents, and preferably 1–5 equivalents provides satisfactory results when chloroform is used as a solvent, while potassium carbonate, sodium carbonate and sodium bicarbonate used in an amount of 1–20 equivalents, and preferably 1–5 equivalents, normally provides favorable results when a mixed solvent of THF and water is used as a solvent. The reaction can be carried out within a range of –80–100° C., and preferable results are obtained from 0° C. to the vicinity of room temperature.

Condensation with an isocyanic acid or isothiocyanic acid derivative can be performed by reacting 1–20 equivalents, and preferably 1–5 equivalents, of a corresponding isocyanate ester with a 6-amino form. Although halocarbons such as dichloromethane, chloroform, carbon tetrachloride and 1,2-dichloroethane, and ethers such as ether, THF, DME and dioxane are used as reaction solvents, chloroform is particularly preferably used. The reaction can be carried out within a range of –80–100° C., and preferable results are obtained from 0° C. to the vicinity of room temperature.

Condensation with a sulfonic acid derivative can be performed by reacting 1–20 equivalents, and preferably 1–5 equivalents, of the corresponding sulfonate chloride with a 6-amino form in the presence of base. Examples of bases that are used include tertiary amines such as triethylamine, diisopropylethylamine and proton sponges, as well as pyridine, dimethylaminopyridine and imidazole. Although halocarbons such as dichloromethane, chloroform, carbon tetrachloride and 1,2-dichloroethane, ethers such as ether, THF, DME and dioxane, and pyridine are used as bases, pyridine is particularly preferably used as both base and solvent. The reaction can be carried out within a range of –80–100° C., and preferable results are obtained from 0° C. to the vicinity of room temperature in particular.

Chart 8

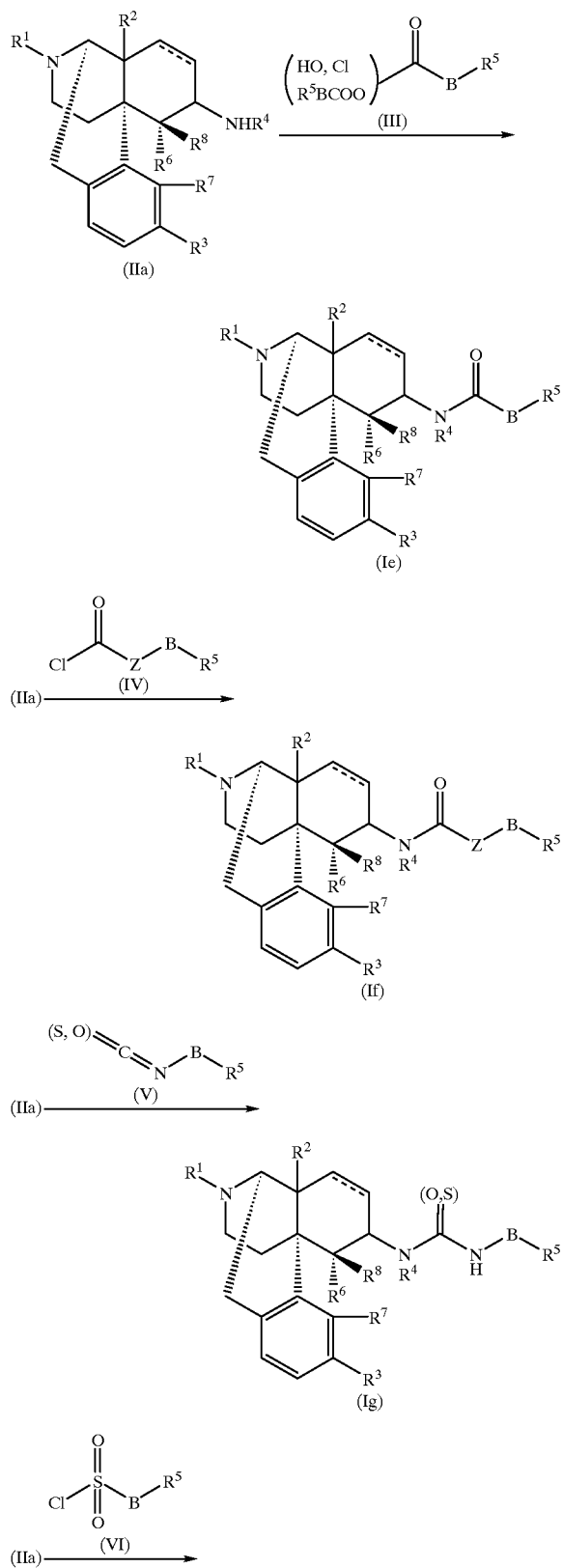

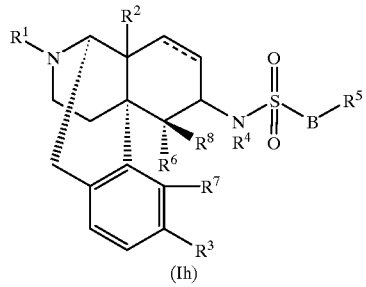

In the case of compounds wherein $R^3$ is a hydroxy group in particular, since there are cases in which phenolic hydroxyl groups may react simultaneously, after carrying out step 1 in the same manner as shown in Chart 8, as shown in Charts 9–11 with carboxylic acid derivative, formic acid derivative and isocyanic acid or isothiocyanic acid derivative, the target compound can be obtained by performing alkaline treatment for step 2. Examples of solvents used for a reaction solvent of step 2 include water, alcohols such as methanol and ethanol, ethers such as ether, THF, DME and dioxane, or mixed solvents of those solvents. When solubility is inadequate, halocarbons such as dichloromethane and chloroform can be suitably added. Examples of bases used include inorganic bases such as potassium carbonate, sodium carbonate, sodium bicarbonate, sodium hydroxide and potassium hydroxide. Normally, 1–20 equivalents, and preferably 1–10 equivalents, of potassium carbonate, sodium hydroxide and so forth are used preferably. The reaction can be carried out within a range of −80–100° C., and favorable results are obtained from 0–50° C. in particular.

Chart 9

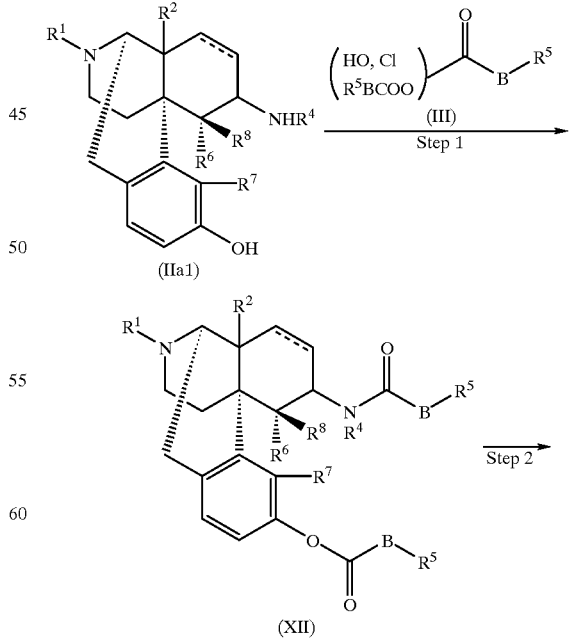

-continued

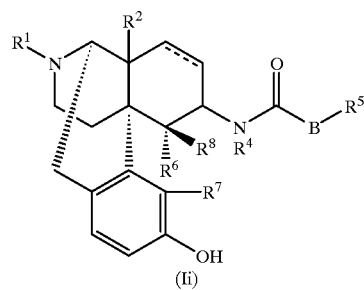
(Ii)

Chart 10

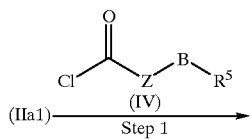

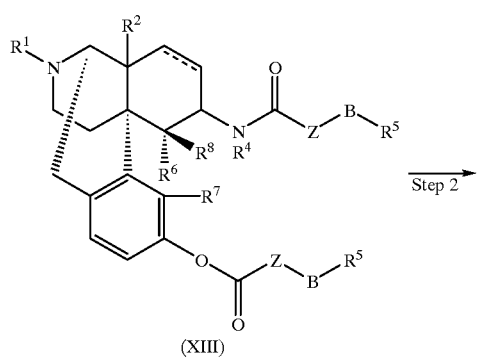
(XIII)

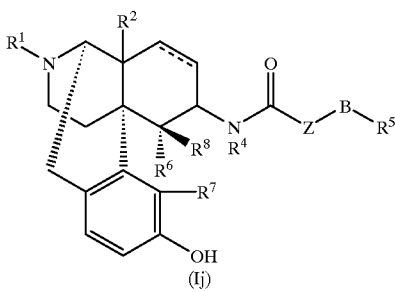
(Ij)

Chart 11

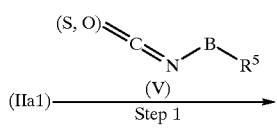

-continued

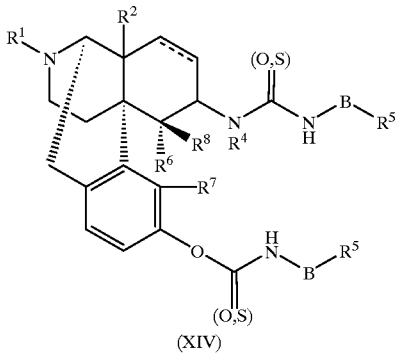
(XIV)

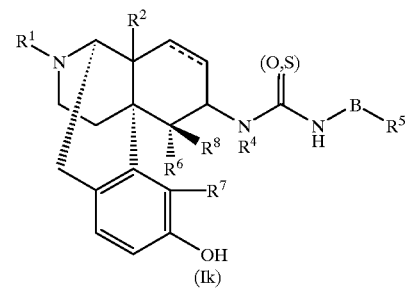
(Ik)

When condensing compounds wherein $R^3$ is a hydroxy group with sulfonic acid derivative, as shown in Chart 12, preferable results are obtained by using a 3-siloxy-6-amino form, wherein phenolic hydroxyl groups are protected in advance with silylether groups and so forth, represented by the general formula (IIc) (wherein R1, R2, R4, R6, R7, R8 and G are the same as previously defined). Naturally, the following method can also be applied to condensation with a carboxylic acid derivative, formic acid derivative and isocyanic acid or isothiocyanic acid derivative. Namely, this method involves removing silyl groups after carrying out step 1 in the same manner as shown in Chart 8. Although quaternary ammonium salts such as tetrabutylammonium fluoride, tetrabutylammonium chloride and pyridinium hydrofluoride, or acids such as acetic acid, hydrochloric acid, sulfuric acid and hydrofluoric acid, are used for removal of silyl groups in step 2, normally 1–20 equivalents, and preferably 1–5 equivalents, of tetrabutylammonium fluoride are used. Although ethers such as THF, ether, DME and dioxane, halocarbons such as dichloromethane and chloroform, and acetonitrile are used as solvents, THF is particularly preferably used. Although the reaction can be carried out at −20–100° C., satisfactory results can normally be obtained at room temperature.

Chart 12

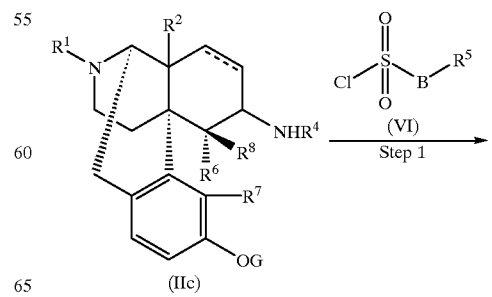
(IIc)

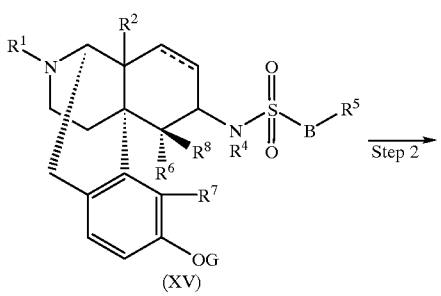

(XV)

Step 2

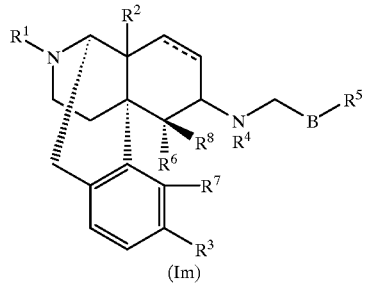

(Im)

As shown in Chart 14, compounds wherein X is O can be obtained by condensing a 6-hydroxy form represented by the general formula (IIb) (wherein $R^1$, $R^2$, $R^3$, $R^6$, $R^7$ and $R^8$ are the same as previously defined) obtained in Charts 4 and 5, with a carboxylic acid derivative (III), a formic acid derivative (IV), an isocyanic acid, an isothiocyanic acid derivative (V), or sulfonic acid derivative (VI) and so forth.

Condensation with a carboxylic acid derivative can be performed by treatment of a 6-hydroxy compound with 1–20 equivalents, and preferably 1–5 equivalents of an acid chloride or acid anhydride in the presence of base. Although halocarbons such as dichloromethane, chloroform, carbon tetrachloride and 1,2-dichloroethane, ethers such as ether, THF, DME and dioxane, and pyridine are used as a reaction solvents, chloroform is used preferably wnen using acid chloride, while pyridine is used preferably in the case of using acid anhydride. Although tertiary amines such as triethylamine, diisopropylethylamine and proton sponge, as well as pyridine, dimethylaminopyridine and imidazole are used as bases, the use of both diisopropylethylamine and dimethylaminopyridine in an amount of 1–20 equivalents, and preferably 1–5 equivalents, normally provides satisfactory results. The reaction can be carried out at −80 to 100° C., and preferable results are obtained at a temperature of from the vicinity of room temperature to 80° C. in particular.

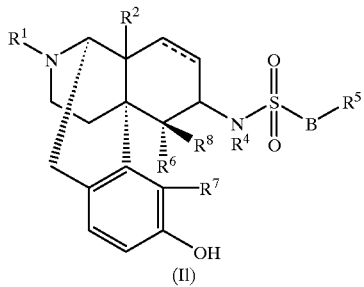

(II)

In addition, a 6-amino form represented by the general formula (Im) (wherein $R^1$, $R^2$, $R^3$, $R^4$, B, $R^5$, $R^6$, $R^7$ and $R^8$ are the same as previously defined), in which A is —$NR^4$—, is obtained by reducing an amide form represented by the general formula (Ie') (wherein $R^1$, $R^2$, $R^3$, $R^4$, $R^5$, $R^6$, $R^7$, $R^8$ and B are the same as previously defined) using a metal hydride reducing agent. Examples of reducing agents used include metal hydride compounds having a strong reducing activity such as lithium aluminum hydride, aluminum diisobutylaluminumhydride, aluminum hydride, lithium borohydride and diborane, 1–20 equivalents, and preferably 1–5 equivalents of diborane are particularly preferably used. Ethers such as THF, DME, ether and dioxane are used preferably as a solvent when using lithium aluminum hydride, lithium borohydride or diborane, with THF being used particularly preferably. Aromatic hydrocarbons such as benzene and toluene are used preferably as a solvent when diisobutylaluminumhydride or aluminum hydride are used. The reaction can be carried out within a range of −40 to 100° C., and a temperature from 0° C. to the vicinity of room temperature is preferable.

Condensation with a formic acid derivative can be performed by reacting a 6-hydroxy form with 1–20 equivalents, and preferably 1–5 equivalents, of an acid chloride that reacts in the presence of a base. Although halocarbons such as dichloromethane, chloroform, carbon tetrachloride and 1,2-dichloroethane, and ethers such as ether, THF, DME and dioxane are used as reaction solvents, chloroform and carbon tetrachloride are used particularly preferably. Although tertiary amines such as triethylamine, diisopropylethylamine and proton sponges, as well as pyridine, dimethylaminopyridine and imidazole are used as bases, the use of both diisopropylethylamine and dimethylaminopyridine in an amount of 1–20 equivalents, and preferably 1–5 equivalents, normally provides satisfactory results. The reaction can be carried out within a range of −80 to 100° C., and preferable results are obtained from the vicinity of room temperature to 80° C. in particular.

Condensation with an isocyanic acid or isothiocyanic acid derivative can be performed by reacting 1–20 equivalents, and preferably 1–5 equivalents, of the corresponding isocyanate ester with a 6-hydroxy form. Although halocarbons such as dichloromethane, chloroform, carbon tetrachloride and 1,2-dichloroethane, and ethers such as ether, THF, DME and dioxane are used as reaction solvent, chloroform is used particularly preferably. The reaction can be carried out within a range of −80 to 100° C., and preferable results are obtained at a temperature of from the vicinity of room temperature to 80° C. in particular.

Condensation with a sulfonic acid derivative can be carried out by treatment of 1–20 equivalents, and preferably Chart 13

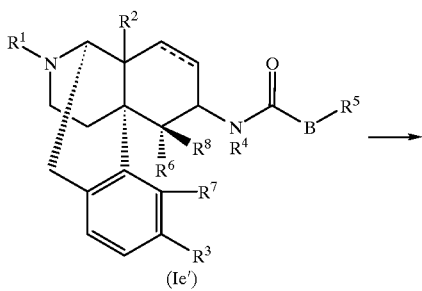

(Ie')

1–5 equivalents, of a corresponding sulfonic chloride with a 6-hydroxy form in the presence of a base. Examples of a base used include tertiary amines such as triethylamine, diisopropylethylamine and proton sponges, as well as pyridine, dimethylaminopyridine and imidazole. Although halocarbons such as dichloromethane, chloroform, carbon tetrachloride and 1,2-dichloroethane, ethers such as THF, DME and dioxane, and pyridine are used as reaction solvent, pyridine is used particularly preferably, both as base and solvent. The reaction can be carried out within a range of −80 to 100° C., and preferable results are obtained at a temperature of the vicinity of room temperature to 80° C. in particular.

Chart 14

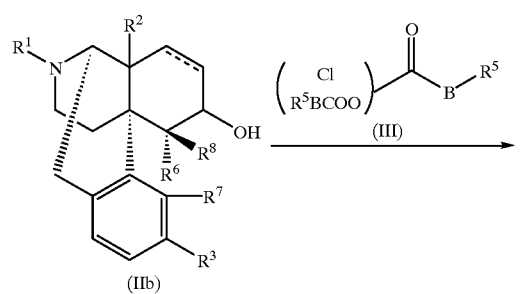

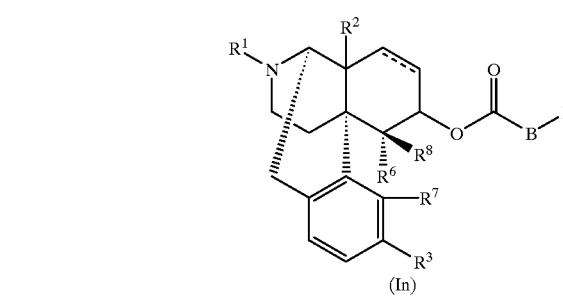

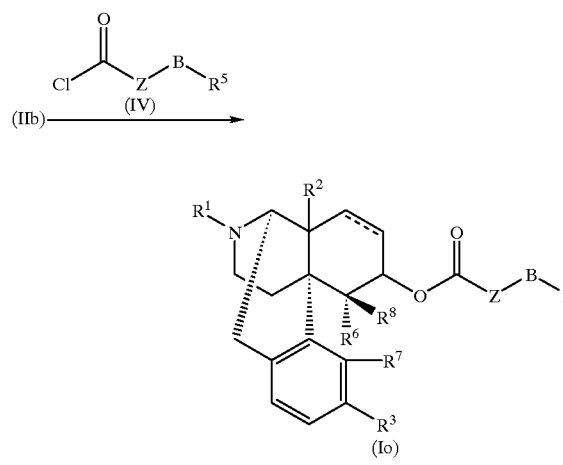

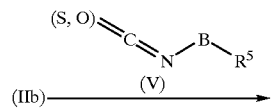

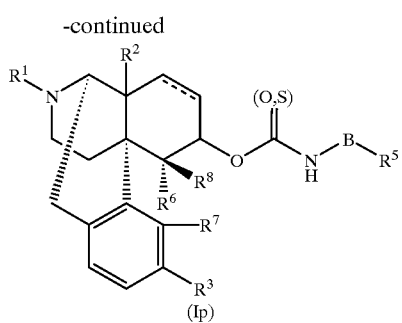

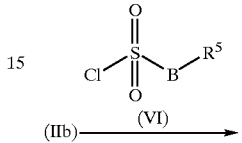

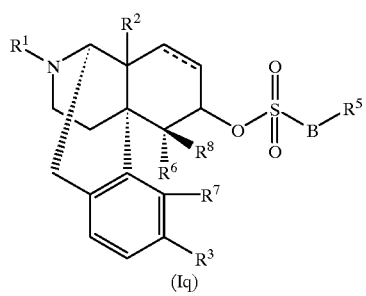

In the case of compounds wherein $R^3$ is a hydroxy group in particular, since phenolic hydroxyl group also reacts simultaneously, in the case of carboxylic acid derivative, formic acid derivative, and isocyanic acid or isothiocyanic acid derivative, after performing a condensation reaction in the same manner as shown in Chart 14 as step 1, the target compound can be obtained by performing alkaline treatment for step 2 as shown in Charts 15–17. Examples of solvents used as reaction solvent of step 2 include alcohols such as methanol and ethanol, and when solubility is not adequate, halocarbons such as dichloromethane, and chloroform can ben suitably added. Examples of a base used include inorganic bases such as potassium carbonate, sodium carbonate, sodium bicarbonate, sodium hydroxide and potassium hydroxide, with potassium carbonate normally being used preferably. The reaction can be carried out within a range of −80 to 100° C., and preferable results are obtained at −20 to 50° C. in particular. However, since solvolysis of functional group at the 6 position may also proceed, in such cases, this problem is solved by either lowering the reaction temperature or shortening the reaction time.

Chart 15

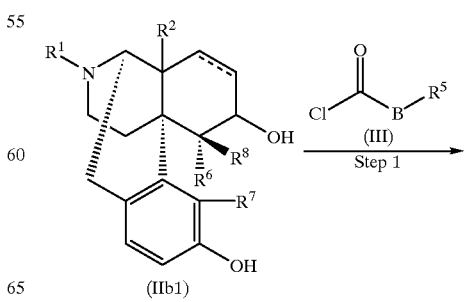

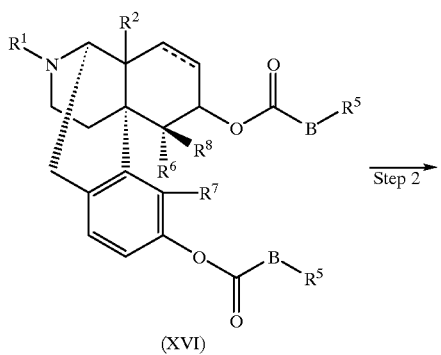

(XVI)

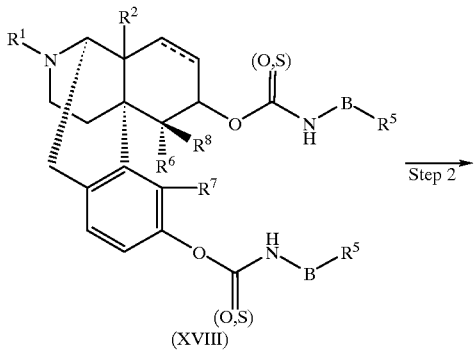

(XVIII)

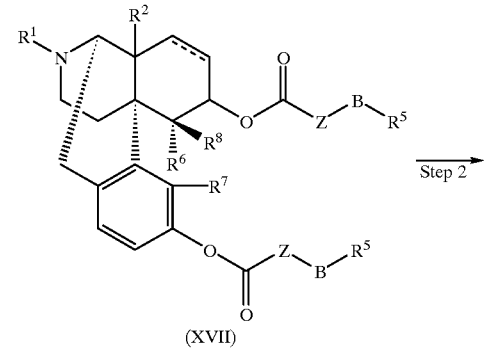

(Ir)

Chart 16

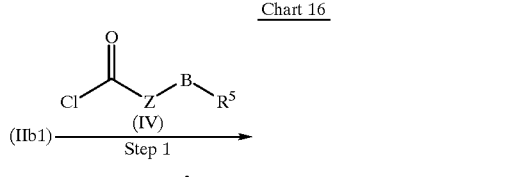

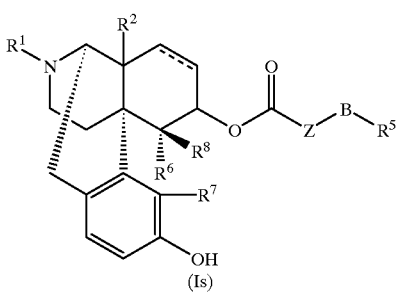

(XVII)

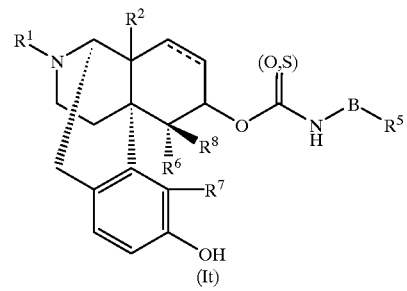

(It)

The use of a 3-siloxy-6-hydroxy form represented by the general formula (IId) (wherein $R^1$, $R^2$, $R^6$, $R^7$, $R^8$ and G are the same as previously defined), in which phenolic hydroxyl groups are protected in advance with silylether group and so forth, for condensation with a sulfonic acid derivative yields preferable results. Naturally, this method can be carried out for condensation with a carboxylic acid derivative, a formic acid derivative, an isocyanic acid or an isothiocyanic acid derivative. After performing condensation in the same manner as shown in Chart 14 as step 1, silyl group is removed in step 2. Although quaternary ammonium salts such as tetrabutylammonium fluoride, tetrabutylammonium chloride and pyridinium hydrofluoride, or acids such as acetic acid, hydrochloric acid, sulfuric acid and hydrofluoric acid, may be used for removal of silyl groups, normally 1–20 equivalents, and preferably 1–5 equivalents, of tetrabutylammonium fluoride are used. Examples of solvents used include ethers such as THF, DME and dioxane, acetonitrile and halocarbons such as dichloromethane and chloroform, though THF is used particularly preferably. Although the reaction can be carried out at –20–100° C., satisfactory results are normally obtained at room temperature.

Chart 18

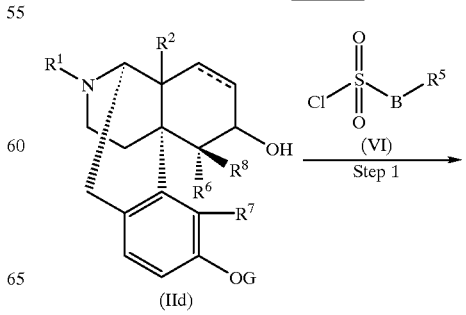

(IId)

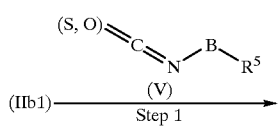

(Is)

Chart 17

-continued

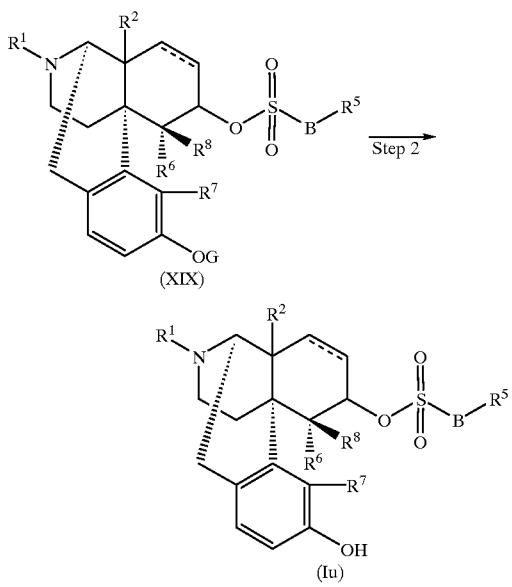

The free base obtained in the above steps can be converted into the salts with pharmacologically acceptable acids specifically by the methods shown below. Namely, a resulting free base is dissolved or suspended in a solvent followed by addition of acid and filtering of the precipitated solid or crystal, or in the case of not precipitating, a solvent of lower polarity is added, or the solvent is substituted with a solvent of lower polarity and filtering after precipitation. Alternatively, concentration and drying are performed after forming a salt. However, in the case organic solvent remains in these methods, drying under reduced pressure may be performed after freeze-drying in an aqueous solution. Examples of solvents used to dissolve or suspend the above free base include water, alcohols such as methanol, ethanol and isopropyl alcohol, halocarbons such as dichloromethane and chloroform, ethers such as ether, THF, DME and dioxane, esters such as ethyl acetate and methyl acetate, or their mixed solvents, while preferable examples include methanol, ethanol, isopropyl alcohol, ethyl acetate, chloroform, chloroform-methanol, water-methanol, and water-ethanol. Preferable examples of solvents used for precipitating solid include ether and ethyl acetate. Although it is desirable that an equivalent amount of acid be added, when it is possible to remove excess acid after washing the resulting salt, 1–10 equivalents may be used. In addition, acid may be added as is or suitably dissolved in the above-mentioned solvents and then added. For example, hydrochloric acid can be added in the form of concentrated hydrochloric acid, 1 N aqueous solution, a saturated methanol solution or a saturated ethyl acetate solution, while tartaric acid can be added in the form of a solid, an aqueous solution or a methanol solution. At the time of salt formation, since the temperature of the system may rise due to the heat of neutralization, there are cases in which favorable results are obtained if a water bath or ice bath is used.

As a result of in vitro and in vivo pharmacological testing, the compounds of the present invention represented by the general formula (I) are known to have strong analgesic and diuretic activity as an opioid κ-agonist, and it became clear that it can be expected to be used as a useful analgesic and diuretic. In addition, based on the properties of κ-agonists, it is also possible to use this compound as a hypotensive and sedative. Moreover, it was also found that the compounds of the present invention also include agonists highly selective for δ-receptors, thus suggesting the possibility of their use as an immunoenhancer, anti-HIV agent and so forth.

At the time of clinical use of the analgesic or diuretic of the present invention, it may be used as in the form of a free base or its salt, or suitably mixed with vehicles such as stabilizer, buffer, diluent, isotonic agents and preservatives. Examples of administration forms include injection preparations; oral preparations such as capsules, powders, granules and syrup, transintestinal administration in the form of suppositories; or topical administration in the form of ointments, creams and plasters. It is desirable that the analgesic of the present invention contain 1–90% by weight, and preferably 30–70% by weight of the above-mentioned active ingredient. Although the amount used is suitably selected according to symptoms, age, body weight and administration method, the adult dose as the amount of active ingredient in the case of an injection preparation is 0.0001 mg–1 g per day, and 0.005 mg–10 g per day in the case of an oral preparation. In both cases, administration may be performed in a single dose or divided among several administrations.

EXAMPLES

Although the following provides an explanation of the present invention in the form of the specific examples described below, the present invention is not limited to these examples.

Reference Example 1

N-Acetylbenzylamine 10 g of benzylamine was dissolved in 200 ml of methylene chloride followed by the addition of 26 ml of triethylamine and dropwise addition of 7.3 ml of acetyl chloride at 0° C. After stirring for 1 hour at room temperature, 2 ml of methanol was added to the reaction system at 0° C. followed by 120 ml of water and separation of the phases. The aqueous layer was extracted with 100 ml of chloroform, and the resulting organic layer was concentrated after drying with anhydrous sodium sulfate to obtain 8.55 g of the target compound (yield: 61%).
NMR (90 MHz, CDCl$_3$)
  δ 1.9 (3H, s), 4.3 (2H, d, J=4.8 Hz), 6.8 (1H, br s), 7.3 (5H, s).
IR (liquid film method)
  υ 3296, 1649, 1543, 1499, 1377, 1359, 1284, 1077, 1033 cm$^{-1}$ Reference Example 2

N-Benzylethylamine 2.96 g of the N-acetylbenzylamine obtained in reference example 1 was dissolved in 45 ml of anhydrous tetrahydrofuran followed by the addition of 1.73 g of lithium aluminum hydride at 0° C. After stirring for 2 hours at room temperature, the reaction mixture was refluxed while heating for 2 hours. After cooling the reaction mixture to 0° C., 22.8 g of sodium fluoride was added followed by dropwise addition of 91 ml of 10% aqueous tetrahydrofuran and stirred for 1 hour at room temperature. The precipitate was removed using Celite and the filtrate was concentrated to obtain 2.5 g of the target compound in liquid form (yield: 93%).
NMR (90 MHz, CDCl$_3$)
  δ 1.10 (3H, t, J=7.3 Hz), 1.4 (1H, brs), 2.65 (2H, q, J=7.3 Hz), 3.75 (2H, s), 7.15–7.4 (5H, m).

Reference Example 3

3-tert-butyldimethylsilyloxy-17-cyclopropylmethyl-4,5α-epoxy-14β-hydroxy-6-oxomorphinan 2

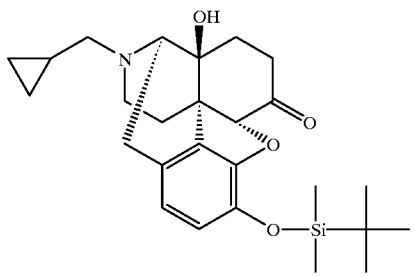

3.49 g of naltrexone hydrochloride was suspended in 10.5 ml of N,N-dimethylformamide. After adding 3.46 g of imidazole, 3.48 g of tert-butyldimethylchlorosilane was added followed by stirring for 35 minutes at room temperature. 30 ml of water and 50 ml of diethyl ether were added to the reaction system followed by separation. The aqueous layer was extracted twice with 30 ml of diethyl ether. The combined extracts were dried over anhydrous sodium sulfate and concentrated. The resulting residue was recrystallized from ethanol to obtain 3.2 g of the target compound (yield: 76%).

NMR (90 MHz, CDCl$_3$)

δ 0.0–1.2 (5H, m), 0.2 (3H, s), 0.3 (3H, s), 1.0 (9H, s), 1.3–2.0 (3H, m), 2.0–3.2 (8H, m), 2.4 (2H, d, J=4.4 Hz), 4.60 (1H, s), 6.5 (1H, d, J=6.4 Hz), 6.6 (1H, d, J=6.4 Hz).

Reference Example 4

3-Dehydroxynaltrexone 3

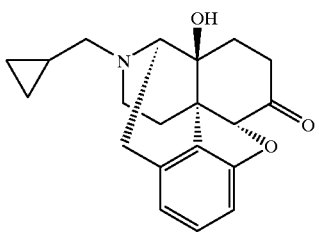

Naltrexone (5 g) was dissolved in dichloromethane (50 ml) followed by the addition of 2,6-lutidine (2.56 ml) and anhydrous trifluoromethanesulfonic acid (2.96 ml) at 0° C. After reacting for 15 minutes at the same temperature, distilled water (40 ml) and saturated aqueous sodium bicarbonate (20 ml) were added followed by extraction with chloroform (20+30 ml). After washing with saturated brine, the extracts was dried with anhydrous sodium sulfate and the solvent was distilled off. Ether (20 ml) was added and the precipitating solid was filtered out using Celite followed by initial purification with silica gel column chromatography (Merk 7734, 300 g; chloroform→1% methanol/chloroform).

The initially purified product was dissolved in anhydrous DMF (25 ml) and reacted with triethylamine (5.9 ml), palladium acetate (0.06 g), DPPF (0.16 g) and formic acid (1.1 ml) for 15 minutes at 60° C. After distilling off the solvent, saturated aqueous sodium bicarbonate (20 ml) and distilled water (10 ml) were added followed by extraction with chloroform (30 ml×2). After washing with saturated brine and drying with anhydrous sodium sulfate, the solvent was distilled off and the resulting black oily substance was purified with silica gel column chromatography (Merk 7734, 300 g; chloroform) to obtain the target compound (3.32 g, yield: 62%).

NMR (400 MHz, CDCl$_3$)

δ 0.26 (2H, m), 0.57 (2H, m), 0.88 (1H, m), 1.54 (1H, dd, J=12.7, 2.0 Hz), 1.63 (1H, dt, J=14.7, 3.9 Hz), 1.89 (1H, m), 2.13 (1H, dt, J=12.7, 3.9 Hz), 2.31 (1H, dt, J=14.7, 2.9 Hz), 2.42 (3H, m), 2.63 (1H, dd, J=18.6, 5.7 Hz), 2.70 (1H, dd, J=12.7, 4.9 Hz), 3.04 (1H, dt, J=14.7, 4.9 Hz), 3.11 (1H, d, J=19.5 Hz), 3.21 (1H, d, J=5.9 Hz), 4.65 (1H, s), 5.0–5.5 (1H, br), 6.69 (1H, d, J=6.8 Hz), 6.75 (1H, d, J=6.8 Hz), 7.07 (1H, t, J=6.8 Hz)

IR (neat)

υ 3406, 1729, 1630, 1607, 1458, 1052, 938, 781 cm$^{-1}$

Mass (EI)

m/z 325 (M+)

Example 1

17-cyclopropylmethyl-4,5α-epoxy-3,14β-dihydroxy-6α-methylaminomorphinan 4

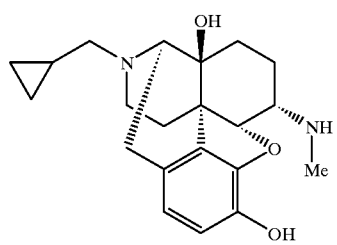

Naltrexone (1.0 g) and methylamine hydrochloride (0.99 g, 5 equivalents) were dissolved in methanol (15 ml) followed by stirring for 20 minutes at room temperature. This reaction solution was added to platinum oxide (0.05 g, 5 w %) in methanol (10 ml) activated in advance in a hydrogen atmosphere followed by hydrogenation for 4 hours at room temperature and atmospheric pressure. The catalyst was removed by Celite filtration and the solvent was distilled off. After adding saturated aqueous sodium bicarbonate (20 ml) and extracting with chloroform (20 ml×2), the extract was washed with saturated brine and dried with anhydrous sodium sulfate, and the solvent was distilled off. The resulting dark reddish-violet oily substance was dissolved in chloroform (2 ml) followed by addition of ethyl acetate (4 ml) to obtain the target compound (0.83 g, yield: 79%) by crystallization. A portion of this compound was removed and various spectra were measured in the form of a hydrochloride.

mp 270° C. (decomposition)

NMR (500 MHz, DMSO-d$_6$)

δ 0.40 (1H, m), 0.48 (1H, m), 0.61 (1H, m), 0.69 (1H, m), 0.95 (1H, m), 1.08 (1H, m), 1.47 (1H, m), 1.70 (1H, d, J=13.2 Hz), 1.81 (1H, m), 1.92 (1H, m), 2.49 (1H, m), 2.68 (3H, s), 2.72 (1H, m), 3.00 (1H, m), 3.08 (2H, m), 3.26 (2H, m), 3.57 (1H, m), 4.01 (3H, m), 4.97 (1H, brs), 6.50 (1H, s), 6.65 (1H, d, J=8.3 Hz), 6.78 (1H, d, J=8.3 Hz), 9.20 (2H, m)

1R (KBr)

υ 3200, 1510, 1464, 1238, 1116, 982, 859 cm$^{-1}$

Mass (EI)

m/z 356 (M+) (measured in the free form)

Elementary Analysis: AS $C_{21}H H_{28}N_2O_3 \cdot 2HCl \cdot 0.2H_2O$

Calculated values: C 58.25; H 7.08; N 6.47; Cl 16.38

Measured values: C 58.35; H 7.20; N 6.44; Cl 16.14

Example 2

17-Cyclopropylmethyl-4,5α-epoxy-3, 14β-dihydroxy-6α-isobutylaminomorphinan a was obtained by following the procedure of example 1 but using isobutylaline instead of methylamine.

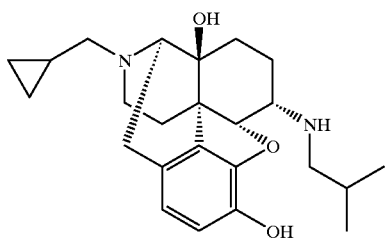

5

NMR (500 MHz, CDCl$_3$)

δ 0.22 (2H, m), 0.53 (2H, m, 0.84 (1H, m, 0.92 (1H, m), 0.94 (3H, d, J=6.7 Hz), 0.95 (3H, d, J=6.1 Hz), 1.40 (1H, dd, J=14.7, 10.4 Hz), 1.57 (1H, m), 1.68 (2H, m), 1.83 (1H, m), 2.30 (4H, m), 2.55 (2H, m), 2.63 (2H, m), 3.00 (1H, d, J=18.3 Hz), 3.06 (1H, d, J=6.7 Hz), 3.18 (1H, dt, J=13.4, 3.7 Hz), 4.3–5.2 (3H, br), 4.66 (1H, d, J=3.7 Hz), 6.46 (1H, d, J=7.9 Hz), 6.64 (1H, d, J=7.9 Hz)

IR (neat)

υ 3350, 1609, 1460, 1249, 1118, 913 cm$^{-1}$

Mass (EI)

m/z 398 (M+)

Example 3

17-Cyclopropylmethyl-14β-hydroxy-4,5α-epoxy-6α-methylaminomorphinan 6 (yield: 75%) was obtained by following the procedure of example 1 but using 3-dehydroxynaltrexone 3 instead of naltrexone hydrochloride.

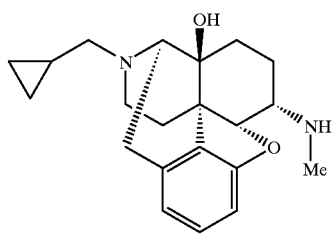

6

NMR (500 MHz, CDCl$_3$)

δ 0.13 (2H, m), 0.54 (2H, m), 0.75 (1H, m), 0.86 (1H, m), 1.40 (1H, dd, J=14.7, 5.5 Hz), 1.57 (1H, m), 1.63 (1H, m), 1.72 (2H, m), 2.25 (2H, m), 2.36 (2H, m), 2.52 (3H, s), 2.65 (2H, m), 3.08 (3H, m), 4.70 (1H, dd, J=3.7, 1.8 Hz), 4.9–5.1 (1H, br), 6.56 (1H, d, J=7.9 Hz), 6.61 (1H, d, J=7.3 Hz), 7.04 (1H, t, J=7.9 Hz)

IR (neat)

υ 3372, 1605, 1560, 1543, 1458, 1104, 864 cm$^{-1}$

Mass (EI)

m/z 340 (M+)

Example 3

3-tert-butyldimethylsilyloxy-17-cyclopropylmethyl-4,5α-epoxy-14β-hydroxy-6α-methylaminomorphinan 7 (yield: 50%) was obtained by following the procedure of example 1 but using 3-tert-butyldimethylsilyloxy-17-cyclopropylmethyl-4,5α-epoxy-14β-hydroxy-6-oxomorphinan 2 instead of Naltrexone hydrochloride.

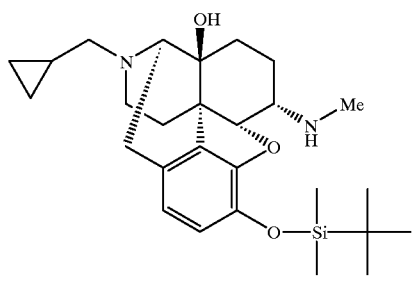

7

NMR (90 MHz, CDCl$_3$)

δ 0.0–1.2 (5H, m), 0.19 (3H, s), 0.2 (3H, s), 1.0 (9H, s), 1.3–1.9 (4H, m), 2.2–2.8 (7H, m), 2.56 (3H, s), 3.0 (1H, d, J=7.6 Hz), 3.0–3.3 (2H, m), 4.75 (1H, d, J=3.6 Hz), 6.5 (1H, d, J=7.2 Hz), 6.63 (1H, d, J=7.2 Hz)

Example 4

6β-(N-Benzyl)methylamino-17-cyclopropylmethyl-4,5α-epoxy-3, 14β-dihydroxymorphinan 8

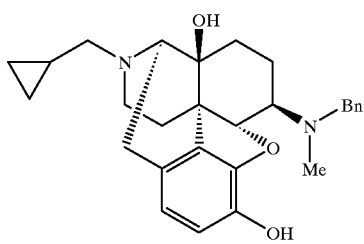

8

10.1 g of Naltrexone hydrochloride was separated with 150 ml of a 4:1 solution of chloroform and methanol and 150 ml of saturated aqueous sodium bicarbonate. The aqueous layer was extracted twice with 100 ml of a 4:1 solution of chloroform and methanol. The resulting organic layer was dried with anhydrous sodium sulfate followed by the addition of 3.26 g of benzoic acid and concentration after completely dissolving. After adequately drying the residue with a vacuum pump, the residue was suspended in 400 ml of benzene. After adding 5.2 ml of benzylmethylamine, 4.9 g of benzoic acid and 0.23 g of p-toluenesulfonic acid, the resulting mixture was stirred for 18 hours in a 110° C. oil bath while boiling off the water. After distilling off 330 ml of benzene at atmospheric pressure, 330 ml of ethanol and 4 g of molecular sieves 4A were added to the reaction mixture followed by cooling to 0° C. Next, 2.52 g of sodium cyanoborohydride was added followed by stirring for 2 hours at room temperature. After adding 200 ml of methanol to the reaction system, the molecular sieves was filtered out and the filtrate was concentrated. 200 ml of chloroform and 150 ml of saturated aqueous sodium bicarbonate were added to the resulting residue and the resulting precipitate was filtered followed by separation. The aqueous layer was extracted twice with 100 ml of chloroform, and the organic layer was concentrated after drying with anhydrous sodium sulfate. The resulting crude product was purified with silica gel column chromatography (480 g ammonia saturated ammonium chloroform/chloroform=2/1) to obtain 10.87 g of the oily target compound (yield: 91%). This was then recrystallized from methanol.

mp 71–80° C. (decomposition)

NMR (400 MHz, CDCl$_3$)

δ (0.09–0.13 (2H, m), 0.49–0.55 (2H, m), 0.79–0.88 (1H, m), 1.25–1.35 (1H, m), 1.43–1.49 (1H, m), 1.59–1.66 (2H, m), 1.87–2.00 (1H, m), 2.11 (1H, dt, J=3.4, 11.7 Hz), 2.19–2.27 (1H, m), 2.34 (3H, s), 2.35 (2H, d, J=6.8 Hz), 2.50–2.59 (1H, m), 2.56 (1H, dd, J=5.4, 18.1 Hz), 2.62 (1H, dd, J=4.4, 11.7 Hz), 2.99 (1H, d, J=18.1 Hz), 3.04 (1H, d, J=5.4 Hz), 3.53 (1H, d, J=13.2 Hz), 3.82 (1H, d, J=13.7 Hz), 4.68 (1H, d, J=8.3 Hz), 6.51 (1H, d, J=8.3 Hz), 6.65 (1H, d, J=8.3 Hz), 7.20–7.35 (5H, m).

IR (KBr)

υ 3428, 3220, 1638, 1615, 1502, 1458, 1375, 1330, 1238, 1147, 1116, 1033, 990, 917, 857, 735 cm$^{-1}$

Mass (EI)

m/z 446 (M+), 355, 286, 160.

Elementary Analysis: As $C_{28}H_{34}N_2O_3 \cdot 0.5H_2O$

Calculated values: C, 73.82; H, 7.74; N, 6.15.

Measured values: C, 73.94; H, 7.79; N, 6.08.

Example 5

17-Cyclopropylmethyl-4,5α-epoxy-6β-(N-benzyl) ethylamino-3,14β-dihydroxymorphinan 9 (yield: 46%) was obtained by following the procedure of example 4 but using benzylethylamine instead of benzylmethylamine.

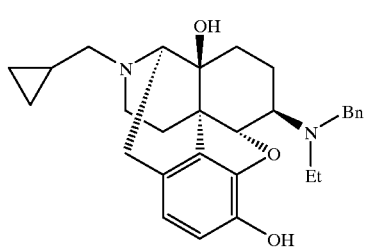

9

NMR (400 MHz, CDCl$_3$)

δ 0.05–0.18 (2H, m), 0.46–0.58 (2H, m), 0.77–0.89 (1H, m), 1.03 (3H, t, J=7.1 Hz), 1.22–1.33 (1H, m), 1.41–1.48 (1H, m), 1.55–1.65 (2H, m), 1.86–1.99 (1H, m), 2.11 (1H, dt, J=3.9, 12.2 Hz), 2.20 (1H, dt, J=4.9, 12.2 Hz), 2.33 (1H, dd, J=6.8, 12.7 Hz), 2.36 (1H, dd, J=6.8, 12.7 Hz), 2.50–2.75 (5H, m), 2.98 (1H, d, J=18.6 Hz), 3.03 (1H, d, J=5.9 Hz), 3.56 (1H, d, J=14.4 Hz), 3.87 (1H, d, J=14.4 Hz), 4.59 (1H, d, J=7.8 Hz), 4.85 (2H, brs), 6.50 (1H, d, J=7.8 Hz), 6.63 (1H, d, J=7.8 Hz), 7.18–7.32 (3H, m), 7.40 (2H, d, J=6.8 Hz).

Mass (EI)

m/z 460 M+

Example 6

17-Cyclopropylmethyl-4,5α-epoxy-3,14β-dihydroxy-6β-methylaminomorphinan 10

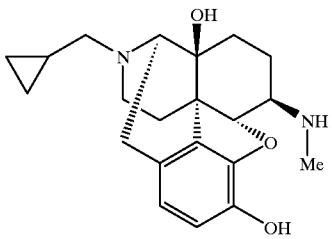

10

12.65 g of 6β-(N-benzyl)methylamino-17-cyclopropylmethyl-4,5α-epoxy-3,14α-dihydroxymorphinan 8.2 hydrochloride (converted to a hydrochloride by established methods) was dissolved in 250 ml of methanol followed by the addition of 2.53 g of 5% palladium-carbon and stirring for 4 hours in a hydrogen atmosphere. After removing the catalyst using Celite, the filtrate was concentrated. 100 ml of a 4:1 solution of chloroform and ethanol and 100 ml of saturated aqueous sodium bicarbonate were added to the resulting residue to separate, and the aqueous layer was then extracted twice with 100 ml of a 4:1 solution of chloroform and ethanol. After drying the organic layer with anhydrous sodium sulfate, the dried organic layer was concentrated to obtain 8.00 g of crude product. This was then recrystallized from methanol to obtain 5.84 g of the target compound (yield: 67%).

NMR (400 MHz, CDCl$_3$)

δ 0.10–0.14 (2H, m), 0.50–0.55 (2H, m), 0.79–0.86 (1H, m), 1.38 (1H, dt, J=2.9 Hz, 12.8 Hz), 1.41–1.48 (1H, m), 1.58–1.72 (2H, m), 1.78–1.91 (1H, m), 2.08–2.25 (2H, m), 2.36 (1H, d, J=6.6 Hz), 2.45 (3H, s), 2.49–2.65 (3H, m), 3.00 (1H, d, J=18.3 Hz), 3.05 (1H, d, J=5.9 Hz), 4.48 (1H, d, J=7.7 Hz), 6.54 (1H, d, J=8.1 Hz), 6.66 (1H, d, J=8.1 Hz).

IR (KBr)

υ 3380, 2926, 1638, 1607, 1462, 1255, 1180, 795 cm$^{-1}$

Mass (EI)

m/e 356 M+

Elementary Analysis: $C_{21}H_{28}O_3N_2$

Calculated values: C, 70.76; H, 7.92; N, 7.86.

Measured values: C, 70.51; H, 7.94; N, 7.84.

Example 7

17-Cyclopropylmethyl-4,5α-epoxy-6β-ethylamino-3,14β-dihydroxymorphinan 11 (yield: 95%) was obtained by following the procedure of example 6 but using 6β-(N-benzyl)ethylamino-17-cyclopropylmethyl-4,5α-epoxy-3,14β-dihydroxymorphinan 9.2 hydrochloride for the starting material instead of 6β-(N-benzyl)methylamino-17-cyclopropylmethyl-4,5α-epoxy-3,14β-dihydroxymorphinan 8.2 hydrochloride.

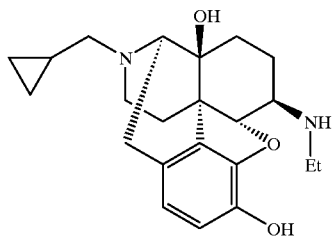

NMR (500 MHz, CDCl₃+D20)

δ 0.08–0.17 (2H, m), 0.49–0.56 (2H, m), 0.78–0.87 (1H, m), 1.16 (3H, t, J=7.1 Hz), 1.37 (1H, dt, J=2.9, 13.2 Hz), 1.40–1.45 (1H, m), 1.57–1.61 (1H, m), 1.66–1.71 (1H, m), 1.83 (1H, dq, J=2.9, 13.2 Hz), 2.13 (1H, dt, J=12.1, 3.3 Hz), 2.20 (1H, dt, J=12.1, 4.8 Hz), 2.34 (1H, dd, J=12.8, 6.6 Hz), 2.37 (1H, dd, J=12.8, 6.6 Hz), 2.52–2.69 (4H, m), 2.80 (1H, dq, J=11.4, 7.0 Hz), 3.00 (1H, d, J=18.3 Hz), 3.05 (1H, d, J=5.9 Hz), 4.46 (1H, d, J=7.7 Hz), 6.54 (1H, d, J=8.1 Hz), 6.67 (1H, d, J=8.1 Hz).

Mass (EI)

m/e 370 M+

Reference Example 6

17-Allyl-3,14β-dihydroxy-4,5α-epoxy-6α-methylamino-morphinan 12

17-Allyl-3,14β-dihydroxy-4,5β-epoxy-6-methylamino-morphinan 13

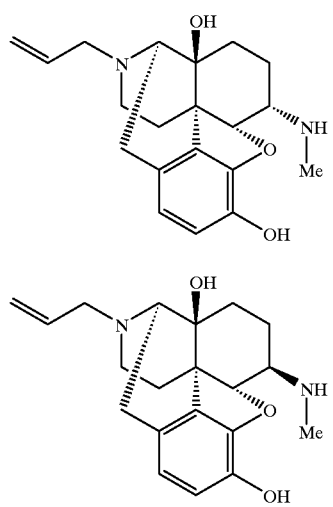

Naloxone hydrochloride (3.0 g), methylamine hydrochloride (5.57 g) and sodium cyanoborohydride (0.33 g) were suspended in anhydrous methanol (40 ml) and stirred for 17 hours at room temperature. After addition of concentrated hydrochloric acid (1.0 ml) and removal of solvent by distillation, distilled water (50 ml) was added followed by washing with chloroform (20 ml). Saturated aqueous sodium bicarbonate (10 ml) was added to make the solution basic followed by extraction with chloroform (30 ml×3). After drying with anhydrous magnesium sulfate, the solvent was distilled off. The resulting crude product was purified with silica gel column chromatography (Merk 7734 100 g; ethyl acetate/methanol/aqueous ammonia=90/10/1→80/20/2) to obtain the target compound in the form of a pure fraction (12 0.4 g, 12%; 13 0.8 g, 24%).

Compound 12

NMR (400 MHz, CDCl₃)

δ 0.87 (1H, m), 1.39 (1H, m), 1.66 (3H, m), 2,19 (1H, dt, J=12.2, 4.9 hz), 2.29(1H, dt, J=12.7, 3.4 Hz), 2.55 (3H, m), 2.59 (3H, s), 2.90 (1H, d, J=6.4 Hz), 3.09 (2H, m), 3.18 (1H, m), 4.76 (1H, d, J=3.4 Hz), 4.7–4.9 (1H, br), 5.17 (2H, m), 5.80 (1H, m), 6.50 (1H, d, J=7.8 Hz), 6.69 (1H, d, J=7.8 Hz)

IR (neat)

3400, 1618, 1450, 1386, 1160, 1067, 750 cm⁻¹.

Mass (EI)

m/z 342 (M+)

Compound 13

NMR (500 MHz, CDCl₃)

δ 1.42 (2H, m), 1.61 (2H, m), 1.91 (1H, dq, J=12.8, 3.1 Hz), 2.16 (2H, m), 2.47 (3H, s), 2.56 (3H, m), 2.87 (1H, d, J=5.5 Hz), 3.03 (1H, d, J=18.3 Hz), 3.11 (2H, d, J=6.7 Hz), 4.51 (1H, d, J=7.9 Hz), 4.7–5.2 (3H, br), 5.18 (2H, m), 5.79 (1H, m), 6.55 (1H, d, J=7.9 Hz), 6.64 (1H, d, J=7.9 Hz)

IR (neat)

υ 3400, 1560, 1543, 1458, 1255, 1036, 731 cm⁻¹.

Mass (EI)

m/z 342 (M+)

Reference Example 7

17-Cyclopropylmethyl-7,8-didehydro-4,5α-epoxy-14β-hydroxy-3-methoxy-6α-(N-methylamino)morphinan (yield: 40%) 14, and 17-cyclopropylmethyl-4,5α-epoxy-14β-hydroxy-3-methoxy-6β-(N-methylamino)morphinan (yield: 23%) 15 were obtained by following the procedure of reference example 6 but using 17-cyclopropylmethyl-7,8-didehydro-4,5α-epoxy-14β-hydroxy-3-methoxymorphinan-6-one instead of naloxone hydrochloride.

Compound 14

NMR (500 MHz, CDCl₃)

δ 0.13–0.18 (2H, m), 0.53–0.59 (2H, m), 0.88 (1H, m), 1.78 (1H, d, J=7.8 Hz), 2.38 (2H, d, J=7.8 Hz), 2.40 (1H, d, J=6.3 Hz), 2.44 (1H, dd, J=12.7, 6.3 Hz), 2.50 (1H, dd, J=18.6, 6.8 Hz), 2.58 (3H, s), 2.72 (1H, d, J=7.8 Hz), 3.08 (1H, d, J=18.6 Hz), 3.35 (1H, d, J=6.8 Hz), 3.65 (1H, m), 3.84 (3H, s), 4.97 (1H, br), 4.99 (1H, dd, J=5.9, 1.5 Hz), 5.54 (1H, dd, J=9.8, 2.9 Hz), 5.88 (1H, dt, J=9.8, 1.5 Hz), 6.51 (1H, d, J=7.8 Hz), 6.63 (1H, d, J=7.8 Hz).

IR (neat)

υ 3342, 2938, 1508, 1456, 1284, 1205, 1123, 1054, 1017, 748 cm⁻¹

Mass (EI)

m/z 368 (M+)

Compound 15

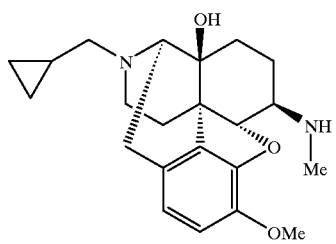

mp 121.5–123.5° C. (ethylacetate-ether)
NMR (400 MHz, CDCl₃)

δ 0.09–0.16 (2H, m), 0.50–0.56 (2H, m), 0.84 (1H, m), 1.36 (1H, td, J=12.7, 3.9 Hz), 1.44 (1H, dd, J=12.7, 2.4 Hz), 1.61 (1H, dt, J=13.2, 3.4 Hz), 1.66–1.83 (2H, m), 2.10 (1H, td, J=12.2, 3.9 Hz), 2.23 (1H, td, J=12.2, 4.9 Hz), 2.36 (2H, dd, J=6.4, 1.5 Hz), 2.43 (1H, m), 2.48 (3H, s), 2.57–2.66 (2H, m), 3.03 (1H, d, J=18.6 Hz), 3.08 (1H, d, J=5.9 Hz), 3.87 (3H, s), 4.45 (1H, d, J=6.8 Hz), 6.61 (1H, d, J=8.3 Hz), 6.72 (1H, d, J=8.3 Hz).

IR (KBr)

υ 3390, 3344, 2944, 2802, 1632, 1611, 1504, 1446, 1282, 1263, 1044, 980, 901 cm⁻¹

Mass (EI)

m/z 370 (M+).

Reference Example 8

3-tert-butyldimethylsilyloxy-17-cyclopropylmethyl-4, 5α-epoxy-14β-hydroxy-6α-(N-methyl-3,4-dichlorophenylmethanesulfonamido)morphinan 16

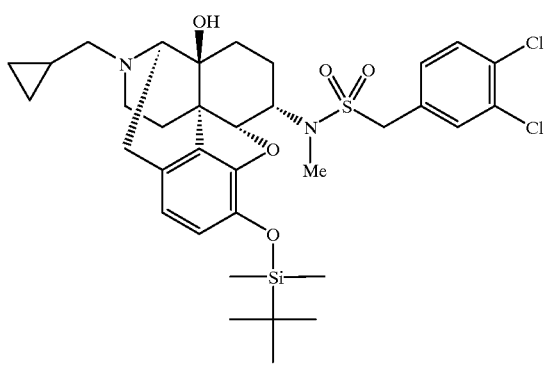

203.9 mg of 3-tert-butyldimethylsilyloxy-17-cyclopropylmethyl-4,5α-epoxy-14β-hydroxy-6α-methylaminomorphinan 7 obtained in reference example 5 was dissolved in 3 ml of pyridine followed by the addition of 124 mg of 3,4-dichlorophenylmethanesufonylchloride and stirring for 30 minutes at room temperature. After concentrating the reaction system, 3 ml of saturated aqueous sodium bicarbonate and 3 ml of chloroform were added to separate layers, after which the aqueous layer was extracted twice with 3 ml of chloroform. After drying with anhydrous sodium sulfate, the organic layer was concentrated to obtain the oily crude product. This was then purified with silica gel column chromatography (30 g benzene/ethyl acetate=5/1) to obtain 235.4 mg of the target compound (yield: 78%).

NMR (500 MHz, CDCl₃)

δ 0.09–0.16 (2H, m), 0.15 (3H, s), 0.21 (3H, s), 0.51–0.57 (2H, m), 0.80–0.89 (1H, m), 0.97 (9H, s), 1.21–1.30 (2H, m), 1.42–1.49 (2H, m), 1.71 (1H, dt, J=14.7, 9.5 Hz), 2.15 (1H, dt, J=12.5, 5.1 Hz), 2.22 (1H, dt, J=12.5, 3.7 Hz), 2.30 (1H, dd, J=12.8, 6.6 Hz), 2.35 (1H, dd, J=12.8, 6.6 Hz), 2.56 (1H, dd, J=18.7, 7.0 Hz), 2.60–2.65 (1H, m), 2.89 (3H, s), 3.01 (1H, d, J=18.7 Hz), 3.05 (1H, d, J=7.0 Hz), 4.16 (1H, d, J=13.9 Hz), 4.19 (1H, d, J=13.9 Hz), 4.22–4.28 (1Hm), 4.41 (1H, d, J=3.3 Hz), 4.90 (1H, brs), 6.48 (1H, d, J=8.1 Hz), 6.62 (1H, d, J=8.1 Hz), 7.31 (1H, dd, J=8.1, 2.2 Hz), 7.46 (1H, d, J=8.1 Hz), 7.53 (1H, d, J=2.2 Hz).

Mass (EI)

m/z 692 M+

Reference Example 9

3-tert-butyldimethylsilyloxy-17-cyclopropylmethyl-4, 5α-epoxy-14β-hydroxy-6α-(N-methylphenylmethanesulfonamido)morphinan 17 (yield: 50%) was obtained by following the procedure of reference example 8 but using phenylmethanesulfonylchloride instead of 3,4-dichlorophenylmethanesulfonylchloride.

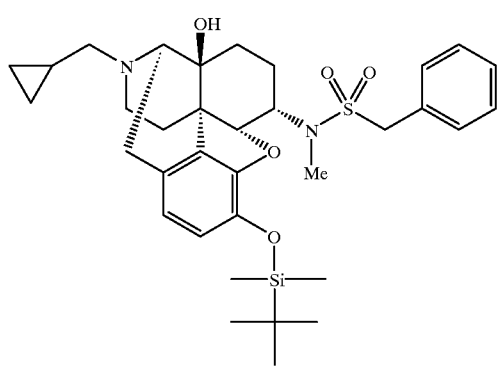

NMR (500 MHz, CDCl₃)

δ 0.08–0.13 (2H, m), 0.14 (3H, s), 0.20 (3H, s), 0.50–0.55 (2H, m), 0.79–0.87 (1H, m), 0.97 (9H, s), 1.10–1.22 (2H, m), 1.37–1.43 (2H, m), 1.64 (1H, dt, J=15.0, 9.5 Hz), 2.12 (1H, dt, J=12.5, 5.1 Hz), 2.20 (1H, dt, J=12.5, 3.3 Hz), 2.29 (1H, dd, J=12.5, 6.6 Hz), 2.33 (1H, dd, J=12.5, 6.6 Hz), 2.54 (1H, dd, J=18.7, 7.0 Hz), 2.59–2.63 (1H, m), 2.83 (3H, s), 2.99 (1H, d, J=18.7 Hz), 3.02 (1H, d, J=7.0 Hz), 4.19–4.24 (1H, m), 4.24 (1H, d, J=13.9 Hz), 4.28 (1H, d, J=13.9 Hz), 4.34 (1H, d, J=2.9 Hz), 4.88 (1H, brs), 6.46 (1H, d, J=8.1 Hz), 6.61 (1H, d, J=8.1 Hz), 7.32–7.40 (3H, m), 7.42–7.47 (2H, m).

Mass (EI)

m/z 624 M+

Reference Example 10

5β-Methylnaltrexone-O-methyloxime(17-cyclopropylmethyl-3,14β-dihydroxy-4,5α-epoxy-5β-methyl-6-methoxyiminomorphinan) 18

18

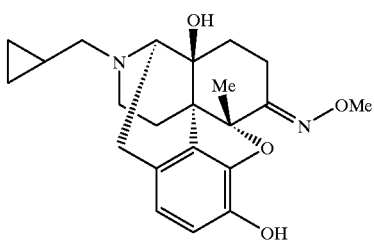

109.3 mg of 5β-methylnaltrexone (0.326 mmol) and 37.2 mg of methoxyamine hydrochloride (0.445 mmol) were dissolved in 1.6 ml of methanol followed by the addition of 0.17 ml of 10% aqueous sodium hydroxide to this solution and refluxing while heating. After 8.5 hours part way through the refluxing period, a solution of 36.1 mg (0.432 mmol) of methoxyamine hydrochloride in 0.5 ml of methanol was added and refluxing was continued until a total of 23 hours had elapsed. After allowing the reaction solution to cool to room temperature by standing, 5 ml of water and 1 ml of saturated aqueous sodium bicarbonate were added followed by extraction with 2×5 ml of chloroform. The organic layers were combined and dried with anhydrous sodium sulfate followed by concentration to obtain 107.4 mg of the unpurified target compound. This unpurified compound was used in the following reaction without being purified.

NMR (400 MHz, CDCl$_3$)

δ 0.13 (2H, m), 0.53 (2H, m), 0.84 (1H, m), 1.37 (1H, m), 1.43 (1H, dd, J=14.1, 3.4 Hz), 1.62 (1H, m), 1.71 (3H, s), 2.23–2.30 (3H, m), 2.30 (1H, br s, OH), 2.37 (2H, d, J=6.5 Hz), 2.55 (1H, dd, J=18.3, 6.1 Hz), 2.71 (1H, m),3.00 (1H, d, J=18.3 Hz), 3.04 (1H, d, J=6.1 Hz), 3.14 (1H, ddd, J=14.7, 3.2, 3.2 Hz), 3.80 (3H, s), 4.95 (1H, br s, OH), 6.55 (1H, d, J=8.0 Hz), 6.70 (1H, d, J=8.0 Hz).

IR (KBr)

υ 3380, 1638, 1620, 1510, 1460, 1377, 1336, 1241, 1118, 1038, 953, 866, 752 cm$^{-1}$

Mass (EI)

m/z 384 (M+).

Reference Example 11

17-Cyclopropylmethyl-3,14β-dihydroxy-4,5α-epoxy-5β-methyl-6α-aminomorphinan 19

19

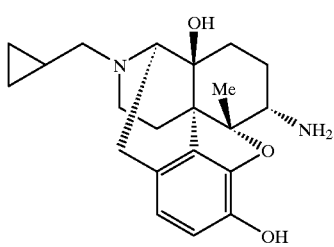

101.0 mg (approximately 0.26 mmol) of the unpurified 5β-methylnaltrexone-O-methyloxime 18 a obtained in reference example 10 was dissolved in 2.5 ml of anhydrous THF in the presence of argon gas followed by cooling to 0° C. After adding 1.31 ml of an anhydrous THF solution of 1.0 M borane.THF complex to this solution, the solution was refluxed for 18.5 hours while heating. After cooling the reaction solution to 0° C. and slowly adding 10 ml of 2 N hydrochloric acid, the solution was again refluxed for 40 minutes while heating. The reaction solution was cooled to 0° C. followed by the addition of 4 ml of 5 N aqueous ammonia and 2 ml of saturated aqueous sodium bicarbonate, and extraction with 3×5 ml of chloroform-methanol (4:1). The organic layers were combined and dried with anhydrous sodium sulfate followed by concentration to obtain 89.6 mg of the unpurified target compound. This unpurified compound was then used in the following reaction without being purified.

NMR (400 MHz, CDCl$_3$)

δ 0.12 (2H, m), 0.53 (2H, m), 0.83 (1H, m), 1.37–1.84 (5H, m), 1.63 (3H, s), 2.15–2.28 (2H, m) 2.33 (2H, d, J=5.7 Hz), 2.60 (1H, dd, J=18.5, 6.3 Hz), 2.67 (1H, m), 2.99 (1H, d, J=18.5 Hz), 3.00 (3H, br s, OH, NH2), 3.02 (1H, d, J=6.3 Hz), 3.14 (1H, dd, J=8.8, 3.8 Hz), 4.90 (1H, br s, OH), 6.49 (1H, d, J=8.0 Hz), 6.63 (1H, d, J=8.0 Hz).

IR (KBr)

υ 3376, 3082, 1611, 1502, 1460, 1379, 1332, 1245, 1122, 1038, 944, 868, 803 cm$^{-1}$.

Mass (EI)

m/z 356 (M+).

Example 8

6β-(N-Benzyl)methylamino-17-cyclopropylmethyl-4,5α-epoxy-3,14β-dihydroxymorphinan 8

8

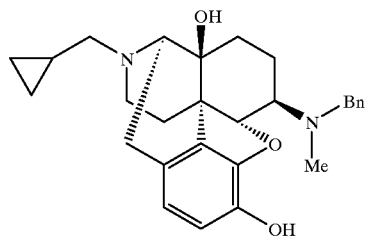

50.08 g (0.108 mol) of naltrexone benzoate was suspended in THF (350 ml) followed by the addition of 19.61 g (0.162 mol) of benzylmethylamine. A Soxhlet extractor containing molecular sieves 4A (50 g) was attached followed by refluxing for 23 hours while heating. After adding methanol (200 ml) to the reaction system, 10.2 g (0.162 mol) of sodium cyanoborohydride was dissolved in methanol (50 ml) and added to the reaction mixture followed by stirring for 30 minutes. After stirring, the solvent was distilled off and ethylacetate (400 ml) and 1% aqueous sodium bicarbonate (400 ml) were added to the residue to separate layers. The aqueous layer was re-extracted with ethylacetate (80 ml). The resulting organic layer was washed with saturated brine (250 ml) and concentrated after drying. Methanol (240 ml) was added to the resulting residue to recrystallize and obtain 42.68 g of the target substance (yield: 88%). The data of this compound is the same as that shown in example 4.

Example 9

An isomer mixture of 17-cyclopropylmethyl-4,5α-epoxy-3-hydroxy-6β-methylaminomorphinan 20 and 17-cyclopropylmethyl-4,5α-epoxy-3-hydroxy-6α-methylaminomorphinan 21 (20:21=approximately 2:1, 44%) was obtained by following the procedure of example 8 but using 14-dehydroxynaltrexone instead of naltrexone benzoate.

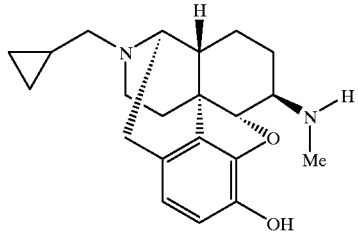

20

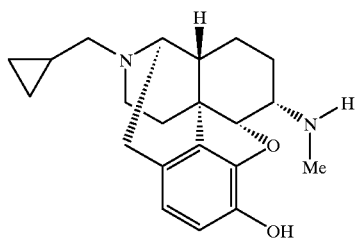

21

Mixture of Compound 20 and Compound 21
NMR (400 MHZ, CDCl₃)

δ 0.08–0.17 (2H, m), 0.49–0.55 (2H, m), 0.8–2.5 (12H), 2.42 (2.1H, s), 2.54 (0.9H, s), 2.7–2.9 (2H), 3.36 (0.7H, m), 3.41 (0.3H, m), 4.36 (0.7H, d, J=7.3 Hz), 4.78 (0.3H, d, J=2.9 Hz), 6.48–6.56 (1H, m), 6.64–6.68 (1H, m)

IR (neat)
υ 2932, 1609, 1454, 1325, 1259, 911, 731 cm⁻¹

Mass (EI)
m/z 340 (M+)

Example 10

17-Cyclopropylmethyl-4,5α-epoxy-3,14β-dihydroxy-6β-methylaminomorphinan 10. phthalate

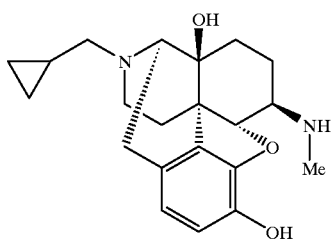

10

42.58 g (0.0953 mol) of 6β-(N-benzyl)methylamino-17-cyclopropylmethyl-4,5α-epoxy-3,14β-dihydroxymorphinan 8 and 17.42 g (0.105 mol) of phthalic acid were dissolved in 500 ml of methanol followed by the addition of 12.7 g of 10% palladium-carbon and stirring for 12 hours in a hydrogen atmosphere. After the atmospheric hydrogen was replaced to nitrogen, 300 ml of methanol was added followed by refluxing while heating. After dissolving the precipitated crystals, the catalyst was filtered out during heating using Celite. After distilling off 200 ml of filtrate by atmospheric pressure condensation, the remaining filtrate was allowed to stand undisturbed to recrystallize and obtain 26.82 g of the target compound (yield: 54%).

mp 151–164° C. (decomposition)

NMR (400 MHz, D2O)

δ 0.40–0.50 (2H, m), 0.73 (1H, m), 0.82 (1H, m), 1.08 (1H, m), 1.56 (1H, m), 1.67 (1H, m), 1.85 (1H, m), 1.89–2.02 (2H, m), 2.52 (1H, ddd, J=13.2, 13.2, 4.9 Hz), 2.75 (1H, ddd, J=12.9, 12.9, 4.2 Hz), 2.78 (3H, s), 2.93–3.04 (2H, m), 3.16–3.25 (2H, m), 3.32–3.43 (2H, m), 4.07 (1H, br d, J=5.9 Hz), 4.99 (1H, d, J=7.3 Hz), 6.85 (1H, d, J=8.0 Hz), 6.90 (1H, d, J=8.0 Hz), 7.34–7.39 (2H, m), 7.43–7.48 (2H, m).

IR (KBr)

υ 3388, 3032, 1605, 1557, 1510, 1460, 1367, 1330, 1243, 1168, 1120, 1035, 992, 936, 859, 770 cm⁻¹.

Mass (FAB)

m/z 357 ((M+H)+).

Elementary Analysis: As $C_{21}H_{28}N_2O_3 \cdot C_8H_6O_4 \cdot 0.8H_2O$

Calcd.: C, 64.86; H, 6.68; N, 5.22.

Found.: C, 64.93; H, 6.61; N, 5.23.

Example 11

17-Cyclopropylmethyl-4,5α-epoxy-3,14β-dihydroxy-6α-N-methyl-3,4-dichlorophenylacetoamido)morphinan.hydrochlorid

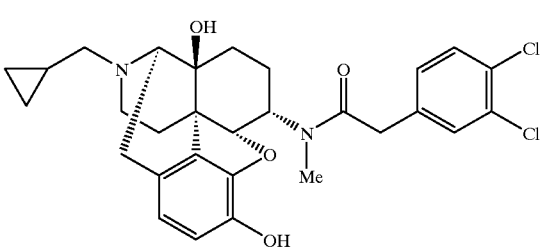

1

8.9 g of 17-cyclopropylmethyl-4,5α-epoxy-3,14β-dihydroxy-6α-methylaminomorphinan 4 obtained in example 1 was dissolved in 180 ml of chloroform. After adding 10.4 ml of triethylamine, 10.4 ml of 3,4-dichlorophenylacetyl chloride (obtained by converting commercially available carboxylic acid into an acid chloride by established methods) was added dropwise at 0° C. After completion of dropwise addition, the reaction solution was stirred for 1 hour at room temperature followed by the addition of 150 ml of saturated aqueous sodium bicarbonate to the reaction system to separate. The aqueous layer was then extracted twice with 100 ml of chloroform. After drying with anhydrous sodium sulfate, the organic layer was concentrated. The resulting residue was dissolved in a mixed solvent of 140 ml of methanol and 14 ml of chloroform followed by the addition of 1.7 g of potassium carbonate at room temperature and stirring for 30 minutes. 100 ml of water and 350 ml of chloroform were then added to the reaction solution to separate layers, and the aqueous layer was extracted twice with 80 ml of chloroform. After drying with anhydrous sodium sulfate, the resulting organic layer was concentrated. The resulting residue was recrystallized from a 2:1 mixture of ethylacetate and methanol to obtain 8.15 g of the free base form. This was then dissolved in a mixed solvent of chloroform and methanol followed by concentration after adjusting to pH 3 by addition of methanol solution of hydrochloride. This solution was re-precipitated from chloroform, methanol and ether to obtain 8.44 g of the target compound (yield: 58%).

mp 252–254° C.

NMR (400 MHz, DMSO-$d_6$)

δ 0.43 (2H, m), 0.65 (2H, m), 1.05 (1H, m), 1.16 (1.5H, m), 1.37 (1H, m), 1.58 (2H, m), 1.92 (1H, m), 2.43 (1H, m), 2.68 (1H, m), 2.81 (0.5H, s), 2.96 (2.5H, s), 3.05 (2.5H, m), 3.30 (2H, m), 3.85 (3H, m), 4.48 (0.2H, m), 4.62 (0.8H, d, J=3.9 Hz), 4.75 (0.2H, m), 4.96 (0.8H, m), 6.21 (0.8H, m), 6.46 (0.2H, m), 6.58 (1H, d, J=8.3 Hz), 6.72 (1H, d, J=8.3 Hz), 7.25 (1H, m), 7.55 (2H, m), 8.80 (1H, brs), 9.32 (1H, brs)

IR (KBr)

υ 3370, 1620, 1510, 1473, 1120, 1035, $cm^{-1}$.

Mass (FAB)

m/z 543 (M+H)+

Elementary Analysis: As $C_{29}H_{32}N_2O_4Cl_2 \cdot HCl \cdot 0.5H_2O$

Calcd.: C, 59.14; H, 5.82; N, 4.75; Cl, 18.06

Found.: C, 59.34; H, 5.78; N, 4.78; Cl, 17.78

Examples 12–40

17-Cyclopropylmethyl-4,5α-epoxy-3,14β-dihydroxy-6α-(N-methyl-3-phenylpropionamido)morphinan.tartrate 22 (yield: 84%), 17-cyclopropylmethyl-3,14β-dihydroxy-4,5α-epoxy-6α-(N-methylphenylacetamido) morphinan.hydrochloride 23 (yield: 70%), 17-cyclopropylmethyl-3,14β-dihydroxy-4,5α-epoxy-6α-(N-methylcinnamamido)morphinan.hydrochloride 24 (yield: 74%), 17-cyclopropylmethyl-3,14β-dihydroxy-4,5α-epoxy-6α-(N-methylacetamido)morphinan.hydrochloride 25 (yield: 93%), 17-cyclopropylmethyl-3,14β-dihydroxy-4,5α-epoxy-6α-(N-methyl-3-bromophenylacetamido) morphinan.hydrobromate 26 (yield: 85%), 17-cyclopropylmethyl-3,14β-dihydroxy-4,5α-epoxy-6α-(N-methyl-3,4-dichlorobenzamido) morphinan.hydrochloride 27 (yield: 58%), 17-cyclopropylmethyl-3,14β-dihydroxy-4,5α-epoxy-6α-(N-methyl-4-bromophenylacetamido)morphinan.hydrochloride 28 (yield: 73%), 17-cyclopropylmethyl-4,5α-epoxy-3,14β-dihydroxy-6α-[(R)-N-methyl-2-phenylpropionamido] morphinan.hydrochloride 29 (yield: 52%), 17-cyclopropylmethyl-3,14β-dihydroxy-4,5α-epoxy-6α ([(R)-N-methylmethoxyphenylacetamido] morphinan.hydrochloride 30 (yield: 98%), 17-cyclopropylmethyl-3,14β-dihydroxy-4,5α-epoxy-6α-[(s)-N-methylmethoxyphenylacetamido] morphinan.hydrochloride 31 (yield: 70%), 17-cyclopropylmethyl-4,5α-epoxy-3,14β-dihydroxy-6α-[(s)-N-methyl-2-phenylpropionamido]morphinan.tartrate 32 (yield: 85%), 17-cyclopropylmethyl-3,14β-dihydroxy-4,5α-epoxy-6α-(N-methylcyclohexylcarboxyamido) morphinan.hydrochloride 33 (yield: 58%), 17-cyclopropylmethyl-3,14β-dihydroxy-4,5α-epoxy-6α-(N-methyl benzamido) morphinan.hydrochloride 34 (yield: 52%), 17-cyclopropylmethyl-3,14β-dihydroxy-4,5α-epoxy-6α-(N-methyl-4-phenylbutyramido)morphinan.hydrochloride 35 (yield: 80%), 17-cyclopropylmethyl3,14β-dihydroxy-4,5α-epoxy-6α-(N-methyl-6-phenylhexanamido) morphinan.hydrochloride 36 (yield: 63%), 17-cyclopropylmethyl-3,14β-dihydroxy-4,5α-epoxy-6α-(N-methyl-3-fluorophenylacetamido) morphinan.hydrochloride 37 (yield: 57%), 17-cyclopropylmethyl-3,14β-dihydroxy-4,5α-epoxy-6α-(N-methylphenoxyacetamido) morphinan.hydrochloride M (yield: 86%), 17-cyclopropylmethyl-3,14β-dihydroxy-4,5α-epoxy-6α-(N-methylhexanamido)morphinan.tartrate 39 (yield: 68%), 17-cyclopropylmethyl-3,14β-dihydroxy-4,5α-epoxy-6α-(N-methylheptanamido)morphinan.tartrate 40 (yield: 81%), 17-cyclopropylmethyl-3,14,β-dihydroxy-4,5α-epoxy-6α- [N-methyl-3-(3-pyridyl)propionamido] morphinan.tartrate 41 (yield: 65%), 17-cyclopropylmethyl-3,14β-dihydroxy-4,5α-epoxy-6α-(N-methylbenzyloxycarbamido)morphinan.tartrate 42 (yield: 61%), 17-cyclopropylmethyl-3,14β-dihydroxy-4,5α-epoxy-6α-(N-methyl-4-nitrobenzyloxycarbamido) morphinan.hydrochloride 43 (yield: 68%), 17-cyclopropylmethyl-4,5α-epoxy-3,14β-dihydroxy-6α-[N-methyl-(3-pyridyl)methyloxycarbamido] morphinan.tartrate 44 (yield: 31%), 17-cyclopropylmethyl-4,5α-epoxy-3,14,β-dihydroxy-6α-(N-methylthiophenoxyacetamido)morphinan.tartrate 45 (yield: 50%), 17-cyclopropylmethyl-3,14β-dihydroxy-4,5α-epoxy-6α-(N-methylheptanamido)morphinan.hydrochloride 46 (yield: 62%), 17-cyclopropylmethyl-4,5α-epoxy-3,14β-dihydroxy-6α-(N-methylbutyroxycarbamido) morphinan.tartrate 47 (yield: 70%), 17-cyclopropylmethyl-4,5α-epoxy-3,14β-dihydroxy-6α-(N-methyl-3-cyclopentylpropionamido) morphinan.tartrate 48 (yield: 84%), 17-cyclopropylmethyl-4,5α-epoxy-3,14β-dihydroxy-6α-(N-methyl-2-methoxyethoxycarbamido) morphinan.tartrate 49 (yield: 70%), and 17-cyclopropylmethyl-4,5α-epoxy-3,14β-dihydroxy-6α-(N-methyl-trans-3-cyclohexylacrylamido) morphinan.hydrochloride 50 (yield: 72%) were obtained by following the procedure of example 11, but using 3-phenylpropionyl chloride, phenylacetyl chloride, trans-cinnamoyl chloride, acetyl chloride, 3-bromophenylacetyl chloride, 3,4-dichlorobenzoyl chloride, 4-bromophenylacetyl chloride, R-(−)-2-phenylpropionyl chloride, R-(−)-methoxyphenylacetyl chloride, S-(+)-methoxyphenylacetyl chloride, S-(+)-2-phenylpropionyl chloride, cyclohexanecarbonyl chloride, benzoyl chloride, 4-phenylbutanoyl chloride, 6-phenylhexanoyl chloride, 3-fluorophenylacetyl chloride, phenoxyacetyl chloride, hexanoyl chloride, heptanoyl chloride, 3-(3-pyridyl)propionyl chloride, benzyl chloroformate, 4-nitrobenzyl chloroformate, 3-pyridylmethyl chloroformate, thiophenoxyacetyl chloride, heptanoyl chloride, butyl chloroformate, 3-cyclopentylpropionyl chloride, 2-methoxyethyl chloroformate and trans-3-cyclohexylacryloyl chloride instead of 3,4-dichlorophenylacetyl chloride.

Compound 22

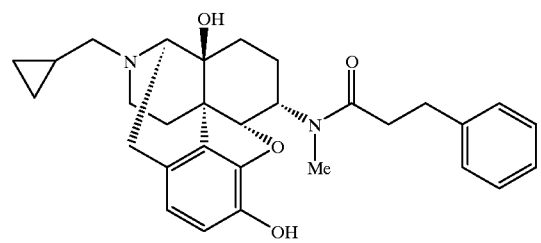

22 mp>203° C. (decomposition)

NMR (500 MHz, DMSO-$d_6$)

δ 0.13–0.27 (2H, m), 0.47–0.59 (2H, m), 0.80–0.95 (1H, m), 1.06–1.57 (5H, m), 1.68–1.79 (1H, m), 1.95–2.33 (2H, m), 2.57–2.89 (6H, m), 2.88 (2.1H, s), 3.17 (0.9H, s), 3.00–3.53 (3H, m), 3.45 (3H, brs), 4.09 (1H, s), 4.29–4.36 (0.3H, m), 4.54 (0.7H, d, J=3.7 Hz).

4.54–4.59 (0.3H, m), 4.92 (0.7H, m), 6.51 (0.7H, d, J=8.0 Hz), 6.49–6.52 (0.3H, m), 6.62 (1H, d, J=8.0 Hz), 7.05–7.31 (5H, m), 9.10 (1H, brs).
IR (KBr)
  υ 3420, 1605, 1460, 1174, 1120, 1073, 1036 cm$^{-1}$.
Mass (EI)
  m/z=488 M+.
Elementary Analysis: As $C_{30}H_{36}N_2O_4 \cdot 0.5C_4H_6O_6 \cdot 0.2H_2O$
  Calcd.: C, 67.75; H, 7.00; N, 4.94.
  Found.: C, 67.79; H. 7.09; N, 5.04.
Compound 23

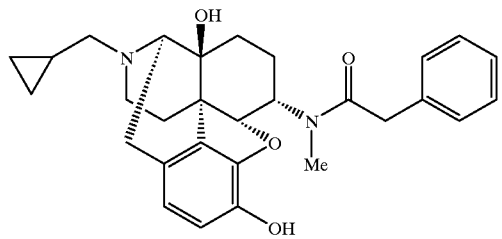

mp 253.0–257.0° C. (decomposition, ether)
NMR (400 MHz, DMSO-$d_6$)
  δ 6 0.40 (1H, m)), 0.47 (1H, m), 0.60 (1H, m), 0.69 (1H, m), 1.05 (1H, m), 1.09 (1H, m), 1.34 (1H, m), 1.47 (1H, m), 1.56 (1H, dd, J=14.7, 9.3 Hz), 1.61 (1H, d, J=13.7 Hz), 1.91 (1H, m), 2.36~2.52 (2H, m), 2.69 (1H, m), 2.80 (0.8H, s), 2.93 (1H, m), 2.95 (2.2H, s), 3.15 (1H, d, J=12.2 Hz), 3.09 (1H, dd, J=19.8, 7.1 Hz), 3.76 (2H, s), 3.89 (1H, br s), 4.27 (0.27H, s), 4.51 (0.27H, m), 4.63 (0.73H, d, J=3.4 Hz), 5.00 (0.73H, dt, J=13.7, 3.4 Hz), 6.20 (0.73H, brs), 6.40 (0.27H, m), 6.58 (1H, d, J=8.3 Hz), 6.72 (1H, dd, J=8.3, 2.0 Hz), 7.22~7.29 (2H, m), 7.30~7.38 (3H, m), 8.80 (1H, br s), 9.29 (1H, d, J=5.9 Hz).
IR (KBr)
  υ 3400, 3100, 2952, 1620, 1508, 1475, 1319, 1120, 1036, 806 cm$^{-1}$.
Mass (FAB)
  m/z 475 (M+H)+.
Elementary Analysis: As $C_{29}H_{35}N_2O_4Cl \cdot 0.3H_2O$
  Calcd.: C, 67.44; H, 6.95; N, 5.43; Cl, 6.86.
  Found.: C, 67.45; H, 7.15; N, 5.40; Cl, 6.99.
Compound 24

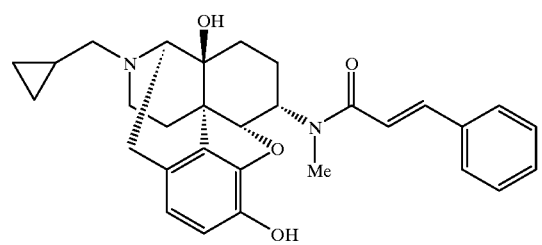

mp 254–257° C.
NMR (400 MHz, DMSO-$d_6$)
  δ 0.21 (2H, m), 0.52 (2H, m), 0.91 (1H, m), 1.20 (1.5H, m), 1.48 (3H, m), 1.78 (1H, m), 2.26 (2.5H, m), 2.58 (1H, m), 2.73 (2H, m), 2.91 (0.5H, s), 3.06 (1H, m), 3.09 (2.5H, m), 3.20–3.90 (4H, br), 4.03 (1H, s), 4.5–5.1 (2H, m), 6.52 (1H, d, J=7.9 Hz), 6.62 (1H, d, J=7.9 Hz), 7.09 (0.2H, d, J=15.9 Hz), 7.23 (0.8H, d, J=15.9 Hz), 7.40–7.60 (4H, m), 7.60–7.80 (2H, m), 8.80–9.20 (1H, br).
IR (KBr)
  υ 3400, 1644, 1593, 1317, 1118, 1038, 768 cm$^{-1}$.
Mass (FAB)
  m/z 487 (M+H)
Elementary Analysis: As $C_{32}H_{37}N_2O_7 \cdot 0.8H_2O$
  Calcd.: C, 66.72; H, 6.75; N, 4.86
  Found.: C, 66.56; H, 6.74; N, 5.08
Compound 25

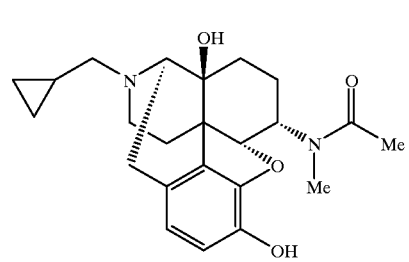

mp>300.0° C. (decomposition, ether)
NMR (400 MHz, DMSO-$d_6$)
  δ 0.40 (1H, m), 0.48 (1H, m), 0.61 (1H, m), 0.69 (1H, m), 1.05 (1H, m), 1.13 (1H, m), 1.33 (1H, m), 1.55 (1H, dd, J=15.3, 9.8 Hz), 1.59 (1H, d, J=14.0 Hz),1.92 (1H, dt, J=15.3, 9.5 Hz), 2.05 (2.5H, s), 2.13 (0.5H, s), 2.43 (1H, dt, J=13.4, 4.9 Hz), 2.69 (1H, m), 2.77 (0.5H, s), 2.89 (2.5H, s), 2.94 (1H, dd, J=13.1, 7.0 Hz), 3.03 (1H, br d, J=10.3 Hz), 3.09 (1H, dd, J=20.1, 7.3 Hz), 3.24~3.38 (2H, m), 3.91 (1H, d, J=6.7 Hz), 4.37 (0.17H, br d, J=12.2 Hz), 4.61 (0.83H, d, J=4.3 Hz), 4.81 (0.17H, d, J=4.3 Hz), 4.94 (0.83H, dt, J=14.0, 3.7 Hz), 6.26 (0,83H, s), 6.46 (0.17H, s), 6.58 (1H, d, J=8.2 Hz), 6.73 (1H, dd, J=8.2, 1.8 Hz), 8.82 (1H, br s), 9.31 (1H, s).
IR (KBr)
  υ 3400, 3100, 2866, 1618, 1500, 1301, 1172, 1120, 1038, 920 cm$^{-1}$.
Mass (FAB)
  m/z 399 (M+H)+.
Elementary Analysis: As $C_{23}H_{30}N_2O_4 \cdot 1.12HCl \cdot 0.5H_2O$
  Calcd.: C, 61.61; H, 7.22; N, 6.25; Cl, 8.86.
  Found.: C, 61.43; H, 7.21; N, 6.33; Cl, 9.00.
Compound 26

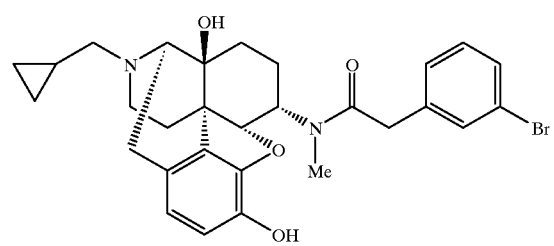

mp 200.0–205.0° C. (decomposition, ether)
NMR (400 MHz, DMSO-$d_6$)
  δ 0.40 (1H, m), 0.46 (1H, m), 0.60 (1H, m), 0.68 (1H, m), 1.03 (1H, m), 1.15 (1H, m), 1.36 (1H, m), 1.53~1.65 (2H, m), 1.87 (1H, m), 2.41 (1H, m), 2.68 (1H, m), 2.80 (0.4H, s), 2.96 (2.6H, s), 2.87~3.12 (3H, m), 3.20~3.35

(2H, m), 3.79 (2H, s), 3.85 (1H, m), 4.63 (0.87H, d, J=3.4 Hz), 4.65 (0.13H, m), 4.97 (1H, dt, J=13.7, 3.4 Hz), 6.13 (0.87H, s), 6.22 (0.13H, s), 6.59 (1H, d, J=8.3 Hz), 6.71 (1H, d, J=8.3 Hz), 7.25 (1H, d, J=7.8 Hz), 7.29 (1H, t, J=7.8 Hz), 7.45 (1H, d, J=7.8 Hz), 7.46 (1H, s), 8.76 (1H, br s), 9.29 (1H, s).

IR (KBr)
  υ 3400, 2952, 1626, 1506, 1407, 1319, 1120, 1036, 919, 772, 748 cm$^{-1}$

Mass (FAB)
  m/z 553 (M+H)+.

Elementary Analysis: As $C_{29}H_{34}N_2O_4Br_2 \cdot 0.4H_2O$
  Calcd.: C, 54.29; H. 5.48; N, 4.37; Br, 24.91.
  Found.: C, 54.04; H, 5.63; N, 4.34; Br, 25.19.

Compound 27

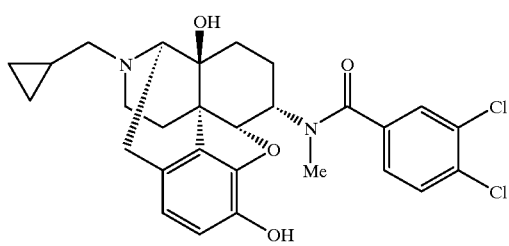

mp 230° C. (decomposition)
NMR (500 MHz, DMSO-$d_6$)
  δ 0.32–0.74 (4H, m), 0.93–1.11 (1H, m), 1.12–1.42 (2H, m), 1.45–1.78 (3H, m), 1.94–2.22 (1H, m), 2.65–2.76 (1H, m), 2.86 (2.4H, s), 2.91–3.15 (3.6H, m), 3.20–3.40 (2H, m), 3.79 (0.2H, m), 3.94 (0.8H, m), 4.24 (0.2H, m), 4.62 (0.2H, m), 4.85 (0.8H, m), 4.98 (0.8H, m), 5.97 (0.2H, br s), 6.35 (0.8H, br s), 6.59 (1H, d, J=7.9 Hz), 6.73 (1H, d, J=7.9 Hz), 7.40–7.50 (1H, m), 7.69–7.79 (2H, m), 8.66 (0.2H, br s), 8.88 (0.8H, br s), 9.31 (0.8H, br s), 9.38 (0.2H, br s).

IR (KBr)
  υ 3152, 1626, 1508, 1473, 1408, 1379, 1315, 1033 cm$^{-1}$.

Mass (FAB)
  m/z 529 ((M+H) +)

Elementary Analysis: As $C_{28}H_{30}N_{O4}Cl_2 \cdot HCl \cdot 0.2H_2O$
  Calcd.: C, 59.05; H, 5.56; N, 4.92; Cl, 18.67.
  Found.: C, 58.93; H, 5.68; N, 4.90; Cl 18.54.

Compound 28

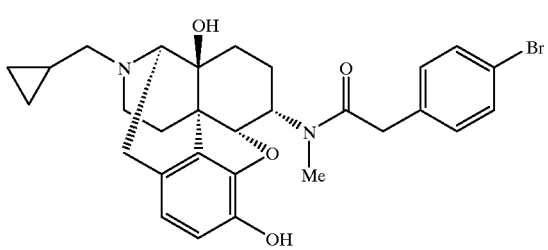

mp 210° C. (decomposition)
NMR (500 MHz, DMSO-$d_6$)
  δ 0.45 (2H, m), 0.64 (2H, m), 1.07 (1H, m), 1.15 (2H, m), 1.35 (1H, m), 1.58 (2H, m), 1.90 (1H, m), 2.42 (1H, m), 2.67 (1H, m), 2.80 (0.5H, s), 2.92 (1H, m), 2.95 (2.5H, s), 3.10 (2H, m), 3.31 (1H, m), 3.80 (3H, m), 4.4–5.0 (2H, m), 6.14 (0.8H, brs), 6.23 (0.2H, brs), 6.59 (1H, d, J=8.6 Hz), 6.72 (1H, d, J=8.6 Hz), 7.21 (2H, m), 7.52 (2H, m), 8.76 (1H, brs), 9.0–9.5 (1H, br)

IR (KBr)
  υ 3320, 1620, 1466, 1321, 1120, 803 cm$^{-1}$.

Mass (FAB)
  m/z 553 (M+H)

Elementary Analysis: As $C_{29}H_{33}N_2O_4Br \cdot HBr \cdot 0.5H_2O$
  Calcd.: C, 54.14; H, 5.48; N, 4.35; Br, 24.84
  Found.: C, 53.90; H, 5.42; N, 4.30; Br, 25.21

Compound 29

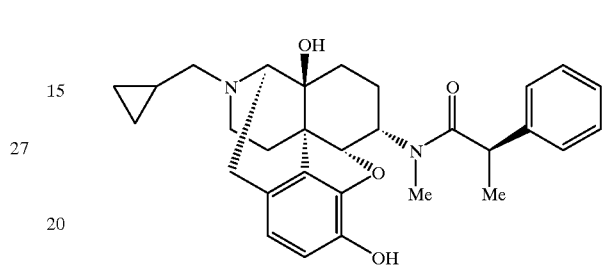

mp>203° C. (decomposition)
NMR (400 MHz, DMSO-$d_6$)
  δ 0.35–0.75 (4H, m), 1.07–1.15 (3H, m), 1.33 (3H, d, J=6.8 Hz), 1.40–1.67 (2H, m), 1.84–2.15 (1.4H, m), 2.43–2.75 (0.6H, m), 2.80 (0.9H, s), 2.81 (2.1H, s), 2.90–3.15 (3H, m), 3.20–3.50 (3H, m), 3.85–3.95 (1H, m)r, 4.12–4.28 ($1_H$, m), 4.53–4.70 (1.3H, m), 4.95–5.05 (0.7H, m), 6.25 (0.7H, brs), 6.40–6.60 (1.3H, m), 6.66 (0.3H, d, J=8.3 Hz), 6.71 (0.7H, d, J=7.8 Hz), 7.18–7.42 (5H, m), 8.80–8.95 (1H, brs), 9,21 (0.3H, s), 9.30 (0.7H, s).

IR (KBr)
  υ 3420, 1620, 1508, 1460, 1120, 1067, 1036, 704 cm$^{-1}$

Mass (FAB)
  m/z 489 (M+H)+.

Elementary Analysis: As $C_{30}H_{36}N_2O_4 \cdot HCl \cdot 3H_2O$
  Calcd.: C, 67.92; H, 7.14; N, 5.28; Cl, 6.68.
  Found.: C, 68.05; H, 7.21; N, 5.39; Cl, 6.31.

Compound 30

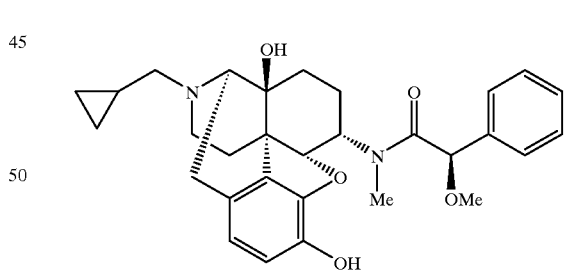

mp 207.0–211.0° C. (decomposition, ether)
NMR (400 MHz, DMSO-$d_6$)
  δ 0.39 (1H, m), 0.47 (1H, m), 0.61 (1H m), 0.68 (1H, m), 1.07 (1H, m), 1.22 (1H, m), 1.39 (1H, m), 1.50 (1H, dd, J=15.1, 9.3 Hz), 1.63 (1H, d, J=11.2 Hz), 1.90 (1H, m), 2.30 (0.15H, dt, J=13.2, 4.9 Hz), 2.47 (0.85H, dt, J=13.2, 4.9 Hz), 2.64 (1H, m), 2.81 (0.45H, s), 2.88 (2.55H, s), 2.95~3.10 (3H, m), 3.20–3.35 (2H, m), 3.30 (0.45H, s), 3.40 (2.55H, s), 3.78 (0.15H, br s), 3.92 (0.85H, br d, J=6.8 Hz), 4.64 (0.15H, br d, J=12.7 Hz), 4.69 (1H, d, J=3.4 Hz), 4.95 (0.85H, br d, J=13.7 Hz), 5.26 (0.85H, s), 5.35 (0.15H, s), 6.28 (0.85H, s), 6.54

(0.15H, d, J=8.3 Hz), 6.57 (0.85H, d, J=8.3 Hz), 6.63 (0.15H, s), 6.69 (0.15H, d, J=8.3 Hz), 6.72 (0.85H, d, J=8.3 Hz), 7.31~7.46 (5H, m), 8.86 (0.85H, br s), 8.92 (0.15H, br s), 9,27 (0.15H, s), 9.34 (0.85H, s).

IR (KBr)
 υ  3400, 1638, 1460, 1321, 1120, 1035, 600, 418 cm$^{-1}$

Mass (FAB)
 m/z 505 (M+H)+.

Elementary Analysis: As $C_{30}H_{37}N_2O_5Cl.0.4H_2O$
 Calcd.: C, 65.72; H, 6.95; N, 5.11; Cl, 6.47.
 Found.: C, 65.77; H, 7.14; N, 5.23; Cl, 6.41.

Compound 31

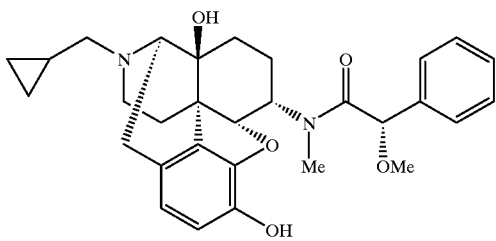

mp 270.0–275.0° C. (decomposition, ether)
NMR (400 MHz, DMSO-d$_6$)
 δ 0.40 (1H, m), 0.48 (1H, m), 0.62 (1H, m), 0.69 (1H, m), 1.07 (1H, m), 1.11 (1H, m), 1.35 (1H, m), 1.50 (1H, t, J=14.5 Hz), 1.57 (1H, t, J=15.6 Hz), 1.86 (0.22H, m), 1.97 (0.78H, m), 2.44 (1H, dt, J=13.2, 4.4 Hz), 2.66 (1H, m), 2.80 (0.66H, s), 2.88 (2.34H, s), 2.96~3.12 (3H, m), 3.24~3.37 (2H, m), 3.30 (2.34H, s), 3.38 (0.66H, s), 3.92 (1H, d, J=5.9 Hz), 4.27 (0.22H, d, J=1.5 Hz), 4.56 (0.78H, d, J=3.4 Hz), 4.75 (0.22H, m), 5.07 (0.78H, br d, J=13.7 Hz), 5.19 (0.78H, s), 5.24 (0.22H, s), 6.31 (0.78H, s), 6.50 (0.22H, s), 6.56 (1H, d, J=8.3 Hz), 6.71 (1H, d, J=8.3 Hz), 7.34~7.43 (5H, m), 8.85 (1H, br s), 9.27 (0.78H, s), 9.30 (0.22H, s).

IR (KBr)
 υ 3500, 3100, 2942, 2346, 1638, 1508 1475, 1319, 1176, 1120, 1036, 905 cm$^{-1}$.

Mass (FAB)
 m/z 505 (M+H)+.

Elementary Analysis: As $C_{30}H_{37}N_2O_5Cl.0.3H_2O$
 Calcd.: C, 65.93; H, 6.94; N, 5.13; Cl, 6.49.
 Found.: C, 65.89; H. 7.02; N, 5.12; Cl, 6.53.

Compound 32

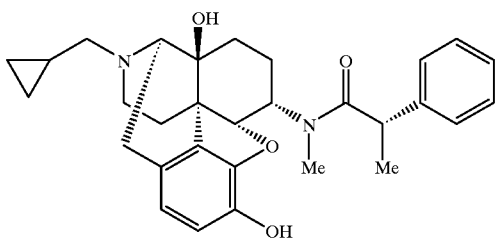

mp 162–165° C.
NMR (400 MHz, DMSO-d$_6$)
 δ 0.21 (2H, m), 0.53 (2H, m), 0.91 (1H, m), 1.09 (1H, m), 1.28 (3H, d, J=6.4 Hz), 1.3–1.5 (3.3H, m), 1.75 (0.7H, m), 2.2–2.3 (2H, m), 2.4–2.8 (4H, m), 2.78 (1H, s), 2.84 (2H, s), 3.0–3.3 (2H, m), 4.04 (1H, s), 4.0–4.1 (1H, m), 4.4–5.1 (2H, m), 6.47 (1H, m), 6.59 (1H, m), 7.2–7.4 (5H, m)

IR (KBr)
 υ  3400, 1620, 1462, 1120, 1067, 702 cm$^{-1}$.

Mass (FAB)
 m/z 489 (M+H)

Elementary Analysis: As $C_{32}H_{39}N_2O_7.0.4H_2O$
 Calcd.: C, 67.33; H. 7.03; N, 4.91
 Found.: C, 67.28; H, 7.26; N, 4.90

Compound 33

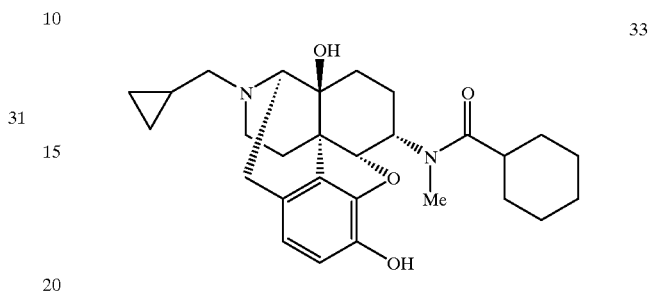

mp>260° C. (decomposition, methanol-ether)
NMR (400 MHz, CD$_3$OD; data only for major amide form (approximately 90%))
 δ 0.49 (2H, m), 0.73 (1H, m), 0.83 (1H, m), 1.08 (1H, m), 1.22–1.57 (7H, m), 1.62–1.98 (8H, m), 2.57–2.74 (2H, m), 2.83–3.02 (2H, m), 3.04–3.20 (2H, m), 3.06 (3H, s), 3.22–3.39 (2H, m), 3.97 (1H, m), 4.74 (1H, m), 5.08 (1H, ddd, J=14.7, 3.9, 3.9 Hz), 6.67 (1H, d, J=8.3 Hz), 6.75 (1H, d, J=8.3 Hz).

IR (KBr)
 υ  3366, 1607, 1510, 1473, 1319, 1197, 1118, 1038, 907, 804 cm$^{-1}$.

Mass (FAB)
 m/z 467 ((M+H)+)

Elementary Analysis: As $C_{28}H_{38}N_2O_4.HCl$
 Calcd.: C, 66.85; H, 7.81; N 5.57; Cl, 7.05.
 Found.: C, 66.87; H, 7.90; N, 5.53; Cl, 7.03.

Compound 34

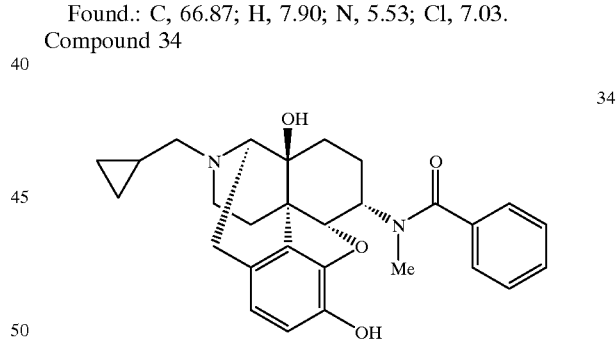

mp 235° C. (decomposition)
NMR (500 MHz, DMSO-d$_6$)
 δ 0.35–0.76 (4H, m), 0.96–1.14 (1H, m), 1.16–1.42 (2H, m), 1.43–1.82 (3H, m), 1.96–2.20 (1H, m), 2.58–2.77 (1H, m), 2.78–3.07 (6H, m), 3.20–3.35 (2H, m), 3.79 (0.2H, m), 3.96 (0.8H, m), 4.35 (0.2H, m), 4.58 (0.2H, m), 4.87 (0.8H, m), 5.01 (0.8H, m), 5.95 (0.2H, br s), 6.38 (0.8H, br s), 6.59 (1H, d, J=7.3 Hz), 6.73 (1H, d, J=7.3 Hz), 7.40–7.50 (5H, m), 8.63 (0.2H, br s), 8.88 (0.8H, br s), 9.31 (0.8H, br s), 9.38 (0.2H, br s).

IR (KBr)
 υ 3270, 3072, 1613, 1506, 1475, 1321, 1120, 1069, 905, 806, 710 cm$^{-1}$

Mass (FAB)
 m/z 461 ((M+H) +).

Elementary Analysis: As $C_{28}H_{32}N_2O_4 \cdot HCl \cdot 0.7H_2O$
  Calcd.: C, 65.99; H, 6.80; N, 5.49; Cl, 6.96.
  Found.: C, 65.97; H, 6.86; N, 5.55; Cl, 6.94.
Compound 35

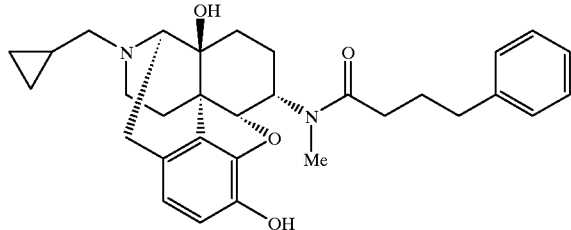

mp 235° C. (decomposition)
NMR (400 MHz, DMSO-$d_6$)
  δ 0 0.40 (1H, m), 0.47 (1H, m), 0.61 (1H, m), 0.68 (1H, m), 1.01–1.09 (2H, m), 1.36 (1H, m), 1.50–1.64 (2H, m), 1.80–1.98 (3H, m), 2.34–2.46 (3H, m), 2.60–2.75 (3H, m), 2.80 (0.6H, s), 2.85 (2.4H, s), 2.88–3.14 (3H, m), 3.22–3.35 (2H, m), 3.90 (1H, m), 4.41 (0.2H, m), 4.61 (0.8H, d, J=3.9 Hz), 4.68 (0.2H, m), 4.97 (0.8H, m), 6.24 (0.8H, br s), 6.46 (0.2H, m), 6.58 (1H, d, J=8.1 Hz), 6.75 (1H, m), 7.16–7.26 (3H, m), 7.30 (2H, m), 8.82 (1H, br s), 9.30 (0.8H, s), 9.33 (0.2H, s).
IR (KBr)
  υ 3068, 1618, 1508, 1475, 1369, 1317, 1118, 1036, 919, 806, 750, 704 cm$^{-1}$.
Mass (FAB)
  m/z 503 ((M+H)+).
Elementary Analysis: As $C_{31}H_{38}N_2O_4 \cdot HCl$
  Calcd.: C, 69.06; H, 7.29; N, 5.19; Cl, 6.58.
  Found.: C, 69.05; H, 7.43; N, 5.27; Cl, 6.43.
Compound 36

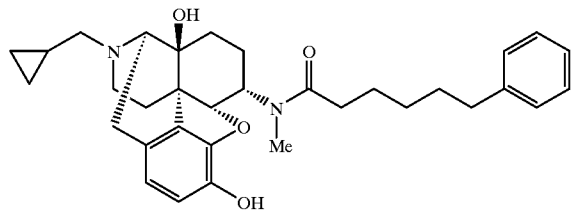

mp 225° C. (decomposition)
NMR (400 MHz, DMSO-$d_6$)
  δ 0.40 (1H, m), 0.47 (1H, m), 0.61 (1H, m), 0.68 (1H, m), 1.01–1.20 (2H, m), 1.25–1.37 (3H, m), 1.50–1.64 (6H, m), 1.91 (1H, m), 2.33 (2H, t, J=7.1 Hz), 2.42 (1H, m), 2.58 (2H, t, J=7.5 Hz), 2.68 (1H, m), 2.78 (0.6H, s), 2.87 (2.4H, s), 2.93 (1H, m), 2.99–3.14 (2H, m), 3.24–3.35 (2H, m), 3.89 (1H, m), 4.42 (0.2H, m), 4.59 (0.8H, d, J=3.4 Hz), 4.76 (0.2H, m), 4.96 (0.8H, m), 6.22 (0.8H, s), 6.44 (0.2H, m), 6.58 (1H, d, J=7.8 Hz), 6.72 (1H, d, J=7.8 Hz), 7.16–7.23 (3H, m), 7.24–7.30 (2H, m), 8.81 (1H, br s), 9.29 (0.8H, s), 9.31 (0.2H, s).
IR (KBr)
  υ 3086, 1618, 1508, 1460, 1315, 1174, 1120, 1038, 748, 700 cm$^{-1}$.
Mass (FAB)
  m/z 531 ((M+H)+).

Elementary Analysis: As $C_{33}H_{42}N_2O_4 \cdot HCl$
  Calcd.: C, 69.88; H, 7.64; N. 4.94; Cl, 6.25.
  Found.: C, 69.70; H, 7.64; N, 4.98; Cl, 6.25.
Compound 37

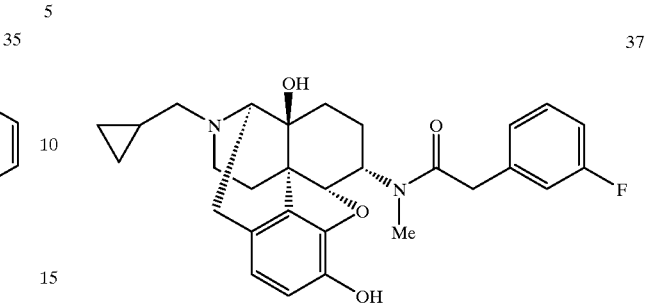

mp 225° C. (decomposition)
NMR (400 MHz, DMSO-$d_6$)
  δ 0.40 (1H, m), 0.47 (1H, m), 0.61 (1H, m), 0.69 (1H, m), 1.01–1.20 (2H, m), 1.35 (1H, m), 1.50–1.64 (2H, m), 1.90 (1H, m), 2.41 (1H, m), 2.67 (1H, m), 2.70 (0.6H, s), 2.95 (2.4H, s), 2.89–3.13 (3H, m), 3.23–3.35 (2H, m), 3.80 (1.6H, s), 3.85–3.94 (1.4H, m), 4.47 (0.2H, m), 4.51 (0.2H, m), 4.63 (0.8H, d, J=3.9 Hz), 4.98 (0.8H, m), 6.20 (0.8H, s), 6.43 (0.2H, br s), 6.58 (1H, d, J=8.3 Hz), 6.72 (1H, d, J=8.3 Hz), 7.05–7.15 (3H, m), 7.35 (1H, m), 8.80 (1H, br s), 9.30 (0.2H, s), 9.31 (0.8H, s)
IR (KBr)
  υ 3120, 1620, 1510, 1460, 1321, 1118, 777, 683, 518 cm$^{-1}$.
Mass (FAB)
  m/z 493 ((M+H)+).
Elementary Analysis: As $C_{29}H_{33}N_2O_4F \cdot HCl$
  Calcd.: C, 65.83; H, 6.48; N, 5.29; Cl, 6.70; F, 3.59.
  Found.: C, 65.69; H, 6.59; N, 5.44; Cl, 6.43; F, 3.60.
Compound 38

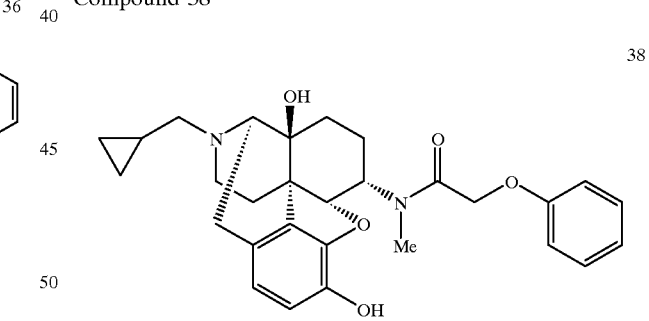

mp 198.0–206.0° C. (decomposition, diethylether)
NMR (400 MHz, DMSO-$d_6$) δ 0.10–0.30 (2H, m), 0.44–0.63 (2H, m), 0.83–0.99 (11H, m), 0.90–1.28 (1H, m), 1.28–1.39 (1H, m), 1.39–1.57 (2I1, m), 1.66–1.84 (1H, m), 2.12–2.38 (2H, m), 2.41–2.65 (2H, m), 2.65–2.80 (2H, m), 2.84 (0.6H, s), 2.95 (2.4H, s), 3.00–3.13 (1H, m), 3.20–3.34 (1H, m), 2.50–4.25 (3H, br s), 4.05 (1H, s), 4.38 (0.2H, dt J=11.2, 3.4 Hz), 4.54 (0.8H, d, J=3.4 Hz), 4.85 (2H, s), 4.76–4.96 (1H, m), 6.51 (1H, d, J=7.8 Hz), 6.64 (1I1, d, J=8.3 Hz), 6.86–7.02 (3H, m), 7.22–7.37 (2H, m), 8.65–9.60 (1H, br s)
IR (KBr)
  υ 1601, 1562, 1497, 1460, 1321, 1236, 1120, 1067, 919, 758 cm$^{-1}$ Mass (FAB)

m/z 491 ((M+H)).

Elementary Analysis: As $C_{31}H_{37}N_2O_8 \cdot 0.8H_2O$
Calcd.: C, 64.19; H, 6.70; N, 4.83
Found.: C, 64.16; H, 6.64; N, 4.89

Compound 39

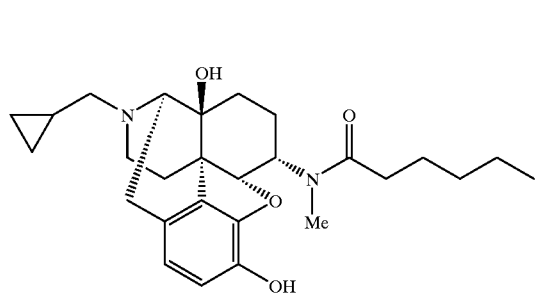

mp 205–207° C.

NMR (400 MHz, DMSO-$d_6$)

δ 0.18–0.30 (2H, m), 0.47–0.60 (2H, m), 0.82–0.97 (4H, m), 1.13 (1H, m), 1.24–1.38 (5H, m), 1.38–1.60 (4H, m), 1.75 (1H, m), 2.20–2.40 (4H, m), 2.57 (1H, m), 2.70–2.79 (3H, m), 2.80 (0.6H, s), 2.88 (2.4H, s), 3.00–3.63 (5H, m), 4.10 (1H, s), 4.36 (0.2H, m), 4.53 (0.8H, d, J=3.4 Hz), 4.62 (0.2H, m), 4.95 (0.8H, m), 6.52 (1H, d, J=8.3 Hz), 6.63 (1H, d, J=8.3 Hz), 9.10 (1H,

IR (KBr)

υ 3230, 1609, 1460, 1317, 1122 cm$^{-1}$.

Mass (FAB)

m/z 455 ((M+H)+).

Elementary Analysis: As $C_{27}H_{38}N_2O_4 \cdot 0.5C_4H_6O_6 \cdot 0.5H_2O$
Calcd.: C, 64.66; H, 7.86; N, 5.20.
Found.: C, 64.54; H, 7.76; N. 5.31.

Compound 40

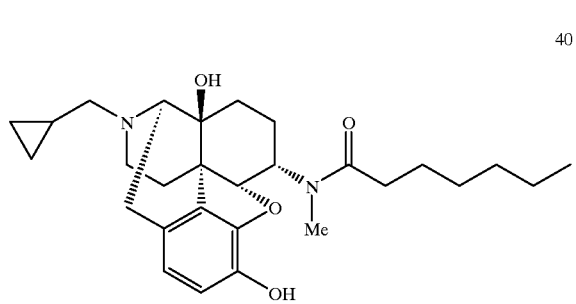

mp 210–212° C. (decomposition)

NMR (500 MHz, DMSO-$d_6$)

δ 0.25–0.35 (2H, m), 0.45–0.57 (2H, m), 0.84–0.96 (4H, m), 1.11 (1H, m), 1.21–1.35 (8H, m), 1.39–1.580 (4H, m), 1.72 (1H, m), 2.15–2.25 (2H, m), 2.27–2.35 (2H, m), 2.51 (1H, m), 2.65–2.76 (2H, m), 2.79 (0.6H, s), 2.88 (2.4H, s), 2.95–3.80 (5H, m), 4.03 (1H, s), 4.34 (0.2H, m), 4.51 (0.8H, d, J=3.4 Hz), 4.61 (0.2H, m), 4.89 (0.8H, m), 6.50 (1H, d, J=8.3 Hz), 6.62 (1H, d, J=8,3 Hz), 9.20 (1H, br s).

IR (KBr)

υ 3180, 1607, 1460, 1359, 1317, 1122 cm$^{-1}$.

Mass (FAB)

m/z 469 ((M+H)+).

Elementary Analysis: As $C_{28}H_{40}N_2O_4 \cdot 0.5C_4H_6O_6$
Calcd.: C, 66.27; H, 7.97; N, 5.15.
Found.: C, 66.38; H, 8.14; N, 5.33.

Compound 41

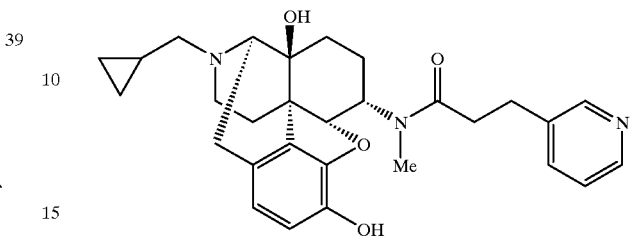

mp 195–210° C.

NMR (400 MHz, DMSO-$d_6$)

δ 0.15–0.28 (2H, m), 0.47–0.60 (2H, m), 0.92 (1H, m), 1.12 (1H, m), 1.24 (1H, m), 1.40–1.55 (2H, m), 1.73 (1H, m), 2.20–2.35 (2H, m), 2.55 (1H, m), 2.60–2.92 (9H, m), 3.05 (1H, m), 3.15–3.95 (5.7H, m), 4.10 (1.7H, s), 4.32 (0.2H, m), 4.54 (0.8H, d, J=3.4 Hz), 4.61 (0.2H, m), 4.90 (0.8H, m), 6.52 (1H, d, J=8.3 Hz), 6.63 (1H, d, J=8.3 Hz), 7.33 (1H, m), 7.71 (1H, m), 8.40 (1H, m), 8.50 (1H, n), 9.08 (1.7H, br s).

IR (KBr)

υ 3220, 1607, 1460, 1311, 1120 cm$^{-1}$.

Mass (FAB )

m/z 490 ((M+H)+).

Elementary Analysis: As $C_{29}H_{35}N_3O_4 \cdot 0.85C_4H_6O_6 \cdot 0.3H_2O$
Calcd.: C, 62.50; H, 6.59; N, 6.75.
Found.: C, 62.33; H, 6.77; N, 6.78.

Compound 42

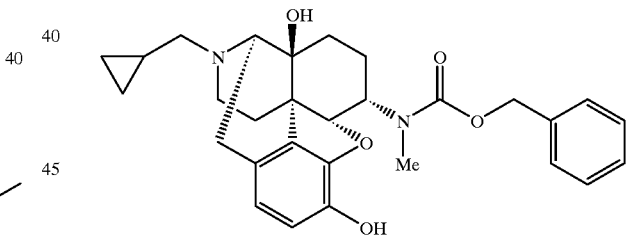

mp 254.0–259.0° C. (decomposition, ether)

NMR (400 MHz, DMSO-$d_6$)

δ 150.40 (1H, J), 0.47 (4H, m), 0.60 (2H, m), 0.69 (1H, m), 1.06 (1H, m), 1.40~1.64 (3H, m), 1.90 (1H, m), 2.44 (1H, m), 2.69 (1H, m), 2.85 (3H, s), 2.92 (1H, m), 3.03 (1H, m), 3.09 (1H, dd, J=20.0, 6.4 Hz), 3.23~3.38 (3H, m), 3.89 (1H, br d, J=5.4 Hz), 4.59, 4.63, 4.67 (2H, each br s), 5.13~5.23 (2H, m), 6.23 (1H, s), 6.58 (1H, d, J=8.1 Hz), 6.71 (1H, d, J=8.1 Hz), 7.35 (1H, m), 7.39, 7.40 (4H, each s), 8.80 (1H, br s), 9.29 (1H, br s).

IR (KBr)

υ 3500, 3100, 2850, 1663, 1470, 1350, 1317, 1156, 1120, 1035 cm$^{-1}$.

Mass (FAB)

m/z 491 (M+H)+.

Elementary Analysis: As $C_{29}H_{35}N_2O_5Cl \cdot 0.2H_2O$
Calcd.: C, 65.64; H, 6.72; N, 5.28; Cl, 6.68.
Found.: C, 65.66; H, 6.71; N, 5.30; Cl, 6.70.

Compound 43

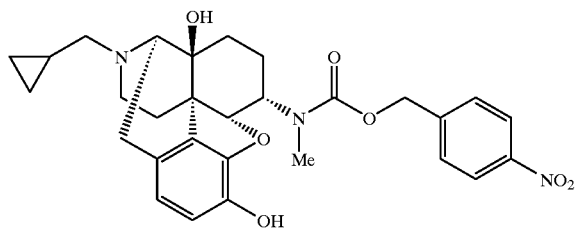

mp 198.0–206.0° C. (decorosition, diethylether)
NMR (400 MHz, DMSO-$d_6$)
 δ 0.31–0.43 (1H, m), 0.43–0.57 (1H, m), 0.57–0.65 (1H, m), 0.65–0.77 (1H, m), 1.00–1.25 (2H, m), 1.38–1.70 (3H, m), 1.87–2.09 (1H, m), 2.35–2.50 (1H, m), 2.60–2.79 (1H, m), 2.89–3.18 (3H, m), 2.87 (1.4H, s), 2.90 (1.6H, s), 3.18–3.38(2H, m), 3.95 (1H, br s), 4.57–4.80 (2H, m), 5.29 (1.2H, s), 5.22–5,40 (0.8H, m), 6.35 (0.6H, brs), 6.45 (0.4H, br s), 6.59 (1H, d, J=7.8 Hz), 6.74 (1H, dd, J=8.3, 2.0 Hz), 7.60–7.74 (2H, m), 8.20–8.36 (2H, m), 8.87 (1H, br s), 9.34 (0.4H, s), 9.35 (0.6H, s)
IR (KBr)
 υ 1686, 1638, 1560, 1543, 1522, 1460, 1346, 1120, 1035 cm$^{-1}$.
Mass (FAB)
 m/z 536 ((M4H)+).
Elementary Analysis: As $C_{29}H_{34}N_3O_7Cl0.3H_2O$
 Calcd.: C, 60.21; H, 6.20; N, 7.26; Cl, 6.13.
 Found.: C, 60.29; H, 6.18; N, 7.16; Cl, 6.24.

Compound 44

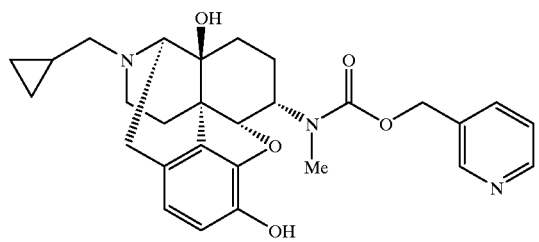

mp>130° C. (decomposition)
NMR (400 MHz, DMSO-$d_6$)
 δ 0.15–0.30 (2H, m), 0.45–0.60 (2H, m), 0.85–0.98 (1H, m), 1.05–1.20 (1H, m), 1.30–1.53 (3H, m), 1.68–1.82 (1H, m), 2.10–2.40 (2H, m), 2.45–2.90 (4H, m), 2.85 (3H, s), 3.00–3.18 (1H, m), 3.21–3.42 (1H, m), 4.11 (2H, s), 4.49–4.62 (2H, m), 5.10–5.30 (2H, m), 6.51 (1H, d, J=8.0 Hz), 6.62 (1H, d, J=8.0 Hz), 7.39–7.48 (1H, m), 7.81 (1H, d, J=7.3 Hz), 8.55 (1H, d, J=3.4 Hz), 8.62 (1H, s), 9.00 (2H, brs).
IR (KBr)
 υ 3312, 1692, 1603, 1406, 1350, 1311, 1267, 1122, 1069, 1035 cm$^{-1}$
Mass (EI)
 m/z 492 (M+H)+.
Elementary Analysis: As $C_{28}H_{33}N_3O_5 \cdot C_4H_6N_6 \cdot 0.3H_2O$
 Calcd.: C, 59.40; H. 6.17; N, 6.50.
 Found.: C, 59.39; H, 6.27; N, 6.52.

Compound 45

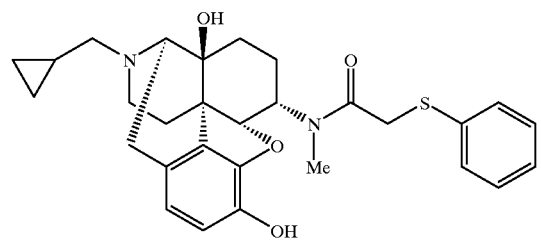

mp 197.0° C. (decomposition, diethylether)
NMR (400 MHz, DMSO-$d_6$)
 δ 0.10–0.30 (2H, m), 0.44–0.63 (2H, m), 0.83–0.99 (1H, m), 1.00–1.20 (1H, m), 1.20–1.35 (1H, m), 1.35–1.57 (2H, m), 1.66–1.84 (1H, m), 2.10–2.34 (2H, m), 2.39–2.62 (2H, m), 2.62–2.79 (2H, m), 2.82 (0.6H, s), 2.99 (2.4H, s), 3.00–3.13 (1H, m), 3.20–3.34 (1H, m), 2.00–3.98 (3H, br s), 4.05 (1H, s), 3.95–4.13 (2H, m), 4.41 (0.2H, br d, J=12.2 Hz), 4.52 (0.8H, d, J=3.7 Hz), 4.80–4.90 (1H, m), 6.51 (1H, d, J=8.6 Hz), 6.63 (1H, d, J=7.9 Hz), 7.15–7.27 (1H, m), 7.27–7.38 (2H, m), 7.38–7.46 (2H, m), 8.65–9.50 (1H, br s)
IR (KBr)
 υ 3430, 1618, 1508, 1460, 1400, 1120, 1036, 917, 746, 692 cm$^{-1}$.
Mass (FAB)
 m/z 507 ((M+H)+).
Elementary Analysis: As $C_{31}H_{37}N_2O_7S \cdot 0.5H_2O$
 Calcd.: C, 63.03; H, 6.48; N, 4.74; S, 5.43
 Found.: C, 63.14; H, 6.51; N, 4.65; S, 5.33

Compound 46

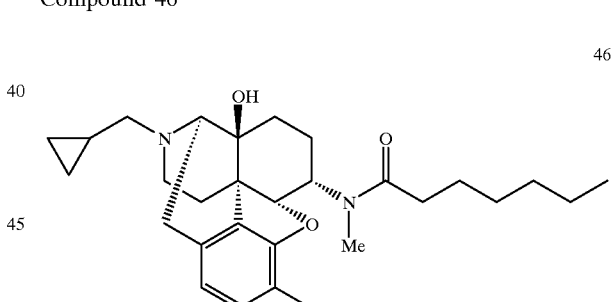

mp >230° C. (decomposition)
NMR (400 MHz, $CD_3OD$)
 δ 0.50 (2H, m), 0.73 (1H, m), 0.83 (1H, m), 0.92 (3H, t, J=6.8 Hz), 1.09 (1H, m), 1.28–1.55 (8H, m), 1.59–1.79 (4H, m), 1.93 (1H, m), 2.38–2.56 (2H, m), 2.64 (1H, m), 2.84–3.05 (2H, m), 2.93 (0.45H, s), 3.02 (2.55H, s), 3.05–3.22 (2H, m), 3.23–3.40 (2H, m), 3.98 (1H, m), 4.57 (0.15H, m), 4.76 (1H, br d, J=2.9 Hz), 5.09 (0.85H, ddd, J=13.7, 3.9, 3.9 Hz), 6.67 (0.85H, d, J=8.3 Hz), 6.68 (0.15H, d, J=8.3 Hz), 6.75 (0.85H, d, J=8.3 Hz), 6.76 (0.15H, d, J=8.3 Hz).
IR (KBr)
 υ 3400, 3158, 1624, 1508, 1468, 1317, 1174, 1120, 1038, 907, 808 cm$^{-1}$.
Mass (FAB)
 m/z 469 ((M+H)+)

Elementary Analysis: As $C_{28}H_{40}N_2O_4 \cdot HCl \cdot 0.2H_2O$
  Calcd.: C, 66.11; H, 8.20; N, 5.51; Cl, 6.97.
  Found.: C, 66.02; H, 8.07; N, 5.64; Cl, 7.02.
Compound 47

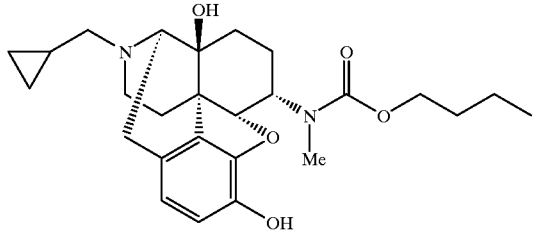

mp 169–170° C. (ethylacetate-methanol)
NMR (400 MHz, DMSO-$d_6$)
  δ 0.18 (2H, m), 0.44–0.56 (2H, m), 0.84–0.96 (4H, m), 1.10 (1H, m), 1.30–1.53 (5H, m), 1.53–1.62 (2H, m), 1.73 (1H, m), 2.12–2.38 (2H, m), 2.41–2.57 (2H, m), 2.63–2.75 (2H, m), 2.80 (3H, s), 3.04 (1H, d, J=18.6 Hz), 3.24 (1H, m), 3.45 (3H, br s, 3×OH), 3.95–4.15 (2H, m), 4.04 (1H, s), 4.48 (1H, m), 4.56 (1H, m), 6.50 (1H, d, J=7.8 Hz), 6.61 (1H, d, J=7.8 Hz), 9.05 (1H, br s, NH+).
IR (KBr)
  υ 3366, 1678, 1613, 1462, 1406, 1350, 1317, 1176, 1122, 1069, 1035, 861, 808 $cm^{-1}$.
Mass (FAB)
  m/z 457 ((M+H) +).
Elementary Analysis: As $C_{26}H_{36}N_2O_5 \cdot 0.5C_4H_6O_6 \cdot 0.5H_2O$
  Calcd.: C, 62.21; H, 7.46; N, 5.18.
  Found.: C, 62.40; H, 7.15; N, 5.23.
Compound 48

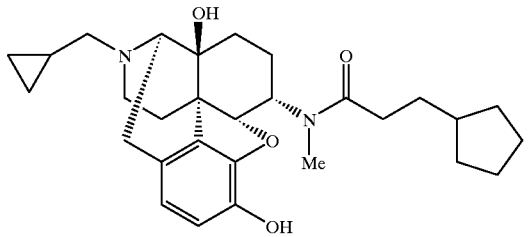

mp 200–212° C. (decomposition)
NMR (400 MHZ, DMSO-$d_6$)
  δ 0.19 (2H, m), 0.45–0.57 (2H, m), 0.90 (1H, m), 1.03–1.18 (3H, m), 1.27 (1H, m), 1.34–1.63 (8H, m), 1.66–1.82 (4H, m), 2.16–2.56 (6H, m) 2.63–2.77 (2H, m), 2.79 (0.6H, s), 2.89 (2.4H, s), 3.03 (1H, br d, J=18.6 Hz), 3.25 (1H, m), 3.45 (3H, br s, 3×OH), 4.03 (1H, s), 4.35 (0.2H, m), 4.52 (0.8H, d, J=3.4 Hz), 4.59 (0.2H, m), 4.88 (0.8H, dt, J=14.1, 3.9 Hz), 6.50 (1H, d, J=8.3 Hz), 6.62 (0.8H, d, J=8.3 Hz), 6.63 (0.2H, d, J=8.3 Hz), 9.06 (1H, br s, NH+).
IR (KBr)
  υ3316, 1719, 1603, 1462, 1408, 1361, 1321, 1172, 1122, 1071, 1038, 917, 808 $cm^{-1}$.
Mass (FAB)
  m/z 481 ((M+H) +).

Elementary Analysis: As $C_{29}H_{40}N_2O_4 \cdot 0.5C_4H_6O_6 \cdot 0.2H_2O$
  Calcd.: C, 66.57; H, 7.82; N, 5.01.
  Found.: C, 66.63; H, 7.83; N, 5.06.
Compound 49

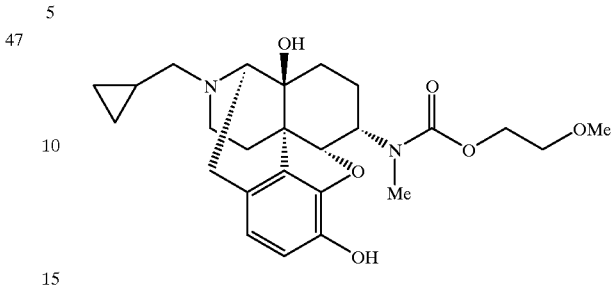

mp>132° C. (decomposition)
NMR (400 MHz, DMSO-$d_6$)
  δ 0.20 (2H, m) ) 0.48–0.58 (2H, m), 0.9 1 (1H, M), 1.10 (1H, m), 1.22–1.54 (3H, 1), 1.73 (6H, m), 2.06–2.34 (2H, m), 2.45–2.62 (2H, m), 2.65–2.78 (2H, m), 2.81 (3H, s), 3.06 ( 2H, br d, J=18.6 Hz), 3.27 (1H, m), 3.29 (3H, br s), 3.50 (3.2H, br s, 3.1×OH +0.1×COOH), 3.52–3.59 (2H, (1), 4.06 (1.1 H, m), 4.07–4.30 (2H, m), 4.40–4.64 (2H, 4), 6.51 (0H, d, J=8.0 Hz), 6.62 (1H, d, J=8.0 Hz), 9.06 (1H, brs, NH+).
IR (KBr)
  υ 3342, 1686, 1609, 1462, 1406, 1346, 1317, 1249, 1176, 1120, 1069, 1036, 924, 903, 806 $cm^{-1}$.
Mass (FAB)
  m/z 459 ((M+H) +)
Elementary Analysis: As $C_{25}H_{34}N_2O_6 \cdot 0.55C_4H_6O_6 \cdot 0.9H_2O$
  Calcd.: C, 58.62; H, 7.07; N, 5.03.
  Found.: C, 58.67; H, 7.06; N, 4.91.
Compound 50

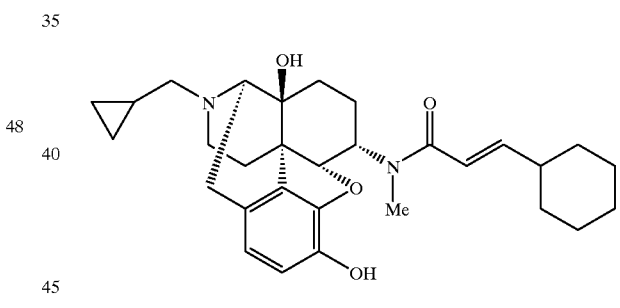

mp 260.0° C. (decomposition)
NMR (400 MHz, DMSO-$d_6$)
  δ 0.08–0.32 (2H, m), 0.40–0.64 (2H, m), 0.80–1.00 (1H, 6), 1.00–1.38 (7H, m), 1.38–1.83 (6H, 35), 2.05–2.38 (3H, m), 2.40–2.65 (2H, m), 2.65–2.81 (3H, m), 2.83 (0.9H, s), 2.95 (2.1H, s), 2.98–3.15 (1H, m), 3.15–3.44 (1H, m), 4.47 (0.3H, m), 4.56 (0.3H, m), 4.58 (0.7H, d, J=3.4 Hz), 4.90 (0.7H, m), 3.50–6.20 (5H, br s), 6.29 (0.3H, d, J=15.1 Hz), 6.37 (0.7H, d, J=14.7 Hz), 6.51 (1H, d, J=8.3 Hz), 6.57–6.74 (2H, m)
IR (KBr)
  υ 3420, 1651, 1599, 1450, 1408, 1321, 1120, 1036, 922, 441 $cm^{-1}$.
Mass (FAB)
  m/z 493 ((M+H) +)
Elementary Analysis: As $C_{30}H_{43}N_2O_8P1 \cdot 1.3H_2O$
  Calcd.: C, 58.68; H, 7.48; N, 4.56; P, 5.04.
  Found.: C, 58.60; H, 7.44; N, 4.61; P, 5.12.

Embodiments 41–44

17-cyclopropylmethyl-4,5α-epoxy-3,14β-dihydroxy-6α-(N-isobutyl-3,4-dichlorophenylacetoamido)

morphinan.hydrochloride 51 (yield: 78%), 17-cyclopropylmethyl-4,5α-epoxy-3,14β-dihydroxy-6α-(3,4-dichlorophenylacetoamido) morphinan.hydrochloride 52 (yield: 92%), 17-cyclopropylmethyl-4,5α-epoxy-3,14β-dihydroxy-6β-(N-methyl-3,4-dichlorophenylacetoamido) morphinan.hydrochloride 51 (yield: 51%), and 17-cyclopropylmethyl-4,5α-epoxy-3,14β-dihydroxy-6β-(N-ethyl-3,4-dichlorophenylacetoamido) morphinan.hydrochloride 54 (yield: 56%) were obtained by following the procedure of example 11 but using 17-cyclopropylmethyl-4,5α (5-epoxy-3,14β-dihydroxy-6α-isobutylaminomorphinan 5, 17-cyclopropylmethyl-4,5α-epoxy-3,14β-dihydroxy-6α-aminomorphinan (J. B. Jiang, R. N. Hanson, P. S. Portoghese, and A. E. Takemori, J. Med. Chem., 20, 1100 (1977).), 17-cyclopropylmethyl-4,5α-epoxy-3,14β-dihydroxy-6β-methylaminomorphinan 10, and 17-cyclopropylmethyl-4,5α-epoxy-3,14β-dihydroxy-6β-ethylaminomorphinan 11 instead of the starting material 17-cyclopropylmethyl-4,5α-epoxy-3,14β-dihydroxy-6α-methylaminomorphinan 4.

Compound 51

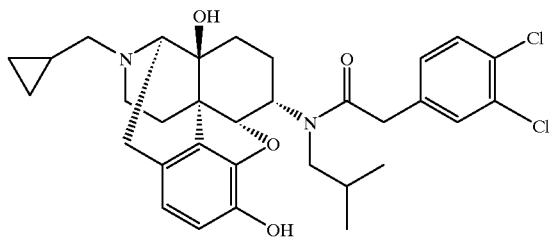

51 mp 185–188C

NMR (400 MHz, DMSO-$d_6$)

δ 0.40 (1H, m), 0.48 (1H, m), 0.61 (1H, m), 0.72 (4H, m), 0.88 (4H, m), 1.06 (2H, m), 1.57 (3H, m), 1.90 (2H, m), 2.42 (1H, m), 2.68 (1H, m), 3.00 (3H, m), 3.36 (2H, m), 3.45 (1H, m), 3.86 (3H, m), 4.4–5.1 (2H, m), 6.19 (0.7H, s), 6.50 (0.3H, s), 6.58 (1H, m), 6.73 (1H, d, J=7.8 Hz), 7.27 (1H, m), 7.52 (1H, d, J=4.4 Hz), 7.59 (1H, t, J=8.3 Hz), 8.82 (1H, brs), 9.26 (0.7H, s), 9.30 (0.3H, s)

IR (KBr)

υ 3370, 1620, 1510, 1468, 1120, 1035 cm$^{-1}$.

Mass (FAB)

m/z 585 (M+H)

Elementary Analysis: As $C_{32}H_{38}N_2O_4Cl_2 \cdot HCl \cdot 0.2H_2O$

Calcd.: C, 61.43; H, 6.35; N, 4.48; Cl, 17.00.

Found.: C, 61.44; H, 6.42; N, 4.45; Cl, 16.82.

Compound 52

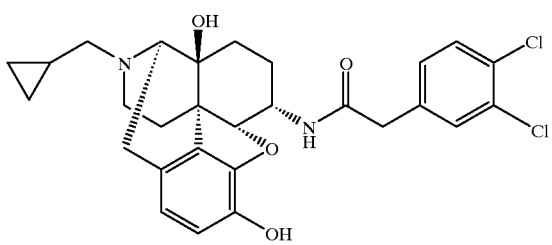

52 mp 212.0–215.0° C. (decomposition, ether)

NMR (400 MHz, DMSO-$d_6$)

δ 0.39 (1H, m), 0.47 (1H, m), 0.60 (1H, m), 0.68 (1H, m), 0.97 (1H, m), 1.05 (1H, m), 1.40 (2H, dd, J=14.7, 9.8 Hz), 1.60 (1H, d, J=10.7 Hz), 1.84 (1H, dt, J=15.1, 9.3 Hz), 2.44 (1H, dt, J=13.2, 4.9 Hz), 2.70 (1H, br q, J=12.7 Hz), 2.94 (1H, m), 3.04 (2H, dd, J=19.5, 6.8 Hz), 3.25~3.35 (2H, m), 3.55 (2H, s), 3.89 (1H, d, J=6.8 Hz), 4.38 (1H, m), 4.59 (1H, d, J=3.4 Hz), 6.25 (1H, s), 6.56 (1H, d, J=8.3 Hz), 6.73 (1H, d, J=8.3 Hz), 7.29 (1H, dd, J=8.3, 2.0 Hz), 7.56 (1H, d, J=2.0 Hz), 7.57 (1H, d, J=8.3 Hz), 8.14 (1H, d, J=8.3 Hz), 8.83 (1H, br s), 9.28 (1H,

IR (KBr)

υ 3400, 2942, 1651, 1510, 1460, 1236, 1120, 1035, 903, 787 cm$^{-1}$.

Mass (FAB)

m/z 529 (M+H)+.

Elementary Analysis: As $C_{28}H_{31}N_2O_4Cl_3 \cdot 0.3H_2O$

Calcd.: C, 58.86; H, 5.58; N, 4.90; Cl, 18.62.

Found.: C, 58.99; H, 5.79; N, 4.93; Cl, 18.61.

Compound 53

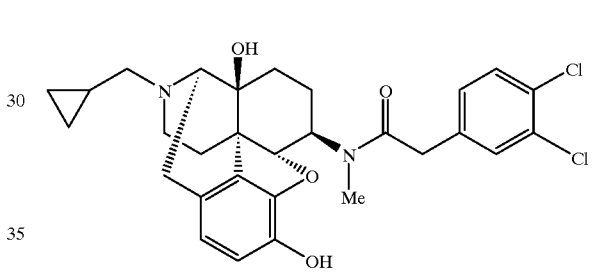

53 mp 194–196° C. (decomposition)

NMR (400 MHz, $CDCl_3$+D20, Data for free base)

δ 0.09–0.17 (2H, m), 0.49–0.57 (2H, m), 0.78–0.89 (2H, m), 1.05 (0.7H, dt, J=13.2, 3.4 Hz), 1.42–1.51 (0.3H, m), 1.49 (2H, brd, J=13.2 Hz), 1.97–2.29 (3H, m), 2.36 (2H, d, J=6.4 Hz), 2.56–2.69 (2H, m), 2.92 (2.1H, s), 2.99 (0.9H, s), 3.00– 3.08 (2H, m), 3.48 (0.7H, d, J=15.6 Hz), 3.49–3.56 (1H, m), 3.66 (0.7H, d, J=15.6 Hz), 3.70 (0.6H, s), 4.55 (0.3H, d, J=8.3 Hz), 4.58 (0.7H, d, J=8.3 Hz), 6.57 (0.3H, d, J=8.3 Hz), 6.73 (0.3H, d, J=8.3 Hz), 6.78–6.82 (1.4H, m), 6.83 (0.7H, d, J=8.3 Hz), 7.11 (0.3H, dd, J=8.3, 2.5 Hz), 7.23 (0.7H, d, J=8.3 Hz), 7.36 (0.3H, d, J=2.0 Hz), 7.39 (0.3H, d, J=8.3 Hz).

IR (KBr)

υ 3420, 1620, 1321, 1127, 1035 cm$^{-1}$.

Mass (FAB)

m/z 543 (M+H)+.

Elementary Analysis: As $C_{29}H_{32}N_2O_4Cl_2 \cdot HCl \cdot 0.7H_2O$

Calcd.: C, 58.78; H, 5.85; N, 4.73; Cl, 17.95.

Found.: C, 58.72; H, 5.86; N, 4.71; Cl, 18.03.

Compound 54

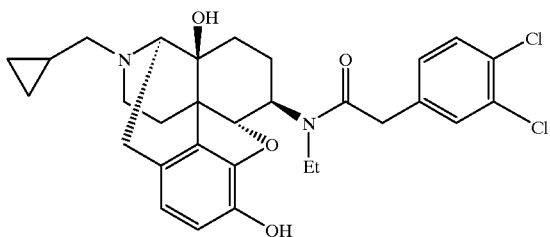

mp 184–187° C. (decomposition)
NMR (500 MHz, DMSO-d$_6$)

δ 0.35–0.75 (4H, m), 1.00–1.53 (4H, m), 1.09 (2.25H, t, J=6.8 Hz), 1.15 (0.75H, t, J=6.8 Hz), 1.60–1.75 (1H, m), 1.93–2.10 (1H, m), 2.38–2.50 (1H, m), 2.80–2.93 (1H, m), 2.96–3.08 (2H, m), 3.15–3.35 (3H, m), 3.40–3.60 (2H, m), 3.56 (2.25H, s), 3.76 (0.75H, s), 3.76–3.87 (1H, m), 4.76 (0.75H, brd, J=7.9 Hz), 5.07 (0.25H, brd, J=7.9 Hz), 6.08 (0.25H, brs), 6.45 (0.75H, brs), 6.63 (0.25H, d, J=7.9 Hz), 6.71 (0.25H, d, J=7.9 Hz), 6.72 (0.75H, d, J=8.1 Hz), 6.80 (0.75 H, d, J=8.1 Hz), 6.98 (0.75H, dd, J=8.3, 2.0 Hz), 7.03 (0.75H, d, J=2.0 Hz), 7.24 (0.25H, dd, J=8.3, 2.0 Hz), 7.51 (0.75H, d, J=8.3 Hz), 7.53 (0.25H, d, J=2.0 Hz), 7.57 (0.25H, d, J=8.3 Hz), 8.80 (1H, brs) 9.31 (0.25H, s), 9.65 (0.75H, s).

IR (KBr)

υ 3420, 1626, 1508, 1319, 1127, 1033 cm$^{-1}$.

Mass (FAB)

m/z 557 (M+H)+.

Elementary Analysis: As $C_{30}H_{34}N2O_4Cl_2 \cdot HCl \cdot 0.3H_2O$
Calcd.: C, 60.12; H, 5.99; N, 4.67; Cl, 17.74.
Found.: C, 60.14; H, 6.17; N, 4.70; Cl, 17.70.

Examples 45–63

17-cyclopropylmethyl-3,14β-dihydroxy-4,5α-epoxy-6β-(N-methylphenylacetamido)morphinan.hydrochloride 55 (yield: 57%), 17-cyclopropylmethyl-3,14β-dihydroxy-4,5α-epoxy-6O-(N-methylbenzyloxycarbamido) morphinan.hydrochloride 56 (yield: 43%), 17-cyclopropylmethyl-3,14β-dihydroxy-4,5α-epoxy-6O-(N-methyl-3-phenylpropionamido) morphinan.hydrochloride 57 (yield: 84%), 17-cyclopropylmethyl-3,4β-dihydroxy-4,5α-epoxy-6β-(N-methylphenoxyacetamido) morphinan.tartrate 58 (yield: 75%), 17-cyclopropylmethyl-3,14β-dihydroxy-4,5α-epoxy-6β-(N-methylbutyroxycarbamido)morphinan.tartrate 5 (yield: 81%), 17-cyclopropylmethyl-3,14β-dihydroxy-4,5α-epoxy-6O-(N-methyl-3-trifluoromethylcinnaiamido) morphinan.tartrate 60 (yield: 84%), 17-cyclopropylmethyl-3,14β-dihydroxy-4,5α-epoxy-6β-[N-methyl-trans-3-(3-furyl)acrylamido]morphinan.tartrate 61 (yield: 91%), 17-cyclopropylmethyl-3,14β-dihydroxy-4,5α-epoxy-6β-(N-methylhexanamido)morphinan.tartrate 62 (yield: 43%), 17-cyclopropylmethyl-3,14β-dihydroxy-4,5α-epoxy-6β-(N-methyl-3-methylcinnamamido) morphinan.tartrate 63 (yield: 88%), 17-cyclopropylmethyl-3,14β-dihydroxy-4,5α-epoxy-6β-(N-methyl-3-cyclopentylpropionamido) morphinan.tartrate 64 (yield: 39%), 17-cyclopropylmethyl-3,14β-dihydroxy-4,5α-epoxy-6β-(N-methylthiophenoxyacetamido)morphinan.tartrate 65 (yield: 75%), 17-cyclopropylmethyl-3,14β-dihydroxy-4,5α-epoxy-6β-(N-methyl-2-naphthamido)morphinan.hydrochloride 66(yield: 95%), 17-cyclopropylmethyl-3,14β-dihydroxy-4,5α-epoxy-6β-(N-methyl-2-methoxyethoxycarbamido) morphinan.tartrate 67 (yield: 63%), 17-cyclopropylmethyl-3,14,β-dihydroxy-4,5α-epoxy-6β-(N-methyl-3-cyclohexylacrylamido) morphinan.tartrate 68 (yield: 77%), 17-cyclopropylmethyl-3,14β-dihydroxy-4,5α-epoxy-6β-(N-methyl-3-methylcinnamamido) morphinan.hydrochloride 69 (yield: 87%), 17-cyclopropylmethyl-3,14β-dihydroxy-4,5α-epoxy-62.[N-methyl-trans-3-(2-furyl)acrylamido] morphinan.hydrochloride 70 (yield: 80%), 17-cyclopropylmethyl-3,14,β-dihydroxy-4,5α-epoxy-6β-[N-methyl-trans-3-(3-thienyl)acrylamido]morphinan.methanesulfonate 71 (yield: 88%), 17-cyclopropylmethyl-3,14β-dihydroxy-4,5α-epoxy-6Oβ (N-methyl-2-trifluoromethylcinnamamido) morphinan.hydrochloride 72 (yield: 93%), and 17-cyclopropylmethyl-3,14,β-dihydroxy-4,5α-epoxy-6β-(N-methyl-4-trifluoromethylcinnamamido) morphinan.tartrate 73 (yield: 84%) were obtained by following the procedure of example 11 but using 17-cyclopropylmethyl-4,5α-epoxy-3,14β-dihydroxy-6β-methylaminomorphinan 10 instead of the starting material 17-cyclopropylmethyl-4,5α-epoxy-3,14β-dihydroxy-6α-methylaminomorphinan 4, and using phenylacetyl chloride, benzyl chloroformate, 3-phenylpropionyl chloride, phenoxyacetyl chloride, butyl chloroformate, 3-trifluoromethylcinnamoyl chloride, trans-3-(3-furyl)acryloyl chloride, hexanoyl chloride, 3-methoxycinnamoyl chloride, 3-cyclopentylpropionyl chloride, thiophenoxyacetyl chloride, 2-naphthoyl chloride, 2-methoxyethyl chloroformate, trans-3-cyclohexylacryloyl chloride, 3-methylcinnamoyl chloride, trans-3-(2-furyl)acryloyl chloride, trans-3-(3-thienyl)acryloyl chloride, 2-trifluoromethylcinnamoyl chloride and 4-trifluoromethylcinnamoyl chloride instead of 3,4-dichlorophenylacetyl chloride.

Compound 55

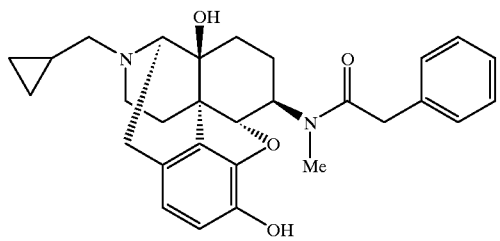

mp 205–207° C.
NMR (500 MHz, DMSO-d$_6$)

δ 0.40 (1H, m), 0.50 (1H, m), 0.57 (1H, m), 0.67 (1H, m), 0.81 (1H, m), 1.00–1.08 (2H, m), 1.37–1.56 (2H, m), 1.97 (1H, m), 2.42–2.53 (2H, m), 2.83 (3H, s), 2.85 (1H, m), 2.45–3.07 (3H, m), 3.25–3.37 (2H, m), 3.46–3.57 (2H, m), 3.81 (0.8H, m), 4.04 (0.2H, m), 4.81 (0.8H, m), 4.88 (0.2H, m), 6.31 (0.2H, br s), 6.42 (0.8H, br s), 6.63 (0.2H, d, J=8.1 Hz), 6.70 (0.2H, d, J=8.1 Hz), 6.75 (0.8H, d, J=8.1 Hz), 6.77–6.80 (1.4H, m), 6.84 (0.8H, d, J=8.1 Hz), 7.12–7.33 (3.6H, m), 8.80 (1H, br s), 9.27 (0.2H, s), 9.65 (0.8H, s).

IR (KBr)

υ 3400, 1620, 1502, 1460, 1321, 1125, 1033, 920, 859, 748, 719 cm$^{-1}$

Mass (FAB)

m/z 475 ((M+H)+)

Elementary Analysis: As C29H34N2O4·HCl·0.5H2O
  Calcd.: C, 66.98; H, 6.98; N, 5.38; Cl, 6.82.
  Found.: C, 67.25; H, 7.05; N, 5.40; Cl, 6.43.
Compound 56

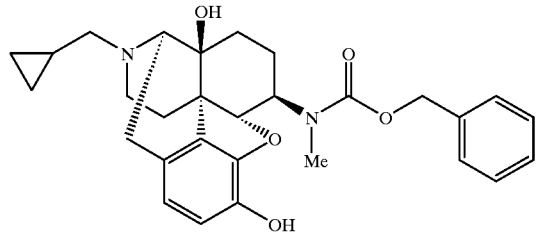

mp 189.0–192.0° C. (decomposition, diethylether)
NMR (400 MHz, DMSO-d6)
  δ 0.31–0.47 (1H, m), 0.47–0.56 (1H, m), 0.56–0.63 (1H, m), 0.63–0.76 (1H, m), 1.00–1.14 (1H, m), 1.20–1.52 (3H, m), 1.63–1.82 (1H, m), 2.03–2.22 (1H, m), 2.34–2.59 (1H, m), 2.80–2.90 (1H, m), 2.90 (1.7H, s), 2.93 (1.3H, s), 2.98–3.17 (2H, m), 3.22–3.40 (2H, m), 3.60–3.72 (0.6H, m), 3.72–3.80 (0.4H, m), 3.84 (1H, d, J=4.9 Hz), 4.83 (1H, brt), 4.98 (0.4H, d, J=13.2 Hz), 5.04 (1H, d, J=12.7 Hz), 5.09 (0.6H, d, J=13.2 Hz), 6.42 (1H, brs), 6.72 (0.6H, d, J=8.3 Hz), 6.77 (0.4H, d, J=7.8 Hz), 7.37 (5H, s), 7.16–7.45 (2H, m), 8.83 (1H, brs), 9.32 (0.4H, s), 9.45 (0.6H, s)
IR (KBr)
  υ 1678, 1560, 1543, 1460, 1315, 1152, 1033 cm$^{-1}$.
Mass (FAB)
  m/z 491 ((M+H)+).
Elementary Analysis: As C29H35N2O5Cl
  Calcd.: C, 66.09; H, 6.69; N, 5.31; Cl, 6.73
  Found.: C, 66.10; H, 6.64; N, 5.18; Cl, 6.56
Compound 57

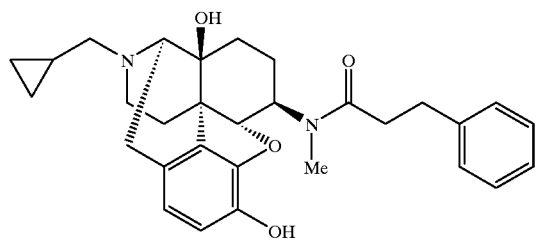

mp 207.0° C. (decomposition)
NMR (400 MHz, DMSO-d6)
  δ 0.31–0.47 (1H, m), 0,47–0.55 (1H, m), 0.55–0.63 (1H, m), 0.63–0.75 (1H, m), 0.99–1.13 (1H, m), 1.13–1.50 (3H, m), 1.60–1.78 (1H, m), 1.98–2.16 (1H, m), 2.28–2.52 (3H, m), 2.52–2.95 (4H, m), 2.83 (2.4H, s), 2.96 (0.6H, s), 2.95–3,16 (2H, m), 3.22–3.35 (2H, m), 3.36–3.53 (1H, m), 3.83 (1H, m), 4.79 (0.8H, d, J=7.8 Hz), 4.85 (0.2H, d, J=8.3 Hz), 6.38 (0.2H, m), 6.46 (0.8H, m), 6.60–6.80 (2H, m), 7.02–7.32 (5H, m), 8.82 (1H, br s), 9.29 (0.2H, s), 9.56 (0.8H, s)
IR (KBr)
  υ 3416, 1622, 1502, 1454, 1410, 1383, 1321, 1125 cm$^{-1}$.
Mass (FAB)
  m/z 489 (M+).

Elementary Analysis: As C30H37N2O4Cl1·0.2H2O
  Calcd.: C, 67.92; H, 7.11; N, 5.28; Cl, 6.68
  Found.: C, 67.96; H, 7.06; N, 5.27; Cl, 6.85
Compound 58

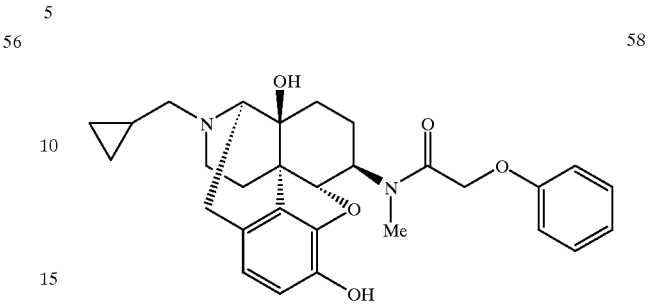

mp 150–200° C. (decomposition)
NMR (500 MHz, DMSO-d6)
  δ 0.21 (2H, m), 0.46–0.58 (2H, m), 0.90 (1H, m), 1.15–1.46 (3H, m), 1.57 (1H, m), 2.03–2.17 (2H, m), 2.28 (1H, m), 2.58–2.78 (3H, m), 2.82 (2.4H, s), 3.00 (0.6H, s), 3.08 (1H, d, J=18.9 Hz), 3.24 (1H, m), 3.45 (1H, m), 3.50 (3H, br s, 3×OH), 4.00–4.05 (1H, m), 4.04 (1H, s), 4.63–4.82 (3H, m), 6.54–6.67 (2H, m), 6.78–6.95 (3H, m), 7.18–7.29 (2H, m), 9.34 (1H, br s, NH+).
IR (KBr)
  υ 3390, 1638, 1601, 1497, 1323, 1241, 1118, 1064, 1035, 922, 859 cm$^{-1}$.
Mass (FAB)
  m/z 491 ((M+H)+).
Elementary Analysis: As C29H34N2O5·0.5C4H6O6·1.1H2O
  Calcd.: C, 63.60; H, 6.75; N, 4.78.
  Found.: C, 63.69; H, 6.63; N, 4.72.
Compound 59

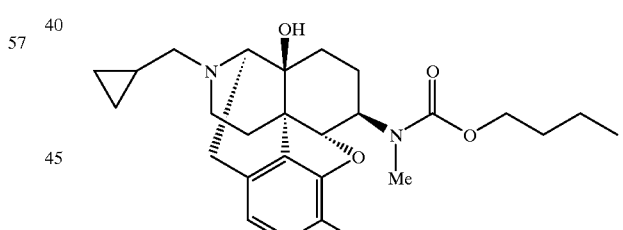

mp 110–150° C. (decomposition)
NMR (400 MHz, DMSO-d6)
  d 0.20 (2H, m), 0.45–0.56 (2H, m), 0.76–0.96 (4H, m), 1.14–1.40 (5H, m), 1.40–1.60 (3H, m), 2.01–2.15 (2H, m), 2.25 (1H, m), 2.55–2.77 (3H, m), 2.82 (3H, s), 3.06 (1H, d, J=18.6 Hz), 3.23 (1H, m), 3.53 (3H, br s, 3×OH), 3.53–3.68 (2H, m), 3.84–3.98 (2H, m), 4.01 (1H, s), 4.67 (1H, m), 6.55 (1H, d, J=8.1 Hz), 6.61 (1H, d, J=8.1 Hz), 9.10 (1H, br s, NH+).
IR (KBr)
  υ 3420, 1678, 1607, 1460, 1408, 1359, 1315, 1164, 1122, 1067, 1035, 922, 861 cm$^{-1}$.
Mass (FAB)
  m/z 457 ((M+H)+).
Elementary Analysis: As C26H36N2O5·0.5C4H6O6·0.5H2O
  Calcd.: C, 62.21; H, 7.46; N, 5.18.
  Found.: C, 62.21; H, 7.59; N, 5.33.

Compound 60

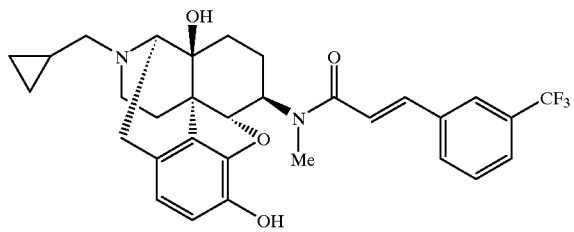

mp 156–159° C.
NMR (400 MHz, DMSO-$d_6$)
  δ 0.21 (2H, m), 0.52 (2H, m), 0.91 (1H, m), 1.2–1.5 (3H, m), 1.57 (1H, d, J=13.2 Hz), 2.12 (2H, m), 2.29 (1H, m), 2.49 (1H, m), 2.6–2.8 (3H, m), 2.90 (2H, s), 3.08 (1H, d, J=18.6 Hz), 3.17 (1H, s), 3.26 (1H, m), 3.67 (0.7H, m), 4.02 (1H, s), 4.21 (0.3H, m), 4.68 (0.7H, d, J=7.8 Hz), 4.79 (0.3H, d, J=8.3 Hz), 6.6–6.8 (2.6H, m), 7.37 (1H, dd, J=7.3, 16.1 Hz), 7.5–7.8 (3.8H, m), 8.02 (0.3H, d, J=7.8 Hz), 8.14 (0.3H, s)
IR (KBr)
  υ 3350, 1649, 1601, 1336, 1168, 1127 cm$^{-1}$.
Mass (FAB)
  m/z 555 (M+H)
Elementary Analysis: As $C_{31}H_{33}N_2O_4F_3 \cdot 0.5(C_4H_6O_6) \cdot 0.3H_2O$
  Calcd.: C, 62.41; H, 5.81; N, 4.41; F, 8.98
  Found.: C, 62.32; H, 5.99; N, 4.48; F, 8.88

Compound 61

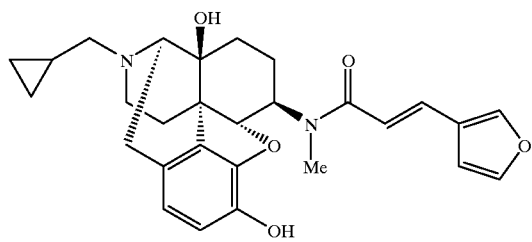

mp 168–172° C.
NMR (400 MHz, DMSO-$d_6$)
  δ 0.20 (2H, brs), 0.52 (2H, m), 0.90 (1H, m), 1.2–1.4 (3H, m), 1.56 (1H, d, J=13.2 Hz), 2.12 (2H, m), 2.24 (1H, m), 2.47 (1H, m), 2.5–2.8 (3H, m), 2.86 (2H, s), 3.08 (1H, d, J=19.6 Hz), 3.10 (1H, s), 3.22 (1H, m), 3.60 (0.7H, m), 4.00 (1H, s), 4.19 (0.3H, m), 4.66 (0.7H, d, J=8.3 Hz), 4.76 (0.3H, d, J=8.3 Hz), 6.39 (0.7H, d, J=15.6 Hz), 6.5–6.7 (2H, m), 6.74 (0.7H, d, J=8.3 Hz), 6.89 (0.3H, d, J=15.1 Hz), 7.00 (0.3H, s), 7.21 (0.7H, d, J=15.6 Hz), 7.36 (0.3H, d, J=15.1 Hz), 7.66 (0.7H, s), 7.72 (0.3H, s), 7.92 (0.7H, s), 8.03 (0.3H, s)
IR (KBr)
  υ 3370, 1651, 1599, 1323, 1158, 1114 cm$^{-1}$.
Mass (FAB)
  m/z 477 (M+H)
Elementary Analysis: As $C_{28}H_{32}N_2O_5 \cdot 0.5(C_4H_6O_6) \cdot 0.2H_2O$
  Calcd.: C, 64.90; H, 6.43; N, 5.04.
  Found.: C, 64.79; H, 6.59; N, 5.01.

Compound 62

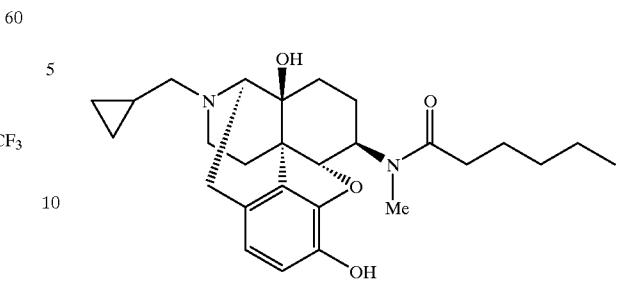

mp 150–158° C. (decomposition)
NMR (400 MHz, DMSO-$d_6$)
  δ 0.23 (2H, m), 0.48–0.59 (2H, m), 0.79 (2.1H, br t, J=6.8 Hz), 0.88 (0.9H, br t, T=6.8 Hz), 0.92 (1H, m), 1.11–1.22 (3H, m), 1.23–1.51 (6H, m), 1.58 (1H, m), 1.98–2.33 (5H, m), 2.52 (1H, m), 2.67–2.82 (3H, m), 2.77 (2.1H, s), 2.93 (0.9H, s), 3.11 (1H, br d, J=19.1 Hz), 3.33 (1H, m), 3.48 (1H, m), 3.50 (5H, br s, 5×OH), 4.08 (2H, s), 4.60 (0.7H, d, J=8.3 Hz), 4.72 (0.3H, d, J=8.3 Hz), 6.56 (0.3H, d, J=7.8 Hz), 6.60 (0.7H, d, J=7.8 Hz), 6.62 (0.3H, d, J=7.8 Hz), 6.67 (0.7H, d, J=7.8 Hz), 9.26 (1H, br s, NH+).
IR (KBr)
  υ 3314, 1719, 1618, 1460, 1412, 1311, 1267, 1120, 1069, 1035, 922, 859 cm$^{-1}$.
Mass (FAB)
  m/z 455 ((M+H)+).
Elementary Analysis: As $C_{27}H_{38}N_2O_4 \cdot C_4H_6O_6 \cdot 1.0H_2O$
  Calcd.: C, 59.79; H, 7.45; N, 4.50.
  Found.: C, 59.59; H, 7.46; N, 4.67.

Compound 63

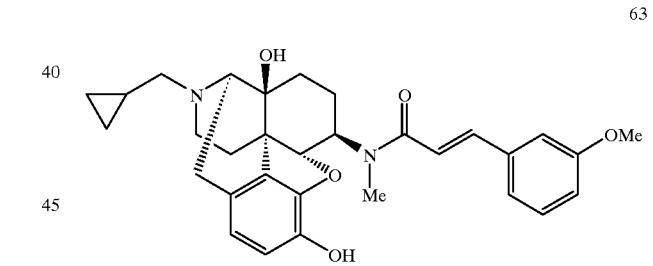

mp 160° C. (decomposition)
NMR (400 MHz, DMSO-$d_6$)
  δ 0.15–0.35 (2H, m), 0.45–0.65 (2H, m), 0.85–1.05 (1H, m), 1.20–1.50 (3H, m), 1.52–1.70 (1H, m), 2.00–2.25 (2H, m), 2.25–2.42 (1H, m), 2.63–2.77 (3H, m), 2.90 (1.8H, s), 2.90–4.20 (3H, br s), 3.05–3.22 (1H, m), 3.15 (1.2H, s), 3.22–3.42 (1H, m), 3.50–3.74 (1.6H, m), 3.77 (1.8H, s), 3.80 (1.2H, s), 4.00 (1H, s), 4.20 (0.4H, br s), 4.71 (0.6H, d, J=7.8 Hz), 4.80 (0.4H, d, J=8.3 Hz), 6.55–6.71 (2.6H, m), 6.92 (0.6H, dd, J=8.3, 2.5 Hz), 6.95–7.03 (1H, m), 7.10 (0.6H, d, J=7.3 Hz), 7.17 (0.4H, d, J=15.1 Hz), 7.23–7.35 (2.4H, m), 7.42 (0.4H, d, J=15.6 Hz), 9.07 (0.4H, br s), 9.37 (0.6H, br s)
IR (KBr)
  υ 3390, 1642, 1599, 1460, 1408, 1313, 1272, 1127, 1035, 787, 683 cm$^{-1}$.
Mass (FAB)
  m/z 517 ((M+H)+).

Elementary Analysis: As $C_{33}H_{39}N_2O_8 \cdot 0.7H_2O$
Calcd.: C, 65.59; H, 6.74; N, 4.64
Found.: C, 65.46; H, 6.78; N, 4.70

Compound 64

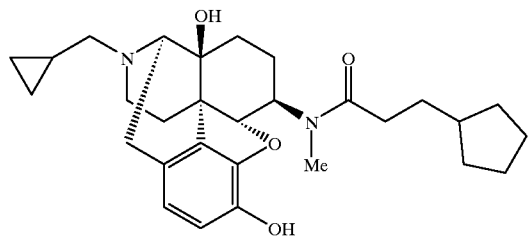

64 mp 145–160° C. (decomposition)
NMR (400 MHz, DMSO-$d_6$)
  δ 0.23 (2H, m), 0.48–0.59 (2H, m), 0.82–1.12 (3H, m), 1.14–1.78 (13H, m), 2.00–2.33 (5H, m), 2.52 (1H, m), 2.66–2.81 (3H, m), 2.76 (2.4H, s), 2.93 (0.6H, s), 3.11 (1H, br d, J=18.6 Hz), 3.31 (1H, m), 3.46 (1H, m), 3.50 (5H, br s, 5×OH), 4.07 (2H, s), 4.61 (0.8H, d, J=7.8 Hz), 4.71 (0.2H, d, J=7.8 Hz), 6.56 (0.2H, d, J=8.0 Hz), 6.59 (0.8H, d, J=8.0 Hz), 6.61 (0.2H, d, J=8.0 Hz), 6.66 (0.8H, d, J=8.0 Hz), 9.25 (1H, br s, NH+).

IR (KBr)
  υ 3398, 1721, 1620, 1456, 1408, 1325, 1243, 1125, 1071, 1035, 922, 859 cm$^{-1}$.

Mass (FAB)
  m/z 481 ((M+H)+).

Elementary Analysis: As $C_{29}H_{40}N_2O_4 \cdot C_4H_6O_6 \cdot 0.3H_2O$
Calcd.: C, 62.31; H, 7.38; N, 4.40.
Found.: C, 62.18; H, 7.65; N, 4.57.

Compound 65

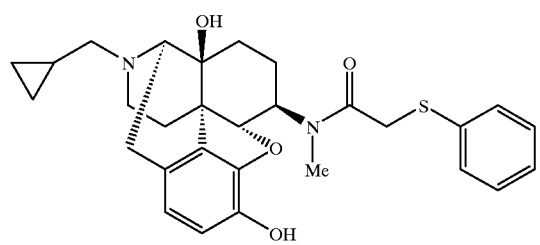

65 mp 145.0° C. (decomposition)
NMR (400 MHz, DMSO-$d_6$)
  δ 0.15–0.30 (2H, m), 0.43–0.60 (2H, m), 0.83–0.98 (1H, m), 1.13–1.26 (1H, m), 1.26–1.41 (2H, m), 1.43–1.62 (1H, m), 1.97–2.19 (2H, m), 2.19–2.33 (1H, m), 2.40–2.55 (1H, m), 2.55–2.78 (3H, m), 2.80 (2.4H, s), 3.03 (0.6H, s), 3.05 (1H, br d, J=13.4 Hz), 3.22 (1H, br s), 2.90–4.30 (3H, br s), 3.42–3.52 (1H, m), 3.74 (0.8H, d, J=14.0 Hz), 3.91 (0.8H, d, J=14.7 Hz), 3.96 (0.2H, d, J=14.6 Hz), 4.02 (0.2H, d, J=14.6 Hz), 4.04 (1H, s), 4.61 (0.8H, d, J=7.9 Hz), 4.73 (0.2H, d, J=7.9 Hz), 6.55 (0.2H, d, J=7.9 Hz), 6.59–6.67 (1H, m), 6.71 (0.8H, d, J=7.9 Hz), 7.08–7.26 (4.2H, m), 7.30 (0.4H, t), 7.35–7.42 (0.4H, m), 9.10–9.60 (1H, br s)

IR (KBr)
  υ 3380, 1620, 1508, 1408, 1313, 1267, 1122, 1035, 690 cm$^{-1}$.

Mass (FAB)
  m/z 507 ((M+H)+).

Elementary Analysis: As $C_{31.4}H_{37.6}N_2O_{7.6}S1.0.6H_2O$
Calcd.: C, 62.08; H, 6.44; N, 4.61; S, 5.28.
Found.: C, 61.84; H, 6.60; N, 4.67; S, 5.35.

Compound 66

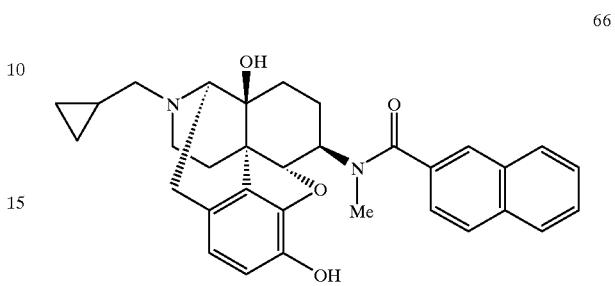

66 mp 220° C. (decomposition)
NMR (400 MHz, DMSO-$d_6$)
  δ 0.34 (1H, m), 0.47 (1H, m), 0.54 (1H, m), 0.62 (1H, m), 0.87 (1H, m), 0.99 (1H, m), 1.28 (1H, m), 1.4–1.6 (2H, m), 2.17 (1H, m), 2.34 (1H, m), 2.52 (1H, m), 2.7–2.9 (2H, m), 3.01 (1H, m), 3.10 (2H, s), 3.2–3.4 (3.7H, m), 3.70 (0.7H, m), 3.87 (0.3H, m), 4.15 (0.3H, m), 5.00 (0.7H, d, J=7.8 Hz), 5.06 (0.3H, m), 6.37 (0.3H, m), 6.39 (0.7H, d, J=7.8 Hz), 6.58 (0.7H, d, J=8.3 Hz), 6.71 (0.3H, m), 7.6–8.0 (7H, m)

IR (KBr)
  υ 3400, 1620, 1319, 1176, 1120, 1035 cm$^{-1}$.

Mass (FAB)
  m/z 511 (M+H)

Elementary Analysis: As $C_{32}H_{34}N_2O_4 \cdot HCl \cdot 0.4H_2O$
Calcd.: C, 69.34; H, 6.51; N, 5.05; Cl, 6.40
Found.: C, 69.13; H, 6.86; N, 4.96; Cl, 6.73

Compound 67

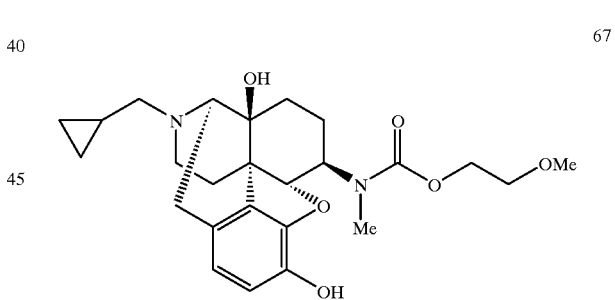

67 mp>130° C. (decomposition)
NMR (400 MHz, DMSO-$d_6$)
  δ 0.23 (2H, m), 0.48–0.58 (2H, m), 0.92 (1H, m), 1.23–1.38 (3H, m), 1.58 (1H, m), 2.02–2.18 (2H, m), 2.27 (1H, m), 2.52 (1H, m), 2.66–2.79 (3H, m), 2.81–2.87 (3H, m), 3.08 (1H, br d, J=18.6 Hz), 3.14 (1.5H, br s), 3,28 (1.5H, br s), 3.30 (1H, m), 3.42–3.57 (2H, m), 3.50 (4H, br s, 3.5×OH+0.5×COOH), 3.61 (1H, m), 4.02–4.13 (2H, m), 4.05 (1.5H, s), 4.69 (1H, m), 6.56 (1H, d, J=8.3 Hz), 6.63 (1H, m), 9.15 (1H, br s, NH+).

IR (KBr)
  υ 3424, 1686, 1609, 1460, 1410, 1313, 1251, 1123, 1066, 1033, 922, 905, 859 cm$^{-1}$.

Mass (FAB)
  m/z 459 ((M+H)+).

Elementary Analysis: As $C_{25}H_{34}N_2O_6 \cdot 0.75C_4H_6O_6 \cdot 0.8H_2O$
  Calcd.: C, 57.44; H, 6.90; N, 4.78.
  Found.: C, 57.41; H, 6.89; N, 4.71.
Compound 68

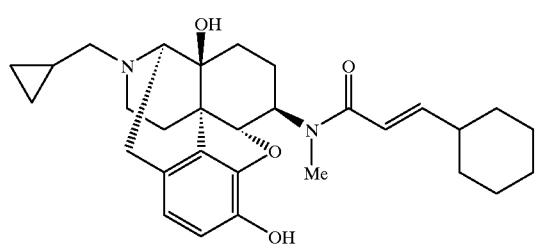

mp 154.0° C. (decomposition)
NMR (500 MHz, DMSO-$d_6$)
  δ 0.16–0.32 (2H, m), 0.42–0.62 (2H, m), 0.82–1.02 (2H, m), 1.02–1.42 (7H, m), 1.42–1.80 (6H, m), 1.88–2.33 (4H, m), 2.42–2.58 (1H, m), 2.58–2.87 (3H, m), 2.60–5.10 (3H, br s), 2.81 (2.1H, s), 3.01 (0.9H, s), 3.09 (1H, br d, J=18.3 Hz), 3.28 (1H, br s), 3.60 (0.7H, m), 4.05 (1H, s), 4.11 (0.3H, m), 4.61 (0.7H, d, J=7.9 Hz), 4.73 (0.3H, d, J=8.5 Hz), 5.93 (0.7H, d, J=15.3 Hz), 6.33 (0.7H, d, J=15.3 Hz), 6.34 (0.3H, d, J=15.3 Hz), 6.52–6.62 (1.6H, m), 6.66 (0.7H, d, J=8.5 Hz), 8.60–9.60 (1H, br s)
IR (KBr)
  υ 3322, 1651, 1601, 1504, 1450, 1410, 1311, 1267, 1216, 1129, 681 cm$^{-1}$.
Mass (FAB)
  m/z 493 ((M+H)+).
Elementary Analysis: As $C_{32.8}H_{44.2}N_2O_{8.2} \cdot 0.8H_2O$
  Calcd.: C, 64.36; H, 7.54; N, 4.58
  Found.: C, 64.37; H, 7.67; N, 4.58
Compound 69

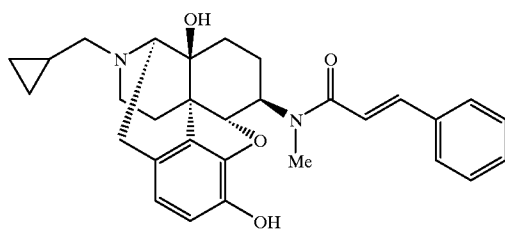

mp 245° C. (decomposition)
NMR (400 MHz, DMSO-$d_6$)
  δ 0.42 (1H, m), 0.50 (1H, rm), 0.59 (1H, m), 0.69 (1H, m), 1.07 (1H, m), 1.2–1.5 (3H, m), 1.72 (1H, d, J=13.7), 2.12 (1H, m), 2.34 (3H, s), 2.4–2.6 (2H, m), 2.88 (1H, m), 2.92 (2H, s), 3.0–3.1 (2H, m), 3.18 (1H, s), 3.3–3.4 (2H, m), 3.66 (0.7H, m), 3.83 (1H, m), 4.20 (0.3H, m), 4.83 (0.7H, d, J=7.8 Hz), 4.90 (0.3H, d, J=8.3 Hz), 6.6–6.8 (2H, m), 6.85 (0.7H, d, J=8.3 Hz), 7.1–7.3 (4.4H, m), 7.41 (0.3H, d, J=15.1 HZ), 7.48 (0.3H, d, J=7.3 Hz), 7.54 (0.3H, brs)
IR (KBr)
  υ 3390, 1647, 1605, 1323, 1127, 1035 cm$^{-1}$.
Mass (FAB)
  m/z 501 (M+H)

Elementary Analysis: As $C_{31}H_{36}N_2O_4 \cdot HCl \cdot 0.8H_2O$
  Calcd.: C, 67.51; H, 7.06; N, 5.08; Cl, 6.43.
  Found.: C, 67.35; H, 7.05; N, 5.17; Cl, 6.53.
Compound 70

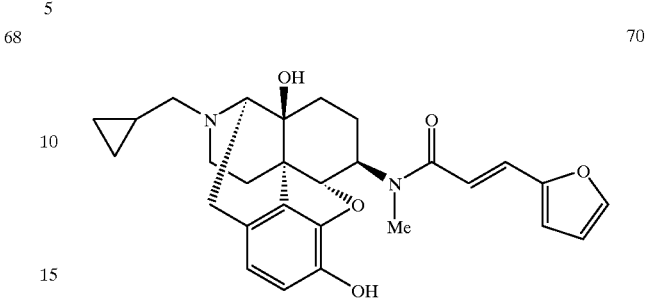

mp 200° C. (decomposition)
NMR (400 MHz, DMSO-$d_6$)
  δ 0.42 (1H, m), 0.53 (1H, m), 0.61 (1H, m), 0.69 (1H, m), 1.08 (1H, m), 1.28 (0.5H, m), 1.3–1.5 (2.5H, m), 1.74 (1H, m), 2.15 (1H, m), 2.4–2.6 (2.5H, m), 2.8–2.9 (1.5H, m), 2.93 (1.5H, s), 3.0–3.1 (2H, m), 3.16 (1.5H, s), 3.3–3.4 (2H, m), 3.61 (0.5H, m), 3.85 (1H, brs), 4.20 (0.5H, m), 4.85 (0.5H, d, J=7.3 Hz), 4.91 (0.5H, d, J=7.8 Hz), 6.4–6.7 (3.5H, m), 6.8–6.9 (1.5H, m), 7.14 (0.5H, d, J=15.1 Hz), 7.28 (0.5H, d, J=15.6 Hz), 7.68 (0.5H, s), 7.80 (0.5H, s)
IR (KBr)
  υ 3390, 1647, 1597, 1321, 1127, 1017 cm$^{-1}$.
Mass (FAB)
  m/z 477 (M+H)
Elementary Analysis: As $C_{28}H_{32}N_2O_5 \cdot HCl \cdot 0.6H_2O$
  Calcd.: C, 64.20; H, 6.58; N, 5.35; Cl, 6.77.
  Found.: C, 64.21; H, 6.84; N, 5.38; Cl, 6.69.
Compound 71

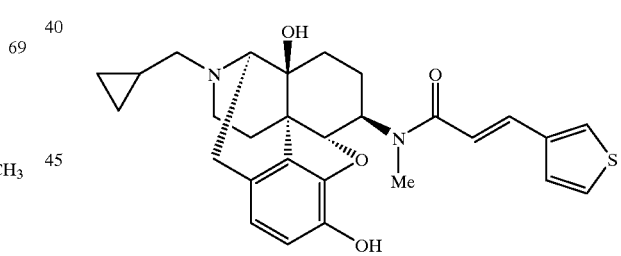

mp 235° C. (decomposition)
NMR (400 MHz, DMSO-$d_6$)
  δ 0.42 (1H, m), 0.51 (1H, m), 0.60 (1H, m), 0.68 (1H, m), 1.08 (1H, m), 1.2–1.5 (3H, m), 1.72 (1H, d, J=12.2 Hz), 2.12 (1H, m), 2.34 (3H, s), 2.4–2.5 (2H, m), 2.86 (1H, m), 2.91 (2H, s), 3.0–3.1 (2H, m), 3.15 (1H, s), 3.3–3.5 (2H, m), 3.61 (0.7H, m), 3.82 (1H, brs), 4.19 (0.3H, m), 4.81 (0.7H, d, J=7.8 Hz), 4.89 (0.3H, d, J=8.3 Hz), 6.46 (0.7H, d, J=15.6 Hz), 6.6–6.7 (1.33H, m), 6.85 (0.7H, d, J=7.8 Hz), 7.00 (0.3H, d, J=15.1 Hz), 7.26 (0.7H, d, J=4.9 Hz), 7.31 (0.7H, d, J=15.6 Hz), 7.46 (0.3H, d, J=15.1 Hz), 7.5–7.7 (2H, m), 7.87 (0.3H, s)
IR (KBr)
  υ 3410, 1642, 1595, 1323, 1127, 1035, 859 cm$^{-1}$.
Mass (FAB)
  m/z 493 (M+H)
Elementary Analysis: As $C_{28}H_{32}N_2O_4S \cdot CH_3SO_3H \cdot 0.2H_2O$ Calcd.: C, 58.80; H, 6.19; N, 4.73; S, 10.83
Found.: C, 58.60; H, 6.42; N, 4.72; S, 10.82
Compound 72

72

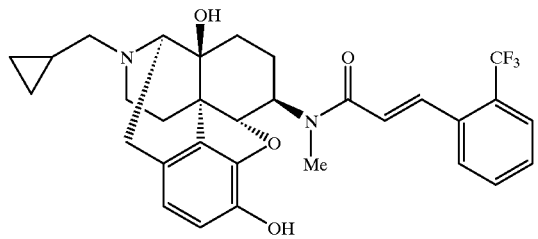

mp 196–199° C.
NMR (400 MHz, DMSO-d$_6$)
δ 0.41 (1H, m), 0,53 (1H, m), 0.59 (1H, m)), 0.67 (1H, m), 1.09 (1H, m), 1.3–1.5 (3H, m), 1.73 (1H, d, J=13.2 Hz), 2.20 (1H, m), 2.4–2.6 (2H, m), 2.88 (1H, m)), 2.97 (2H, s), 3.0–3.1 (2H, m), 3.23 (1H, s), 3.3–3.4 (2H, m), 3.68 (0.7H, m), 3.87 (1H, brs), 4.18 (0.3H, m), 4.88 (0.7H, d, J=7.8 Hz), 4.97 (0.3H, d, J=8.3 Hz), 6.6–6.9 (2.7H, m), 7.28 (0.3H, d, J=15.1 Hz), 7.5–7.7 (1.7H, m), 7.7–7.9 (3H, m), 8.14 (0.3H, d, J=7.8 Hz)
IR (KBr)
υ 3400, 1649, 1605, 1460, 1317, 1125, 1036 cm$^{-1}$.
Mass (FAB)
m/z 555 (M+H)
Elementary Analysis: As $C_{31}H_{33}N_2O_4F_3 \cdot 1.1HCl \cdot 0.4H_2O$
Calcd.: C, 61.86; H, 5.84; N, 4.65; F, 9.47; Cl, 6.48
Found.: C, 61.88; H, 5.94; N, 4.67; F, 9.47; Cl, 6.44
Compound 73

73

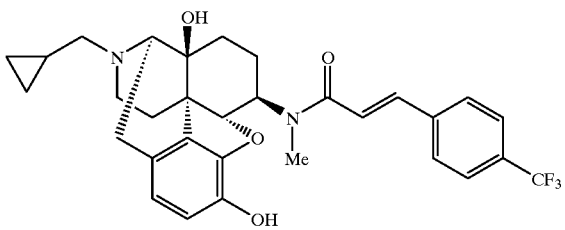

mp 167–170° C.
NMR (400 MHz, DMSO-d$_6$)
δ 0.21 (2H, m), 0.52 (2H, m),0.91 (1H, m), 1.2–1.4 (3H, m), 1.58 (1H, m), 2.1–2.2 (2H, m), 2.30 (1H, m), 2.49 (1H, m), 2.6–2.8 (3H, m), 2.90 (2H, s), 3.18 (1H, d, J=18.6 Hz), 3.16 (1H, s), 3.24 (1H, m), 3.65 (0.7H, m), 4.03 (1H, s), 4.20 (0.3H, m), 4.68 (0.7H, d, J=8.3 Hz), 4.79 (0.3H, d, J=7.8 Hz), 6.5–6.7 (1.3H, m), 6.8–6.9 (1.4H, m), 7.34 (1H, d, J=15.6 Hz), 7.51 (0.3H, d, J=15.6 Hz), 7.7–7.8 (3.7H, m), 7.94 (0.3H, d, J=8.3 Hz)
IR (KBr)
υ 3400, 1649, 1601, 1325, 1168, 1114 cm$^{-1}$.
Mass (FAB)
m/z 555 (M+H)
Elementary Analysis: As $C_{31}H_{33}N_2O_4F_3 \cdot 0.5 (C_4H_6O_6) \cdot 0.3H_2O$
Calcd.: C, 62.41; H, 5.81; N, 4.41; F, 8.98
Found.: C, 62.36; H, 5.80; N, 4.41; F, 8.98

Example 64

17- cyclopropylmethyl-14β-hydroxy-4,5α-epoxy-6α-(N-methylbenzyloxycarbamido)morphinan-phosphate 74 (yield: 82%) was obtained by following the procedure of example 11 but using 17-cyclopropylmethyl-4,5α-epoxy-14β-hydroxy-6α-methylaminomorphinan 6 instead of the starting material 17-cyclopropylmethyl-4,5α-epoxy-3,14β-dihydroxy-6α-methylaminomorphinan 4, and using benzyl chloroformate instead of 3,4-dichlorophenylacetyl chloride.

74

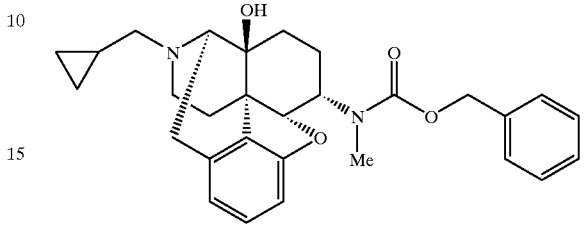

mp 122–125° C.
NMR (400 MHz, DMSO-d$_6$)
δ 0.23 (2H, m), 0.54 (2H, m), 0.93 (1H, m), 1.06 (1H, m), 1.3–1.5 (3H, m), 1.75 (1H, m), 2.2–2.3 (2H, m), 2.5–2.7 (2H, m), 2.80 (3H, s), 2.7–2.9 (2H, m), 3.18 (1H, d, J=19.5 Hz), 3.35 (1H, m), 4.59 (2H, m), 5.1–5.2 (2H, m), 6.60 (1H, d, J=7.3 Hz), 6.70 (1H, d, J=7.3 Hz), 7.10 (1H, t, J=7.3 Hz), 7.3–7.4 (5H, m)
IR (KBr)
υ 3400, 1692, 1462, 1350, 1245, 1120 cm$^{-1}$.
Mass (FAB)
m/z 474 (M+H)
Elementary Analysis: As $C_{29}H_{34}N_2O_4 \cdot H_3PO_4 \cdot 0.7H_2O$
Calcd.: C, 59.52; H, 6.61; N, 4.78; P, 5.29
Found.: C, 59.51; H, 6.56; N, 4.78; P, 5.60

Example 65

17-Cyclopropylmethyl-7,8-didehydro-4,5α-epoxy-14β-hydroxy-3-methoxy-6α-[N-methyl-trans-3-(3-furyl)acrylamido] morphinan 75

75

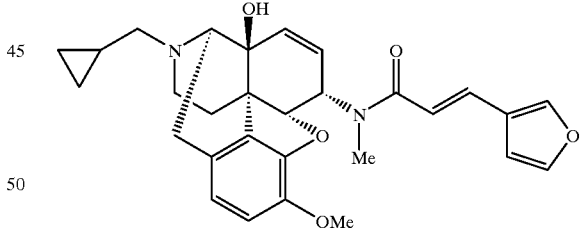

540 mg of 17-cyclopropylmethyl-7,8-didehydro-4,5α-epoxy-14β-hydroxy-3-methoxy-6α-(N-methylamino)morphinan 14 and 0.31 ml of triethylamine was dissolved in 10 ml of chloroform followed by addition of 250 mg of trans-3-(3-furyl)acryloyl chloride and stirring for 30 minutes at room temperature. The resulting solution was neutralized by addition of saturated aqueous sodium bicarbonate followed by extraction with chloroform. The organic layer was washed with saturated brine, dried and concentrated. The resulting residue was separated and purified by column chromatography [silica gel; chloroform=chloroform:methanol (100:1)] to obtain 610 mg of crude crystal. This was then recrystallized from dichloromethane-ether to obtain 580 mg of the target compound (yield: 81%).

mp 199–201° C.

NMR (400 MHz, CDCl₃)

δ 0.19 (2H, m) 0.60 (2H, m), 0.93 (1H, m), 1.58 (1H, m), 1.74 (1H, m), 2.27–2.64 (4H, m), 2.78 (1H, m), 3.00 (3H, s), 3.09 (1H, d, J=18.6 Hz), 3.40 (1H, m), 3.82 (3H, s), 4.97 (1H, br s, OH), 5.14 (1H, d, J=6.8 Hz), 5.70–5.77 (2H, m), 5.83 (1H, m), 6.56 (1H, d, J=8.3 Hz), 6.61 (1H, d, J=1.5 Hz), 6.66 (1H, d, J=15.3 Hz), 6.67 (1H, d, J=8.3 Hz), 7.42 (1H, br s), 7.63 (1H, d, J=15.3 Hz), 7.65 (1H, br s).

IR (KBr)

υ 3338, 1659, 1638, 1404, 1282, 1205, 1160, 1122, 1054, 1017, 980, 808 cm⁻¹.

Mass (EI)

m/z 488 (M+).

Example 66

17-Cyclopropylmethyl-7,8-didehydro-4,5α-epoxy-3,14β-dihydroxy-6α-[N-methyl-trans-3-(3-furyl)acrylamido]morphinan.hydrochloride 76

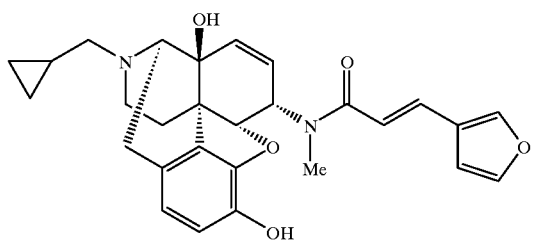

76

300 mg of 17-cyclopropylmethyl-7,8-didehydro-4,5α-epoxy-14β-hydroxy-3-methoxy-6α-[N-methyl-trans-3-(3-furyl)acrylamido] morphinan 75 was dissolved in 5 ml of anhydrous dichloromethane and cooled to 0° C. 3.7 ml of a dichloromethane solution of boron tribromide (1.0 M) was then added followed by stirring for 2 hours (at room temperature.). The reaction solution was cooled to 0° C. followed by addition of 6 ml of 28% aqueous ammonia:water (1:4). After stirring for 30 minutes at 0° C., the reaction solution was extracted with chloroform and methanol (3:1). The organic layer was washed with saturated brine, dried and concentrated, and the resulting residue was purified with column chromatography [silica gel; chloroform~chloroform:methanol:28% aqueous ammonia (100:2:0.2)] to obtain 350 mg of crude crystal. This was then recrystallized from dichloromethane, methanol and ethyl acetate to obtain 265 mg of a free base of the target compound. 238 mg of the resulting crystal was dissolved in 5 ml of methanol and concentrated after adding of an excess amount of methanol solution of hydrochloride. The residue was recrystallized from methanol to obtain 159.3 mg of the target compound (yield: 57%).

mp 251° C. (decomposition)

NMR (400 MHz, DMSO-d₆)

δ 0.43 (1H, m), 0.53 (1H, m), 0.62 (1H, m), 0.72 (1H, m), 1.07 (1H, m), 1.69–1.82 (1H, m), 2.54–3.02 (4H, m), 2.91 (3H, s), 3.08–3.18 (1H, m), 3.30–3.44 (2H, m), 4.07 (0.3H, m), 4.12 (0.7H, m), 4.94 (0.7H, d, J=6.8 Hz), 5.21 (0.3H, d, J=7.3 Hz), 5.49 (0.7H, m), 5.76 (0.3H, m), 5.83–5.94 (2H, m), 6.52–6.57 (1H, m), 6.69–6.76 (1.6H, m), 6.95 (0.7H, d, J=15.3 Hz), 7.05 (0.7H, d, J=2.0 Hz), 7.31 (0.3H, br s, OH), 7.46 (0.7H, br s, OH), 7.51 (1H, d, J=15.3 Hz), 7.70 (0.3H, br s), 7.74 (0.7H, br s), 8.09 (1H, br s), 8.90–9.06 (1H, m, NH+), 9.33 (0.3H, br s, OH), 9.34 (0.7H, br s, OH).

IR (KBr)

υ 3422, 3190, 1653, 1600, 1504, 1473, 1406, 1321, 1160, 1118, 1023, 949, 870, 799 cm⁻¹.

Mass (FAB)

m/z 475 ((M+H)+).

Elementary Analysis: As C₂₈H₃₀N₂O₅.HCl

Calcd.: C, 65.81; H, 6.11; Cl, 6.94; N, 5.48.

Found.: C, 65.62; H, 6.19; Cl, 6.82; N, 5.61.

Example 67

17-Cyclopropylmethyl-3,14β-dihydroxy-4,5α-epoxy-5β-methyl-6α-[trans-3-(3-furyl)acrylamido]morphinan.0.5 tartrate 77 (yield: 40%) was obtained by following the procedure of example 11 but using 17-cyclopropylmethyl-3,14-dihydroxy-4,5α-epoxy-5β-methyl-6α-aminomorphinan 19 instead of the starting material of 17-cyclopropylmethyl-4,5α-epoxy-3,14β-dihydroxy-6α-methylaminomorphinan 4, and using trans-3-(3-furyl)acryloyl chloride instead of 3,4-dichlorophenylacetyl chloride.

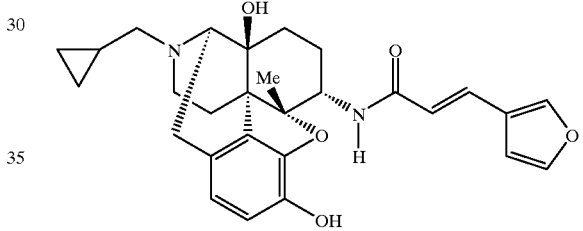

77 mp >170° C. (decomposition)

NMR (400 MHz, DMSO-d₆)

δ 0.31 (2H, m), 0.53 (2H, m), 0.81–0.97 (2H, m), 1.33–1.52 (3H, m), 1.39 (3H, s), 1.70 (1H, m), 2.21–2.33 (2H, m), 2.41–2.83 (4H, m), 3.06 (1H, br d, J=18.6 Hz), 3.25 (1H, m), 3.48 (3H, br s, 30H), 4.03 (1H, s), 4.27 (1H, m), 6.49 (1H, d, J=8.3 Hz), 6.54 (1H, d, J=15.6 Hz), 6.61 (1H, d, J=8.3 Hz), 6.71 (1H, d, J=1.5 Hz), 7.34 (1H, d, J=15.3 Hz), 7.46 (1H, d, J=9.3 Hz), 7.73 (1H, br s), 8.01 (1H, s), 8.85 (1H, br s, NH+).

IR (KBr)

υ 3398, 1665, 1611, 1508, 1462, 1352, 1245, 1158, 1123, 1062, 870, 803 cm⁻¹.

Mass (FAB)

m/z 477 ((M+H)+).

Elementary Analysis: As C₂₈H₃₂N₂O₅.0.5C₄H₆O₆.1.0H₂O

Calcd.: C, 63.26; H, 6.55; N, 4.92.

Found.: C, 63.33; H, 6.43; N, 4.79.

Example 68

17-Cyclopropylmethyl-3,14β-dihydroxy-4,5α-epoxy-6β-[N-methyl-trans-3-(3-furyl)acrylamido]morphinan.hydrochloride 78

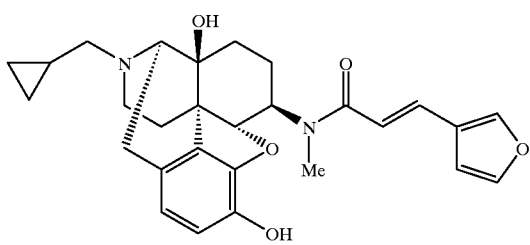

21.12 g (0.0404 mol) of 17-cyclopropylmethyl-4,5α-epoxy-3,14β-dihydroxy-6β-(N-methylamino)morphinan.phthalate 10 was dissolved in 110 ml of water. After adding 110 ml of THF and 8.75 g (0.0808 mol) of sodium carbonate, the atmosphere of reaction system was replaced to argon. Then, 6.96 g of trans-3-(3-furyl)acryloyl chloride (0.04444 mol) was dissolved in 40 ml of THF and added dropwise. After stirring for 30 minutes, 40 ml of methanol and 54 ml of 3 N aqueous sodium hydroxide were added and stirred for 1 hour. 350 ml of ethyl acetate and 250 ml of saturated aqueous sodium bicarbonate were added to the reaction solution to separate, and the aqueous layer was re-extracted with 100 ml of ethyl acetate. After washing with 200 ml of saturated brine, the resulting organic layer was dried with sodium sulfate and concentrated. The residue was dissolved in 630 ml of ethyl acetate while heating, and after dissolving, 150 ml was distilled off while heating. The resulting solution was allowed to stand and recrystallized to obtain 15.47 g of the free base of the target compound. 9.03 g of this free base was suspended in 90 ml of ethanol. After then adding 18.7 ml of 1 N aqueous hydrochloric acid, the resulting solution was concentrated and dried to obtain 9.72 g of the target compound (yield: 80%).

mp 187° C. (decomposition)
NMR (400 MHz, DMSO-$d_6$)
  δ 0.42 (1H, m), 0.51 (1H, m), 0.60 (1H, m), 0.68 (1H, m), 1.07 (1H, m), 1.26 (0.4H, m), 1.32–1.50 (3.6H, m), 1.73 (1H, br d, J=13.7 Hz), 2.13 (1H, m), 2.40–2.60 (3H, m), 2.88 (1H, m), 2.92 (1.8H, s), 3.06 (1H, br d, J=13.18 Hz), 3.16 (1.2H, s), 3.59 (0.6H, m), 3.86 (1H, m), 4.19 (0.4H, m), 4.86 (0.6H, d, J=7.8 Hz), 4.92 (0.4H, d, J=7.8 Hz), 6.35 (0.6H, d, J=15.6 Hz), 6.40 (0.4H, br s), 6.50 (0.6H, br s), 6.62 (0.6H, s), 6.64 (0.4H, d, J=8.3 Hz), 6.71 (1H, d, J=8.3 Hz), 6.85 (0.6H, d, J=8.3 Hz), 6.90 (0.4H, d, J=15.1 Hz), 6.99 (0.4H, s), 7.22 (0.6H, d, J=15.6 Hz), 7.36 (0.4H, d, J=15.1 Hz), 7.66 (0.6H, s), 7.72 (0.4H, s), 7.92 (0.6H, s), 8.03 (0.4H, s), 8.85 (1H, br s), 9.28 (0.4H, s), 9.68 (0.6H, s)
IR (KBr)
  υ 3376, 1653, 1506, 1599, 1410, 1323, 1158, 1127, 1033, 872, 799 cm$^{-1}$.
Mass (FAB)
  m/z 477 (M+H)
Elementary Analysis: As $C_{28}H_{32}N_2O_5 \cdot HCl \cdot 0.2H_2O$
  Calcd.: C, 65.10; H, 6.52; N, 5.42; Cl, 6.86.
  Found.: C, 65.11; H, 6.63; N, 5.60; Cl, 6.80.

Examples 69–71

17-Cyclopropylmethyl-3,14β-dihydroxy-4,5α-epoxy-6β-[trans-3-(3-furyl)acrylamido]morphinan.hydrochloride 79, 17-cyclopropylmethyl-3-hydroxy-4,5α-epoxy-6β-[N-methyl-trans-3-(3-furyl)acrylamido]morphinan.hydrochloride 80, and 17-cyclopropylmethyl-3-hydroxy-4,5α-epoxy-6α-[N-methyl-trans-3-(3-furyl)acrylamido]morphinan.hydrochloride 81 were obtained by following the procedure of example 68 but using 17-cyclopropylmethyl-4,5α-epoxy-3,14β-dihydroxy-6β-aminomorphinan (J. B. Jiang, R. N. Hanson, P. S. Portoghese and A. E. Takemori, J. Med. Chem., 20, 1100 (1977)), 17-cyclopropylmethyl-3-hydroxy-4,5α-epoxy-6β-methylaminomorphinan 20, and 17-cyclopropylmethyl-3-hydroxy-4,5α-epoxy-6α-methylaminomorphinan 21 instead of 17-cyclopropylmethyl-4,5α-epoxy-3,14β-dihydroxy-6β-(N-methylamino)morphinan 10.phthalate.

Compound 79

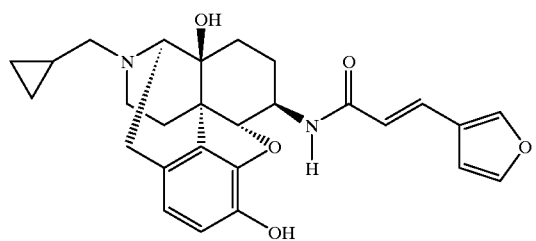

mp 240° C. (decomposition)
NMR (400 MHz, DMSO-$d_6$)
  δ 0.41 (1H, m), 0.52 (1H, m), 0.59 (1H, m), 0.67 (1H, m), 1.07 (1H, m), 1.32–1.49 (2H, m), 1.57 (1H, m), 1.68–1.83 (2H, m), 2.37–2.47 (2H, m), 2.86 (1H, m), 2.98–3.12 (2H, m), 3.27–3.39 (2H, m), 3.52 (1H, m), 3.86 (1H, br d, J=4.9 Hz), 4.60 (1H, d, J=7.8 Hz), 6.23 (1H, br s), 6.33 (1H, d, J=15.6 Hz), 6.65 (1H, d, J=7.8 Hz), 6.72 (1H, d, J=7.8 Hz), 6.73 (1H, br s), 7.32 (1H, d, J=15.6 Hz), 7.74 (1H, br s), 8.01 (1H, s), 8.40 (1H, d, J=7.8 Hz), 8.86 (1H, m, NH+), 9.36 (1H, s, OH).
IR (KBr)
  υ 3376, 3244, 1663, 1620, 1560, 1508, 1460, 1377, 1340, 1241, 1156, 1127, 1035, 980, 872, 795 cm$^{-1}$.
Mass (FAB)
  m/z 463 ((M+H)+).
Elementary Analysis: As $C_{27}H_{30}N_2O_5 \cdot HCl \cdot 0.2H_2O$
  Calcd.: C, 64.52; H, 6.30; Cl, 7.05; N, 5.57
  Found.: C, 64.50; H, 6.39; Cl, 7.00; N, 5.53

Compound 8

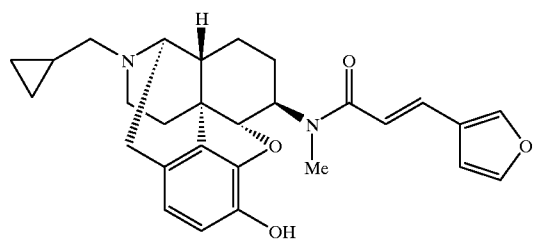

mp 225–230° C. (decomposition)
NMR (400 MHz, DMSO-$d_6$)
  δ 0.38 (1H, m), 0.51 (1H, m), 0.63 (2H, m), 0.97 (1H, m), 1.21 (1H, m), 1.40–1.72 (3.8H, m), 2.29 (1H, m), 2.40–2.52 (1.2H, m), 2.57 (0.2H, m), 2.70 (0.8H, m), 2.80–2.96 (1.2H, m), 2.89 (2.4H, s), 3.00–3.18 (1.6H, m), 3.14 (0.6H, s), 3.18–3.35 (2.2H, m), 3.48 (0.8H, m), 3.95–4.10 (1.2H, m), 4.65–4.95 (1H, m), 6.27–8.32 (7H, m)

IR (KBr)
υ 3370, 1651, 1593, 1321, 1156, 872 cm⁻¹.
Mass (FAB)
m/z 461 (M+H)
Elementary Analysis: As C₂₈H₃₂N₂O₄.1.7HCl.0.5H₂O
Calcd.: C, 63.27; H, 6.58; N, 5.27; Cl, 11.34
Found.: C, 63.24; H, 6.60; N, 5.09; Cl, 11.55
Compound 81

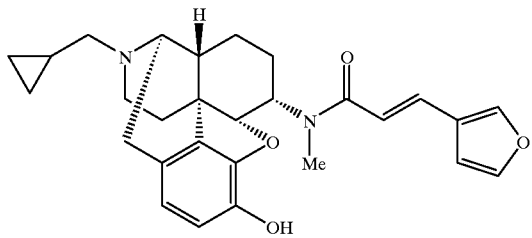

mp 210–215° C. (decomposition)
NMR (400 MHz, DMSO-d₆)
δ 0.38 (1H, m), 0.48 (1H, m), 0.65 (2H, m), 0.98 (1H, m), 1.16 (2H, m), 1.32 (1H, m), 1.62–1.90 (2H, m), 2.23 (1H, m), 2.68 (0.7H, m), 2.8–3.4 (7.2H, m), 3.04 (2.1H, s), 4.01–4.10 (1H, m), 4.52–4.81 (2H, m), 6.6–8.3 (7H, m)
IR (KBr)
υ 3380, 1651, 1591, 1323, 1160, 872 cm⁻¹.
Mass (FAB)
m/z 461 (M+H)
Elementary Analysis: As C₂₈H₃₂N₂O₄.1.4HCl.0.5H₂O
Calcd.: C, 64.60; H, 6.66; N, 5.38; Cl, 9.53
Found.: C, 64.78; H, 6.82; N, 5.01; Cl, 9.29

Example 72

17-cyclopropylmethyl-3,14β-dihydroxy-4,5α-epoxy-6β-[N-methyl-trans-3-(2-thienyl)acrylamido]morphinan.tartrate 82 (yield: 84%) was obtained by following the procedure of example 68 but using trans-3-(2-thienyl)acryloyl chloride instead of trans-3-(3-furyl)acryloyl chloride.

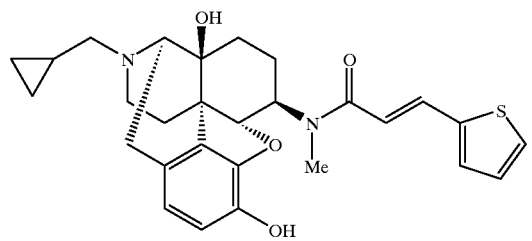

mp 178–181° C.
NMR (400 MHz, DMSO-d₆)
δ 0.22 (2H, brs), 0.53 (2H, m), 0.91 (1H, m), 1.2–1.4 (3H, m), 1.58 (1H, d, J=10.4 Hz), 2.14 (2H, m), 2.27 (1H, m), 2.50 (1H, m), 2.6–2.8 (3H, m), 2.88 (1.8H, s), 3.08 (1H, d, J=17.1 Hz), 3.11 (1.2H, s), 3.24 (1H, m), 3.59 (0.6H, m), 4.02 (1H, s), 4.20 (0.4H, m), 4.66 (0.6H, d, J=8.6 Hz), 4.76 (0.4H, d, J=8.6 Hz), 6.42 (0.6H, d, J=15.3 Hz), 6.48 (0.4H, d, J=12.2 Hz), 6.57 (1H, d, J=7.9 Hz), 6.75 (0.6H, d, J=7.9 Hz), 6.85 (0.4H, d, J=15.3 Hz), 7.07 (0.6H, t, J=3.7 Hz), 7.12 (0.4H, t, J=4.9 Hz), 7.32 (0.6H, d, J=3.1 Hz), 7.45–7.48 (1H, m), 7.58–7.67 (1.4H, m)
IR (KBr)
υ 3350, 1636, 1590, 1460, 1035 cm⁻¹.
Mass (FAB)
m/z 493 (M+H)
Elementary Analysis: As C₂₈H₃₂N₂O₄S.0.5(C₄H₆O₆).0.5H₂O
Calcd.: C, 62.48; H, 6.29; N, 4.86; S, 5.56
Found.: C, 62.32; H, 6.36; N, 4.92; S, 5.57

Example 73

17-Cyclopropylmethyl-3,14-β-dihydroxy-4,5α-epoxy-6α-(N-methyl-3-nitrophenylacetamido)morphinan.hydrochloride 83

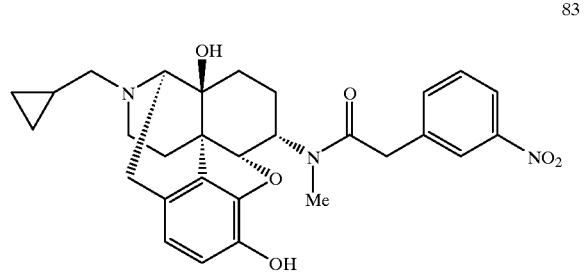

567.1mg (1.59 nmol) of 17-cyclopropylmethyl-3,14β-dihydroxy-4,5α-epoxy-6α-methylaminomorphinan 4 and 577.9 mg (3.19 mmol) of 3-nitrophenylacetic acid were dissolved in 18 ml of chloroform followed by the addition of 657.0 mg (3.18 mmol) of dicyclohexylcarbodiimide and 10.0 mg (0.082 mmol) of 4-(N,N-dimethylamino)pyridine to this solution and stirring for 1 hour at room temperature. The solid that formed in the reaction solution was filtered out, the residue was washed with chloroform, and the filtrate and washing were combined and concentrated. The resulting solid was dissolved in a mixed solution of methanol and chloroform (4:1) followed by the addition of 445 mg (3.22 mmol) of potassium carbonate and stirring for 2 hours at room temperature. 15 ml of water was added to the reaction solution followed by extraction with chloroform (3×15 ml). The organic layers were then combined and concentrated to obtain 2.27 g of solid. This solid was then purified with column chromatography [silica gel 80 g; chloroform-methanol (40:1→20:1)] to obtain 717.4 mg of the free base of the target compound (yield: 87%). This crystal was then dissolved in methanol followed by addition of methanol solution saturated with hydrogen chloride gas. The precipitated crystal was then filtered to obtain 300.5 mg of the target compound (yield: 34%). In addition, the crystal resulting from concentration of this filtrate was then recrystallized from methanol to further obtain 354.0 mg of the target compound (yield: 40%). Both of these compounds were then combined to obtain 654.5 mg of the target compound (yield: 74%).
mp >210° C. (decomposition, methanol)
NMR (400 MHz, DMSO-d₆)
δ 0.39 (1H, m), 0.47 (1H, m), 0.61 (1H, m), 0.68 (1H, m), 1.06 (1H, m), 1.17 (1H, m), 1.37 (1H, m), 1.50–1.64 (2H, m), 1.94 (1H, m), 2.43 (1H, m), 2.68 (1H, m), 2.82 (0.6H, s), 2.90–3.14 (3H, m), 3.00 (2.4H, s), 3.22–3.38 (2H, m), 3.90–4.10 (3H, m), 4.54 (0.2H, m), 4.63

(0.8H, d, J=3.3 Hz), 4.82 (0.2H, m), 4.98 (0.8H, m), 6.28 (1H, br s, OH), 6.58 (1H, d, J=7.8 Hz), 6.75 (1H, d, J=7.8 Hz), 7.62 (0.8H, dd, J=7.8, 7.8 Hz), 7.65 (0.2H, dd, J=7.8, 7.8 Hz), 7.71 (0.8H, d, J=7.8 Hz), 7.75 (0.2H, d, J=7.8 Hz), 8.13 (1H, d, J=7.8 Hz), 8.14 (1H, br s), 8.84 (1H, m, NH+), 9.36 (1H, s, OH).

IR (KBr)

υ 3388, 1618, 1528, 1466, 1352, 1321, 1120, 1036, 920, 806 cm$^{-1}$.

Mass (FAB)

m/z 520 ((M+H)+).

Elementary Analysis: As $C_{29}H_{33}N_3O_6 \cdot HCl$

Calcd.: C, 62.64; H, 6.16; N, 7.56; Cl, 6.38.

Found.: C, 62.25; H, 6.39; N, 7.68; Cl, 6.20.

Examples 74–88

17-cyclopropylmethyl-3,14β-dihydroxy-4,5α-epoxy-6α-(N-methyl-3-phenylpropiolamido)morphinan.hydrochloride 84 (yield: 16%), 17-cyclopropylmethyl-3,14β-dihydroxy-4,5α-epoxy-6α-(N-methylcyclohexylacetamido)morphinan.hydrochloride 85 (yield: 55%), 17-cyclopropylmethyl-3,14β-dihydroxy-4,5α-epoxy-6α-(N-methyl-3,4-dichlorocinnamamido) morphinan.hydrochloride 86 (yield: 78%), 17-cyclopropylmethyl-3,14β-dihydroxy-4,5α-epoxy-6α-(N-methyl-4-nitrophenylacetamido)morphinan.hydrochloride 87 (yield: 83%), 17-cyclopropylmethyl-3,14β-dihydroxy-4,5α-epoxy-6α-(N-methyl-2-bromophenylacetamido)morphinan.hydrochloride 88 (yield: 81%), 17-cyclopropylmethyl-3,14β-dihydroxy-4,5α-epoxy-6α-[N-methyl-trans-3-(3-furyl)acrylamido]morphinane.tartrate 89 (yield: 39%), 17-cyclopropylmethyl-3,14β-dihydroxy-4,5α-epoxy-6α-(N-methyl-4-pyridylacetamido) morphinan.2 hydrochloride 90 (yield: 83%), 17-cyclopropylmethyl-3,14β-dihydroxy-4,5α-epoxy-6α-[N-methyl-trans-3-(3-thienyl)acrylamido]morphinan.tartrate 91 (yield: 40%), 17-cyclopropylmethyl-3,14β-dihydroxy-4,5α-epoxy-6α-(N-methyl-2-pyridylacetamido)morphinan.2 hydrochloride 92 (yield: 82%), 17-cyclopropylmethyl-3,14β-dihydroxy-4,5α-epoxy-6α-(N-methyl-3-pyridylacetamido) morphinan-.hydrochloride 93 (yield: 92%), 17-cyclopropylmethyl-3,14β-dihydroxy-4,5α-epoxy-6α-(N-methyl-3-cyclohexylpropionamido)morphinan.hydrochloride 94 (yield: 45%), 17-cyclopropylmethyl-3,14β-dihydroxy-4,5α-epoxy-6α-(N-methyl-trans-2-hexenamido) morphinan.tartrate 9 (yield: 46%), 17-cyclopropylmethyl-3,14β-dihydroxy-4,5α-epoxy-6α-(N-methyl-3-fluorocinnamamido)morphinan.tartrate 96 (yield: 79%), 17-cyclopropylmethyl-3,14β-dihydroxy-4,5α-epoxy-6α-(N-methyl-3-nitrocinnamamido)morphinanphosphate 97 (yield: 40%) and 17-cyclopropylmethyl-3,14β-dihydroxy-4,5α-epoxy-6α-(N-methylbenzoylacetamido)morphinan.tartrate 98 (yield: 37%) were obtained by following the procedure of example 73 but using phenylpropiolic acid, cyclohexylacetic acid, trans-3,4-dichlorocinnamic acid, 4-nitrophenylacetic acid, 2-bromophenylacetic acid, trans-3-(3-furyl)acrylic acid, 4-pyridylacetic acid, trans-3-(3-thienyl)acrylic acid, 2-pyridylacetic acid, 3-pyridylacetic acid, 3-cyclohexylpropionic acid, trans-2-hexenoic acid, 3-fluorocinnamic acid, 3-nitrocinnamic acid and benzoylacetic acid instead of 3-nitrophenylacetic acid.

Compound 84

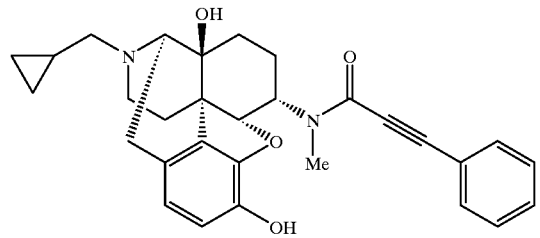

mp 206.0–209.0° C. (decomposition, ether)

NMR (400 MHz, DMSO-d$_6$)

δ 0.41 (1H, m), 0.49 (1H, m), 0.62 (1H, m), 0.69 (1H, m), 1.08 (1H, m), 1.19 (0.5H, m), 1.27 (0.5H, m), 1.45~1.72 (3H, m), 1.95 (0.5H, m) 2.02 (0.5H, m), 2.48 (1H, m), 2.71 (1H, m), 2.92 (1.5H, s), 2.94~3.06 (2H, m), 3.12 (1H, dd, J=19.5, 6.7 Hz), 3.24 (1.5H, s), 3.27~3.38 (2H, m), 3.95 (1H, dd, J=15.6, 6.7 Hz), 4.71 (0.5H, d, J=3.7 Hz), 4.81 (0.5H, d, J=3.7 Hz), 4.92 (0.5H, br d, J=13.4 Hz), 5.09 (0.5H, br d, J=13.4 Hz), 6.32 (0.5H, s), 6.42 (0.5H, s), 6.61 (0.5H, d, J=7.9 Hz), 6.62 (0.5H, d, J=7.9 Hz), 6.74 (0.5H, d, J=7.9 Hz), 6.75 (0.5H, d, J=7.9 Hz), 7.49 (1H, t, J=7.3 Hz), 7.52~7.57 (2H, m), 7.66 (1H, d, J=8.5 Hz), 7.72 (1H, d, J=7.3 Hz), 8.85 (0.5H, br s), 8.93 (0.5H, br s), 9.37 (1H, s)

IR (KBr)

υ 3400, 2952, 2216, 1613, 1493, 1377, 1321, 1120, 1036, 692 cm$^{-1}$.

Mass (FAB)

m/z 485 (M+H)+.

Elementary Analysis: As $C_{30}H_{32}N_2O_4 \cdot 1.5HCl \cdot 0.8H_2O$

Calcd.: C, 66.61; H, 6.48; N, 5.18; Cl, 7.54.

Found.: C, 66.42; H, 6.55; N, 5.19; Cl, 7.72.

Compound 85

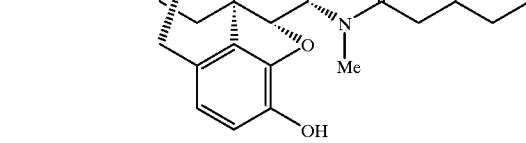

mp 245.0–248.0° C. (decomposition, ether)

NMR (400 MHz, DMSO-d$_6$)

δ 0.40 (1H, m), 0.47 (1H, m), 0.61 (1H, m), 0.68 (1H, m), 0.93~1.35 (8H, m), 1.53~1.74 (8H, m), 1.90 (1H, m), 2.22 (2H, dd, J=6.8, 2.4 Hz), 2.39~2.54 (2H, m), 2.69 (1H, m), 2.79 (0.6H, s) 2.88 (2.4H, s), 2.92 (1H, m), 3.03 (1H, br d, J=13.2 Hz), 3.09 (1H, dd, J=20.4, 7.6 Hz), 3.39 (1H, m), 3.87 (1H, d, J=6.4 Hz), 4.48 (0.2H, m), 4.60 (0.8H, d, J=3.9 Hz), 4.73 (0.2H, br s), 4.98 (0.8H, dt, J=14.2, 3.9 Hz), 6.16 (0.8H, s), 6.38 (0.2H, s), 6.58 (0.8H, d, J=8.3 Hz), 6.59 (0.2H, d, J=7.8 Hz), 6.71 (0.8H, d, J=7.8 Hz), 6.72 (0.2H, d, J=8.3 Hz), 8.79 (1H, br s), 9.28 (0.8H, s), 9.31 (0.2H, s).

IR (KBr)

3400, 2928, 2856, 1615, 1508, 1317, 1120, 804 cm$^{-1}$.

Mass (FAB)

m/z 481 (M+H)+.

Elementary Analysis: As $C_{29}H_{41}N_2O_4Cl\cdot0.4H_2O$
Calcd.: C, 66.43; H, 8.04; N, 5.34; Cl, 6.76.
Found.: C, 66.33; H, 7.81; N, 5.35; Cl, 6.97.

Compound 86

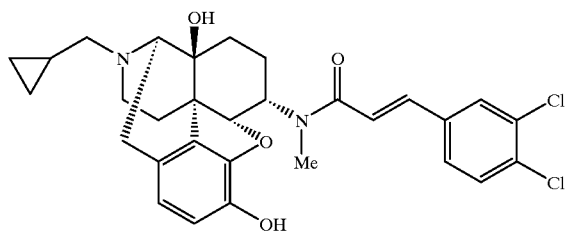

86 mp 249–258° C. (decomposition, methanol)

NMR (400 MHz, DMSO-$d_6$)

δ 0.31–0.43 (1H, m), 0.43–0.54 (1H, m), 0.54–0.66 (1H, m), 0.66–0.76 (1H, m), 0.99–1.12 (1H, m), 1.12–1.33 (1H, m), 1.33–1.50 (1H, m), 1.50–1.70 (2H, m), 1.86–2.03 (1H, m), 2.40–2.50 (1H, m), 2.61–2.78 (1H, m), 2.87–2.99 (1H, m), 2.90 (0.6H, s), 2.99–3.19 (2H, m), 3.09 (2.4H, s), 3.19–3.39 (2H, m), 3.92 (1H, br d, J=5.9 Hz), 4.63 (0.2H, m), 4.73 (0.8H, d, J=3.9 Hz), 4.92 (0.2H, brs), 5.04 (0.8H, dt, J=14.2, 4.0 Hz), 6.27 (0.8H, br s), 6.46 (0.2H, br s), 6.60 (1H, d, J=7.8 Hz), 6.73 (1H, d, J=7.8 Hz), 7.32 (0.2H, d, J=15.1 Hz), 7.38 (0.8H, d, J=15.1 Hz), 7.47 (0.2H, d, J=15.1 Hz), 7.49 (0.8H, d, J=15.1 Hz), 7.64–7.73 (1H, m), 7.75 (1H, dd, J=8.3, 2.0 Hz), 8.04 (0.2H, s), 8.13 (0.8H, d, J=2.0 Hz), 8.82 (1H, br s), 9.31 (0.8H, s), 9.34 (0.2H, s), IR (KBr)

υ 1649, 1599, 1510, 1475, 1377, 1317, 1120, 1033 cm$^{-1}$.

Mass (FAB)

m/z 555 ((M+H)+).

Elementary Analysis: As $C_{30}H_{33}N_2O_4Cl_3$
Calcd.: C, 60.87; H, 5.62; N, 4.73; Cl, 17.97
Found.: C, 60.87; H, 5.82; N, 4.73; Cl, 17.75

Compound 87

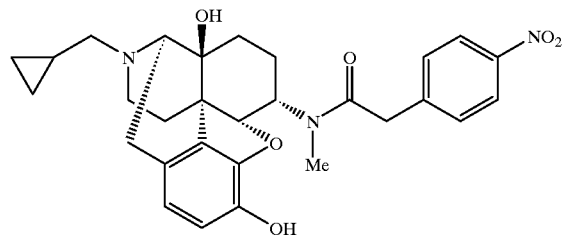

87 mp >190° C. (decomposition)

NMR (400 MHz, DMSO-$d_6$)

d 0.39 (1H, m), 0.47 (1H, m), 0.61 (1H, m),0.68 (1H, m), 1.05 (1H, m), 1.18 (1H, m), 1.37 (1H, m), 1.46–1.63 (2H, m), 1.93 (1H, m), 2.43 (1H, m), 2.67 (1H, m), 2.82 (0.6H, s), 2.90–3.14 (3H, m), 2.98 (2.4H, s), 3.21–3.39 (2H, m), 3.88–4.07 (3H, m), 4.50 (0.2H, m), 4.60–4.67 (1H, m), 4.98 (0.8H, m), 6.27 (0.8H, br s, OH), 6.58 (1H, d, J=7.8 Hz), 6.59 (0.2H, br s, OH), 6.74 (1H, d, J=7.8 Hz), 7.53 (1.6H, d, J=8.8 Hz), 7.58 (0.4H, d, J=8.8 Hz), 8.20 (1.6H, d, J=8.8 Hz), 8.23 (0.4H, d, J=8.8 Hz), 8.83 (1H, m, NH+), 9.34 (1H, br s, OH).

IR (KBr)

υ 3358, 1611, 1520, 1468, 1346, 1323, 1118, 1035, 919, 820 cm$^{-1}$.

Mass (FAB)

m/z 520 ((M+H)+).

Elementary Analysis: As $C_{29}H_{33}N_3O_6\cdot HCl\cdot0.7H_2O$
Calcd.: C, 61.25; H, 6.27; N, 7.39; Cl, 6.23.
Found.: C, 61.24; H, 6.38; N, 7.18; Cl, 6.37.

Compound 88

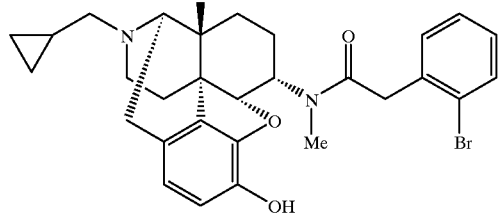

88 mp 230° C. (decomposition)

NMR (400 MHz, DMSO-$d_6$)

δ 0.40 (1H, m), 0.46 (1H, m), 0.60 (1H, m), 0.68 (1H, m), 1.05 (1H, m), 1.18 (1H, m), 1.38 (1H, m), 1.50–1.64 (2H, m), 1.93 (1H, m), 2.42 (1H, m), 2.69 (1H, m), 2.84 (0.6H, s), 2.94 (1H, m), 3.01 (2.4H, s), 3.02–3.14 (2H, m), 3.21–3.33 (2H, m), 3.82–3.97 (3H, m), 4.57 (0.2H, m), 4.61 (0.8H, d, J=3.7 Hz), 4.84 (0.2H, m), 4.98 (0.8H, m), 6.24 (0.8H, br s), 6.46 (0.2H, br s), 6.58 (1H, d, J=7.9 Hz), 6.75 (1H, d, J=7.9 Hz), 7.21 (1H, m), 7.30–7.38 (2H, m), 7.60 (1H, m), 8.82 (1H, br s), 9.34 (0.8H, s), 9.35 (0.2H, s).

IR (KBr)

υ 3120, 1620, 1508, 1473, 1377, 1317, 1118, 1027, 752 cm$^{-1}$.

Mass (FAB)

m/z 553 ((M+H)+).

Elementary Analysis: As $C_{29}H_{33}N_2O_4Br\cdot HCl\cdot0.4H_2O$
Calcd.: C, 58.33; H, 5.87; N, 4.69; Cl, 5.94; Br, 13.38.
Found.: C, 58.52; H, 5.76; N, 4.77; Cl, 6.07; Br, 13.03.

Compound 89

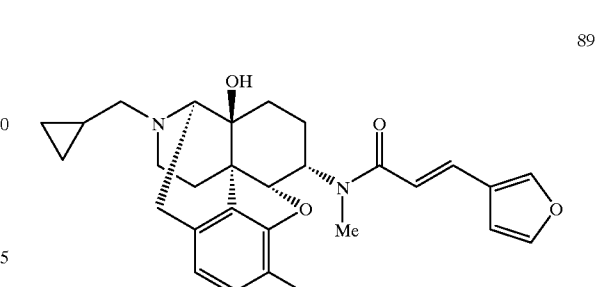

89 mp 243.0–254.0° C. (decomposition, diethylether)

NMR (400 MHz, DMSO-$d_6$)

δ 0.10–0.30 (2H, m), 0.44–0.63 (2H, m), 0.83–0.99 (1H, m), 0.90–1.30 (1H, m), 1.30–1.42 (1H, m), 1.42–1.60 (2H, m), 1.69–1.83 (1H, m), 2.12–2.41 (2H, m), 2.41–2.65 (2H, m), 2.65–2.82 (2H, m), 2.82–2.98 (1H, m), 3.05 (3H, s), 3.05–3.16 (1H, m), 3.16–3.39 (1H, m), 2.80–3.80 (1H, br s), 4.07 (1H, s), 4.55 (0.2H, m), 4.63 (0.8H, d, J=2.9 Hz), 4.68 (0.2H, br s), 4.96 (0.8H, dt, J=13.6, 4.0 Hz), 6.52 (1H, d, J=8.3 Hz), 6.63 (1H, d, J=7.8 Hz), 6.72–6.87 (0.4H, m), 6.96 (0.8H, d, J=15.1 Hz), 7.01 (0.8H, s), 7.43 (1H, d, J=15.1 Hz), 7.72 (0.8H, s), 7.70–7.78 (1H, m), 8.80–9.60 (1H, br s)

IR (KBr)
  υ 1651, 1597, 1510, 1460, 1377, 1160, 1120, 1038, 801 cm$^{-1}$.

Mass (FAB)
  m/z 477 ((M+H)+).

Elementary Analysis: As $C_{30}H_{35}N_2O_8 \cdot 0.8H_2O$
  Calcd.: C, 63.66; H, 6.52; N, 4.95
  Found.: C, 63.42; H, 6.50; N, 4.87

Compound 90

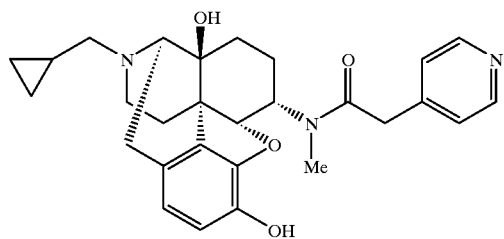

mp 200° C. (decomposition)
NMR (400 MHz, DMSO-$d_6$)
  δ 0.40 (1H, m), 0.47 (1H, m), 0.61 (1H, m), 0.68 (1H, m), 1.06 (1H, m), 1.18 (1H, m), 1.38 (1H, m), 1.50–1.64 (2H, m), 1.95 (1H, m), 2.42 (1H, m), 2.67 (1H, m), 2.83 (0.6H, s), 3.00 (2.4H, s), 2.90–3.13 (3H, m), 3.23–3.36 (2H, m), 3.50–4.30 (4H, m), 4.51 (0.2H, m), 4.62 (0.8H, d, J=3.9 Hz), 4.89 (0.2H, m), 4.97 (0.8H, m), 6.32 (1H, br s), 6.59 (1H, d, J=8.3 Hz), 6.75 (1H, d, J=8.3 Hz), 7.81 (2H, d, J=6.8 Hz), 8.79 (2H, d, J=6.8 Hz), 8.85 (1H, br s), 9.38 (1H, br s).

IR (KBr)
  υ 3390, 1620, 1510, 1460, 1321, 1120, 803 cm$^{-1}$.

Mass (EI)
  m/z 475 (M+).

Elementary Analysis: As $C_{28}H_{33}N_3O_4 \cdot 1.8HCl \cdot 0.4H_2O$
  Calcd.: C, 61.32; H, 6.54; N, 7.66; Cl, 11.64.
  Found.: C, 61.23; H, 6.68; N, 7.55; Cl, 11.59.

Compound 91

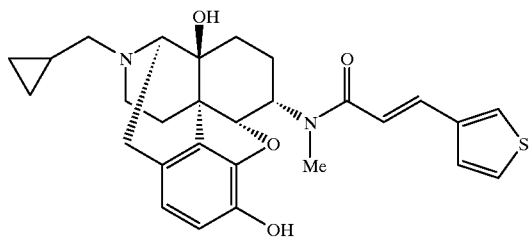

mp 249.0–250.0° C. (decomposition, methanol)
NMR (400 MHz, DMSO-$d_6$)
  δ 0.10–0.30 (2H, m), 0.44–0.63 (2H, m), 0.83–0.99 (1H, m), 1.10–1.32 (2H, m), 1.32–1.42 (1H, m), 1.42–1.67 (3H, m), 1.69–1.86 (1H, m), 2.18–2.41 (2H, m), 2.41–2.66 (2H, m), 2.66–2.84 (2H, m), 2.84–2.96 (1H, m), 3.06 (3H, s), 3.05–3.16 (1H, m), 3.30 (1H, br s), 4.06 (1H, s), 4.59 (0.2H, m), 4.64 (0.8H, d, J=2.9 Hz), 4.65 (0.2H, brs), 4.97 (0.8H, dt, J=13.7, 2.5 Hz), 6.52 (1H, d, J=7.8 Hz), 6.63 (1H, d, J=8.3 Hz), 6.91 (0.2H, m), 7.07 (0.8H, d, J=15.1 Hz), 7.41–7.50 (0.2H, m), 7.53 (1H, d, J=15.1 Hz), 7.61 (1.8H, s), 7.89 (1H, s), 8.52–9.48 (1H, br s)

IR (KBr)
  υ 1638, 1597, 1508, 1460, 1402, 1321, 1118, 1069, 1038, 789 cm$^{-1}$.

Mass (FAB)
  m/z 493 ((M+H)+).

Elementary Analysis: As $C_{30}H_{35}N_2O_7S \cdot 1.2H_2O$
  Calcd.: C, 61.14; H, 6.40; N, 4.75; S, 5.44
  Found.: C, 61.20; H, 6.39; N, 4.69; S, 5.29

Compound 92

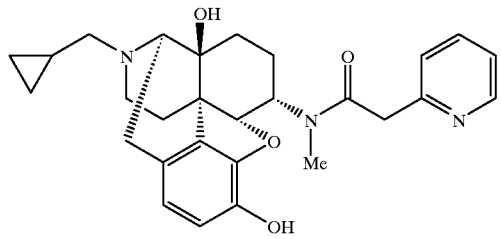

mp 190° C. (decomposition)
NMR (400 MHz, DMSO-$d_6$)
  δ 0.40 (1H, m), 0.47 (1H, m), 0.61 (1H, m), 0.68 (1H, m), 1.06 (1H, m), 1.20 (1H, m), 1.38 (1H, m), 1.48–1.64 (2H, m), 1.95 (1H, m), 2.41 (1H, m), 2.67 (1H, m), 2.83 (0.6H, s), 3.02 (2.4H, s), 2.90–3.15 (3H, m), 3.22–3.36 (2H, m), 3.40–3.85 (1H, br), 3.93–4.40 (3H, m), 4.58 (0.2H, m), 4.60 (0.8H, d, J=3.9 Hz), 4.97 (1H, m), 6.32 (1H, br s), 6.59 (1H, d, J=8.3 Hz), 6.76 (1H, d, J=8.3 Hz), 7.74–7.83 (2H, m), 8.36 (1H, m), 8.79 (1H, br d, J=3.9 Hz), 8.94 (1H, brs), 9.40 (1H, br s).

IR (KBr)
  υ 3380, 1638, 1508, 1460, 1321, 1120, 768 cm$^{-1}$.

Mass (FAB)
  m/z 476 ((M+H)+).

Elementary Analysis: As $C_{28}H_{33}N_3O_4 \cdot 1.8HCl \cdot 0.6H_2O$
  Calcd.: C, 60.92; H, 6.57; N, 7.61; Cl, 11.56.
  Found.: C, 60.91; H, 6.82; N, 7.47; Cl, 11.52.

Compound 93

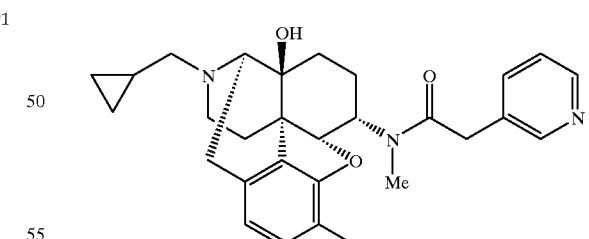

mp 195° C. (decomposition)
NMR (400 MHz, DMSO-$d_6$)
  δ 0.40 (1H, m), 0.47 (1H, m), 0.61 (1H, m), 0.68 (1H, m), 1.08 (I1H, m), 1.19 (1H, m), 1.38 (1H, m), 1.48–1.64 (2$_1$, m), 1.95 (1H, m), 2.42 (1H, m), 2.65 (1H, m), 2.83 (0.6H, s), 3.02 (2.4H, s), 2.88–3.15 (3H, m), 3.22–3.36 (2H, m), 3.45–3.80 (1H, br), 3.95–4.23 (3H, m), 4.60 (1H, m), 4.97 (1H, m), 6.32 (1H, br s), 6.59 (1H, m), 6 .7 7(1H, m), 7.91 (1H, m), 8.32 (1H, m), 8.74–8.82 (2H, m), 8.94 (1H, br s), 9.38 (1H, br s).

IR (KBr)
υ 3410, 1626, 1475, 1321, 1120, 1036, 919, 806, 683 cm$^{-1}$.
Mass (FAB)
m/z 476 ((M+H)+).
Elementary Analysis: As $C_{28}H_{33}N_3O_4 \cdot 1.8HCl \cdot 0.75H_2O$
Calcd.: C, 60.63; H, 6.60; N, 7.57; Cl, 11.50.
Found.: C, 61.01; H, 6.82; N, 7.17; Cl, 11.49.
Compound 94

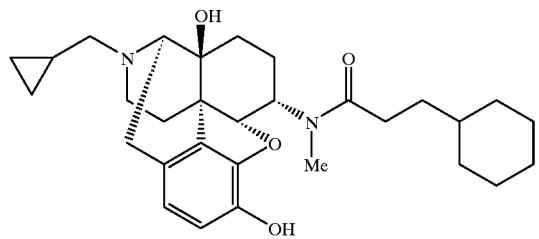

94 mp >265° C. (decomposition)
NMR (400 MHz, CD$_3$OD)
δ 0.49 (2H, m), 0.73 (1H, m), 0.83 (1H, m), 0.90–1.03 (2H, m), 1.09 (1H, m), 1.15–1.41 (5H, m), 1.43–1.58 (3H, m), 1.63–1.83 (7H, m), 1.92 (1H, m), 2.38–2.52 (2H, m), 2.64 (1H, m), 2.84–3.05 (2H, m), 2.93 (0.6H, s), 3.02 (2.4H, s), 3.05–3.21 (2H, m), 3.23–3.40 (2H, m), 3.98 (1H, m), 4.57 (0.2H, m), 4.75 (1H, br d, J=3.4 Hz), 5.08 (0.8H, ddd, J=13.7, 3.9, 3.9 Hz), 6.67 (0.8H, d, J=8.3 Hz), 6.69 (0.2H, d, J=8.3 Hz), 6.75 (0.8H, d, J=8.3 Hz), 6.76 (0.2H, d, J=8.3 Hz).
IR (KBr)
υ 3342, 3140, 1622, 1508, 1470, 1317, 1172, 1118, 1038, 920, 907, 806 cm$^{-1}$.
Mass (FAB)
m/z 495 ((M+H)+).
Elementary Analysis: As $C_{30}H_{42}N_2O_4 \cdot HCl \cdot 0.18H_2O$
Calcd.: C, 67.43; H, 8.18; N, 5.24; Cl, 6.63.
Found.: C, 67.80; H, 8.01; N, 4.84; Cl, 6.69.
Compound 95

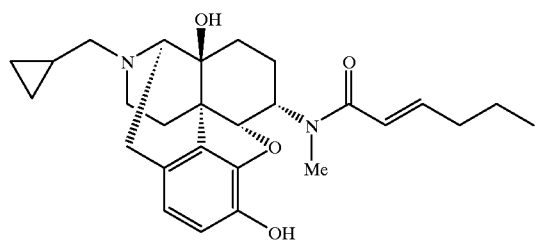

95 mp 230–240° C. (decomposition)
NMR (400 MHz, DMSO-d$_6$)
δ 0.19 (2H, m), 0.45–0.58 (2H, m), 0.90 (1H, m), 0.91 (3H, t, J=7.3 Hz), 1.07–1.37 (2H, m), 1.38–1.55 (4H, m), 1.73 (1H, m), 2.13–2.27 (4H, m), 2.42–2.58 (2H, m), 2.62–2.78 (2H, m), 2.84 (0.6H, s), 2.95 (2.4H, s), 3.03 (1H, br d, J=19.0 Hz), 3.23 (1H, m), 3.50 (3H, br s, 3×OH), 4.02 (1H, s), 4.45 (0.2H, m), 4.56 (0.2H, m), 4.58 (0.8H, d, J=3.4 Hz), 4.90 (0.8H, m), 6.34 (0.2H, d, J=15.1 Hz), 6.45 (0.8H, d, J=15.1 Hz), 6.50 (1H, d, J=8.0 Hz), 6.61 (1H, d, J=8.0 Hz), 6.65–6.73 (1H, m), 9.06 (1H, br s, NH+).

IR (KBr)
υ 3386, 1657, 1591, 1462, 1408, 1359, 1315, 1170, 1122, 1069, 1038, 980, 920, 810 cm$^{-1}$.
Mass (FAB)
m/z 453 ((M+H)+).
Elementary Analysis: As $C_{27}H_{36}N_2O_4 \cdot 0.5C_4H_6O_6 \cdot 0.2H_2O$
Calcd.: C, 65.57; H, 7.48; N, 5.27.
Found.: C, 65.54; H, 7.35; N, 5.37.
Compound 96

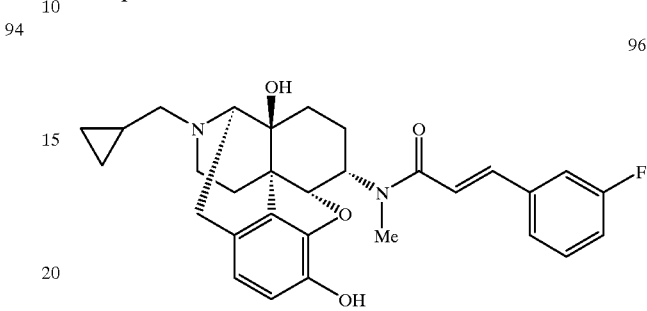

96 mp 225° C. (decomposition)
NMR (400 MHz, DMSO-d$_6$)
δ 0.10–0.23 (2H, m), 0.43–0.60 (2H, m), 0.82–0.98 (1H, m), 1.12–1.60 (4H, m), 1.68–1.82 (1H, m), 2.18–2.40 (2H, m), 2.62–2.80 (2H, m), 2.83–4.00 (10H, m), 4.04 (1H, s), 4.52–4.60 (0.3H, m), 4.65 (0.7H, d, J=3.4 Hz), 4.75 (0.3H, br s), 4.92–5.02 (0.7H, m), 6.51 (1H, d, J=7.8 Hz), 6.62 (1H, d, J=7.8 Hz), 7.10–7.26 (1H, m), 7.31 (1H, d, J=15.6 Hz), 7.40–7.57 (3H, m), 7.67 (1H, d, J=10.3 Hz), 9.07 (1H, br s).
IR (KBr)
υ 3400, 1644, 1586, 1462, 1408, 1359, 1315, 1120, 789 cm$^{-1}$.
Mass (FAB)
m/z 505 ((M+H)+).
Elementary Analysis: As $C_{30}H_{33}N_2O_4F \cdot 0.5C_4H_6O_6$
Calcd.: C, 66.31; H, 6.26; N, 4.83; F, 3.28.
Found.: C, 66.43; H, 6.37; N, 4.87; F, 3.27.
Compound 97

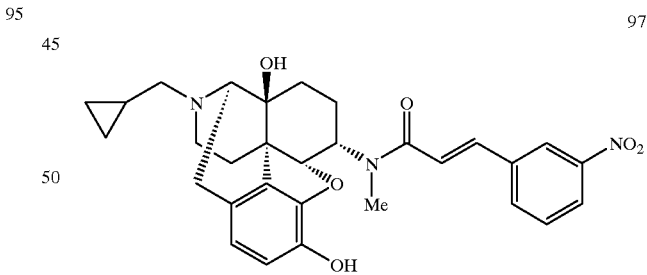

97 mp 185–200° C.
NMR (400 MHz, DMSO-d$_6$)
δ 0.10–0.30 (2H, m), 0.45–0.62 (2H, m), 0.82–1.00 (1H, m), 1.10–1.60 (4H, m), 1.70–1.85 (1H, m), 2.20–2.35 (2H, m), 2.55–2.90 (5H, m), 2.92 (0.6H, s), 2.97–3.10 (1H, m), 3.12 (2.4H, s), 3.23–3.37 (1H, m), 3.50–5.75 (4H, br), 4.55 (0.2H, m), 4.66 (0.8H, d, J=3.4 Hz), 4.78 (0.2H, m), 4.98 (0.8H, m), 6.53 (1H, d, J=8.1 Hz), 6.64 (1H, d, J=8.1 Hz), 7.29 (0.2H, d, J=15.1 Hz), 7.48 (0.8H, d, J=15.4 Hz), 7.58 (0.2H, d, J=15.1 Hz), 7.63 (0.8H, d, J=15.4 Hz), 7.71 (1H, t, J=8.1 Hz), 8.10–8.27 (2H, m), 8.50 (0.2H, s), 8.61 (0.8H, s).

IR (KBr)
  υ 3398, 3360, 3216, 3094, 1649, 1591, 1531, 1350, 1120, 1036, 973, 812, 741
Mass (FAB)
  m/z 532 ((M+H)+).
Elementary Analysis : As C₃₀H₃₃N₃O₆.H₃PO₄.1.6H₂O
  Calcd.: C, 54.73; H, 6.00; N 6.38; P, 4.70.
  Found.: C, 54.66; H, 5.85; N, 6.28; P, 4.45.
Compound 98

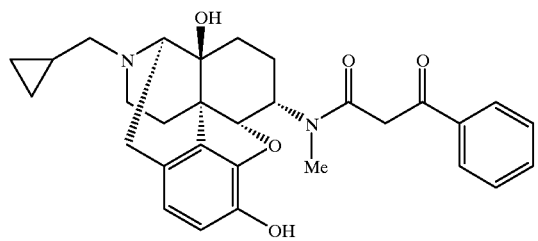

mp >176° C. (decomposition)
NMR (400 MHz, DMSO-d₆)
  δ 0.14–0.24 (2H, m), 0.43–0.57 (2H, m), 0.81–0.95 (1H, m), 1.10–1.58 (4H, m), 1.74 (1H, m), 2.16–2.31 (2H, m), 2.40–2.56 (2H, m), 2.62–2.78 (2H, m), 2.84 (0.27H, s), 2.94 (1.71H, s), 2.99–3.08 (1H, m), 3.04 (1.02H, s), 3.25 (1H, m), 3.50 (3H, br s, 3×OH), 4.03 (1H, s), 4.15–4.25 (0.15H, m), 4.20 (0.51H, d, J=16.6 Hz), 4.29 (0.51H, d, J=16.6 Hz), 4.29 (0.09H, d, J=16.6 Hz), 4.36 (0.09H, d, J=16.6 Hz), 4.52 (0.51H, d, J=3.9 Hz), 4.63 (0.34H, d, J=3.9 Hz), 4.72 (0.06H, m), 4.77 (0.09H, m), 4.91 (0.51H, ddd, J=13.7, 3.9, 3.9 Hz), 4.98 (0.34H, ddd, J=13.7, 3.9, 3.9 Hz), 5.97 (0.06H, s), 6.18 (0.34H, s), 6.50–6.56 (1H, m), 6.61–6.67 (1H, m), 7.45–8.02 (5H, m), 9.10 (1H, br s, NH+), 15.84 (0.34H, s), 15.92 (0.06H, s).
IR (KBr)
  υ 3400, 1688, 1611, 1464, 1359, 1323, 1214, 1172, 1120, 1069, 1038, 919, 806 cm⁻¹.
Mass (FAB)
  m/z 503 ((M+H)+).
Elementary Analysis: As C₃₀H₃₄N₂O₅.0.5C₄H₆O₆.0.7H₂O
  Calcd.: C, 65.12; H, 6.56; N, 4.75.
  Found.: C, 65.15; H, 6.43; N, 4.74.

Examples 89–94

17-cyclopropylmethyl-3,14β-dihydroxy-4,5α-epoxy-6β-(N-methylcinnamamido)morphinan.hydrochloride 99 (yield: 46%), 17-cyclopropylmethyl-3,14β-dihydroxy-4,5α-epoxy-6β-(N-methyl-trans-2-hexenamido)morphinan.tartrate 100 (yield: 52%), 17-cyclopropylmethyl-3,14β-dihydroxy-4,5α-epoxy-6β-(N-methyl-3-phenylpropiolamido)morphinan.hydrochloride 101 (yield: 49%), 17-cyclopropylmethyl-3,14β-dihydroxy-4,5α-epoxy-6β-(N-methyl-3-fluorocinnamamido)morphinan.tartrate 102 (yield: 81%), 17-cyclopropylmethyl-3,14β-dihydroxy-4,5α-epoxy-6β-(N-methylbenzoylacetamido)morphinan.tartrate 103 (yield: 52%) and 17-cyclopropylmethyl-3,14β-dihydroxy-4,5α-epoxy-6β-(N-methyl-3-nitrocinnamamido)morphinan.tartrate 104 (yield: 47%) were obtained by following the procedure of example 73 but using 17-cyclopropylmethyl-4,5α-epoxy-3,14β-dihydroxy-6β-methylaminomorphinan 10 instead of the starting material of 17-cyclopropylmethyl-4,5α-epoxy-3,14β-dihydroxy-6α-methylaminomorphinan 4, and using cinnamic acid, trans-2-hexenoic acid, phenylpropiolic acid, 3-fluorocinnamic acid, benzoylacetic acid and 3-nitrocinnamic acid instead of 3-nitrophenylacetic acid.

Compound 99

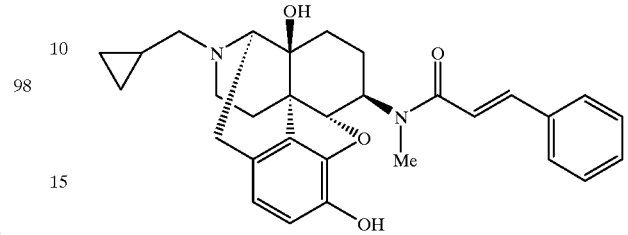

mp 225° C. (decomposition)
NMR (400 MHz, DMSO-d₆)
  δ 0.42 (1H, m), 0.50 (1H, m), 0.59 (1H, m), 0.68 (1H, m), 1.07 (1H, m), 1.20–1.50 (3.5H, m), 1.72 (1H, m), 2.13 (1H, m), 2.40–2.60 (2.5H, m), 2.87 (1H, m), 2.92 (2H, s), 3.06 (2H, m),3.19 (1H, s), 3.32 (2H, m), 3.6–4.3 (2H, m), 4.85 (0.7H, m), 4.92 (0.3H, m), 6.30 (1H, m), 6.68 (2H, m) 6.88 (0.5H, d, J=8.3 Hz), 7.30–7.50 (5H, m), 7.71 (0.5H, d, J=6.4 Hz), 8.79 (1H, m), 9.29 (0.3H, s), 9.70 (0.7H, s)
IR (KBr)
  υ 3380, 1642, 1599, 1499, 1321, 1127, 768 cm⁻¹.
Mass (FAB)
  m/z 487 (M+H)
Elementary Analysis: As C₃₀H₃₄N₂O₄.HCl.0.3H₂O
  Calcd.: C, 68.18; H, 6.79; N, 5.30; Cl, 6.71
  Found.: C, 68.06; H, 7.11; N, 5.46; Cl, 6.37

Compound 100

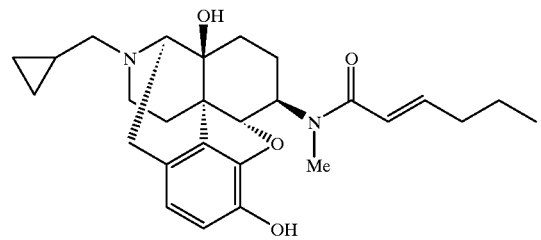

mp >145° C. (decomposition)
NMR (400 MHz, DMSO-d₆)
  δ 0.25 (2H, m), 0.48–0.59 (2H, m), 0.79 (2.1H, t, J=7.3 Hz), 0.90 (0.9H, t, J=7.3 Hz), 0.92 (1H, m), 1.20–1.48 (5H, m), 1.58 (1H, m), 1.91–2.20 (4H, m), 2.29 (1H, m), 2.53 (1H, m), 2.67–2.85 (3H, m), 2.81 (2.1H, s), 3.01 (0.9H, s), 3.11 (1H, br d, J=18.6 Hz), 3.31 (1H, m), 3.45 (4.2H, br s, 3.6×OH+0.6×COOH), 3.57 (1H, m), 4.06 (1.6H, s), 4.62 (0.7H, d, J=7.8 Hz), 4.74 (0.3H, d, J=7.8 Hz), 6.05 (0.7H, d, J=15.1 Hz), 6.35–6.44 (1.0H, m), 6.54–6.71 (2.3H, m), 9.26 (1H, br s, NH+).
IR (KBr)
  υ 3396, 1736, 1655, 1601, 1460, 1410, 1319, 1123, 1067, 1035, 922, 859 cm⁻¹.
Mass (FAB)
  m/z 453 ((M+H)+).

Elementary Analysis: As $C_{27}H_{36}N_2O_4 \cdot 0.8C_4H_6O_6 \cdot 1.1H_2O$
  Calcd.: C, 61.22; H, 7.32; N, 4.73.
  Found.: C, 61.13; H, 7.23; N, 4.82.

Compound 101

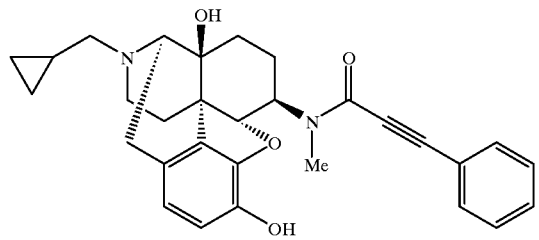

mp 208.0–225.0° C. (decomposition, ether)
NMR (400 MHz, DMSO-$d_6$) (data for 0.5 tartrate)
  δ 0.25 (2H, br s), 0.54 (2H, m), 0.93 (1H, m), 1.27~1.47 (3H, m), 1.66 (1H, m), 1.88~5.20 (3H, br OH×2), 2.08~2.19 (2H, m), 2.30 (1H, m), 2.44~2.53 (2H, m), 2.58~2.80 (3H, m), 2.93 (2.1H, s), 3.12 (1H, m), 3.17 (0.9H, s), 3.27 (1H, br s), 4.00 (1H, s), 4.06 (0.3H, m), 4.20 (0.7H, m), 4.73 (0.7H, d, J=8.3 Hz), 4.82 (0.3H, d, J=8.3 Hz), 6.55–6.67 (2H, m), 7.19 (1.55H, d, J=7.3 Hz), 7.37 (1.55H, t, J=7.3 Hz), 7.45~7.56 (1.40H, m), 7.60 (0.5H, d, J=6.8 Hz), 9.15 (1H, br s).
IR (KBr) (Data for free base)
  υ 3218, 2218, 1618, 1458 cm$^{-1}$.
Mass (FAB)
  m/z 485 (M+H)+.
Elementary Analysis: As $C_{30}H_{33}N_2O_4Cl \cdot 0.7H_2O$
  Calcd.: C, 67.52; H, 6.50; N, 5.25; Cl, 6.64.
  Found.: C, 67.43; H, 6.65; N, 5.25; Cl, 6.67.

Compound 102

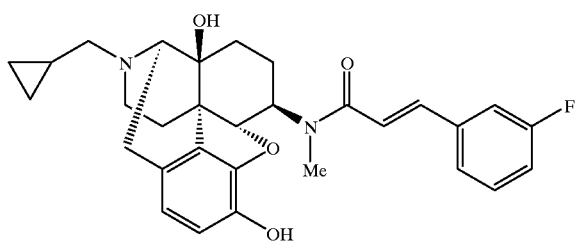

mp 145–153° C.
NMR (400 MHz, DMSO-$d_6$)
  δ 0.20–0.32 (2H, m), 0.46–0.62 (2H, m), 0.88–1.00 (1H, m), 1.20–1.50 (3H, m), 1.55–1.65 (1H, m), 2.00–2.40 (3H, m), 2.42–2.60 (2H, m), 2.70–2.88 (3H, m), 2.90 (2.1H, s), 3.15 (0.9H, m), 3.05–4.00 (7H, m), 4.11 (2H, s), 4.71 (0.7H, d, J=8.1 Hz), 4.81 (0.3H, d, J=8.1 Hz), 6.58–6.68 (3H, m), 7.14–7.68 (5H, m), 9.15 (0.3H, br s), 9.45 (0.7H, br s).
IR (KBr)
  υ 3320, 1731, 1647, 1586, 1412, 1311, 1270, 1127, 1077, 1033, 980, 859, 789, 677 cm$^{-1}$.
Mass (FAB)
  m/z 505 ((M+H)+).
Elementary Analysis: As $C_{30}H_{33}N_2O_4F \cdot C_4H_6O_6 \cdot H_2O$
  Calcd.: C, 60.71; H, 6.14; N, 4.16; F, 2.82.
  Found.: C, 60.63; H, 6.22; N, 4.07; F, 2.81.

Compound 103

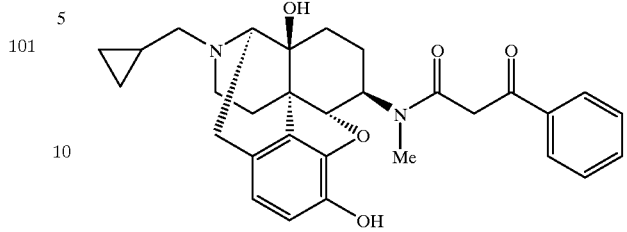

mp >161° C. (decomposition)
NMR (400 MHz, DMSO-$d_6$)
  δ 0.17–0.27 (2H, m), 0.45–0.58 (2H, m), 0.89(1H, m), 1.16–1.44 (3H, m), 1.50–1.61 (1H, m), 2.02–2.18 (2H, m), 2.28 (1H, m), 2.43 (1H, m), 2.53–2.78 (3H, m), 2.81 (1.68H, s), 2.93 (0.18H, s), 2.98 (0.72H, s), 3.04 (1H, br d, J=19.1 Hz), 3.10 (0.42H, s), 3.17–3.28 (1H, m), 3.35 (1H, m), 3.50 (3H, br s, 3×OH), 3.98–4.37 (1.4H, m), 4.04 (1H, s), 4.67 (0.8H, d, J=7.8 Hz), 4.76 (0.14H, d, J=8.3 Hz), 4.77 (0.06H, d, J=8.3 Hz), 5.62 (0.06H, s), 6.12 (0.24H, s), 6.52 (0.56H, d, J=8.3 Hz), 6.52–6.78 (0.88H, m), 6.61 (0.56H, d, J=8.3 Hz), 7.41–7.96 (5H, m), 9.02–9.60 (1H, m, NH+), 15.50 (0.06H, s), 15.76 (0.24H, s).
IR (KBr)
  υ 3390, 1686, 1626, 1452, 1323, 1278, 1125, 1035, 926, 859 cm$^{-1}$.
Mass (FAB)
  m/z 503 ((M+H)+).
Elementary Analysis: As $C_{30}H_{34}N_2O_5 \cdot 0.5C_4H_6O_6 \cdot 1.2H_2O$
  Calcd.: C, 64.14; H, 6.63; N, 4.67.
  Found.: C, 64.20; H, 6.57; N, 4.61.

Compound 104

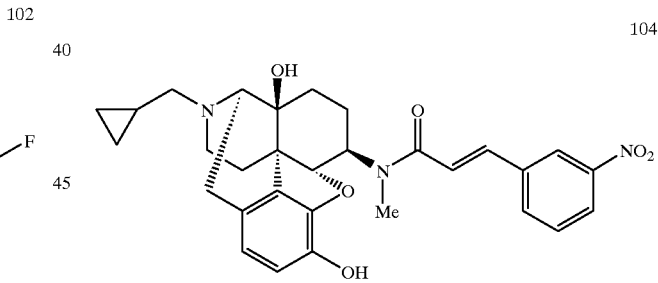

mp 161–164° C.
NMR (400 MHz, DMSO-$d_6$)
  d 0.18–0.30 (2H, m), 0.46–0.60 (2H, m), 0.85–0.97 (1H, m), 1.22–1.50 (3H, m), 1.53–1.62 (1H, m), 2.03–2.21 (2H, m), 2.23–2.35 (1H, m), 2.50–2.90 (4H, m), 2.91 (2.1H, s), 3.18 (0.9H, s), 3.10–4.20 (3H, m), 4.05 (1H, s), 4.67 (0.7H, d, J=8.3 Hz), 4.81 (0.3H, d, J=8.3 Hz), 6.58 (0.3H, d, J=7.8 Hz), 6.63 (1H, d, J=7.8 Hz), 6.73 (0.7H, d, J=7.8 Hz), 6.84 (0.7H, d, J=15.6 Hz), 7.42 (0.3H, d, J=15.9 Hz), 7.45 (0.7H, d, J=15.6 Hz), 7.57 (0.3H, d, J=15.6 Hz), 7.66 (0.7H, dd, J=8.3, 7.8 Hz), 7.71 (0.3H, dd, 8.3, 7.8 Hz), 7.93 (0.7H, d, J=7.8 Hz), 8.15–8.27 (2H, m), 8.60 (0.3H, s), 9.12 (0.7H, br s), 9.28 (0.7H, br s).
IR (KBr)
  υ 3380, 1649, 1601, 1531, 1352, 1127, 1035, 922, 859, 810, 743 cm$^{-1}$.

Mass (FAB)

m/z 532 ((M+H)+).

Elementary Analysis: AS $C_{30}H_{33}N_3O_6 \cdot 0.5C_4H_6O_6 \cdot 2.2H_2O$

Calcd.: C, 59.47; H, 6.30; N, 6.50.

Found.: C, 59.42; H, 5.96; N, 6.25.

Example 95

17-cyclopropylmethyl-3,14β-dihydroxy-4,5α-epoxy-6α-(N-methyl-3,4-difluorophenylacetamido)morphinan.hydrochloride 105

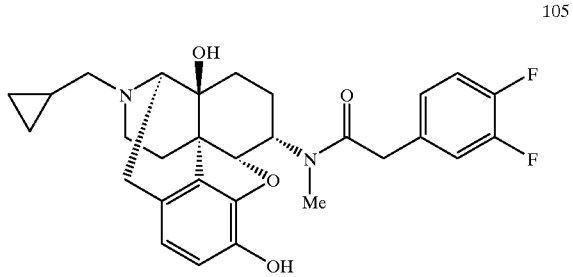

105

128 mg of 3,4-difluorophenylacetic acid and 131 mg of carbonyl diimidazole were dissolved in 2.5 ml of anhydrous tetrahydrofuran. After refluxing while heating for 30 minutes, the solution was cooled to room temperature. A solution of 200 mg of 17-cyclopropylmethyl-4,5α-epoxy-3,14β-dihydroxy-6α-methylaminomorphinan 4 dissolved in 13 ml of anhydrous tetrahydrofuran was added to the reaction solution followed by refluxing while heating for 1 hour. After cooling to room temperature, the reaction solution was concentrated and the resulting residue was dissolved in 16 ml of methanol and stirred for 1 hour following the addition of 1 ml of 1 N aqueous sodium hydroxide. The reaction system was then concentrated followed by the addition of 40 ml of ethylacetate to the residue and sequential washing with 25 ml of water and 25 ml of saturated brine. After drying with anhydrous sodium sulfate, the organic layer was concentrated to obtain 439 mg of crude product. This was then recrystallized from ethylacetate to obtain 190 mg of the free base of the target compound. The mother liquor was then purified with silica gel column chromatography (25 g chloroform/methanol=19/1) to obtain 177 mg of the free base of the target compound. The free base obtained in this manner was then dissolved in a mixed solvent of chloroform and methanol, and this solution was concentrated after adding methanol solution of hydrochloride to adjust to pH 4. The residue was re-precipitated with ether and filtered to obtain 176 mg of the target compound (yield: 57%).

mp 194–208° C. (decomposition, diethylether)

NMR (400 MHz, DMSO-$d_6$)

δ 25 0.31–0.43 (1H, m), 0.43–0.53 (1H, m), 0.53–0.64 (1H, m), 0.64–0.76 (1H, m), 0.99–1.12 (1H, m), 1.12–1.28 (1H, m), 1.28–1.45 (1H, m), 1.45–1.67 (2H, m), 1.86–2.03 (1H, m), 2.35–2.50 (1H, m), 2.59–2.77 (1H, m), 2.80 (0.6H, s), 2.88–3.18 (3H, m), 2.96 (2.4H, s), 3.18–3.39 (2H, m), 3.78 (1.6H, s), 3.88 (0.4H, s), 3.91 (1H, d, J=6.8 Hz), 4.49 (0.2H, m), 4.62 (1H, d, J=3.4 Hz), 4.97 (0.8H, dt, J=14.2, 3.4 Hz), 6.25 (0.8H, br s), 6.56 (0.2H, br s), 6.58 (1H, d, J=7.8 Hz), 6.73 (1H, d, J=7.8 Hz), 7.03–7.18 (1H, m), 7.25–7.45 (2H, m), 8.82 (1H, br s) 9.32 (1H, s)

IR (KBr)

υ 1620, 1560, 1520, 1460, 1278, 1172, 1120, 1036, 774 cm$^{-1}$.

Mass (FAB)

m/z 511 ((M+H)+).

Elementary Analysis: As $C_{29}H_{33}N_2O_4ClF_2 \cdot 0.7H_2O \cdot 0.25AcOEt$

Calcd.: C, 61.95; H, 6.31; N, 4.82; Cl, 6.09; F, 6.53

Found.: C, 61.91; H, 6.47; N, 4.81; Cl, 6.04; F, 6.53

Examples 96–98

17-cyclopropylmethyl-3,14β-dihydroxy-4,5α-epoxy-6α-(N-methyl-4-benzo[b]thienylacetamido)morphinane.hydrochloride 106 (yield: 74%), 17-cyclopropylmethyl-3,14β-dihydroxy-4,5α-epoxy-6α-(N-methyl-3-benzo[b]thienylacetamido)morphinan.hydrochloride 107 (yield: 71%) and 17-cyclopropylmethyl-3,14β-dihydroxy-4,5α-epoxy-6α-(N-methyl-3-trifluoromethylphenylacetamido) morphinan.hydrochloride 108 (yield: 78%) were obtained by following the procedure of example 95 but using 4-benzo[b]thienylacetic acid, 3-benzo[b]thienylacetic acid and 3-trifluoromethylphenylacetic acid instead of 3,4-difluorophenylacetic acid.

Compound 106

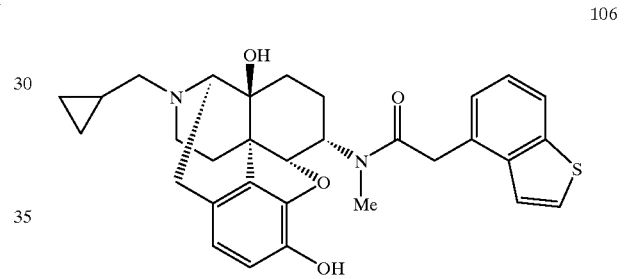

106 mp 207.0–215.0° C. (decomposition, diethylether)

NMR (400 MHz, DMSO-$d_6$)

δ 0.31–0.42 (1H, m), 0.42–0.53 (1H, m), 0.53–0.65 (1H, m), 0.65–0.74 (1H, m), 1.00–1.11 (1H, m), 1.11–1.29 (1H, m), 1.29–1.48 (1H, m), 1.55 (1H, dd, J=15.1, 9.3 Hz), 1.61 (1H, br d, J=12.2 Hz), 1.88–2.00 (1H, m), 2.42 (1H, dq, J=13.2, 4.9 Hz), 2.60–2.75 (1H, m), 2.81 (0.6H, s), 2.89–2.99 (1H, m), 3.02 (2.4H, s), 3.01–3.15 (2H, m), 3.19–3.32 (2H, m), 3.90 (1H, d, J=6.7 Hz), 4.11 (1.6H, s), 4.20 (0.4H, s), 4.51 (0.2H, br s), 4.63 (0.8H, d, J=3.9 Hz), 4.66 (0.2H, br s), 5.00 (0.8H, dt, J=13.7, 3.4 Hz), 6.22 (0.8H, br s), 6.49 (0.2H, br s), 6.58 (1H, d, J=8.3 Hz), 6.74 (1H, d, J=8.3 Hz), 7.22 (1H, d, J=6.8 Hz), 7.36 (0.8H, t, J=7.6 Hz), 7.35–7.40 (0.2H, m), 7.52 (0.8H, d, J=4.9 Hz), 7.64 (0.2H, d, J=5.9 Hz), 7.76 (0.8H, d, J=5.4 Hz), 7.77 (0.2H, d, J=5.9 Hz), 7.90 (0.8H, d, J=8.3 Hz), 7.92 (0.2H, m), 8.82 (1H, br s), 9.29 (0.2H, s), 9.32 (0.8H, s)

IR (KBr)

υ 1620, 1543, 1508, 1460, 1321, 1120, 1036, 764 cm$^{-1}$.

Mass (FAB)

m/z 531 ((M+H)+).

Elementary Analysis: As $C_{31}H_{35}N_2O_4ClS \cdot 0.7H_2O$

Calcd.: C, 64.22; H, 6.33; N, 4.83; Cl, 6.12; S, 5.53

Found.: C, 64.13; H, 6.43; N, 4.79; Cl, 6.43; S, 5.24

Compound 107

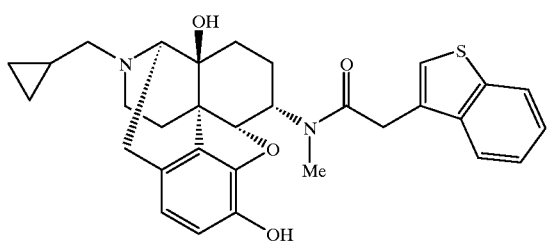

mp 239–250° C. (decomposition, ethylacetate)
NMR (400 MHz, DMSO-$d_6$)

δ 0.31–0.43 (1H, m), 0.43–0.53 (1H, m), 0.53–0.63 (1H, m), 0.63–0.74 (1H, m), 0.98–1.12 (1H, m), 1.12–1.31 (1H, m), 1.31–1.47 (1H, m), 1.47–1.69 (2H, m), 1.82–2.07 (1H, m), 2.29–2.49 (1H, m), 2.59–2.77 (1H, m), 2.81 (0.6H, s), 2.84–2.98 (1H, m), 3.03 (2.4H, s), 2.98–3.18 (2H, m), 3.18–3.42 (2H, m), 3.81–3.96 (1H, m), 4.00 (1.6H, s), 4.02–4.27 (0.4H, m), 4.32–4.43 (0.2H, m), 4.66 (0.8H, d, J=3.4 Hz), 4.66–4.74 (0.2H, m), 5.00 (1H, dt, J=14.2, 3.3 Hz), 6.22 (0.8H, brs), 6.59 (1H, d, J=7.8 Hz), 6.73 (1H, d, J=8.3 Hz), 7.31–7.48 (2H, m), 7.52 (0.8H, s), 7.64 (0.2H, brs), 7.81 (0.8H, d, J=7.3 Hz), 7.91–8.04 (1.2H, m), 8.81 (1H, br s), 9.28 (0.2H, s), 9.33 (0.8H, s).

IR (KBr)
υ 1620, 1510, 1460, 1321, 1120, 1038 $cm^{-1}$.

Mass (FAB)
m/z 531 ((M+H)+).

Elementary Analysis: As $C_{31}H_{35}N_2O_4ClS \cdot 0.5H_2O$
Calcd.: C, 64.62; H, 6.29; N, 4.86; Cl, 6.15; S, 5.57
Found.: C, 64.62; H, 6.50; N, 5.00; Cl, 6.08; S, 5.62

Compound 108

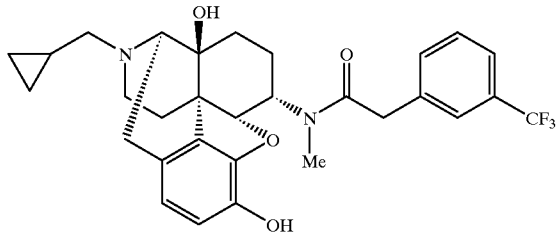

mp 192.0–200.0° C. (decomposition, ethylacetate)
NMR (400 MHz, DMSO-$d_6$)

δ 0.31–0.42 (1H, m), 0.42–0.53 (1H, m), 0.53–0.62 (1H, m), 0.62–0.77 (1H, m), 0.96–1.12 (1H, m), 1.12–1.31 (1H, m), 1.31–1.47 (1H, m), 1.47–1.69 (2H, m), 1.82–2.04 (1H, m), 2.30–2.49 (1H, m), 2.59–2.78 (1H, m), 2.81 (0.4H, s), 2.86–3.18 (3H, m), 2.99 (2.6H, s), 3.18–3.40 (2H, m), 3.90 (2H, s), 3.90–4.1 (1H, m), 4.53 (0.2H, m), 4.62 (0.8H, d, J=3.9 Hz), 4.77 (0.2H, br s), 4.98 (0.8H, dt, J=13.7, 3.9 Hz), 6.24 (1H, br s), 6.58 (1H, d, J=7.8 Hz), 6.74 (1H, d, J=8.3 Hz), 7.49–7.68 (4H, m), 8.82 (1H, br s), 9.33 (1H, s)

IR (KBr)
υ 1620, 1508, 1460, 1334, 1166, 1120, 1077, 1036, 801, 702 $cm^{-1}$.

Mass (FAB)
m/z 543 ((M+H)+).

Elementary Analysis: As $C_{30}H_{34}N_2O_4ClF_3 \cdot 0.5H_2O$
Calcd.: C, 61.27; H, 6.00; N, 4.76; Cl, 6.02; F, 9.69
Found.: C, 61.37; H, 6.08; N, 4.75; Cl, 5.89; F, 9.92

Examples 99–110

17-cyclopropylmethyl-3,14β-dihydroxy-4,5α-epoxy-6β-(N-methyl-4-chlorophenylacetamido) morphinan.hydrochloride 109 (yield: 78%), 17-cyclopropylmethyl-3,14β-dihydroxy-4,5α-epoxy-6β-(N-methyl-3-chlorophenylacetamido) morphinan.hydrochloride 110 (yield: 84%), 17-cyclopropylmethyl-3,14β-dihydroxy-4,5α-epoxy-6β-(N-methyl-1-naphthylacetamido)morphinan.hydrochloride 111 (yield: 61%), 17-cyclopropylmethyl-3,14β-dihydroxy-4,5(α-epoxy-6β-(N-methyl-2-naphthylacetamido) morphinan.hydrochloride 112 (yield: 63%), 17-cyclopropylmethyl-3,14β-dihydroxy-4,5α-epoxy-6β-(N-methyl-3-thienylacetamido)morphinan.hydrochloride 113 (yield: 61%), 17-cyclopropylmethyl-3,14β-dihydroxy-4,5α-epoxy-6β-(N-methyl-3,4-methylenedioxyphenylacetamido)morphinan.hydrochloride 114 (yield: 45%), 17-cyclopropylmethyl-3,14β-dihydroxy-4,5α-epoxy-6β-(N-methyl-3-benzo[b]thienylacetamido) morphinan.hydrochloride 115 (yield: 55%), 17-cyclopropylmethyl-3,14β-dihydroxy-4,5α-epoxy-6β-(N-methyl- 3-trifluoromethylphenylacetamido) morphinan.hydrochloride 116 (yield: 57%), 17-cyclopropylmethyl-3,14β-dihydroxy-4,5α-epoxy-6β-(N-methyl-9-fluorenamido)morphinane.hydrochloride 117 (yield: 65%), 17-cyclopropylmethyl-3,14β-dihydroxy-4,5α-epoxy-6β-(N-methyl-2,3,4,5,6-pentafluorophenylacetamido)morphinan.hydrochloride 118 (yield: 68%), 17-cyclopropylmethyl-3,14β-dihydroxy-4,5α-epoxy-6β-[N-methyl-3-(5-chlorobenzo[b]thienyl) acetamido] morphinan.hydrochloride 119 (yield: 83%) and 17-cyclopropylmethyl-3,14β-dihydroxy-4,5α-epoxy-6β-(N-methyl-4-benzo[b]thienylacetamido) morphinan.hydrochloride 120 (yield: 76%) were obtained by following the procedure of example 95 but using 17-cyclopropylmethyl-4,5α-epoxy-3,14β-dihydroxy-6β-methylaminomorphinan 10 instead of the starting material of 17-cyclopropylmethyl-4,5α-epoxy-3,14β-dihydroxy-6α-methylaminomorphinan 4, and using 4-chlorophenylacetic acid, 3-chlorophenylacetic acid, 1-naphthylacetic acid, 2-naphthylacetic acid, 3-thienylacetic acid, 3,4-methylenedioxyphenylacetic acid, 3-benzo[b] thienylacetic acid, 3-trifluoromethylphenylacetic acid, 9-fluorenecarboxylic acid, 2,3,4,5,6-pentafluorophenylacetic acid, 3-(5-chlorobenzo[b]thienyl) acetic acid and 4-benzo[b]thienylacetic acid instead of 3,4-difluorophenylacetic acid.

Compound 109

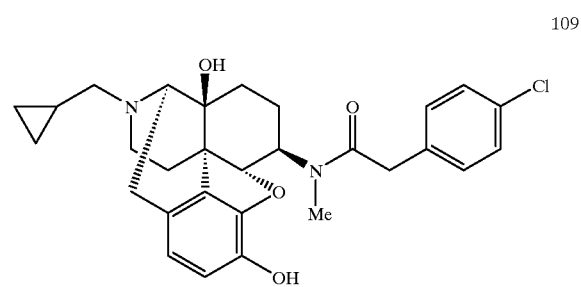

mp 201.0–205.0° C. (decomposition, methanol)
NMR (400 MHz, $CD_3OD$)

δ 0.31–0.58 (2H, m), 0.61–0.75 (1H, m), 0.75–0.87 (1H, m), 0.87–1.00 (1H, m), 1.00–1.12 (1H, m), 1.12–1.27 (1H, m), 1.35–1.82 (3H, m), 2.06 (1H, dq, J=13.4, 2.7 Hz), 2.42–2.73 (2H, m), 2.73–2.88 (1H, m), 2.92

(2.5H,s), 3.07 (0.5H, s), 2.97–3.20 (3H, m), 3.68 (2H, dd, J=28.8, 15.6 Hz), 3.51–4.38 (2H, m), 4.75 (1H, d, J=8.3 Hz), 6.82 (2H, d, J=8.8 Hz), 6.87 (1H, d, J=7.8 Hz), 7.18 (2H, d, J=8.8 Hz), 7.22 (1H, m)

IR (KBr)

υ 1626, 1493, 1460, 1321, 1125, 1035, 924, 808 cm$^{-1}$.

Mass (FAB)

m/z 509 ((M+H)+).

Elementary Analysis: As $C_{29}H_{34}N_2O_4Cl_3 \cdot 0.6H_2O$
 Calcd.: C, 62.61; H, 6.38; N, 5.04; Cl, 12.74
 Found.: C, 62.56; H, 6.49; N, 5.02; Cl, 12.64

Compound 110

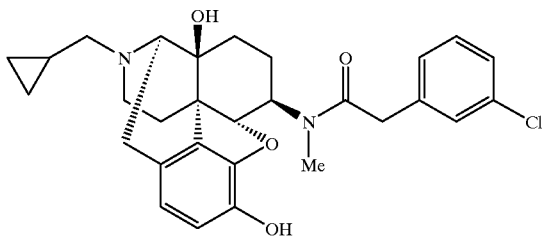

mp 200.0–209.0° C. (decomposition, methanol)

NMR (400 MHz, CD$_3$OD)

δ 0.31–0.58 (2H, m), 0.61–0.75 (1H, m), 0.75–0.89 (2H, m), 0.96–1.24 (2H, m), 1.34–1.82 (3H, m), 2.03 (1H, dq, J=13.2, 2.9 Hz), 2.42–2.73 (2H, m), 2.73–2.88 (1H, m), 2.91 (2.5H, s), 3.09 (0.5H, s), 2.97–3.20 (3H, m), 3.54–3.65 (1H, m), 3.68 (2H, s), 3.73–4.97 (1H, m), 4.75 (1H, d, J=8.3 Hz), 6.62–7.39 (6H, m)

IR (KBr)

υ 1620, 1502, 1460, 1321, 1125, 1035, 924, 808 cm$^{-1}$.

Mass (FAB)

m/z 509 ((M+H)+).

Elementary Analysis: As $C_{29}H_{34}N_2O_4Cl_3 \cdot 0.3H_2O$
 Calcd.: C, 63.22; H, 6.33; N, 5.08; Cl, 12.87
 Found.: C, 63.20; H, 6.50; N, 5.03; Cl, 12.69

Compound 111

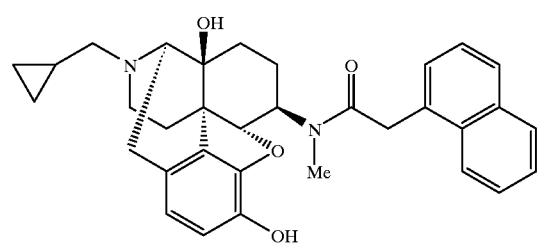

mp 210.0–215.0° C. (decomposition, diethylether)

NMR (400 MHz, CD$_3$OD)

δ 0.31–0.60 (3H, m), 0.61–0.91 (3H, m), 0.91–1.18 (1H, m), 1.31 (1H, brd, J=14.2 Hz), 1.43–1.81 (2H, m), 1.89 (1H, dq, J=13.2, 2.9 Hz), 2.42–2.73 (2H, m), 2.73–3.00 (2H, m), 2.92 (2.6H, s), 3.15 (0.4H, s), 3.00–3.19 (2H, m), 3.54–3.85 (2H, m), 3.99 (1H, d, J=16.1 Hz), 4.23 (1H, d, J=16.1 Hz), 4.75 (1H, d, J=8.3 Hz), 6.80 (1H, d, J=8.30 Hz), 6.90 (1H, d, J=7.82 Hz), 7.00 (1H, d, J=6.84 Hz), 7.27 (1H, t, J=7.6 Hz), 7.31–7.59 (2H, m), 7.70 (2H, t, J=8.30 Hz), 7.80 (1H, d, J=8.3 Hz)

IR (KBr)

υ 1620, 1510, 1502, 1460, 1402, 1321, 1125, 1035, 924, 797 cm$^{-1}$.

Mass (FAB)

m/z 525 ((M+H)+).

Elementary Analysis: As $C_{33}H_{37}N_2O_4Cl \cdot 0.3H_2O$
 Calcd.: C, 69.96; H, 6.69; N, 4.94; Cl, 6.26
 Found.: C, 70.04; H, 6.68; N, 5.03; Cl, 6.20

Compound 112

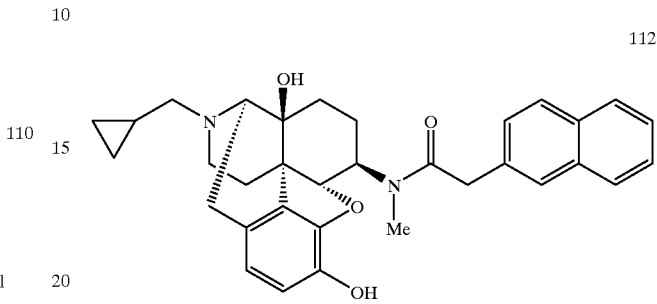

mp 207.0–214.0° C. (decomposition, diethylether)

NMR (400 MHz, CD$_3$OD)

δ 0.35–0.58 (3H, m), 0.61–0.91 (3H, m), 0.91–1.18 (1H, m), 1.23 (1H, brd, J=14.2 Hz), 1.39–1.81 (2H, m), 1.89 (1H, dq, J=13.2, 2.9 Hz), 2.42–2.76 (2H, m), 2.76–3.02 (2H, m), 2.92 (2.6H, s), 3.10 (0.4H, s), 3.02–3.20 (2H, m), 3.60–3.82 (2H, m), 3.86 (1H, d, J=21.5 Hz), 3.95 (1H, d, J=18.1 Hz), 4.75 (1H, d, J=8.3 Hz), 6.87–7.00 (2H, m), 7.00–7.13 (2H, m), 7.35–7.49 (2H, m), 7.49–7.58 (1H, m), 7.70 (1H, d, J=8.3 Hz), 7.73–7.80 (1H, m)

IR (KBr)

υ 1620, 1504, 1460, 1408, 1321, 1125, 1035, 859, 803, 748 cm$^{-1}$.

Mass (FAB)

m/z 525 ((M+H)+).

Elementary Analysis: As $C_{33}H_{37}N_2O_4Cl$
 Calcd.: C, 70.64; H, 6.65; N, 4.99; Cl, 6.32
 Found.: C, 70.39; H, 6.75; N, 5.05; Cl, 6.00

Compound 113

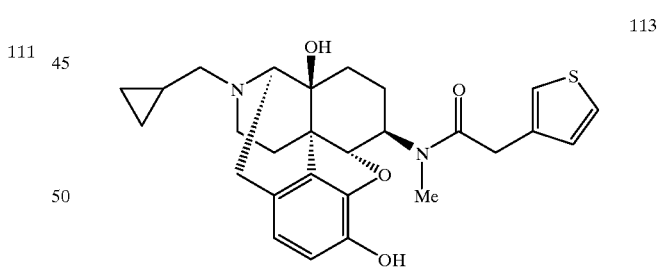

mp 208.0–219.0° C. (decomposition, diethylether)

NMR (400 MHz, DMSO-d$_6$)

δ 0.31–0.45 (1H, m), 0.45–0.53 (1H, m), 0.53–0,63 (1H, m), 0.63–0.78 (1H, m), 0.84–1.30 (3H, m), 1.30–1.80 (2H, m), 1.90–2.14 (1H, m), 2.30–2.61 (3H, m), 2.83 (2.4H, s), 3.00 (0.6H, s), 2.75–2.91 (1H, m), 2.91–3.17 (3H, m), 3.40–3.57 (2H, m), 3.57–3.72 (1H, m), 3.72–3.88 (1H, m), 4.81 (0.8H, d, J=8.3 Hz), 4.87 (0.2H, d, J=8.3 Hz), 6.30 (0.2H, s), 6.40 (0.8H, s), 6.62 (1H, d, J=4.9 Hz), 6.72 (1H, s), 6.73 (1H, d, J=8.3 Hz), 6.82 (1H, d, J=8.3 Hz), 7.38 (0.8H, dd, J=4.9, 2.9 Hz), 7.47 (0.2H, dd, J=4.9, 2.9 Hz), 8.80 (1H, br s), 9.28 (0.2H, s), 9.65 (0.8H, s)

IR (KBr)

υ 1620, 1508, 1460, 1321, 1125, 1035, 922, 859 cm$^{-1}$.

Mass (FAB)

m/z 481 ((M+H)+).

Elementary Analysis: As $C_{27}H_{33}N_2O_4Cl\cdot0.5H_2O$

Calcd.: C, 61.64; H, 6.51; N, 5.32; Cl, 6.74; S, 6.10

Found.: C, 61.77; H, 6.50; N, 5.19; Cl, 6.65; S, 5.83

Compound 114

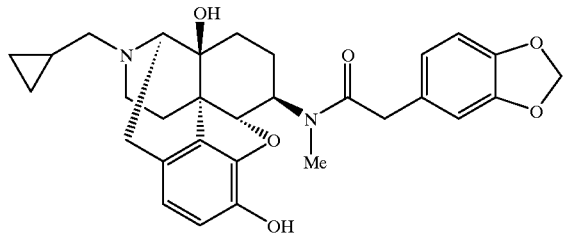

mp 203.0–208.0° C. (decomposition, ethylacetate, diethylether)

NMR (400 MHz, DMSO-d$_6$)

δ 0.31–0.45 (1H, m), 0.45–0.54 (1H, m), 0.54–0.63 (1H, m), 0.63–0.73 (1H, m), 0.85–0.99 (1H, m), 0.99–1.10 (1H, m), 1.10–1.29 (1H, m), 1.32–1.80 (3H, m), 1.92–2.13 (1H, m), 2.36–2.55 (2H, m), 2.72–2.92 (1H, m), 2.82 (2.4H, s), 2.99 (0.6H, s), 2.92–3.13 (2H, m), 3.25–3.41 (1H, m), 3.44 (2H, s), 3.48–3.70 (1H, m), 3.82 (1H, br d, J=4.9 Hz), 4.81 (0.8H, d, J=8.3 Hz), 4.87 (0.2H, d, J=8.3 Hz), 5.93 (1.6H, d, J=0.98 Hz), 5.98 (0.4H, s), 6.23 (1H, dd, J=1.3, 8.1 Hz), 6.34 (1H, s), 6.40 (1H, br s), 6.58–6.90 (3H, m), 8.80 (1H, brs), 9.26 (0.2H, s), 9.63 (0.8H, s)

IR (KBr)

υ 1620, 1504, 1491, 1323, 1249, 1125, 1036 cm$^{-1}$.

Mass (FAB)

m/z 519 ((M+H)+).

Elementary Analysis: As $C_{30}H_{35}N_2O_6Cl\cdot0.4H_2O$

Calcd.: C, 64.08; H, 6.41; N, 4.98; Cl, 6.31

Found.: C, 64.00; H, 6.43; N, 5.01; Cl, 6.27

Compound 115

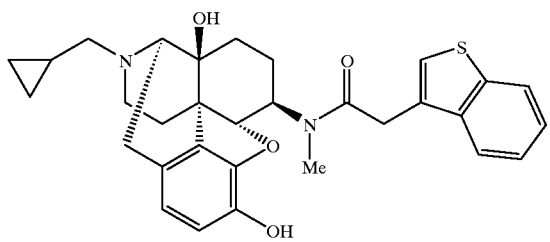

mp 215.0–225.0° C. (decomposition, ethylacetate, diethylether)

NMR (400 MHz, DMSO-d$_6$)

δ 0.31–0.45 (1H, m), 0.45–0.53 (1H, m), 0.53–0.62 (1H, m), 0.62–0.73 (1H, m), 0.79–0.89 (1H, m), 0.89–1.12 (2H, m), 1.34–1.60 (2H, m), 1.98–2.07 (1H, m), 2.39–2.55 (2H, m), 2.73–2.98 (1H, m), 2.85 (2.4H, s), 3.07 (0.6H, s), 2.98–3.13 (2H, m), 3.17–3.39 (2H, m), 3.50–3.61 (1H, m), 3.68 (1H, d, J=16.1 Hz), 3.78 (1H, br d, J=3.9 Hz), 3.88 (1H, d, J=16.1 Hz), 4.83 (0.8H, d, J=8.3 Hz), 4.90 (0.2H, d, J=8.3 Hz), 6.29 (0.2H, s), 6.35 (0.8H, s), 6.03 (0.2H, d, J=8.3 Hz), 6.70 (0.2H, d, J=8.3 Hz), 6.74 (0.8H, d, J=8.3 Hz), 6.82 (0.8H, d, J=8.3 Hz), 7.08 (0.8H, s), 7.21–7.42 (2.8H, m), 7.48 (0.2H, s), 7.77–7.82 (0.2H, m), 7.92 (0.8H, d, J=7.8 Hz), 7.97–8.02 (0.2H, m), 8.78 (1H, br s), 9.28 (0.2H, s), 9.68 (0.8H, s)

IR (KBr)

υ 1626, 1502, 1460, 1319, 1125, 1035 cm$^{-1}$.

Mass (FAB)

m/z 531 ((M+H)+).

Elementary Analysis: As $C_{31}H_{35}N_2O_4Cl\cdot0.4H_2O$

Calcd.: C, 64.83; H, 6.28; N, 4.88; Cl, 6.17; S, 5.58

Found.: C, 64.85; H, 6.42; N, 4.89; Cl, 6.15; S, 5.53

Compound 116

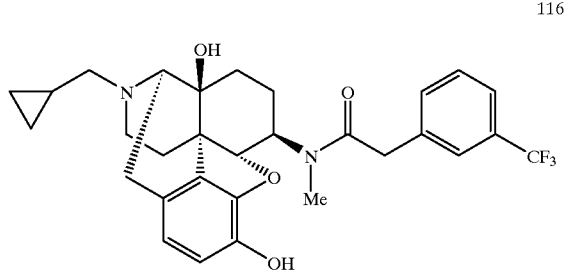

mp 195.0–203.0° C. (decomposition, methanol)

NMR (400 MHz, DMSO-d$_6$)

δ 0.31–0.45 (1H, m), 0.45–0.53 (1H, m), 0.53–0.63 (1H, m), 0.63–0.77 (1H, m), 0.96–1.12 (2H, m), 1.12–1.30 (1H, m), 1.30–1.80 (3H, m), 2.06 (1H, br q, J=13.2 Hz), 2.39–2.59 (2H, m), 2.85 (2.4H, s), 3.05 (0.6H, s), 2.71–2.92 (1H, m), 2.92–3.12 (2H, m), 3.41–3.58 (1H, m), 3.68 (1H, d, J=3.4 Hz), 3.58–3.77 (1H, m), 3.77–4.10 (2H, m), 4.84 (0.8H, br d, J=5.4 Hz), 4.88 (0.2H, br d, J=5.4 Hz), 6.30 (0.2H, br s), 6.42 (0.8H, br s), 6.62 (0.2H, d, J=8.3 Hz), 6.69 (0.2H, d, J=8.3 Hz), 6.72 (0.8H, d, J=8.3 Hz), 6.81 (0.8H, d, J=8.3 Hz), 7.13 (0.8H, s), 7.17 (0.2H, d, J=6.8 Hz), 7.22–7.28 (0.2H, m), 7.30 (0.8H, d, J=7.8 Hz), 7.48 (1H, t, J=7.8 Hz), 7.52–7.63 (1H, m), 8.80 (1H, br s), 9.25 (0.2H, s), 9.64 (0.8H, s)

IR (KBr)

υ 1628, 1508, 1460, 1334, 1166, 1127, 1077, 1035, 922, 704 cm$^{-1}$.

Mass (FAB)

m/z 543 ((M+H)+).

Elementary Analysis: As $C_{30}H_{34}N_2O_4ClF_3$

Calcd.: C, 62.23; H, 5.92; N, 4.84; Cl, 6.12; F, 9.84

Found.: C, 62.19; H, 6.04; N, 4.82; Cl, 5.76; F, 9.87

Compound 117

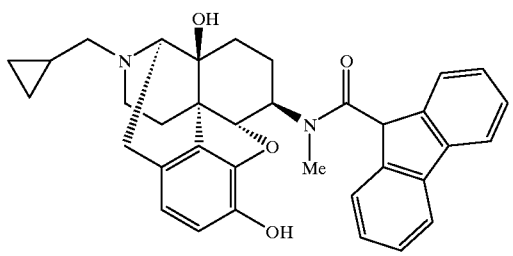

mp 215.0–224.0° C. (decomposition, ethylacetate)
NMR (400 MHz, DMSO-d$_6$)

δ 0.31–0.47 (1H, m), 0.47–0.57 (1H, m), 0.57–0.64 (1H, m), 0.64–0.77 (1H, m), 0.98–1.13 (1H, m), 1.20–1.60 (2H, m), 1.60–1.92 (2H, m), 2.31–2.70 (2H, m), 2.79–2.91 (1H, m), 2.97 (2.1H, s), 2.99–3.15 (2H, m), 3.36 (0.9H, s), 3.37–3.60 (2H, m), 3.81 (0.3H, br d, J=5.2 Hz), 3.89 (0.7H, br d, J=5.2 Hz), 3.72–3.93 (0.3H, m), 4.12–4.29 (0.7H, m), 4.90–5.02 (0.3H, m), 5.04 (0.7H, d, J=7.3 Hz), 5.09 (0.7H, s), 5.38 (0.3H, m), 6.17 (0.3H, br s), 6.46 (0.7H, br s), 6.61 (1H, s), 6.55–6.78 (1H, m), 7.08–7.52 (6H, m), 7.64 (1H, d, J=7.3 Hz), 7.84 (1H, dd, J=7.8, 4.4 Hz), 7.91 (1H, d, J=7.3 Hz), 8.77 (0.3H, br s), 8.83 (0.7H, br s), 9.24 (0.3H, s), 9.26 (0.7H, s)

IR (KBr)

υ 1620, 1510, 1460, 748 cm$^{-1}$.

Mass (FAB)

m/z 549 ((M+H)+).

Elementary Analysis: AS C$_{35}$H$_{37}$N$_2$O$_4$Cl.0.6H$_2$O
Calcd.: C, 70.54; H, 6.46; N, 4.70; Cl, 5.95
Found.: C, 70.77; H, 6.54; N, 4.71; Cl, 5.58

Compound 118

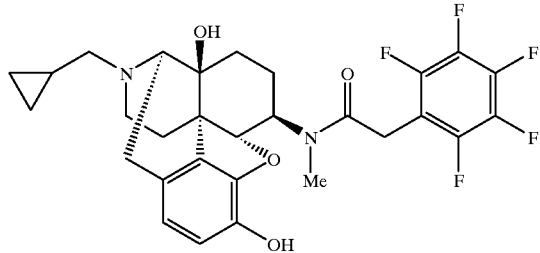

mp 208.0–214.0° C. (decomposition, methanol)
NMR (400 MHz, DMSO-d$_6$)

δ 0.31–0.47 (1H, m), 0.47–0.56 (1H, m), 0.56–0.63 (1H, m), 0.63–0.77 (1H, m), 1.00–1.13 (1H, m), 1.20–1.65 (3H, m), 1.74 (1H, br t, J=13.4 Hz), 2.16 (1H, br q, J=12.7 Hz), 2.39–2.62 (2H, m), 2.89 (2.4H, s), 2.76–2.96 (1H, m), 2.96–3.12 (2H, m), 3.17 (0.6H, s), 3.20–3.45 (2H, m), 3.62–3.75 (1H, m), 3.75–3.98 (3H, m), 4.85 (0.8H, d, J=7.8 Hz), 4.94 (0.2H, d, J=7.8 Hz), 6.38 (0.2H, br s), 6.52 (0.8H, brs), 6.62 (0.2H, d, J=8.3 Hz), 6.68 (1H, d, J=8.3 Hz), 6.74 (0.8H, d, J=7.8 Hz), 8.85 (1H, br s), 9.27 (0.2H, s), 9.41 (0.8H, s)

IR (KBr)

υ 1638, 1510, 1315, 1127, 1009, 919, 859 cm$^{-1}$.

Mass (FAB)

m/z 565 ((M+H)+).

Elementary Analysis: As C$_{29}$H$_{30}$N$_2$O$_4$ClF$_5$.0.2H$_2$O
Calcd.: C, 57.61; H, 5.07; N, 4.63; Cl, 5.86; F, 15.71
Found.: C, 57.60; H, 5.36; N, 4.74; Cl, 5.94; F, 15.51

Compound 119

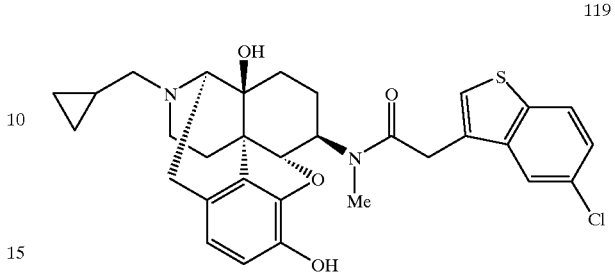

mp 210.0–219.0° C. (decomposition, diethylether)
NMR (400 MHz, DMSO-d$_6$)

δ 0.31–0.45 (1H, m), 0.45–0.54 (1H, m), 0.54–0.62 (1H, m), 0.62–0.73 (1H, m), 1.00–1.12 (1H, m), 1.19–1.57 (3H, m), 1.61–1.78 (1H, m), 2.00–2.18 (1H, m), 2.40–2.60 (2H, m), 2.73–2.92 (1H, m), 2.87 (2.4H, s), 3.09 (0.6H, s), 2.92–3.13 (2H, m), 3.23–3.41 (2H, m), 3.59–3.69 (0.8H, m), 3.76 (0.8H, d, J=16.5 Hz), 3.80–3.90 (1H, m), 3.89 (0.8H, d, J=16.5 Hz), 3.95 (0.4H, s), 4.00–4.12 (0.2H, m), 4.88 (0.8H, d, J=7.9 Hz), 4.90 (0.2H, d, J=7.9 Hz), 6.35 (0.2H, br s), 6.47 (0.8H, br s), 6.63 (0.2H, d, J=7.9 Hz), 6.69 (1H, d, J=8.5 Hz), 6.78 (0.8H, d, J=7.9 Hz), 7.23 (0.8H, s), 7.36 (0.8H, dd, J=8.6, 1.8 Hz), 7.40 (0.2H, dd, J=8.6, 1.8 Hz), 7.60 (0.2H, s), 7.66 (0.8H, d, J=1.8 Hz), 7.86 (0.2H, d, J=1.8 Hz), 7.97 (0.8H, d, J=8.6 Hz), 8.01 (0.2H, d, J=8.5 Hz), 8.82 (1H, br s), 9.25 (0.2H, s), 9.60 (0.8H, s)

IR (KBr)

υ 1628, 1508, 1427, 1321, 1127, 1079, 1035, 859, 835 cm$^{-1}$.

Mass (FAB)

m/z 565 ((M+H)+).

Elementary Analysis: As C$_{31}$H$_{34}$N$_2$O$_4$Cl$_2$S.0.3H$_2$O
Calcd.: C, 61.34; H, 5.75; N, 4.62; Cl, 11.68; S, 5.28
Found.: C, 61.40; H, 5.81; N, 4.63; Cl, 11.38; S, 5.20

Compound 120

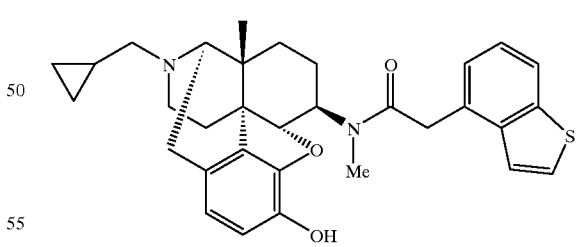

mp 219.0–226.0° C. (decomposition, diethylether)
NMR (400 MHz, DMSO-d$_6$)

δ 0.31–0.45 (1H, m), 0.45–0.53 (1H, m), 0.53–0.62 (2H, m), 0.62–0.73 (1H, m), 0.77–0.92 (1H, m), 0.97–1.12 (1H, m), 1.43 (1H, d, J=12.2 Hz), 1.47 (1H, d, J=10.3 Hz), 1.91 (1H, br q, J=13.2 Hz), 2.48 (2H, d, J=8.6 Hz), 2.77–2.89 (1H, m), 2.83 (2.4H, s), 2.92 (1H, dd, J=19.5, 6.1 Hz), 3.06 (0.6H, s), 2.99–3.11 (1H, m), 3.25–3.39 (1H, m), 3.51–3.61 (1H, m), 3.78 (1H, d, J=5.4 Hz), 3.85 (1H, d, J=15.4 Hz), 3.89 (1H, d, J=15.4 Hz), 4.83

(0.8H, d, J=8.3 Hz), 4.91 (0.2H, d, J=8.3 Hz), 6.31 (0.2H, br s), 6.37 (0.8H, br s), 6.63 (0.2H, d, J=8.3 Hz), 6.70 (0.2H, dd, J=7.8, 2.0 Hz), 6.77 (0.8H, d, J=8.3 Hz), 6.80–6.90 (1.8H, m), 6.98 (1H, d, J=5.4 Hz), 7.18 (0.8H, t, J=7.8 Hz), 7.31 (0.2H, t, J=7.8 Hz), 7.36 (0.8H, s), 7.50 (0.2H, d, J=4.9 Hz), 7.60 (0.8H, d, J=5.4 Hz), 7.73 (0.2H, d, J=5.9 Hz), 7.82 (0.8H, d, J=8.3 Hz), 7.88 (0.2H, d, J=7.8 Hz), 8.78 (1H, br s), 9.25 (0.2H, s), 9.66 (0.8H, s)

IR (KBr)

υ 1620, 1543, 1516, 1460, 1125, 1033, 766 cm$^{-1}$.

Mass (FAB)

m/z 531 ((M+H)+).

Elementary Analysis: As $C_{31}H_{35}N_2O_4ClS \cdot 0.4H_2O$
Calcd.: C, 64.83; H, 6.28; N, 4.88; Cl, 6.17; S 5.58
Found.: C, 65.03; H, 6.49; N, 4.78; Cl, 6.03; S, 5.19

Examples 111–113

17-Cyclopropylmethyl-3,14β-dihydroxy-4,5α-epoxy-6β-(3,4-dichlorophenylacetamido)morphinan.hydrochloride 121 (yield: 54%) and 17-allyl-3,14β-dihydroxy-4,5α-epoxy-6α-(N-methyl-3,4-dichlorophenylacetamido)morphinan.hydrochloride 122 (yield: 63%), 17-allyl-3,14β-dihydroxy-4,5α-epoxy-6β-(N-methyl-3,4-dichlorophenylacetamido) morphinan.hydrochloride 123 (yield: 76%) were obtained by following the procedure of example 95 but using 17-cyclopropylmethyl-4,5α-epoxy-3,14β-dihydroxy-6β-aminomorphinan (J. B. Jiang, R. N. Hanson, P. S. Portoghese and A. E. Takemori, J. Med. Chem., 20, 1100 (1977)), 17-allyl-4,5α-epoxy-3,14β-dihydroxy-6α-methylaminomorphinan 12 and 17-allyl-4,5α-epoxy-3,14β-dihydroxy-6β-methylaminomorphinan 13 instead of the starting material of 17-cyclopropylmethyl-4,5α-epoxy-3,14β-dihydroxy-6αmethylaminomorphinan 4, and using 3,4-dichlorophenylacetic acid instead of 3,4-difluorophenylacetic acid. Compound 121

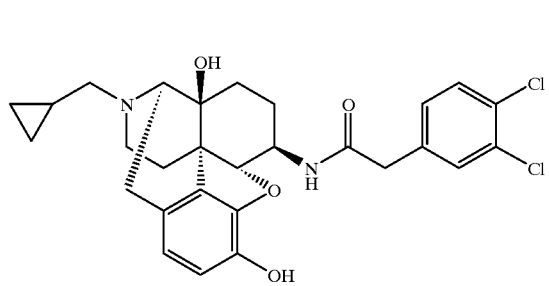

121 mp 245.0–254.0° C. (decomposition, methanol)

NMR (400 MHz, DMSO-d$_6$)

δ 0.31–0.46 (1H, m), 0.46–0.53 (1H, m), 0.53–0.63 (1H, m), 0.63–0.75 (1H, m), 0.98–1.12 (1H, m), 1.21–1.39 (1H, m), 1.39–1.57 (2H, m), 1.57–1.80 (2H, m), 2.28–2.48 (2H, m), 2.77–2.92 (1H, m), 3.02 (1H, brd, J=6.4 Hz), 3.07 (1H, br d, J=5.9 Hz), 3.19–3.41 (3H, m), 3.45 (1H, d, J=14.7 Hz), 3.50 (1H, d, J=14.7 Hz), 3.82 (1H, br s), 4.58 (1H, d, J=7.8 Hz), 6.17 (1H, br s), 6.63 (1H, d, J=7.8 Hz), 6.71 (1H, d, J=8.3 Hz), 7.25 (1H, dd, J=8.3, 2.0 Hz), 7.53 (1H, d, J=2.0 Hz), 7.57 (1H, d, J=8.3 Hz), 8.45 (1H, br s), 8.82 (1H, br s), 9.34 (1H, d, J=1.5 Hz)

IR (KBr)

υ 1655, 1545, 1508, 1461, 1128, 1034, 922 cm$^{-1}$.

Mass (FAB)

m/z 529 ((M+H)+).

Elementary Analysis: As $C_{28}H_{31}N_2O_4Cl_3 \cdot 0.4H_2O$
Calcd.: C, 58.67; H, 5.59; N, 4.89; Cl, 18.56
Found.: C, 58.70; H, 5.65; N, 4.88; Cl, 18.63

Compound 122

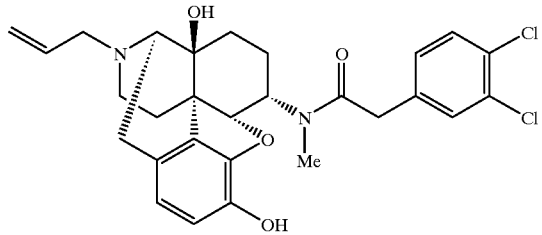

122 mp 214–2160° C.

NMR (400 MHz, DMSO-d$_6$)

δ 1.16 (1H, m), 1.34 (1H, m), 1.51 (1H, m), 1.62 (1H, m), 1.86 (1H, m), 2.41 (1H, m), 2.72 (1H, m), 2.80 (0.5H, s), 2.95 (2.5H, s), 3.0–3.3 (2H, m), 3.40 (1H, m), 3.52 (1H, m), 3.88 (3H, m), 4.45 (0.2H, m), 4.61 (0.8H, d, J=3.9 Hz), 4.73 (0.2H, m), 4.95 (0.8H, m), 5.57 (2H, m), 5.89 (1H, m), 6.14 (0.8H, brs), 6.48 (0.2H, brs), 6.59 (1H, d, J=8.3 Hz), 6.72 (1H, d, J=8.3 Hz), 7.23 (1H, m), 7.52 (1H, d, J=2.0 Hz), 7.58 (1H, m), 9.12 (1H, brs), 9.32 (1H, s)

IR (KBr)

υ 3300, 1624, 1473, 1118, 1035, 804 cm$^{-1}$.

Mass (FAB)

m/z 529 (M+H)

Elementary Analysis: As $C_{28}H_{30}N_2O_4Cl_2 \cdot HCl \cdot 0.4H_2O$
Calcd.: C, 58.68; H, 5.59; N, 4.89; Cl, 18.56
Found.: C, 58.77; H, 5.66; N, 4.87; Cl, 18.29

Compound 123

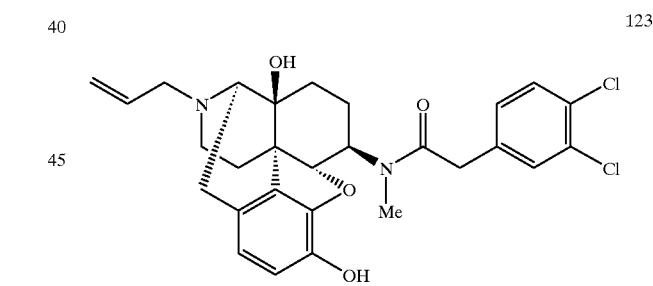

123 mp 185° C. (decomposition)

NMR (500 MHz, DMSO-d$_6$)

δ 1.15–1.39 (2H, m), 1.44 (0.2H, brd, J=9.2 Hz), 1.51 (0.8H, brd, J=9.8 Hz), 1.61–1.68 (1H, m), 2.00–2.11 (1H, m), 2.44–2.57 (2H, m), 2.83 (2.4H, s), 2.90–3.00 (1H, m), 3.02 (0.6H, s), 3.07–3.15 (1H, m), 3.35–3.39 (0.2H, m), 3.37 (0.8H, d, J=6.7 Hz), 3.43–3.55 (2H, m), 3.57 (1.6H, d, J=3.1 Hz), 3.70–3.79 (1.4H, m), 3.88–4.05 (1H, m), 4.80–4.88 (1H, m), 5.52 (1H, brd, J=11.0 Hz), 5.62 (1H, d, J=7.1 Hz), 5.83–5.96 (1H, m), 6.10–6.38 (1H, m), 6.64 (0.2H, d, J=8.2 Hz), 6.69 (0.2H, d, J=8.2 Hz), 6.73 (0.8H, d, J=8.2 Hz), 6.80 (0.8H, d, J=8.2 Hz), 6.99 (0.8H, dd, J=8.6, 1.8 Hz), 7.10 (0.8H, d, J=1.8 Hz), 7.19–7.23 (0.2H, m), 7.47–7.50 (0.2H, m), 7.50 (0.8H, d, J=8.5 Hz), 7.55 (0.2H, d, J=8.6 Hz), 9.18 (1H, brs), 9.25 (0.2H, s), 9.63 (0.8H, s).

IR (KBr)
υ 3380, 1620, 1502, 1475, 1321, 1125, 1033 cm$^{-1}$.

Mass (EI)
m/z 528 (M+).

Elementary Analysis: As $C_{28}H_{30}N_2O_4Cl_2 \cdot HCl \cdot H_2O$
Calcd.: C, 57.59; H, 5.70; N, 4.80; Cl, 18.21
Found.: C, 57.93; H, 5.80; N, 4.82; Cl, 17.85

Example 114

17-Cyclopropylmethyl-3,14β-dihydroxy-4,5α-epoxy-6β-[N-methyl-3-(3-trifluoromethylphenyl)propiolamido] morphinan.hydrochloride 124

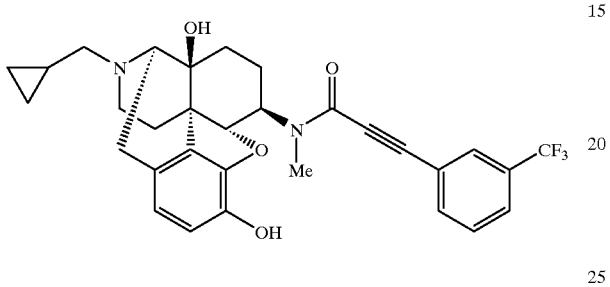

400 mg (1.12 mmol) of 17-cyclopropylmethyl-4,5α-epoxy-3,14β-dihydroxy-6β-methylaminomorphinan 10 and 360 mg (1.68 mmol) of 3-(3-trifluoromethylphenyl)propiolic acid were dissolved in 12 ml of chloroform followed by sequential addition of 0.40 ml (2.91 mmol) of N-ethylpiperidine and 428 mg (1.68 mmol) of bis-(2-oxo-3-oxazolidinyl)phosphinic chloride and stirring for 12 hours at room temperature. Then, 15 ml of 1 N aqueous sodium hydroxide were added to separate layers, and the organic layer was washed with 10 ml each of water and saturated brine, dried and concentrated. The residue was dissolved in 10 ml of methanol followed by the addition of 2 ml of 1 N aqueous sodium hydroxide and stirring for 3 hours. 30 ml of ethylacetate were then added to separate layers, and the resulting organic layer was washed with 20 ml of saturated brine, dried and concentrated. The residue was purified with silica gel column chromatography (Merk 9385, 30 g, chloroform/methanol=30/1) to obtain 562.8 mg of the free base of the target compound. This was then re-precipitated from hexane and ethylacetate, and the resulting solid was dissolved in ethylacetate. An excess amount of ethylacetate solution of hydrochloride solution was added followed by stirring and filtration of the resulting precipitate to obtain 274 mg of the target compound (yield: 42%).

mp>195° C. (decomposition)

NMR (400 MHz, DMSO-d$_6$)
δ 0.42 (1H, m), 0. 52 (1H, m), 0. 59 (1H, m), 0.67 (1H, m), 1.07 (1H, m), 1.29–1.51 (3H, m), 1.73–1.83 (1H, m), 2.09–2.26 (1H, m), 2.40–2.58 (2H, m), 2.86 (1H, m), 2.98 (2.4H, s), 3.02–3.11 (2H, m), 3.31 (0.6H, s), 3.30–3.38 (2H, m), 3.87 (1H, br d, J=5.9 Hz), 4.13 (1H, m), 4.89 (0.8H, d, J=8.3 Hz), 4.96 (0.2H, d, J=8.3 Hz), 6.40 (0.2H, s, OH), 6.46 (0.8H, d, J=7.3 Hz, OH), 6.53 (0.8H, s, OH), 6.60 (0.8H, d, J=7.3 Hz), 6.66 (0.2H, d, J=7.3 Hz), 6.72 (0.2H, d, J=7.3 Hz), 7.47 (0.8H, br s), 7.57 (0.8H, d, J=7.8 Hz), 7.63 (0.8H, dd, J=7.8, 7.8 Hz), 7.73 (0.2H, dd, J=7.8, 7.8 Hz),7.83 (0.8H, d, J=7.8 Hz), 7.90 (0.2H, d, J=7.8 Hz), 7.97 (0.2H, d, J=7.8 Hz), 8.06 (0.2H, br s), 8.81 (1H, m, NH+), 9.30 (0.8H, s, OH), 9.31 (0.2H, s, OH).

IR (KBr)
υ 3400, 2224, 1620, 1439, 1334, 1170, 1127, 1073, 1035, 924, 806 cm$^{-1}$.

Mass (FAB)
m/z 553 ((M+H)+).

Elementary Analysis: As $C_{31}H_{31}F_3N_2O_4 \cdot HCl \cdot 0.5H_2O$
Calcd.: C, 62.26; H, 5.56; Cl, 5.93; F, 9.53; N, 4.68
Found.: C, 62.25; H, 5.64; Cl, 5.78; F, 9.49; N, 4.73

Example 115

17-cyclopropylmethyl-3,14β-dihydroxy-4,5α-epoxy-6α-[N-methyl-3-(3-trifluoromethylphenyl)propiolamido] morphinan. hydrochloride 125 was obtained by following the procedure of example 114 but using 17-cyclopropylmethyl-4,5α-epoxy-3,14β-dihydroxy-6α-methylaminomorphinan 4 instead of 17-cyclopropylmethyl-4,5α-epoxy-3,14β-dihydroxy-6β-methylaminomorphinan 10.

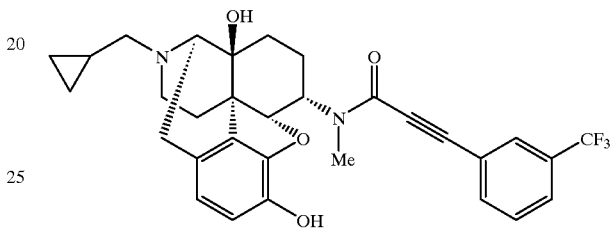

mp>190° C. (decomposition)

NMR (400 MHz, DMSO-d$_6$)
δ 0.41 (1H, m), 0.48 (1H, m), 0.62 (1H, m), 0.68 (1H, m), 1.07 (1H, m), 1.14–1.33 (1H, m), 1.48–1.70 (3H, m), 1.92–2.07 (1H,m), 2.47 (1H, m), 2.70 (1H, m), 2.92–3.15 (3H, m)), 2.93 (1.2H, s), 3.22–3.38 (2H, m), 3.26 (1.8H, s), 3.96 (1H, m), 4.72 (0.6H, d, J=3.4 Hz), 4.85 (0.4H, d, J=3.4 Hz), 4.92 (0.6H, ddd, J=14.2, 3.9, 3.9 Hz), 5.07 (0.4H, ddd, J=13.2, 3.9, 3.9 Hz), 6.34 (0.6H, s, OH), 6.43 (0.4H, s, OH), 6.61 (0.6H, d, J=7.8 Hz), 6.61 (0.4H, J=7.3 Hz), 6.75 (0.6H, d, J=7.8 Hz), 6.75 (0.4H, d, J=7.3 Hz), 7.73 (0.6H, dd, J=7.8, 7.3 Hz), 7.82 (0.4H, dd, J=7.8, 7.3 Hz), 7.91 (0.6H, d, J=7.3 Hz), 7.92 (0.4H, d, J=7.3 Hz), 7.98 (0.6H, d, J=7.8 Hz), 8.06 (0.6H, br s), 8.06 (0.4H, d, J=7.8 Hz), 8.08 (0.4H, br s), 8.82–8.94 (1H, m, NH+), 9.38 (0.4H, s, OH), 9.38 (0.6H, s, OH).

IR (KBr)
υ 3400, 2220, 1611, 1460, 1334, 1172, 1122, 1071, 1036, 922, 806 cm$^{-1}$.

Mass (FAB)
m/z 553 ( (M+H)+).

Elementary Analysis: As $C_{31}H_{31}F_3N_2O_4 \cdot HCl \cdot 0.6H_2O$
Calcd.: C, 62.07; H, 5.58; Cl, 5.91; F, 9.50; N, 4.67
Found.: C, 61.96; H, 5.64; Cl, 6.06; F, 9.47; N, 4.69

Example 116

17-Cyclopropylmethyl-3,14β-dihydroxy-4,5α-epoxy-6α-[N-methyl-3-(4-trifluoromethylphenyl)propiolamido] morphinan.0.5 tartrate 126 was obtained by following the procedure of example 114 but using 17-cyclopropylmethyl-4,5α-epoxy-3,14β-dihydroxy-6α-methylaminomorphinan 4 instead of 17-cyclopropylmethyl-4,5α-epoxy-3,14β-dihydroxy-6β-methylaminomorphinan 10, and using 3-(4-trifluoromethylphenyl)propiolic acid instead of 3-(3-trifluoromethylphenyl)propiolic acid.

126

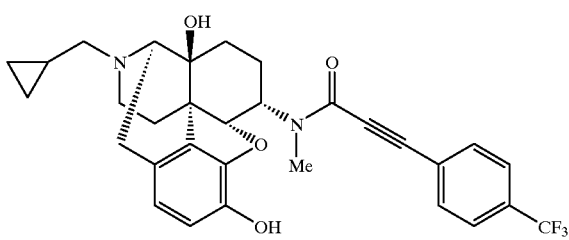

mp 197.0° C. (decomposition)
NMR (400 MHz, DMSO-d$_6$)

δ 0.10–0.30 (2H, m), 0.44–0.63 (2H, m), 0.83–0.99 (1H, m), 1.10–1.35 (1H, m), 1.40–1.60 (3H, m), 1.70–1.88 (1H, m), 2.15–2.34 (2H, m), 2.39–2.62 (2H, m), 2.62–2.84 (2H, m), 2.93 (1.5H, s), 3.00–3.13 (1H, m), 3.25 (1.5H, s), 3.20–3.34 (1H, m), 2.40–4.40 (3H, br s), 4.10 (1H, s), 4.62 (0.5H, br d, J=3.4 Hz), 4.70 (0.5H, br d, J=2.9 Hz), 4.85 (0.5H, ddd, J=14.2, 3.9, 3.9 Hz), 5.03 (0.5H, ddd, J=13.2, 3.9, 3.9 Hz), 6.53 (1H, d, J=8.3 Hz), 6.64 (0.5H, d, J=7.8 Hz), 6.65 (0.5H, d, J=8.3 Hz), 7.85 (1H, d, J=8.3 Hz), 7.89 (1H, d, J=8.3 Hz), 7.90 (1H, d, J=8.3 Hz), 7.93 (1H, d, J=8.3 Hz), 8.80–9.60 (1H, br s).

IR (KBr)

υ 3416, 2222, 1609, 1508, 1406, 1325, 1125, 1067 cm$^{-1}$.

Mass (FAB)

m/z 553 ( (M+H)+)

Elementary Analysis: As C$_{31}$H$_{31}$F$_3$N$_2$O$_4$.0.5C$_4$H$_6$O$_6$.0.5H$_2$O
Calcd.: C, 62.26; H, 5.54; F, 8.95; N, 4.40
Found.: C, 62.14; H, 5.58; F, 8.91; N, 4.43

Example 17

17-Cyclopropylmethyl-3,14β-dihydroxy-4,5α-epoxy-6β-[N-methyl-3-(4-trifluoromethylphenyl)propiolamido] morphinan.hydrochloride 127 was obtained by following the procedure of example 114 but using 3-(4-trifluoromethylphenyl)propiolic acid instead of 3-(3-trifluoromethylphenyl)propiolic acid.

127

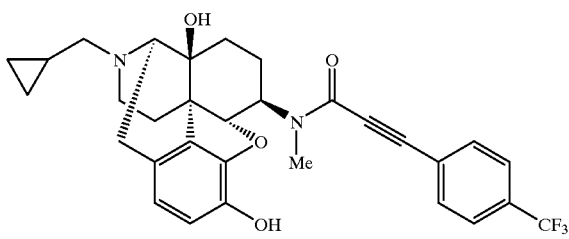

mp 197.0° C. (decomposition)
NMR (400 MHz, DMSO-d$_6$)

δ 0.35–0.46 (1H, m), 0.46–0.56 (1H, m),0.56–0.64 (1H, m), 0.64–0.75 (1H, m), 1.01–1.15 (1H, m), 1.27–1.37 (0.6H, m), 1.37–1.52 (2.4H, m), 1.70–1.85 (1H, m), 2.05–2.30 (1H, m), 2.36–2.62 (2H, m), 2.80–2.92 (1H, m), 2.99 (2.4H, s), 3.00–3.16 (2H, m), 3.32 (0.6H, s), 3.30–3.40 (2H, m), 3.86 (1H, br d, J=4.4 Hz), 4.05–4.18 (1H, m), 4.90 (0.8H, d, J=8.3 Hz), 4.97 (0.2H, d, J=8.8 Hz), 6.43 (0.2H, s), 6.55 (0.8H, s), 6.57 (0.8H, d, J=7.8 Hz), 6.66 (1H, d, J=8.3 Hz), 6.72 (0.2H, d, J=7.8 Hz), 7.43 (1.6H, d, J=7.8 Hz), 7.74 (1.6H, d, J=8.3 Hz), 7.85 (0.4H, d, J=8.8 Hz), 7.89 (0.4H, d, J=8.8 Hz), 8.83 (1H, br s), 9.32 (0.2H, s), 9.35 (0.8H, s).

IR (KBr)

υ 3416, 2224, 1618, 1508, 1408, 1325, 1172, 1127, 1067 cm$^{-1}$.

Mass (FAB)

m/z 553 ((M+H)+).

Elementary Analysis: As C$_{31}$H$_{31}$F$_3$N$_2$O$_4$. HCl.0.6H$_2$O
Calcd.: C, 62.07; H, 5.58; Cl, 5.91; F, 9.50; N, 4.67
Found.: C, 62.14; H, 5.62; Cl, 5.90; F, 9.29; N, 4.62

Example 118

17-cyclopropylmethyl-4,5α-epoxy-3,14β-dihydroxy-6α-(N-methyl-3,4-dichlorophenylmethanesulfonamido) morphinan.tartrate 128

128

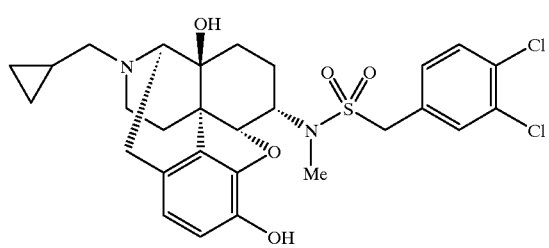

227 mg of 3-tert-butyldimethylsilyloxy-17-cyclopropylmethyl-4,5α-epoxy-14β-hydroxy-6α-(N-methyl-3,4-dichlorophenylmethanesulfonamido)morphinan 16 obtained in reference example 8 was dissolved in 4.5 ml of tetrahydrofuran followed by the addition of 0.39 ml of tetrabutylammonium fluoride and stirring for 30 minutes. 15 ml of ethylacetate and 10 ml of saturated aqueous ammonium chloride were added to separate layers, and the aqueous layer was extracted twice with 10 ml of ethylacetate. The resulting organic layer was concentrated after drying with anhydrous sodium sulfate, and the residue was purified with silica gel column chromatography (25 g chloroform/methanol=20/1) to obtain the crude compound. This was then recrystallized from ethylacetate and methanol to obtain 158 mg of the free base of the target compound. This was dissolved in a mixed solvent of chloroform and methanol, completely dissolved by addition of 20.4 mg of tartaric acid and concentrated. This residue was re-precipitated from methanol and ether followed by filtration to obtain 105 mg of the target compound (yield: 49%).

mp>149° C. (decomposition)
NMR (400 MHz, DMSO-d$_6$)

δ 0.13–0.22 (2H, m), 0.47–0.58 (2H, m), 0.82–0.92 (1H, m), 0.98–1.11 (1H, m), 1.18–1.27 (1H, m), 1.35–1.48 (2H, m), 1.55–1.67 (1H, m), 2.07–2.26 (2H, m), 2.48–2.60 (1H, m), 2.60–2.73 (2H, m), 2.83 (3H, s), 3.01 (1H, brd, J=8.6 Hz), 2.90–4.00 (5H, m, 3×OH), 3.98–4.07 (1H, m), 4.11 (1H, s), 4.35 (1H, d, J=3.4 Hz), 4.49 (1H, d, J=13.7 Hz), 4.53 (1H, d, J=13.7 Hz), 6.49 (1H, d, J=8.3 Hz), 6.61 (1H, d, J=8.3 Hz), 7.44 (1H, dd, J=2.0, 8.3 Hz), 7.67 (1H, d, J=8.3 Hz), 7.71 (1H, d, J=2.0 Hz), 9.08 (1H, brs).

IR (KBr)

υ 3410, 1607, 1470, 1323, 1122, 1035, 959, 917 cm$^{-1}$.

Mass (FAB)

m/z 579 (M+H)+.

Elementary Analysis: As $C_{28}H_{32}N_2O_5Cl_2S \cdot 0.65C_4H_6N_6 \cdot 0.4H_2O$ Calcd.: C, 53.71; H, 5.41; N, 4.09; Cl, 10.36; S, 4.69
Found.: C, 53.79; H, 5.50; N, 4.12; Cl, 10.09; S, 4.58

Example 119

17-Cyclopropylmethyl-4,5α-epoxy-3,14β-dihydroxy-6α-(N-methylphenylmethanesulfonamido)morphinan.tartrate 129 (yield: 87%) was obtained by following the procedure of example 118 but using 3-tert-butyldimethylsilyloxy-17-cyclopropylmethyl-4,5α-epoxy-14β-hydroxy-6α-(N-methyl-phenylmethanesulfonamido)morphinan 17 instead of the starting material of 3-tert-butyldimethylsilyloxy-17-cyclopropylmethyl-4,5α-epoxy-14β-hydroxy-6α-(N-methyl-3,4-dichlorophenylmethanesulfonamido)morphinan 16.

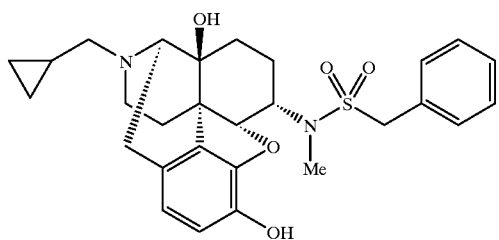

129 mp>147° C. (decomposition)
NMR (400 MHz, DMSO-$d_6$)

δ 0.13–0.22 (2H, m), 0.45–0.58 (2H, m), 0.82–1.07 (2H, m), 1.09–1.19 (1H, m), 1.33–1.42 (2H, m), 1.50–1.62 (1H, m), 2.07–2.27 (2H, m), 2.40–2.72 (3H, m) , 2.79 (3H, s) , 2.99 (1H, brd, J=9.0 Hz), 2.95–4.15 (5H, m, 3×OH), 3.98–4.07 (1H, m), 4.10 (1H, s), 4.34 (1H, d, J=3.4 Hz), 4.40 (1H, d, J=13.9 Hz), 4.45 (1H, d, J=13.9 Hz), 6.47 (1H, d, J=8.0 Hz), 6.61 (1H, d, J=8.0 Hz), 7.31–7.46 (5H, m), 9.10 (1H, brs).

IR (KBr)

υ 3420, 1603, 1460, 1321, 1122, 1069, 1036, 959, 917 cm$^{-1}$.

Mass (FAB)

m/z 511 (M+H)+.

Elementary Analysis: As $C_{28}H_{34}N_2O_5S \cdot 0.5C_4H_6N_6 \cdot H_2O$

Calcd.: C, 59.67; H, 6.51; N, 4.64; S, 5.31
Found.: C, 59.50; H, 6.47; N, 4.68; S, 5.21

Example 120

17-cyploroylmethyl-4,5α-epoxy-3,14β-dihydroxy-6α-(3-phenylpropionyloxy)morphinanan.tartrate 130

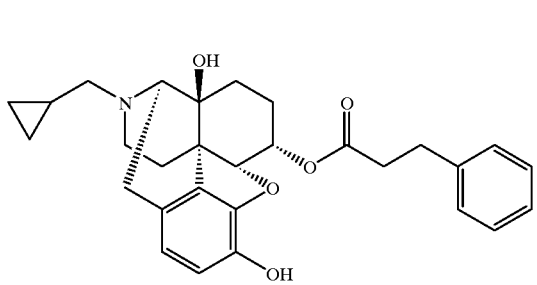

130

148 mg of 17-cyclopropylmethyl-4,5α-epoxy-3,6α,14β-trihydroxymorphinan (N. Chatterjie, C. E. Inturrisi, H. B. Dayton and H. Blumberg, J. Med. Chem., 18, 490 (1975); H.C. Brown and S. Krishnamurthy, J. Am. Chem. Soc., 94, 7159 (1972)) was dissolved in 0.9 ml of carbon tetrachloride and 0.3 ml of methylene chloride followed by the addition of 0.225 ml diisopropylethylamine and 26 mg of 4-dimethylaminopyridine, and the dropwise addition of 0.13 ml of 3-phenylpropionyl chloride at 0° C. After stirring for 20 hours at room temperature, 2 ml of saturated aqueous sodium bicarbonate was added to the reaction system to separate layers, and the aqueous layer was extracted twice with chloroform. The organic layer was concentrated after drying with anhydrous sodium sulfate. The resulting residue was dissolved in a mixed solvent of chloroform and methanol followed by the addition of 30 mg of potassium carbonate and stirring for 1 hour. Water was then added to the reaction mixture to separate layer, and the aqueous layer was extracted twice with chloroform. The resulting organic layer was concentrated after drying with anhydrous sodium sulfate, and the residue was purified with silica gel column chromatography (15 g chloroform/methanol=20/1) to obtain 95.3 mg of the free base of the target compound. This was then dissolved in methanol, completely dissolved by addition of 15 mg of tartaric acid and concentrated. The residue was re-precipitated from ether followed by filtration to obtain 103 mg of the target compound (yield: 43%).

mp >110° C. (decomposition)
NMR (500 MHz, DMSO-$d_6$)

δ 0.18–0.28 (2H, m), 0.47–0.60 (2H, m), 0.83–0.95 (1H, m), 1.19–1.28 (1H, m), 1.32–1.49 (3H, m), 1.74–1.82 (1H, m), 2.19–2.29 (2H, m), 2.40–2.47 (2H, m), 2.55–2.80 (6H, m), 3.08 (1H, brd, J=18.9 Hz), 3.28 (1H, brs), 3.36 (5H, m), 4.10 (2H, s), 4.64 (1H, d, J=4.9 Hz), 5.27–5.31 (1H, m), 6.51 (1H, d, J=8.2 Hz), 6.63 (1H, d, J=8.2 Hz), 7.13–7.19 (3H, m), 7.22–7.28 (2H, m), 9.10 (1H, brs).

IR (KBr)

υ 3400, 1719, 1460, 1307, 1267, 1122, 1069, 1036 cm$^{-1}$.

Mass (FAB)

m/z 476 (M+H)+.

Elementary Analysis: As $C_{29}H_{33}NO_5 \cdot 0.95C_4H_6O_6 \cdot 1/6C_4H_{10}O \cdot 1/6C_2H_6O \cdot 0.4H_2O$ Calcd.: C, 62.91; H, 6.59; N, 2.17
Found.: C, 62.92; H, 6.56; N, 2.32

Example 121

17-Cyclopropylmethyl-3,14β-dihydroxy-4,5β-epoxy-6α[N-methyl-N'-(3,4-dichlorophenyl)ureido]morphinan.hydrochloride 131

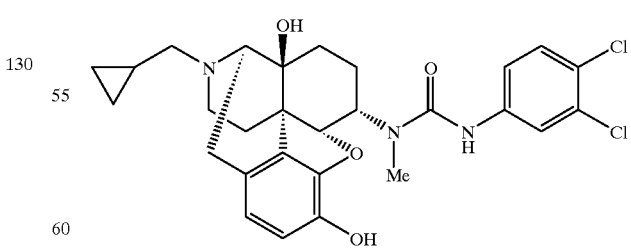

131

17-Cyclopropylmethyl-3,14β-dihydroxy-4,5α-epoxy-6α-methylaminomorphinan A (0.20 g) was dissolved in chloroform (5 ml) followed by the addition of 3,4-dichlorophenylisocyanate (0.26 g, 2.5 equivalents) and reacting for 5 minutes at room temperature. The precipitated solid was filtered out and dissolved in chloroform (8 ml) and methanol (10 ml) followed by the addition of 3 N aqueous sodium hydroxide to carry out hydrolysis for 5 minutes at room temperature. The solvent was distilled off followed by addition of saturated aqueous sodium bicarbonate (10 ml) and distilled water (4 ml), extraction with chloroform and methanol (12/2+10/2 ml), and drying with anhydrous sodium sulfate. After purifying with silica gel column chromatography (Merk 9385, 20 g; chloroform →3% methanol/chloroform), the residue was again dissolved in chloroform and methanol (5/0.5 ml) followed by addition of methanol solution of hydrochloric acid to obtain the target compound (0.23 g, 70%) in the form of its hydrochloride.

mp 210° C. (decomposition)

NMR (400 MHz, DMSO-$d_6$)

δ 0.41 (1H, m), 0.44 (1H, m), 0.62 (1H, m), 0.68 (1H, m), 1.0–1.2 (2H, m), 1.40 (1H, m), 1.60 (2H, m), 1.94 (1H, m), 2.4–2.5 (1H, m), 2.68 (1H, m), 2.92 (3H, s), 2.9–3.2 (3H, m), 3.3–3.4 (2H, m), 3.91 (1H, d, J=6.8 Hz), 4.74 (1H, d, J=3.9 Hz), 4.81 (1H, dt, J=13.7, 3.9 Hz), 6.34 (1H, s), 6.59 (1H, d, J=7.8 Hz), 6.73 (1H, d, J=7.8 Hz), 7.49 (1H, d, J=8.8 Hz), 7.55 (1H, dd, J=9.3, 2.4 Hz), 7.94 (1H, d, J=2.4 Hz), 8.73 (1H, s), 8.82 (1H, brs), 9.32 (1H, s)

IR (KBr)

υ 3300, 1638, 1510, 1477, 1120, 1040 cm$^{-1}$.

Mass (FAB)

m/z 544 (M+H)

Elementary Analysis: As $C_{28}H_{31}N_3O_4Cl_2 \cdot HCl \cdot 0.4H_2O$

Calcd.: C 57.18; H 5.62; N 7.14; Cl 18.08

Found.: C 57.32; H 5.83; N 7.04; Cl 17.85

Examples 122–124

17-Cyclopropylmethyl-3,14β-dihydroxy-4,5α-epoxy-6α-(N-methyl-N'-benzylureido)morphinan.tartrate 132 (yield: 65%), 17-cyclopropylmethyl-3,14β-dihydroxy-4,5α-epoxy-6α-(N-methyl-N'-benzylthioureido)morphinan.tartrate 133 (yield: 88%) and 17-cyclopropylmethyl-3,14β-dihydroxy-4,5α-epoxy-6β-(N-methyl-N'-benzylthioureido) morphinan.tartrate 134 (yield: 74%) were obtained by following the procedure of example 121 but using benzylisocyanate and benzylisothiocyanate instead of 3,4-dichlorophenylisocyanate, and using 17-cyclopropylmethyl-3,14β-dihydroxy-4,5α-epoxy-6β-methylaminomorphinan 10 instead of 17-cyclopropylmethyl-3,14β-dihydroxy-4,5α-epoxy-6α-methylaminomorphinan 4.

Compound 132

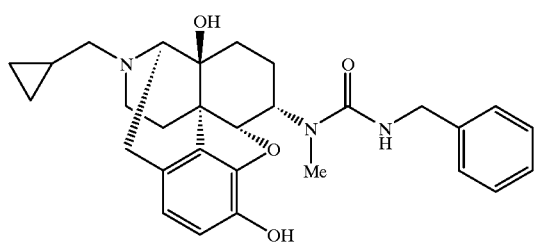

132 mp 202–205° C. (decomposition, methanol-ethylacetate)

NMR (400 MHz, DMSO-$d_6$)

δ 0.28 (2H, m). 0.52 (2H, m), 0.89 (1H, m), 1.10 (1H, m), 1.24 (1H, m), 1.38–1.53 (2H, m), 1.73 (1H, m), 2.15–2.30 (2H, m), 2.62–2.76 (2H, m), 2.78 (3H, s), 3.04 (1H, br d, J=18.6 Hz), 3.24 (1H, m), 3.39–3.52 (2H, m), 3.53 (3H, br s, 3×OH), 3.99 (1H, s), 4.28 (2H, d, J=5.9 Hz), 4.53 (1H, d, J=3.4 Hz), 4.70 (1H, m), 6.49 (1H, d, J=8.1 Hz), 6.61 (1H, d, J=8.1 Hz), 6.89 (1H, t, J=5.9 Hz, NH), 7.18–7.34 (5H, m), 9.03 (1H, br s, NH+).

IR (KBr)

υ 3422, 3204, 1630, 1615, 1589, 1535, 1468, 1359, 1319, 1123, 903, 735 cm$^{-1}$.

Mass (FAB)

m/z 490 ( (M+H)+).

Elementary Analysis: As $C_{29}H_{35}N_3O_4 \cdot 0.5C_4H_6O_6$

Calcd.: C, 65.94; H, 6.78; N, 7.44

Found.: C, 65.95; H, 6.74; N, 7.47

Compound 133

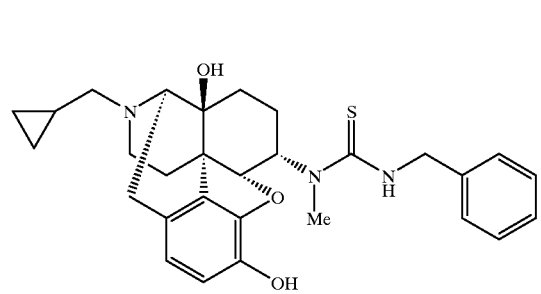

133 mp 155–195° C. (decomposition)

NMR (500 MHz, DMSO-$d_6$)

δ 0.29 (2H, m), 0.52 (2H, m), 0.90 (1H, m), 1.18 (1H, m), 1.35 (1H, m), 1.43 (1H, br d, J=9.1 Hz), 1.50 (1H, dd, J=14.6, 9.1 Hz), 1.77 (1H, m), 2.18–2.28 (2H, m), 2.42–2.57 (2H, m), 2.66–2.78 (2H, m), 2.95 (3H, s), 3.04 (1H, br d, J=18.9 Hz), 3.23 (1H, m), 3.48 (3H, br s, 3×OH), 4.01 (1H, s), 4.80 (1H, d, J=3.6 Hz), 4.82 (1H, dd, J=15.3, 6.1 Hz), 4.89 (1H, dd, J=15.3, 6.1 Hz), 5.81 (1H, m), 6.51 (1H, d, J=7.9 Hz), 6.62 (1H, d, J=7.9 Hz), 7.23 (1H, m), 7.28–7.33 (4H, m), 8.01 (1H, dd, J=6.1, 6.1 Hz, NH), 9.03 (1H, br s, NH+).

IR (KBr)

υ 3374, 1605, 1535, 1460, 1381, 1330, 1243, 1176, 1118, 1067, 1036, 907, 698 cm$^{-1}$.

Mass (FAB)

m/z 506 ( (M+H)+).

Elementary Analysis: As $C_{29}H_{35}N_3O_3S \cdot 0.5C_4H_6O_6 \cdot 0.3H_2O \cdot 0.15CH_3COOC_2H_5$ Calcd.: C, 63.33; H, 6.69; N, 7.01; S, 5.35

Found.: C, 63.44; H, 6.56; N, 6.90; S, 5.35

Compound 134

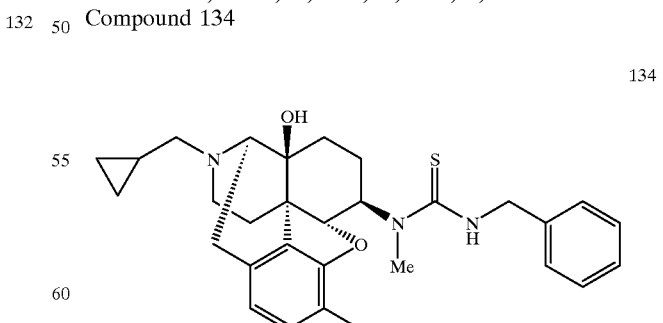

134 mp 160–180° C. (decomposition)

NMR (400 MHz, DMSO-$d_6$)

δ 0.22 (2H, m), 0.47–0.58 (2H, m), 0.91 (1H, m), 1.27–1.47 (3H, m), 1.55 (1H, m), 1.94 (1H, m)), 2.12

(1H, m), 2.28 (1H, m), 2.43–2.78 (5H, m), 3.07 (1H, m), 3.08 (3H, s), 3.26 (1H, m), 3.50 (3.6H, br s, 3.3×OH+0.3×COOH), 4.01 (1.3H, s), 4.60 (1H, dd, J=15.3, 4.9 Hz), 4.74 (1H, d, J=8.3 Hz), 4.93 (1H, dd, J=15.3, 5.9 Hz), 6.55 (1H, d, J=8.3 Hz), 6.60 (1H, d, J=8.3 Hz), 7.19–7.34 (5H, m), 7.95 (1H, dd, J=5.9, 4.9 Hz, NH), 9.11 (1H, br s, NH+).

IR (KBr)

υ 3352, 1721, 1605, 1531, 1456, 1330, 1238, 1125, 1067, 1033, 915, 859 cm$^{-1}$.

Mass (FAB)

m/z 506 ((M+H)+).

Elementary Analysis: As $C_{29}H_{35}N_3O_3S \cdot 0.65C_4H_6O_6 \cdot 0.4H_2O$

Calcd.: C, 62.18; H, 6.56; N, 6.88; S, 5.25

Found.: C, 62.09; H, 6.74; N, 6.83; S, 5.21

Example 125

17-Cyclopropylmethyl-3,14β-dihydroxy-4,5α-epoxy-6α-[N-methyl-N-2-(3,4-dichlorophenyl)ethylamino]morphinan.1.8 hydrochloride 135

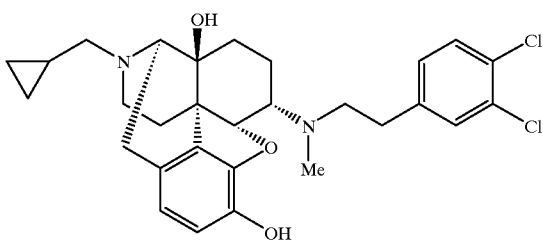

135

234.5 mg (0.431 mmol) of 17-cyclopropylmethyl-3,14β-dihydroxy-4,5α-epoxy-6α-(N-methyl-3,4-dichlorophenylacetamido)morphinan (free base of 1) was dissolved in 5.0 ml of anhydrous THF under argon atmosphere followed by the dropwise addition of 1.1 ml (2.2 mmol) of a 2.0 M anhydrous THF solution of borane-dimethylsulfide complex at 0° C. and refluxing for 1.5 hours. This reaction solution was cooled to 0° C. followed by the addition of 2 ml of 6 N hydrochloric acid and again refluxing for 1 hour. The reaction solution was again cooled to 0° C. and 25 ml of saturated aqueous sodium bicarbonate was added to make the solution basic. The solution was then extracted with chloroform and methanol (4:1) (3×20 ml), and the organic layers were combined, dried and concentrated to obtain 281 mg of an oily substance. This oily substance was purified with column chromatography [silica gel 25 g; chloroform-methanol (50:1→40:1)] to obtain 191.0 mg of the free base of the target compound. This free base was dissolved in methanol followed by the addition of a methanol solution of hydrogen chloride and concentration. The resulting hydrochloride was purified with Sephadex gel column chromatography [methanol] to obtain 193.3 mg of the target compound (yield: 74%).

mp>205° C. (decomposition)

NMR (400 MHz, CDCl$_3$; data for free base)

δ 0.13 (2H, m), 0.53 (2H, m), 0.85 (1H, m), 1.00 (1H, m), 1.49 (1H, dd, J=15.1, 8.8 Hz), 1.53–1.62 (2H, m), 1.71 (1H, ddd, J=15.1, 9.5, 9.5 Hz), 2.0–3.1 (1H, br s, OH), 2.15–2.40 (4H, m), 2.51 (3H, s), 2.55–2.67 (2H, m), 2.72–2.85 (3H, m), 2.89 (1H, m), 2.98–3.10 (3H, m), 4.78 (1H, dd, J=3.0, 2.0 Hz), 4.98 (1H, br s, OH), 6.50 (1H, d, J=8.1 Hz), 6.68 (1H, d, J=8.1 Hz), 7.03 (1H, dd, J=8.3, 2.0 Hz), 7.28 (1H, d, J=2.0 Hz), 7.33 (1H, d, J=8.3 Hz).

IR (KBr)

υ 3422, 1638, 1620, 1508, 1470, 1390, 1323, 1241, 1172, 1122, 1035, 982, 919, 886 cm$^{-1}$.

Mass (FAB)

m/z 529 ( (M+H)+).

Elementary Analysis: As $C_{29}H_{34}Cl_2N_2O_3 \cdot 1.8HCl \cdot 0.4H_2O$

Calcd.: C, 57.83; H, 6.12; N, 4.65; Cl, 22.37

Found.: C, 57.73; H, 6.31; N, 4.60; Cl, 22.38

Example 126

17-Cyclopropylmethyl-3,14β-dihydroxy-4,5α-epoxy-6β-[N-methyl-N-2-(3,4-dichlorophenyl)ethylamino]morphinan.1.9 hydrochloride 136 (yield: 65%) was obtained by following the procedure of example 125 but using 17-cyclopropylmethyl-3,14β-dihydroxy-4,5α-epoxy-6β-(N-methyl-3,4-dichlorophenylacetamido)morphinan (free base of 53) instead of the starting material of 17-cyclopropylmethyl-3,14β-dihydroxy-4,5α-epoxy-6α-(N-methyl-3,4-dichlorophenylacetamido)morphinan (free base of 1).

Compound 136

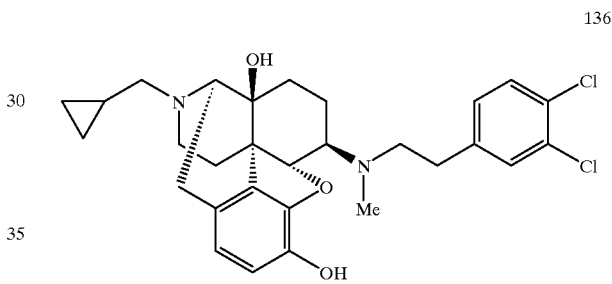

136 mp>185° C. (decomposition)

NMR (400 MHz, CDCl$_3$; data of free base);

δ 0.12 (2H, m), 0.52 (2H, m), 0.83 (1H, m), 1.29 (1H, ddd, J=13.2, 13.2, 2.9 Hz), 1.44 (1H, m), 1.51 (1H, m), 1.61 (1H, ddd, J=13.2, 2.9, 2.9 Hz), 1.86 (1H, m), 2.0–3.8 (2H, br s, 2×OH), 2.11 (1H, ddd, 11.7, 11.7, 3.4 Hz), 2.21 (1H, ddd, J=12.2, 12.2, 4.9 Hz), 2.33–2.38 (2H, m), 2.41 (3H, s), 2.47–2.56 (2H, m), 2.57–2.75 (4H, m), 2.81 (1H, m), 2.97–3.06 (2H, m), 4.56 (1H, d, J=8.3 Hz), 6.56 (1H, d, J=8.1 Hz), 6.71 (1H, d, J=8.1 Hz), 7.01 (1H, dd, J=8.3, 2.0 Hz), 7.29 (1H, d, J=2.0 Hz), 7.30 (1H, d, J=8.3 Hz).

IR (KBr)

υ 3250, 1638, 1618, 1473, 1398, 1330, 1241, 1218, 1116, 1035, 982, 919, 855, 756 cm$^{-1}$.

Mass (FAB)

m/z 529 ((M+H)+).

Elementary Analysis: As $C_{29}H_{34}Cl_2N_2O_3 \cdot 1.9 HCl \cdot 0.5H_2O$

Calcd.: C, 57.31; H, 6.12; N, 4.61; Cl, 22.75

Found.: C, 57.40; H, 6.22; N, 4.55; Cl, 22.54

Example 127

17-cyclopropylmethyl-3,14β-dihydroxy-4,5α-epoxy-6α-(N-methyl-4-aminophenylacetamido)morphinanan.1.6 hydrochloride 137

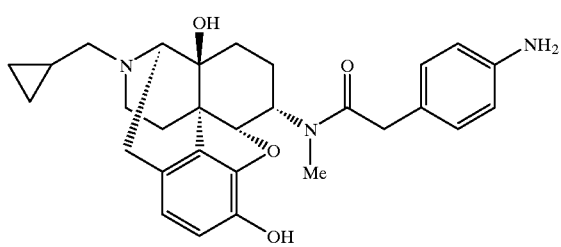

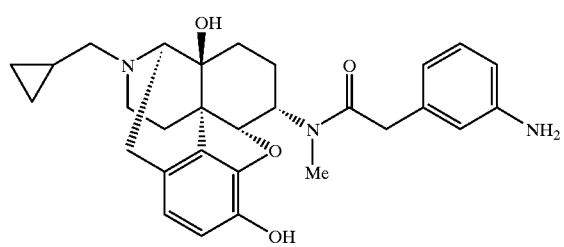

156.8 mg (0.282 mmol) of 17-cyclopropylmethyl-3,14β-dihydroxy-4,5α-epoxy-6α-(N-methyl-4-nitrophenylacetamido) morphinan.hydrochloride 87 was dissolved in 2.1 ml of methanol followed by the addition of roughly 0.2 ml of a saturated methanol solution of hydrogen chloride gas and 5.3 mg of platinum oxide, and stirring for 2.5 hours at room temperature in a hydrogen atmosphere (1 atm). The reaction mixture was filtered by passing through Celite, and the filtration residue was washed with methanol. The filtrate and washing were combined and concentrated to obtain 166 mg of crude product. This crude product was purified twice with Sephadex column chromatography [methanol] to obtain 108.2 mg of the target compound (yield: 68%).

mp>220° C. (decomposition)

NMR (400 MHz, DMSO-d$_6$)

δ 0.39 (1H, m), 0.47 (1H, m), 0.62 (1H, m), 0.69 (1H, m), 1.00–1.23 (2H, m), 1.34 (1H, m), 1.45–1.63 (2H, m), 1.94 (1H, m), 2.44 (1H, m), 2.68 (1H, m), 2.78 (0.9H, s), 2.92–3.13 (3H, m), 2.93 (2.1H, s), 3.21–3.43 (2H, m), 3.67–3.82 (2H, m), 3.92–3.98 (1H, m), 4.38 (0.3H, m), 4.57 (0.3H, m), 4.61 (0.7H, d, J=3.4 Hz), 4.98 (0.7H, m), 6.29 (0.7H, br s, OH), 6.57 (1H, d, J=8.3 Hz), 6.63 (0.3H, br s, OH), 6.72 (0.3H, d, J=8.3 Hz), 6.74 (0.7H, d, J=8.3 Hz), 6.97 (0.6H, d, J=8.3 Hz) 7.00 (1.4H, d, J=8.3 Hz), 7.16 (1.4H, d, J=8.3 Hz), 7.20 (0.6H, d, J=8.3 Hz), 8.53 (2.8H, br s, NH3+), 8.84 (0.8H, m, NH+), 9.30 (0.3H, br s, OH), 9.33 (0.7H, br s, OH).

IR (KBr)

υ 3370, 1620, 1510, 1466, 1321, 1120, 1038, 919, 804 cm$^{-1}$.

Mass (FAB)

m/z 490 ((M+H)+).

Elementary Analysis: As C$_{29}$H$_{35}$N$_3$O$_4$.1.6HCl.0.8H$_2$O

Calcd.: C, 61.94; H, 6.85; N, 7.47; Cl, 10.09.

Found.: C, 62.09; H, 7.02; N, 7.15; Cl, 9.93.

Example 128

17-Cyclopropylmethyl-3,14β-dihydroxy-4,5α-epoxy-6α-(N-methyl-3-aminophenylacetamido)morphinan.1.1 tartrate 138 (yield: 90%) was obtained by following the procedure of example 127 but using 17-cyclopropylmethyl-3,14β-dihydroxy-4,5α-epoxy-6α-(N-methyl-3-nitrophenylacetamido) morphinan.hydrochloride 83 instead of the starting material of 17-cyclopropylmethyl-3,14β-dihydroxy-4,5α-epoxy-6α-(N-methyl-4-nitrophenylacetamido)morphinan.hydrochloride 87.

mp>160° C. (decomposition)

NMR (400 MHz, DMSO-d$_6$)

δ 0.23 (2H, m), 0.53 (2H, m), 0.92 (1H, m), 1.18–1.32 (2H, m), 1.48–1.53 (2H, m), 1.74 (1H, m), 2.14–2.38 (2H, m), 2.54 (1H, m), 2.63–2.84 (2H, m), 2.79 (0.9H, s), 2.90 (2.1H, s), 3.08 (1H, m), 3.26–3.41 (2H, m), 3.51–3.63 (3H, m), 3.60 (7H, br s, 4×OH, NH3+), 4.09 (0.3H, m), 4.11 (2H, s), 4.47 (0.3H, m), 4.56 (0.7H, d, J=3.4 Hz), 4.95 (0.7H, m), 6.37–6.56 (3H, m), 6.58–6.64 (1H, m), 6.62–7.00 (1H, m), 9.10 (1H, br s, NH+).

IR (KBr)

υ 3312, 1736, 1719, 1609, 1510, 1460, 1402, 1309, 1267, 1120, 1069, 1038, 919, 774, 687 cm$^{-1}$.

Mass (FAB)

m/z 490 ((M+H)+).

Elementary Analysis: As C$_{29}$H$_{35}$N$_3$O$_4$.1.1C$_4$H$_6$O$_6$1.8 H$_2$O. 0.5CH$_3$COOC$_2$H$_5$ Calcd.: C, 58.15; H, 6.78; N, 5.75

Found.: C, 58.18; H, 6.76; N, 5.65

Example 129

17-Cyclopropylmethyl-3-acetoxy-4,5α-epoxy-14β-hydroxy-6α-(N-methyl-3,4-dichlorophenylacetamido) morphinan.hydrochloride 139

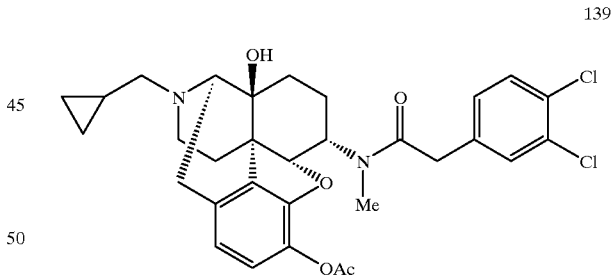

152 mg of 17-cyclopropylmethyl-4, 5α-epoxy-3, 14βdihydroxy-6α-(N-methyl-3,4-dichlorophenylacetamido) morphinan.hydrochloride 1 obtained in example 11 was dissolved in 2.3 ml of pyridine followed by the addition of 0.04 ml of acetic anhydride and stirring for 30 minutes. After concentrating the reaction solvent and removing the pyridine by azeotrope with toluene, the residue was washed with ether to obtain 148 mg of the target compound (yield: 91%).

mp>187° C. (decomposition)

NMR (400 MHz, CDCl$_3$)

δ 0.35–0.58 (1.3H, m), 0.63–0.94 (2.7H, m),1.25–1.75 (5H, m), 2.26 (2.1H, s), 2.27 (0.9H, s), 2.47–2.70 (2H, m), 2.83 (0.9H, S), 2.85 (2.1H, s), 2.90–3.26 (4H, m), 3.27–3.60 (2H, m), 3.69 (1.4H, s), 3.71 (0.6H, s), 4.35–4.60 (1.3H, m), 4.75–4.83 (0.3H, m), 4.86 (0.7H, d, J=2.9 Hz), 5.18–5.28 (0.7H, m), 6.70 (1H, d, J=8.4 Hz), 6.72 (1H, brs), 6.87–6.93 (1H, m), 7.09 (0.7H, dd, J=8.3, 2.0 Hz), 7.30 (0.3H, dd, J=8.3, 2.0 Hz), 7.35 (0.7H, d, J=2.0 Hz), 7.40 (0.7H, d, J=8.3 Hz), 7.48 (0.3H, d, J=2.0 Hz), 7.56 (0.3H, d, J=8.3 Hz), 9.40–9.70 (1H, m).

IR (KBr)

υ 3380, 1765, 1636, 1626, 1475, 1458, 1224, 1201, 1122, 1036 cm$^{-1}$.

Mass (FAB)

m/z 585 (M+H)+.

Elementary Analysis: As $C_{31}H_{34}N_2O_5Cl_2 \cdot HCl$

Calcd.: C, 59.86; H. 5.67; N, 4.50; Cl, 17.10
Found.: C, 59.71; H, 5.70; N, 4.55; Cl, 16.95

Examples 130–131

δ 17-Cyclopropylmethyl-3-acetoxy-14β-hydroxy-4,5α-epoxy-6β-(N-methylcinnamamido)morphinan.tartrate 140 (yield: 70%) and 17-cyclopropylmethyl-3-acetoxy-14β-hydroxy-4,5α-epoxy-6β-(N-methyl-3-trifluoromethylcinnamamido)morphinan.tartrate 141 (yield: 56%) were obtained by following the procedure of example 129 but using 17-cyclopropylmethyl-3,14β-dihydroxy-4,5α-epoxy-6β-(N-methylcinnamamido)morphinan.tartrate 99 and 17-cyclopropylmethyl-3,14β-dihydroxy-4,5α-epoxy-6β-(N-methyl-3-trifluoromethylcinnamamido)morphinan.tartrate 60 instead of 17-cyclopropylmethyl-4,5α-epoxy-3,14β-dihydroxy-6α-(N-methyl-3,4-dichlorophenylacetamido)morphinan.hydrochloride 1

Compound 140

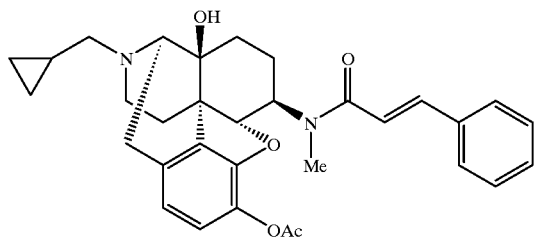

mp 142–146° C. (decomposition, ethylacetate)
PNMR (400 MHz, DMSO-d$_6$)

δ 0.23 (2H, br s), 0.54 (2H, m), 0.92 (1H, m), 1.30 (1H, m), 1.38–1.50 (2H, m), 1.60 (1H, m), 1.85 (1.73H, s), 2.09–2.26 (2H, m), 2.21 (1.27H, s), 2.33 (1H, m), 2.60–4.40 (5H, br OH×5), 2.69 (1H, m), 2.78 (2H, m) 2.90 (1.73H, s), 3.13 (1.27H, s), 3.30 (1H, m), 3.33 (1H, m), 3.72 (1H, m), 3.89 (1H, m), 4.13 (2 H, s), 4.78 (0.67H, d, J=7.8 Hz), 5.00 (0.33 H, d, J=8.3 Hz), 6.72–7.72 (9H, m)

IR ( KBr)

υ 3350, 1760, 1640, 1600, 1493, 1309, 1189 cm$^{-1}$.

Mass (FAB)

m/z 529 (M+H)+.

Elementary Analysis: AS $C_{36}H_{42}N_2O_{11}$

Calcd.: C, 63.71; H, 6.24; N, 4.13.
Found.: C, 63.51; H, 6.37; N, 4.10.

Compound 141

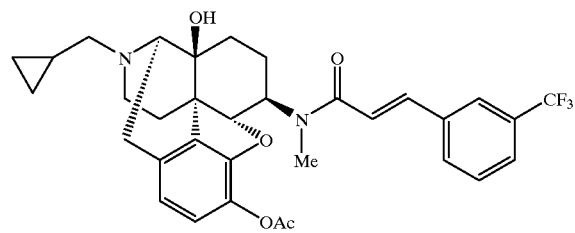

mp 125–128° C.
NMR (400 MHz, DMSO-d$_6$)

δ 0.22 (2H, brs), 0.53 (2H, m), 0.91 (1H, m), 1.3–1.7 (4H, m), 1.76 (2 H, br s), 2.1–2.2 (2H, m), 2.21 (1H, s), 2.35 (1H, m) 2.46 (1H, m), 2.6–2.8 (3H, m), 2.91 (2H, s), 3.15 (1H, s), 3.2–3.9 (3H, m), 4.12 (1.4H, s), 4.75 (0.7H, d, J=7.3 Hz), 5.00 (0.3H, d, J=8.3 Hz), 6.7–7.9 (2.7H, m), 7.36 (0.3H, d, J=15.6 Hz), 7.5–7.7 (2H, m), 7.71 (1H, d, J=7.3 Hz), 7.80 (0.7H, d, J=7.8 Hz), 7.92 (0.7H, s), 8.01 (0.3H, d, J=7.8 Hz), 8.14 (0.33H, s).

IR(KBr)

υ 3400, 1765, 1648, 1605, 1336, 1127 cm$^{-1}$.

Mass (FAB)

m/z 597 (M+H).

Elementary Analysis: As $C_{33}H_{35}N_2O_5F_3 \cdot 0.70(C_4H_6O_6) \cdot 1.0H_2O$ Calcd.: C, 59.74; H, 5.77; N, 3.89; F, 7.92.
Found.: C, 59.83; H. 5.82; N. 3.88; F, 7.88.

Example 132

17-cyclopropylmethyl-4, 5α-epoxy-14β-hydroxy-3-methoxy-6α-(N-methyl-3,4-dichlorophenylacetamido) morphinan.tartrate 142

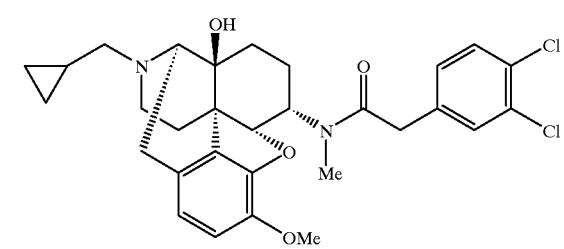

245 mg of 17-cyclopropylmethyl-4,5α-epoxy-3,14β-dihydroxy-6α-(N-methyl-3,4-dichlorophenylacetamido) morphinan (free base of 1) obtained in example 11 was dissolved in 3.5 ml of chloroform followed by the addition of an excess amount of diazomethane and stirring for 1 hour. After concentrating the reaction system, the residue was purified with silica gel column chromatography (20 g hexane/ethylacetate/methanol/aqueous ammonia=5/3/0.2/0.04) to obtain the free base of the target compound. After dissolving this in methanol, 11 mg of tartaric acid was added to completely dissolve followed by concentration. The residue was re-precipitated from ether followed by filtration to obtain 83 mg of the target compound (yield: 30%).

mp>115° C. (decomposition)
NMR(400 MHz, DMSO-d$_6$+D20)

δ 0.15–0.33 (2H, m), 0.48–0.63 (2H, m), 0.87–1.00 (1H, m), 1.05–1.55 (4H, m), 1.69–1.85 (1H, m), 2.20–2.45

(2H, m), 2.55–2.95 (3H, m), 2.79 (0.9H, s), 2.94 (2.1H, s), 3.08–3.22 (1H, m), 3.30–3.58 (2H, m), 3.78 (3H, s), 3.77 (1H, d, J=16.1 Hz), 3.84 (1H, d, J=16.1 Hz), 4.09 (2H, s), 4.38–4.45 (0.3H, m), 4.55–4.63 (0.3H, m), 4.60 (0.7H, d, J=3.4 Hz), 4.88–4.96 (0.7H, m), 6.68 (0.7H, d, J=8.3 Hz), 6.64–6.70 (0.3H, m), 6.86 (0.7H, d, J=8.3 Hz), 6.82–6.88 (0.3H, m), 7.24 (0.7H, dd, J=8.3, 2.0 Hz), 7.24–7.30 (0.3H, m), 7.52 (0.7H, d, J=2.0 Hz), 7.52–7.56 (0.3H, m), 7.57 (0.7H, d, J=8.3 Hz), 7.60 (0.3H, d, J=8.3 Hz).

IR (KBr)

υ 3324, 1628, 1402, 1309, 1267, 1131 cm$^{-1}$.

Mass (II)

m/z=556 M+.

Elementary Analysis: As $C_{30}H_{34}N_2O_4Cl_2 \cdot 0.87C_4H_6O_6 \cdot 0.7H_2O$ Calcd.: C 57.39; H 5.80; N 4.00; Cl 10.12

Found.: C 57.35; H 5.91; N 4.09; Cl 10.19

Example 133

14β-Acetoxy-17-cyclopropylmethyl-4,5α-epoxy-3-hydroxy-6α-(N-methyl-3,4-dichlorophenylacetamido) morphinan.hydrochloride 143

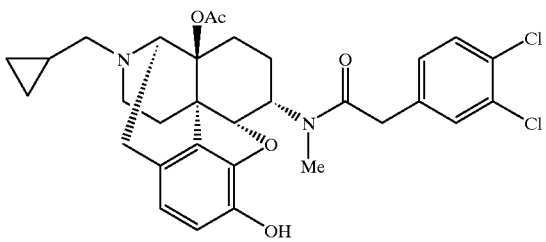

143

443 mg of 17-cyclopropylmethyl-4,5α-epoxy-3,14β-dihydroxy-6α-(N-methyl-3,4-dichlorophenylacetamido) morphinan (free base of 1) obtained in example 11 was dissolved in acetic anhydride followed by stirring for 1 hour at 160° C. with an oil bath. After concentrating the reaction solvent, the acetic anhydride was completely removed by azeotrope with toluene. The residue was dissolved in 10 ml of methanol followed by the addition of 14 ml of 4% aqueous sulfuric acid and stirring for 18 hours. 10 ml of aqueous ammonia and 30 ml of chloroform were then added to the system to separate, and the aqueous layer was extracted twice with 15 ml of chloroform. The organic layer was concentrated after drying with anhydrous sodium sulfate and the residue was purified with silica gel column chromatography (45 g, chloroform/ethylacetate =2/1). This was then recrystallized from chloroform and methanol followed by derivation of the crystals into hydrochloride with methanol solution of hydrochloride to obtain 299 mg of the target compound (yield: 59%).

mp>190° C. (decomposition)

NMR (400 MHz, DMSO-d$_6$)

δ 0.35–0.73 (4H, m), 0.90–1.03 (1H, m), 1.05–1.75 (4H, m), 2.17 (2.25H, s), 2.24 (0.75H, s),2.30–2.62 (2H, m), 2.65–2.83 (1H, m), 2.80 (0.75H, s), 2.96 (2.25H, s), 2.90–3.15 (2H, m), 3.18–3.52 (3H, m), 3.79 (0.75H, d, J=16.1 Hz), 3.84 (0.75H, d, J=16.1 Hz), 3.93–4.07 (0.5H, m), 4.55–4.60 (0.25H, m), 4.72 (0.75H, d, J=3.4 Hz), 4.77–4.85 (1H, m), 5.26 (1H, d, J=6.4 Hz), 6.50 (0.25H, d, J=8.3 Hz), 6.61 (0.75H, d, J=8.3 Hz), 6.77 (1H, d, J=8.3 Hz), 7.19–7.25 (0.25H, m), 7.24 (0.75H, dd, J=8.3, 2.0 Hz), 7.49 (0.25H, d, J=2.0 Hz), 7.52 (0.75H, d, J=2.0 Hz), 7.58 (0.75H, d, J=8.3 Hz), 7.60 (0.25H, d, J=8.3 Hz), 9.20–9.47 (1H, m), 9.42 (0.25H, s), 9.43 (0.75H, s).

IR (KBr)

υ 3420, 1744, 1626, 1473, 1406, 1371, 1321, 1214, 1116, 1035 cm$^{-1}$.

Mass (EI)

m/z 584 M+.

Elementary Analysis: As $C_{31}H_{34}N_2O_5Cl_2 \cdot HCl \cdot 0.2H_2O$

Calcd.: C, 59.52; H, 5.70; N, 4.48; Cl, 17.00.

Found.: C, 59.40; H, 5.90; N, 4.56; Cl, 17.12.

Example 134

17-Cyclopropylmethyl-3-hydroxy-14β-acetoxy-4,5α-epoxy-6β-(N-methylcinnamamido)morphinan.tartrate 144 (yield: 48%) was obtained by following the procedure of example 133 but using 17-cyclopropylmethyl-3,14β-dihydroxy-4,5α-epoxy-6β-(N-methylcinnamamido) morphinan (free base of 99) instead of 17-cyclopropylmethyl-4,5α-epoxy-3,14β-dihydroxy-6α-(N-methyl-3,4-dichlorophenylacetamido) morphinan (free base of 1).

144

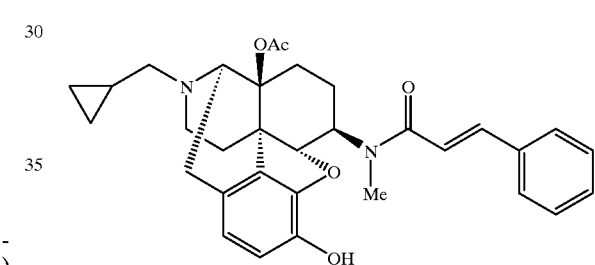

mp 154–157° C.

NMR (400 MHz DMSO-d$_6$)

δ 0.06 (2H, m), 0.42 (2H, d, J=8.3 Hz), 0.72 (1H, m), 1.2–1.4 (3H, m), 1.93 (1H, m), 2.05 (1H, m), 2.11 (3H, s), 2.24 (1H, m), 2.37 (2H, m), 2.43 (1H, m), 2.62 (1H, m), 2.89 (2H, s), 3.03 (1H, d, J=18.1 Hz), 3.15 (1H, s), 3.2–3.4 (1H, m) 3.69 (0.7H, m), 4.15 (0.3H, m), 4.28 (1H, s), 4.70 (0.7H, d, J=7.8 Hz), 4.82 (0.3H, d, J=8.3 Hz), 6.5–6.8 (3H, m), 7.1–7.5 (5.3H, m), 7.71 (0.7H, d, J=6.3 Hz)

IR (KBr)

υ 3390, 1738, 1647, 1590, 1408, 1122 cm$^{-1}$.

Mass (FAB)

m/z 529 (M+H).

Elementary Analysis: As $C_{32}H_{36}N_2O_5 \cdot 0.5(C_4H_6O_6) \cdot 1.0H_2O$

Calcd.: C, 65.68; H, 6.65; N, 4.50.

Found.: C, 65.85; H, 6.66; N, 4.43.

Example 135

17-Cyclopropylmethyl-3,14β-dihydroxy-4,5α-epoxy-6β (N-methyl-3-aminocinnamamido)morphinan.hydrochloride 145

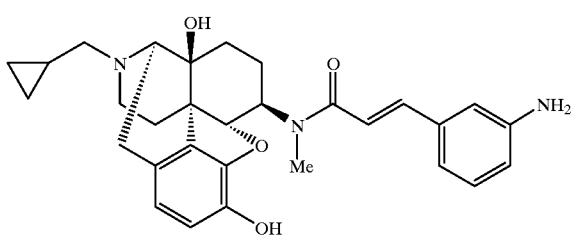

145

360 mg of 17-cyclopropylmethyl-3,14β-dihydroxy-4,5α-epoxy-6β-(N-methyl-3-nitrocinnamamido)morphinan (free base of 104) and 1.07 g of stannic chloride dihydrate was dissolved in 7.5 ml of ethanol followed by heating to 70°0 C. and stirring for 2 hours. After cooling the reaction mixture to room temperature, 2 N aqueous sodium hydroxide was added while cooling with ice to neutralize followed by extraction with dichloromethane. The organic layers were combined and washed with saturated brine. After drying and concentrating, the organic substances were removed by chromatographic filtration [silica gel; chloroform:methanol (9:1)]. The resulting crude target compound was converted into a dihydrochloride to obtain 310 mg.

Mass (FAB)

m/z 502 ( (M+H)+).

Example 136

17-Cyclopropylmethyl-3,14β-dihydroxy-4,5α-epoxy-6β-(N-methyl-3-isothiocyanatocinnamamido)morphinanan.methanesulfonate 146

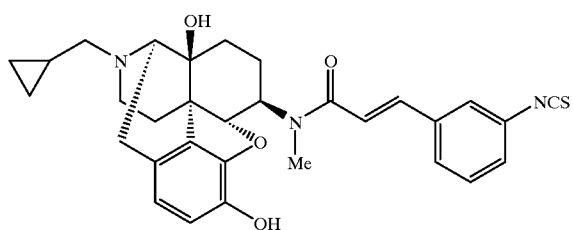

146

300 mg of 17-cyclopropylmethyl-3,14β-dihydroxy-4,5α-epoxy-6β-(N-methyl-3-aminocinnamamido)morphinan.hydrochloride 145 obtained in example 135 was dissolved in 9 ml of water and cooled with ice. 40 μl of thiophosgene dissolved in 2 ml of chloroform was added dropwise followed by stirring for 5 hours at warming to room temperature. Saturated aqueous sodium bicarbonate was then added to neutralize while cooling with ice followed by extraction with chloroform. The organic layers were combined and washed with saturated brine followed by drying and concentrating. The resulting residue was purified with column chromatography [silica gel; chloroform:methanol (97.5:2.5)], to obtain 208 mg of the resulting target compound after converting a methanesulfonate from (yield: 52% 2 steps).

mp 170° C. (decomposition)

NMR (500 MHz, DMSO-d$_6$)

δ 0.42 (1H, m), 0.49 (1H, m), 0.60 (1H, m), 0.69 (1H, m), 1.07 (1H, m), 1.27–1.58 (3H, m), 1.72 (1H, m), 2.11 (1H, m), 2.31 (3H, s), 2.43–2.52 (2H, m), 2.86 (1H, m), 2.92 (2.1H, s), 3.02–3.14 (2H, m), 3.18 (0.9H, s), 3.30–3.38 (2H, m), 3.70 (0.7H, m), 3.83 (1H, m), 4.19 (0.3H, m), 4.80 (0.7H, d, J=8.3 Hz), 4.90 (0.3H, d, J=8.3 Hz), 6.14 (0.3H, br s), 6.22 (0.7H, br s), 6.65–6.84 (2.1H, m), 6.88 (0.7H, d, J=7.8 Hz), 7.29 (1H, d, J=15.6 Hz), 7.40–7.50 (3.6H, m), 7.69 (0.3H, d, J=7.8 Hz), 7.91 (0.3H, S), 8.74 (1H, br s), 9.30 (0.3H, br s), 9.54 (0.7H, br s).

IR (KBr)

υ 3380, 3210, 2124, 1649, 1599, 1197, 1060, 785 cm$^{-1}$.

Mass (FAB)

m/z 544 ((M+H)+).

Elementary Analysis: As $C_{31}H_{33}N_3O_4S \cdot CH_3SO_3H \cdot H_2O$

Calcd.: C, 58.43; H, 5.98; N, 6.39; S, 9.75

Found.: C, 58.67; H, 6.15; N, 6.11; S, 9.78

Example 137

17-Cyclopropylmethyl-3,14β-dihydroxy-4,5α-epoxy-6α-(N-methyl-3-aminocinnamamido)morphinan.hydrochloride 147 was obtained by following the procedure of example 135 but using 17-cyclopropylmethyl-3,14β-dihydroxy-4,5α-epoxy-6α-(N-methyl-3-nitrocinnamamido)morphinan (free base of 97) instead of 17-cyclopropylmethyl-3,14β-dihydroxy-4,5α-epoxy-6β-(N-methyl-3-nitrocinnamamido) morphinan (free base of 104).

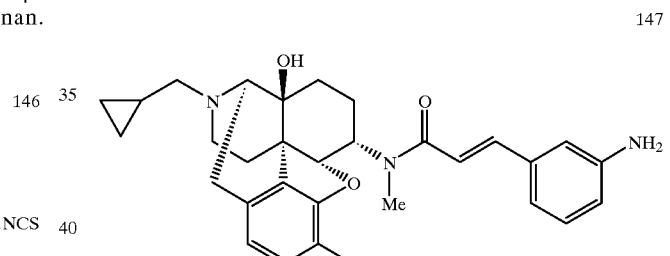

147

Mass (FAB)

m/z 502 ( (M+H)+).

Examples 138–139

17-Cyclopropylmethyl-3,14β-dihydroxy-4,5α-epoxy-6α-(N-methyl-3-isothiocyanatocinnamamido)morphinan.methanesulfonate (yield: 32% 2 steps) 148 and 17-cyclopropylmethyl-3,14β-dihydroxy-4,5α-epoxy-6α-(N-methyl-3-isothiocyanatophenylacetamido)morphinanan.methanesulfonate 149 (yield: 78%) were obtained by following the procedure of example 136 but using 17-cyclopropylmethyl-3,14β-dihydroxy-4,5α-epoxy-6α-(N-methyl-3-aminocinnamamido)morphinan.hydrochloride 147 and 17-cyclopropylmethyl-3,14β-dihydroxy-4,5α-epoxy-6α-(N-methyl-3-aminophenylacetamido)morphinan.hydrochloride 138 instead of 17-cyclopropylmethyl-3,14β-dihydroxy-4,5α-epoxy-6β-(N-methyl-3-aminocinnamamido)morphinan.hydrochloride 145.

Compound 148

148 mp 160° C. (decomposition)
NMR (500 MHz, DMSO-d$_6$)
  δ 0.41 (1H, m), 0.48 (1H, m), 0.62 (1H, m), 0.70 (1H, m), 1.05 (1H, m), 1.20 (1H, m), 1.40–1.67 (3H, m), 1.93 (1H, m), 2.31 (3.3H, s), 2.47 (1H, m), 2.71 (1H, m), 2.91 (0.6H, s), 2.93 (1H, m), 3.01–3.15 (2H, m), 3.10 (2.4H, s), 3.25–3.38 (2H, m), 3.89 (1H, br d, J=5.9 Hz), 4.58 (0.2H, m), 4.73 (0.8H, d, J=3.4 Hz), 4.94 (0.2H, br s), 5.04 (0.8H, m), 6.20 (0.8H, s), 6.25 (0.2H, br s), 6.61 (1H, d, J=7.8 Hz), 6.72 (1H, d, J=7.8 Hz), 7.22 (0.2H, d, J=14.1 Hz), 7.37 (0.8H, d, J=15.6 Hz), 7.42–7.54 (3H, m), 7.68 (0.2H, d, J=7.3 Hz), 7.71 (0.8H, d, J=7.3 Hz), 7.77 (0.2H, s), 7.93 (0.8H, s), 8.77 (1H, br s), 9.30 (1H, br s).
IR (KBr)
  υ 3340, 3200, 2112, 1649, 1599, 1508, 1460, 1210, 1195, 1118, 1060, 1038, 785 cm$^{-1}$.
Mass (FAB)
  m/z 544 ((M+H)+).
Elementary Analysis: As $C_{31}H_{33}N_3O_4S \cdot 1 \cdot CH_3SO_3H \cdot H_2O$
  Calcd.: C 57.77; H 5.95; N 6.29; S 10.09
  Found.: C 57.72; H 6.04; N 6.22; S 10.22

Compound 149

149 mp>155° C. (decomposition)
NMR (500 MHz, DMSO-d$_6$)
  δ 0.38 (1H, m), 0.46 (1H, m), 0.61 (1H, m), 0.70 (1H, rm), 1.04 (1H, m), 1.15 (1H, m), 1.36 (1H, m), 1.55 (1H, m), 1.62 (1H, m), 1.89 (1H, m), 2.30 (3H, s), 2.42 (1H, m), 2.71 (1H, m)), 2.93 (1H, m), 2.96 (3H, s), 3.03 (1H, m), 3.10 (1H, m), 3.23–3.37 (2H, m), 3.73–3.90 (3H, m), 4.44 (0.1H, m). 4.63 (0.9H, d, J=3.7 Hz), 4.71 (0.1H, m), 4.98 (0.9H, ddd, J=14.3, 4.0, 4.0 Hz), 6.12 (0.9H, s, OH), 6.23 (0.1H, s, OH), 6.59 (1H, d, J=8.3 Hz), 6.71 (1H, d, J=8.3 Hz), 7.01–7.44 (4H, m), 8.75 (1H, m, NH+), 9.27 (1H, s, OH).
IR (KBr)
  υ 3258, 2122, 1736, 1625, 1613, 1460, 1402, 1323, 1207, 1160, 1120, 919, 775 cm$^{-1}$.
Mass (FAB)
  m/z 532 ((M+H)+).
Elementary Analysis: As $C_{30}H_{33}N_3O_4S \cdot CH_3SO_3H \cdot 0.9 \ H_2O$
  Calcd.: C 57.82; H 6.07; N 6.52; S 9.96
  Found.: C 58.21; H 6.22; N 6.40; S 9.58

Example 140

Opioid Activity Test Using the Isolated Guinea Pig Preparation

Preparation

A male Hartley guinea pig was used in this test.

After sacrificing the guinea pig and extracting the ileum, the lumen was washed with nutrient solution and only the longitudinal muscle was isolated. This longitudinal muscle was filled with Krebes-Henseleit solution (NaCl 118 mM; KCl 4.7 mM; CaCl$_2$ 2.5 mM; KH$_2$PO$_4$ 1.2 mM; NaHCO$_3$ 25 mM; MgSO$_4$ 1.2 mM and glucose 10 mM) warmed to 37° C. and suspended in a Magnus tube ventilated with 5% carbon dioxide and 95% oxygen. Electrical stimulus was performed at 0.1 Hz for 5.0 ms by means of ring-shaped platinum electrodes located above and below. Tissue contractions were recorded on a polygraph using an isometric transducer.

Initially, the test drug was cumulatively added to a concentration at which specimen contractions caused by electrical stimulus were suppressed by 50% to calculate the IC$_{50}$ value. Then after adequately washing with nutrient solution and the contraction reaction stabilized, naloxone, a μ antagonist, or norBNI, a κ agonist, were added and the test compound was again cumulatively added after roughly 20 minutes. The Ke value was calculated using the following calculation formula from the difference in the efficacies of both agonists.

Ke=[Conc. of added antagonist]/(IC$_{50}$ ratio–1)

IC$_{50}$ ratio=IC$_{50}$ in the presence of antagonist/IC$_{50}$ in the absence of antagonist As a result, when the ratio between the Ke value (μ) and Ke value (κ) was taken, Ke(μ)/Ke(κ)=4063. It was thus found that the compounds of the present invention are highly selective agonists for κ receptors.

|   | | Ke (nM) | |
|---|---|---|---|
|   | IC$_{50}$ (nM) | Naloxone | norBNI |
| 1 | 0.026 | 650 | 0.16 |

Example 141

Opioid Activity Test Using the Isolated Mouse Vas Deference Preparation

A male ddy mouse was used in this test. The isolated vas deference was filled with Krebes-Henseleit solution (NaCl 118 mM; KCl 4.7 mM; CaCl$_2$ 2.5 mM; KH$_2$PO$_4$ 1.1 mM; NaHCO$_3$ 25 mM; and glucose 10 mM) warmed to 37° C. and suspended in a Magnus tube ventilated with 5% carbon dioxide and 95% oxygen. Electrical stimulus was performed at 0.1 Hz for 5.0 ms by means of ring-shaped platinum electrodes located above and below. Tissue contractions were recorded on a polygraph using an isometric transducer.

Initially, the test drug was cumulatively added to a concentration at which specimen contractions caused by electrical stimulus were suppressed by 50% to calculate the IC$_{50}$ value. Then after adequately washing with nutrient solution and the contraction reaction stabilized, naloxone, a $\mu$ agonist, NTI, a $\delta$ agonist, or norBNI, a $\kappa$ agonist, were added and the test compound was again cumulatively added after roughly 20 minutes. The Ke value was calculated using the following calculation formula from the difference in the efficacies of both agonists.

Ke=[Conc. of added agonist]/($IC_{50}$ ratio−1)

$IC_{50}$ ratio $IC_{50}$ in the presence of agonist/$IC_{50}$ in the absence of agonist A portion of the evaluation results of the compounds of the present invention are shown in Table 1. In each cases, there are no large differences in $IC_{50}$ values before and after use of naloxone, and agonist activity by means of p receptors was found to be extremely weak. Namely, compounds 24, 84, 96, 97, 126 are selective agonists for $\delta$ receptors, while compounds 1, 22, 38, 39, 42, 43, 45, 46, 47, 52, 57, 59, 60, 61, 62, 63, 68, 69, 70, 73, 89, 91, 98, 99, 100, 101, 102, 103, 122, 140 and 141 are selective agonists for $\kappa$ receptors.

TABLE 1

Opioid Activity of Compounds

| | | Ke (nM) | |
|---|---|---|---|
| $IC_{50}$ (nM) | Naloxone | NTI | norBNI |
| 1   0.395 | 53 | 17.3 | 0.548 |
| 22  1.20 | 800 | 545 | 5.53 |
| 24  0.121 | 16.5 | 0.426 | 4.90 |
| 38  0.349 | 411 | 16.6 | 4.65 |
| 39  0.568 | 89.9 | 99.3 | 1.01 |
| 42  0.251 | 186 | 63.5 | 0.905 |
| 43  0.650 | 409 | 22.5 | 5.31 |
| 45  0.185 | 26.5 | 135 | 0.416 |
| 46  1.05 | — | — | 0.440 |
| 47  0.439 | 63.5 | 10.4 | 0.140 |
| 53  10.3 | — | 1676 | 0.21 |
| 57  0.0254 | — | 747 | 0.0124 |
| 59  1.14 | 21.3 | 47.3 | 0.151 |
| 60  0.468 | — | 291 | 3.20 |
| 61  0.420 | 14000 | 41.6 | 0.164 |
| 62  14.7 | — | 90.2 | 0.203 |
| 63  0.746 | 60.9 | 96.9 | 1.60 |
| 68  0.457 | 5710 | 143 | 1.08 |
| 69  0.320 | 1780 | 64.5 | 1.95 |
| 70  0.545 | — | — | 0.198 |
| 73  0.072 | 524 | 78 | 0.272 |
| 84  2.07 | 35.4 | 0.309 | 5.69 |
| 89  0.0934 | 18.3 | 15.6 | 0.85 |
| 91  0.378 | — | 450 | 0.699 |
| 96  0.346 | 32.5 | 1.61 | 4.21 |
| 97  0.247 | 163 | 2.92 | 13.9 |
| 98  1.30 | — | — | 1.35 |
| 99  0.674 | 94.5 | — | 0.652 |
| 100 0.647 | 1797 | — | 0.0717 |
| 101 0.269 | 25.4 | 31.6 | 0.0425 |
| 102 1.60 | — | 276 | 2.37 |
| 103 11.0 | — | — | 0.657 |
| 104 0.227 | 185 | 89 | 1.40 |
| 122 3.01 | 59.5 | 42.7 | 0.358 |
| 126 0.969 | 40.2 | 0.0065 | 1.20 |
| 140 0.413 | 320 | 261 | 1.06 |
| 141 0.160 | 142 | 184 | 1.39 |

Example 142

Analgesic Activity Test Using the Acetic Acid-induced Writhing Method 5 week old ddY mice were used in this test. After intraperitoneal administration of 0.1 ml of 0.6% aqueous acetic acid per 10 g of body weight, the number of writhing reactions that occurred in 10 minutes starting 10 minutes after administration was evaluated for the indicator. The test drug was administered subcutaneously into the backs of the animals 15 minutes before administration of acetic acid. A portion of those results are shown in Table 2. In this test, compounds 42, 47, 63 and 96 demonstrating $ED_{50}$ values of 0.00136, 0.00052, 0.0011 and 0.00086 mg/Kg, respectively, indicating particularly strong analgesic activity.

TABLE 2

Analgesic Activity According to Acetia Acid Writhing

| Compound | $ED_{50}$ (mg/kg) | Compound | $ED_{50}$ (mg/kg) |
|---|---|---|---|
| 1 | 0.017 | 22 | 0.0051 |
| 23 | 0.67 | 24 | 0.00575 |
| 26 | 0.099 | 27 | 0.046 |
| 28 | 0.071 | 31 | 0.75 |
| 32 | 0.290 | 33 | 0.080 |
| 34 | 0.210 | 35 | 0.026 |
| 36 | 0.23 | 37 | 0.0041 |
| 38 | 0.00352 | 39 | 0.0088 |
| 41 | 0.39 | 42 | 0.00136 |
| 43 | 0.0055 | 44 | 0.084 |
| 45 | 0.0038 | 46 | 0.013 |
| 47 | 0.00052 | 48 | 0.019 |
| 49 | 0.026 | 50 | 0.011 |
| 51 | 0.19 | 53 | 0.46 |
| 54 | 0.72 | 55 | 0.980 |
| 56 | 0.00802 | 57 | 0.040 |
| 58 | 0.190 | 59 | 0.0028 |
| 60 | 0.0046 | 61 | 0.0044 |
| 62 | 0.077 | 63 | 0.0011 |
| 64 | 0.097 | 65 | 0.15 |
| 67 | 0.36 | 68 | 0.0042 |
| 69 | 0.0049 | 70 | 0.0016 |
| 71 | 0.0042 | 72 | 0.18 |
| 73 | 0.023 | 74 | 0.78 |
| 83 | 0.0080 | 84 | 0.0058 |
| 85 | 0.1128 | 86 | 0.0347 |
| 87 | 0.027 | 89 | 0.00471 |
| 91 | 0.019 | 94 | 0.013 |
| 95 | 0.0081 | 96 | 0.00086 |
| 97 | 0.0019 | 98 | 0.0068 |
| 99 | 0.0018 | 100 | 0.024 |
| 101 | 0.0066 | 102 | 0.0019 |
| 103 | 0.069 | 104 | 0.017 |
| 105 | 0.098 | 106 | 0.25 |
| 107 | 0.023 | 108 | 0.0064 |
| 122 | 0.34 | 128 | 0.63 |
| 132 | 0.073 | 133 | 0.044 |
| 134 | 0.15 | 137 | 0.170 |
| 138 | 0.014 | 139 | 0.040 |
| 140 | 0.0034 | 141 | 0.010 |
| 142 | 0.78 | 144 | 0.024 |
| 149 | 0.013 | Morphine | 0.55 |

Example 143

Evaluation of Diuretic Action

7–8 week old male Wistar rats were used in this test after prohibiting from drinking water for 1 hour before testing. After discharging any urine accumulated in the bladder by gently stimulating the lower abdomens of the animals, the drug was administered subcutaneously. After 30 minutes, the animals were then forcibly given 20 ml/kg of physiological saline orally. The animals were then placed in metabolic cages immediately after administration of the drug (2 animals/cage) and urine output for 5 hours after loading with physiological saline was measured. Drug efficacy was expressed in the form of those doses resulting in urine outputs of 200 and 500, respectively, when the urine output of a non-dosed group was taken to be 100. Those doses were expressed as the $ED_{200}$ and $ED_{500}$ values, respectively. A portion of those results are shown in Table 3. In this test, the $ED_{200}$ values of compounds 22, 24, 42 and 43 were 0.00095, 0.00069, 0.00085 and 0.00054 mg/kg, respectively, indicating that these compounds have extremely strong diuretic action.

TABLE 3

Diuretic Action

| Compound | ED200 | ED500 (mg/kg) | Compound | ED200 | ED500 (mg/kg) |
|---|---|---|---|---|---|
| 1 | 0.0027 | 0.0457 | 22 | 0.00095 | 0.0170 |
| 24 | 0.00069 | 0.0063 | 27 | 0.0248 | 2.075 |
| 28 | 0.0200 | 3.799 | 35 | 0.0245 | 5.19 |
| 37 | 0.365 | — | 38 | 0.0038 | 0.281 |
| 39 | 0.0041 | 0.228 | 42 | 0.00085 | 0.0061 |
| 43 | 0.00054 | 0.0044 | 45 | 0.0081 | 0.857 |
| 47 | 0.0016 | — | 50 | 0.0021 | 0.0325 |
| 53 | 0.135 | 0.658 | 56 | 0.0028 | 0.0518 |
| 57 | 0.0424 | 1.256 | 59 | 0.0105 | 2.364 |
| 60 | 0.0143 | 1.13 | 61 | 0.0032 | 0.157 |
| 62 | 0.101 | 7.04 | 63 | 0.0038 | 0.309 |
| 65 | 0.119 | 5.31 | 68 | 0.0016 | 0.0232 |
| 83 | 0.0261 | 2.99 | 84 | 0.0028 | 0.0469 |
| 86 | 0.0057 | 0.229 | 89 | 0.0012 | 0.0162 |
| 91 | 0.0094 | 0.960 | 95 | 0.0028 | 0.0968 |
| 96 | 0.0013 | 0.0549 | 97 | 0.0045 | 0.0939 |
| 98 | 0.0065 | 0.206 | 99 | 0.0011 | 0.0309 |
| 100 | 0.0159 | 0.811 | 101 | 0.0089 | 0.226 |
| 102 | 0.0014 | 0.0154 | 103 | 0.0827 | 5.65 |
| 105 | 0.0190 | 3.30 | 107 | 0.0061 | 0.20 |
| 108 | 0.0210 | 5.11 | 141 | 0.0319 | 3.45 |

Industrial Applicability

AS a result of in vitro and in vivo tests, the compounds of the present invention were found to have both strong analgesic and diuretic activity as κ-agonists. It was clear that said compounds can be expected to be useful as analgesics and diuretics. Based on the properties of κ-agonists, the compounds of the present invention can also be used as hypotensives and sedatives.

What is claimed is:

1. A morphinan derivative represented by the formula (I) or its pharmacologically acceptable acid addition salt:

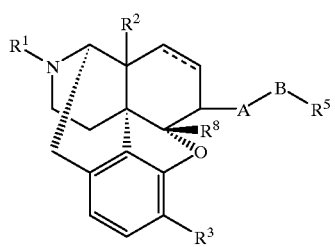

(I)

wherein,—
represents a single or double bond;

$R^1$ represents an alkyl group having 1–5 carbon atoms, a cycloalkylalkyl group having 4–7 carbon atoms, a cycloalkenylalkyl group having 5–7 atoms, an aryl group having 6–12 carbon atoms, an aralkyl group having 7–13 carbon atoms, an alkenyl group having 4–7 carbon atoms, an allyl group, a furan-2-ylalkyl group having 1–5 alkyl carbon atoms, or a thiophen-2-ylalkyl group having 1–5 alkyl carbon atom;

$R^2$ represents a hydrogen atom, a hydroxy group, a nitro group, an alkanoyloxy group having 1–5 carbon atoms, an alkoxy group having 1–5 carbon atoms, or —$NR^9R^{10}$;

$R^9$ represents a hydrogen atom or an alkyl group having 1–5 carbon atoms;

$R^{10}$ represents a hydrogen atom, an alkyl group having 1–5 carbon atoms or —$C(=O)R^{11}$;

$R^{11}$ represents a hydrogen atom, a phenyl group or an alkyl group having 1–5 carbon atoms, $R^3$ represents a hydrogen atom, a hydroxy group, an alkanoyloxy group having 1–5 carbon atoms or an alkoxy group having 1–5 carbon atoms;

A represents —$NR^{4'}C(=Y)$—, —$NR^4C(=Y)Z$—, —$NR^{4'}SO_2$—, —$NR^{4'}$—, or —$OC(OR^4)R^{4'}$— where Y and Z each independently represent $NR^4$, S or O, $R^4$ represents a hydrogen atom, a straight-chain or branched alkyl group having 1–5 carbon atoms or an aryl group having 6–12 carbon atoms, and wherein $R^4$ may be identical or different, and $R^{4'}$ represents a hydrogen atom, a straight-chain or branched alkyl group having 1–5 carbon atoms or an aryl group having 6–12 carbon atoms, B represents a valence bond, a straight-chain or branched alkylene group having 1–14 carbon atoms which may be substituted with one or more types of substituent groups selected from the group consisting of an alkoxy group having 1–5 carbon atoms, an alkanoyloxy group having 1–5 carbon atoms, a hydroxy group, fluorine, a nitro group, a cyano group, a trifluoromethyl group and a phenoxy group, a straight chain or branched acyclic unsaturated hydrocarbon containing 1 to 3 double bonds and/or triple bonds and having 2–14 carbon atoms which may be substituted with one or more substituent groups selected from the group consisting of an alkoxy group having 1–5 carbon atoms, an alkanoyloxy group having 1–5 carbon atoms, a hydroxy group, fluorine, a nitro group, a cyano group, a trifluoromethyl group and a phenoxy group, or a straight-chain or branched saturated or unsaturated hydrocarbon containing from 1 to 5 thioether, ether and/or amino bonds having 1–14 carbon atoms wherein no heteroatom is bonded directly to A;

$R^5$ represents a hydrogen atom or an organic group having the structure below which may be substituted with one or more substituent groups selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, iodine, an amino group, a nitro group, a cyano group, an isothiocyanate group, a trifluoromethyl group and a methylenedioxy group;

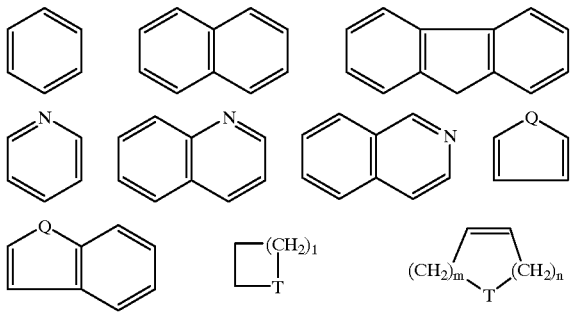

wherein Q is N, O or S, T is CH, N, S or O, 1 is 0–5, m, n≧0 and m+n≦5;

$R^8$ represents a hydrogen atom, an alkyl group having 1–5 carbon atoms or an alkanoyl group having 1–5 carbon atoms;

with proviso that
a) when A represents —NR$^{4'}$C(=Y)—, —NR$^{4'}$C(=Y)Z— or —NR$^4$ SO$_2$—, and NR$^4$ represents a straight-chain or branched alkyl group having 1–5 carbon atoms or an aryl group having 6–12 carbon atoms, then R$^1$ represents an alkyl group having 1–2 carbon atoms, a cycloalkenylalkyl group having 5–7 carbon atoms, an aryl group having 6–12 carbon atoms, an aralkyl group having 7–13 carbon atoms, a furan-2-ylalkyl group having 1–5 carbon atoms or thiophen-2-ylalkyl group having 1–5 carbon atoms;
b) when A represents —NHC(=O)—, and R$^5$ represents a hydrogen atom, then B represents a straight-chain or branched alkylene having 3–14 carbon atoms (which may be substituted with one or more types of substituent groups selected from the group consisting of an alkoxy group having 1–5 carbon atoms, an alkanoyloxy group having 1–5 carbon atoms, a hydroxy group, fluorine, a nitro group, a cyano group, trifluoromethyl group and a phenoxy group), a straight-chain or branched acyclic unsaturated hydrocarbon containing 1 to 3 double bonds and/or triple bonds and having 3–14 carbon atoms, which may be substituted with one or more substituents selected from the group consisting of an alkoxy group having 1–5 carbon atoms, an alkanoyloxy group having 1–5 carbon atoms, a hydroxy group, fluorine, a nitro group, a cyano group, trifluoromethyl group and a phenoxy group, or a straight-chain or branched saturated or unsaturated hydrocarbon containing from 1 to 5 thioether, ether and/or amino bonds having 1–14 carbon atoms wherein no heteratom is bonded directly to A;
c) when A represents —NHC(=O)—, B presents a valence bond, and R$^5$ represents a phenyl group, then R$^5$ must be substituted with at least one substitutent selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, iodine, an amino group, a nitro group, an isothiocyanate group, a trifluoromethyl group and a methylenedioxy group;
d) when A represents —NH—, and R$^5$ represent a hydrogen atom, then B represents a straight-chain or branched alkylene group having 3–14 carbon atoms, which may be substituted with one or more types of substituent groups selected from the group consisting of an alkoxy group having 1–5 carbon atoms, an alkanoyloxy group having 1–5 carbon atoms, a hydroxy group, fluorine, a nitro group, a cyano group, a trifluoromethyl group and a phenoxy group, a straight-chain or branched acyclic unsaturated hydrocarbon containing 1 to 3 double bonds and/or triple bonds and having 2–14 carbon atoms, which may be substituted with one or more substituent groups selected from the group consisting of an alkoxy group having 1–5 carbon atoms, an alkanoyloxy group having 1–5 carbon atoms, a hydroxy group, fluorine, a nitro group, a cyano group, a trifluoromethyl group and a phenoxy group, or a straight-chain or branched saturated or unsaturated hydrocarbon containing from 1 to 5 thieoether, ether and/or amino bonds having 1–14 carbon atoms wherein no heteroatom is bonded directly to A;
e) when A represents —NH—, B represents a straight-chain alkylene having one carbon atom, and R$^5$ represents a phenyl group, then R$^5$ must be substituted with one or more substituents selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, iodine, an amino group, a nitro group, a cyano group, an isothiocyatate group, a trifluoromethyl group and a methylenedioxy group; and
f) when A represents —NR$^{4'}$—, R$^{4'}$ represents a straight-chain alkyl group having 1 or 2 carbon atoms, and R$^5$ represents a hydrogen atom, when B represents a straight-chain or branched alkylene group having 3–14 carbon atoms, which may be substituted with one or more substituent groups selected from the group consisting of an alkoxy group having 1–5 carbon atoms, an alkanoyloxy group having 1–5 carbon atoms, a hydroxy group, fluorine, a nitro group, a cyano group, a trifluoromethyl group and a phenoxy group, a straight-chain or branched acyclic unsaturated hydrocarbon containing 1 to 3 double bonds and/or triple bonds and having 2–14 carbon atoms, which may be substituted with one or more substituent groups selected from the group consisting of an alkoxy group having 1–5 carbon atoms, an alkanoyloxy group having 1–5 carbon atoms, a hydroxy group, fluorine, a nitro group, a cyano group, a trifluoromethyl group and a phenoxy group, or a straight-chain or branched saturated or unsaturated hydrocarbon containing from 1 to 5 thioether, ether and/or amino bonds having 1–14 carbon atoms wherein no heteroatom is bonded to A;

and formula (I) includes the (+) form, (−) form and (±)form.

2. The compound of claim 1, or its pharmacologically acceptable acid addition salt, wherein A is —NR$^{4'}$C(=Y)Z—, —OC(OR$^4$)R$^4$— or —SSO$_2$—, provided that Z represents NR$^4$ or S when Y is O.

3. The compound of claim 1, or its pharmacologically acceptable acid addition salt, wherein A is —NR$^4$ C(=Y)—, wherein Y represents NR$^4$ or S.

4. The compound of claim 1, or its pharmacologically acceptable acid addition salt, wherein A is —N$^{4'}$C(=S)NR$^4$—, NR$^{4'}$C(=O)NR$^4$, —NR$^{4'}$C(=O)O—, —NR$^{4'}$C(=O)—, —NR$^{4'C(=S)}$— or —$^{NR4'}$SO$_2$—, wherein R$^4$ and R$^{4'}$ independently, represent a straight chain or branched alkyl group having 1–5 carbon atoms or an aryl group having 6–12 carbon atoms:

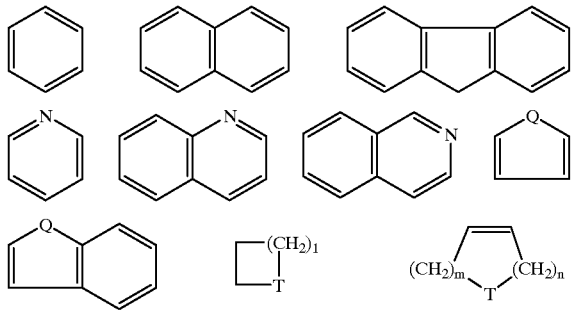

5. The compound of claim 1, or its pharmacologically acceptable acid addition salt, wherein A is —N$^{4'}$C(=O)O— provided that, when p$^{4'}$and R$^5$ are both hydrogen atoms, B represents a straight-chain or branched alkylene group having 3–14 carbon atoms, which may be substituted with one or more types of substituent groups selected from the group consisting of an alkoxy group having 1–5 carbon atoms, an alkanoyloxy group having 1–5 carbon atoms, a hydroxy group, fluorine, a nitro group, a cyano group, a trifluoromethyl group and a phenoxy group, a straight chain or branched acylic unsaturated hydrocarbon containing from 1 to 3 double bonds and/or triple bonds and having 2–14 carbon atoms which may be substituted with one or more substitution groups selected from the group consisting of an alkoxy group having 1–5 carbon atoms, an alkanoyloxy group having 1–5 carbon atoms, a hydroxy group, fluorine, a nitro group, a cyano group, a trifluoromethyl group and a phenoxy group, or a straight-chain or branched saturated or unsaturated hydrocarbon containing from 1 to 5 thioether, ether and/or amino bonds and having 1–14 carbon atoms, wherein no hetero atom is bonded directly to A.

6. The compound of claim 1, or its pharmacologically acceptable acid addition salt, wherein A is —NHC(=O)—, B is a straight-chain or branched alkylene group having 1–14 carbon atoms which may be substituted with one or more types of substituent groups selected from the group consisting of an alkoxy group having 1–5 carbon atoms, an alkanoyloxy group having 1–5 carbon atoms, a hydroxy group, fluorine, a nitro group, a cyano group, a trifluoromethyl group and a phenoxy group, a straight chain or branched acyclic unsaturated hydrocarbon containing from 1 to 3 double bonds and/or triple bonds and having 2–14 carbon atoms which may be substituted with one or more substituent groups selected from the group consisting of an alkoxy group having 1–5 carbon atoms, an alkanoyloxy group having 1–5 carbon atoms, a hydroxy group, fluorine, a nitro group, a cyano group, a trifluoromethyl group and a phenoxy group, or a straight-chain or branched saturated or unsaturated hydrocarbon containing from 1 to 5 thioether, ether and/or amino bonds and having 1–14 carbon atoms, wherein no hetero atom is bonded directly to A, and $R^5$ is an organic group having the following structure:

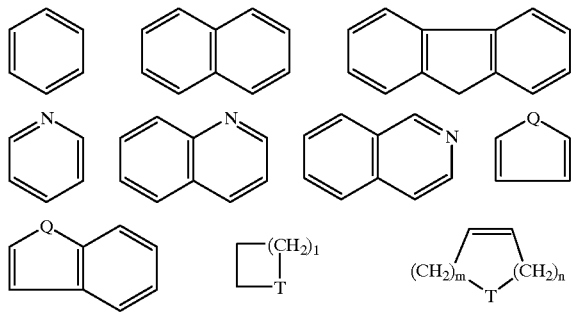

wherein Q is N. O or S. T is CH, N. S or O, l is 0–5, m, n≧0 and m+n≦5; which may be substituted by at least one type of substituent group selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, iodine, an amino group, a nitro group, a cyano group, an isothiocyanato group, a trifluoromethyl group and a methylenedioxy group.

7. The compound of claim 1, or its pharmacologically acceptable acid addition salt, wherein A is —NHC(=O)—, B represents a valence bond, and $R^5$ is an organic group having the following structure:

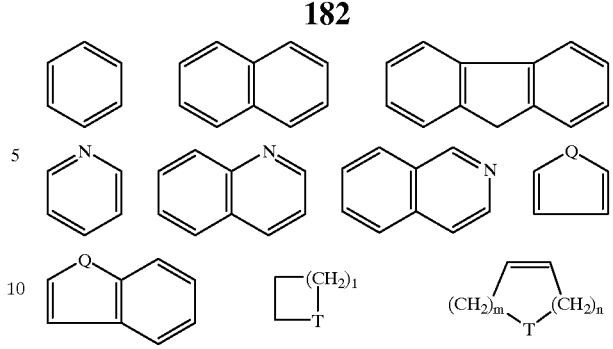

wherein Q is N, O or S, T is CH, N, S or O, l is 0–5, m, n≧0 and m +n≦5;

wherein $R^5$ is substituted by at least one type of substituent group selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, iodine, an amino group, a nitro group, a cyano group, an isothiocyanato group, a trifluoromethyl group and a methylenedioxy group.

8. The compound of claim 6, or its pharmacologically acceptable acid addition salt, wherein $R^1$ is a methyl, ethyl, cyclopropylmethyl, allyl, benzyl or phenethyl group, and $R^2$ and $R^3$ are independently a hydrogen atom, a hydroxy, acetoxy or methoxy group, and $R^8$ is a hydrogen atom or methyl group.

9. The compound of claim 4, or its pharmacologically acceptable acid addition salt, wherein A is —NR$^{4'}$C(=O)— and wherein $R^4$ represents a straight-chain or branched alkyl group having 1–5 carbon atoms or an aryl group having 6–12 carbon atoms.

10. The compound of claim 1, or its pharmacologically acceptable acid addition salt, wherein A is —NR$^{4'}$—, and provided that, when $R^5$ is a hydrogen atom, B is a straight-chain or branched alkylene group having 5–14 carbon atoms which may be substituted with one or more types of substituent groups selected from the group consisting of an alkoxy group having 1–5 carbon atoms, an alkanoyloxy group having 1–5 carbon atoms, a hydroxy group, fluorine, a nitro group, a cyano group, a trifluoromethyl group and a phenoxy group, a straight-chain or branched acyclic unsaturated hydrocarbon containing from 1 to 3 double bonds and/or triple bonds and having 2–14 carbon atoms which may be substituted with one or more substituent groups selected from the group consisting of an alkoxy group having 1–5 carbon atoms, an alkanoyloxy group having 1–5 carbon atoms, a hydroxy group, fluorine, a nitro group, a cyano group, a trifluoromethyl group and a phenoxy group, or a straight-chain or branched saturated or unsaturated hydrocarbon containing from 1 to 5 thioether, ether and/or amino bonds and having 1–14 carbon atoms wherein no hetero atom is bonded directly to A.

11. A pharmaceutical composition containing a morphinan derivative of claim 1, or a pharmacologically acceptable acid addition salt thereof, as an active ingredient.

12. A method for producing analgesia comprising administering an effective amount of a pharmaceutical composition comprising a morphinan derivative of claim 1, or a pharmacologically acceptable acid addition salt thereof, as an active ingredient to a subject requiring pain relief.

13. A method of diuresis comprising administering an effective amount of a pharmaceutical composition comprising a morphinan derivative of claim 1, or a pharmacologically acceptable acid addition salt thereof, as an active ingredient.

* * * * *